(12) United States Patent
Paruch et al.

(10) Patent No.: US 7,449,488 B2
(45) Date of Patent: Nov. 11, 2008

(54) PYRAZOLOPYRIMIDINES AS PROTEIN KINASE INHIBITORS

(75) Inventors: Kamil Paruch, Garwood, NJ (US); Timothy J. Guzi, Chatham, NJ (US); Michael P. Dwyer, Scotch Plains, NJ (US); Gerald W. Shipps, Jr., Stoneham, MA (US)

(73) Assignee: Schering Corporation, Kenilworth, NJ (US)

( * ) Notice: Subject to any disclaimer, the term of this patent is extended or adjusted under 35 U.S.C. 154(b) by 43 days.

(21) Appl. No.: 11/244,628

(22) Filed: Oct. 6, 2005

(65) Prior Publication Data
US 2006/0094706 A1   May 4, 2006

Related U.S. Application Data

(63) Continuation-in-part of application No. 10/452,400, filed on Jun. 2, 2003, now Pat. No. 7,196,111.

(60) Provisional application No. 60/385,837, filed on Jun. 4, 2002.

(51) Int. Cl.
C07D 231/00   (2006.01)
C07D 231/54   (2006.01)
A61K 31/415   (2006.01)
A01N 43/56   (2006.01)

(52) U.S. Cl. ............... 514/405; 514/403; 514/514; 514/406; 546/1; 546/26; 546/112; 546/134; 548/356.1; 548/358.1; 548/360.1

(58) Field of Classification Search ............... 514/405, 514/403, 406; 546/1, 26, 112, 134; 548/356.1, 548/358.1, 360.1
See application file for complete search history.

(56) References Cited

OTHER PUBLICATIONS

Wolff, M.E., "Burger's Medicinal Chemistry", 5th Ed., Part 1, pp. 975-977 (1995).*
Banker et al., "Modern Pharmaceuticals", 3rd Ed., p. 596 (1996).*

* cited by examiner

*Primary Examiner*—James O. Wilson
*Assistant Examiner*—Paul V. Ward
(74) *Attorney, Agent, or Firm*—Palaiyur S. Kalyanaraman

(57) ABSTRACT

In its many embodiments, the present invention provides a novel class of pyrazolo[1,5-a]pyrimidine compounds as inhibitors of protein and/or checkpoint kinases, methods of preparing such compounds, pharmaceutical compositions including one or more such compounds, methods of preparing pharmaceutical formulations including one or more such compounds, and methods of treatment, prevention, inhibition, or amelioration of one or more diseases associated with the protein or checkpoint kinases using such compounds or pharmaceutical compositions. The invention also relates to the inhibition of hepatitis C virus (HCV) replication. In particular, embodiments of the invention provide compounds and methods for inhibiting HCV RNA-dependent RNA polymerase enzymatic activity. The invention also provides compositions and methods for the prophylaxis and treatment of HCV infection.

16 Claims, No Drawings

PYRAZOLOPYRIMIDINES AS PROTEIN KINASE INHIBITORS

CROSS REFERENCE TO RELATED APPLICATIONS

This application is a continuation-in-part of U.S. patent application Ser. No. 10/452,200 filed on Jun. 2, 2003, which claims the benefit of priority from U.S. Provisional Patent Application Ser. No. 60/385,837, filed on Jun. 4, 2002.

FIELD OF THE INVENTION

This invention relates to substituted pyrazolo[1,5-a]pyrimidine compounds useful as protein kinase inhibitors, regulators or modulators, pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases.

This invention also relates to the inhibition of hepatitis C virus (HCV) replication. In particular, the invention relates to compounds and methods for inhibiting HCV RNA-dependent RNA polymerase.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Checkpoint (CHK) kinases (e.g., CHK-1, CHK-2 etc.), AKT kinases and the like. Examples of protein kinase inhibitors are described in WO02/22610 A1 and by Y. Mettey et al in *J. Med. Chem.*, (2003) 46 222-236.

The cyclin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer. Flavopiridol (shown below) is a nonselective CDK inhibitor that is currently undergoing human clinical trials, A. M. Sanderowicz et al, *J. Clin. Oncol*. (1998) 16, 2986-2999.

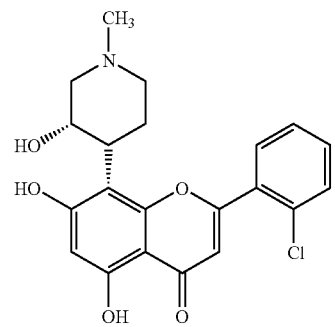

Other known inhibitors of CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b]pyridine compounds as CDK inhibitors. An illustrative compound from the '305 patent is:

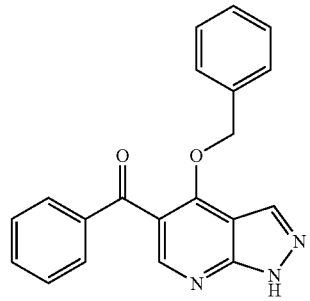

K. S. Kim et al, *J. Med. Chem.* 45 (2002) 3905-3927 and WO 02/10162 disclose certain aminothiazole compounds as CDK inhibitors.

Pyrazolopyrimidines are known. For example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383, 790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. Other publications of interest include: U.S. Pat. Nos. 5,688,949 and 6,313,124, WO 98/54093, WO 03/101993, WO 03/091256, WO 04/089416 and DE 10223917.

Another series of protein kinases are those that play an important role as a checkpoint in cell cycle progression.

Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate $G_2$ arrest induced by DNA damage inflicted by either anticancer agents or endogenous DNA damage, as well as result in preferential killing of the resulting checkpoint defective cells. See, e.g., Peng et al., *Science*, 277, 1501-1505 (1997); Sanchez et al., Science, 277, 1497-1501 (1997), Nurse, *Cell*, 91, 865-867 (1997); Weinert, *Science*, 277, 1450-1451 (1997); Walworth et al., Nature, 363, 368-371 (1993); and Al-Khodairy et al., *Molec. Biol. Cell.*, 5, 147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., Nature, 395, 507-510 (1998); Matsuoka, *Science*, 282, 1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1 (FLK-1), fetal liver kinase-4 (FLK-4) and the fms-like tyrosine kinase-1 (flt-1). For detailed discussion of the receptor-type tyrosine kinases, see Plowman et al., DN&P 7(6): 334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8, 2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Research*, 56, 3540-3545 (1996)), as has been shown with mutants of VEGF-R2 which fail to mediate signal transduction. Millauer et al, Cancer Research, 56, 1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17, 5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., Science, 277, 55-60 (1997).

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja—Ser. D Osa —Tom. 616, (Aug. 30, 2005), http://kiriasto.utu.fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

There is a need for effective inhibitors of protein kinases in order to treat or prevent disease states associated with abnormal cell proliferation. Moreover, it is desirable for kinase inhibitors to possess both high affinity for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF, CDKs or CDK/cyclin complexes and both receptor and non-receptor tyrosine kinases.

Hepatitis C virus (HCV) is a positive strand RNA virus in the Flaviviridae family. Its 9.6 kb genome encodes for approximately 10 proteins, including the structural capsid and envelope proteins, as well as the nonstructural proteins NS3 (protease and helicase) and NS5B (polymerase). Ishii et al., Hepatology, 1227 (1999), teaches that the viral RNA-dependent RNA polymerase (RdRp) is responsible both for generating the intermediate minus-strand RNA template and for the synthesis of progeny positive-strand genomic RNA. The authors point out that RdRp is used only in the replication of RNA viruses and has very strict template specificities. The authors conclude that RNA-dependent RNA polymerase enzymes, including HCV RdRp, are ideal targets for antiviral drugs.

HCV is a major human pathogen and is believed to have infected approximately 3% of the worldwide population. Bressanelli et al., Proc. Natl. Acad. Sci. USA, 96: 13034-13039 (1999), teaches that HCV is capable of establishing a persistent infection that can cause chronic hepatitis leading to cirrhosis and hepatocellular carcinoma.

Existing therapies for HCV are limited, and only a few inhibitors of HCV RNA-dependent RNA polymerase are known. There is thus a need to identify additional HCV RdRp inhibitors and to identify the structural features required for potent HCV RdRp inhibitory activity.

SUMMARY OF THE INVENTION

In its many embodiments, the present invention provides substituted pyrazolo[1,5-a]pyrimidine compounds, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the protein kinases using such compounds or pharmaceutical compositions.

In one aspect, the present invention provides compounds represented by the structural formula (VII):

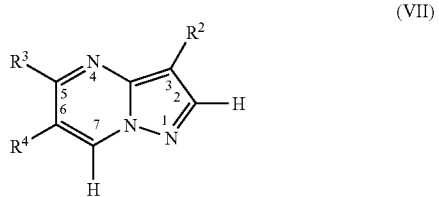

or a pharmaceutically acceptable salt, solvate, ester, or prodrug of the compound of Formula (VII), wherein:

$R^2$ is halo;

$R^3$ is a saturated or partially unsaturated heterocyclic radical; and $R^4$ is selected from the group consisting of H, halo, haloalkyl, alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —$NR^8R^9$, —$NR^8COR^9$, —$NR^8SO_2R^9$, —$COR^8$, —$CO_2R^8$, —$CONR^8R^9$, —$CH_2OR^8$, —$OR^8$, —$SR^8$, —$SO_2R^8$, —$S(O_2)NR^8R^9$, —$S(O_2)$aryl, —$S(O_2)$heteroaryl, —$C(O)OR^9$, —$C(O)$aryl, —$C(O)$heteroaryl, —$(CHR^5)_n$-aryl, —$(CHR^5)_n$-heteroaryl,

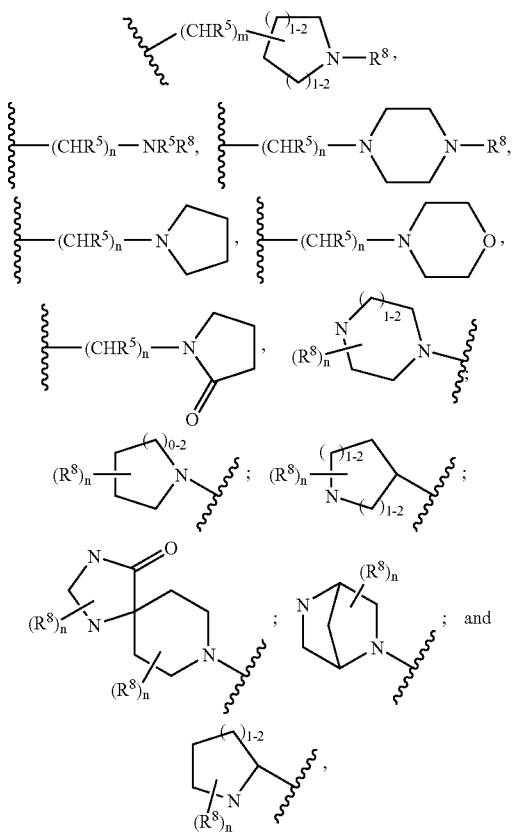

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for $R^4$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$;

$R^5$ is selected from the group consisting of H, alkyl, aryl or cycloalkyl;

$R^6$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —$CF_3$, —$OCF_3$, —CN, —$OR^5$, —$NR^5R^{10}$, —$C(R^5R^{11})_p$—$R^9$, —$N(R^5)$Boc, —$(CR^5R^{11})_p OR^5$, —$C(O_2)R^5$, —$C(O)R^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^7$ is selected from the group consisting of alkyl, cycloalkyl, aryl, arylalkenyl, heteroaryl, arylalkyl, heteroarylalkyl, heteroarylalkenyl, and heterocyclyl, wherein each of the alkyl, cycloalkyl, heteroarylalkyl, aryl, arylalkenyl, heteroaryl, arylalkyl, heteroarylalkyl, heteroarylalkenyl, and heterocyclyl can be unsubstituted or optionally independently substituted with one or more moieties which can be the same or different, each moiety being independently selected from the group consisting of halo, alkyl, aryl, cycloalkyl, CF$_3$, OCF$_3$, CN, —OR$^5$, —NR$^5$R$^{10}$, —CH$_2$OR$^5$, —C(O$_2$)R$^5$, —C(O)NR$^5$R$^{10}$, —C(O)R$^5$, —SR$^{10}$, —S(O$_2$)R$^{10}$, —S(O$_2$)NR$^5$R$^{10}$, —N(R$^5$)S(O$_2$)R$^{10}$, —N(R$^5$)C(O)R$^{10}$ and —N(R$^5$)C(O)NR$^5$R$^{10}$;

R$^8$ is selected from the group consisting of H, —OR$^6$, —NR$^5$R$^6$, —C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, —S(O$_2$)R$^7$,

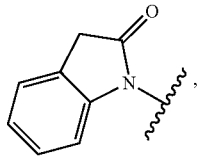

—OR$^{10}$, —CF$_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{10}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^9$ is selected from the group consisting of H, —OR$^6$, —NR$^5$R$^6$, —C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, —S(O$_2$)R$^7$,

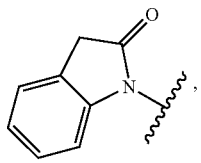

—OR$^{10}$, —CF$_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{10}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^{10}$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{11}$, —C(R$^5$R$^{11}$)$_p$—R$^9$, —N(R$^5$)Boc, —(CR$^5$ R$^{11}$)$_p$OR$^5$, —C(O$_2$)R$^5$, —C(O)R$^5$, —C(O)NR$^5$R$^{11}$, —SO$_3$H, —SR$^{11}$, —S(O$_2$)R$^7$, —S(O$_2$)NR$^5$R$^{11}$, —N(R$^5$)S(O$_2$)R$^7$, —N(R$^5$)C(O)R$^7$ and —N(R$^5$)C(O)NR$^5$R$^{11}$;

or optionally (i) R$^5$ and R$^{11}$ in the moiety —NR$^5$R$^{11}$, or (ii) R$^5$ and R$^6$ in the moiety —NR$^5$R$^6$, may be joined together to form a cycloalkyl or heterocyclyl moiety, with each of the cycloalkyl or heterocyclyl moiety being unsubstituted or optionally independently being substituted with one or more R$^9$ groups; and R$^{11}$ is H, halo or alkyl;

m is 0 to 4;

n is 1 to 4; and p is 1 to 4.

In another aspect, the present invention provides compounds represented by the structural formula (VIII):

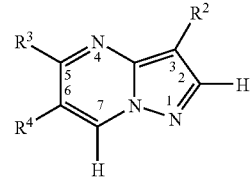

or a pharmaceutically acceptable salt, solvate, ester, or prodrug of the compound of Formula (VIII), wherein:

R$^2$ is halo;

R$^3$ is alkyl; and

R$^4$ is alkyl or alkoxy.

The compounds of Formulae VII and VIII can be useful as protein kinase inhibitors and can be useful in the treatment and prevention of proliferative diseases, for example, cancer, inflammation and arthritis, neurodegenerative diseases such Alzheimer's disease, cardiovascular diseases, viral diseases and fungal diseases.

The present invention also provides compounds and methods useful for the prophylaxis or treatment of HCV infection. In particular, embodiments of the invention provide compounds and methods for inhibiting HCV RNA-dependent RNA polymerase (RdRp) enzymatic activity.

In one aspect, embodiments of the invention provide novel HCV RdRp inhibitors of formula (I):

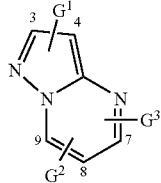

or a pharmaceutically acceptable salt thereof, wherein:

$G^1$ is selected from the group consisting of —OH, cyano, —C(O)—OH, —C(O)—OR$^8$, —C(O)—NR$^2$R$^3$, —N(R)—C(O)R$^8$, —S(O)$_2$ NR$^2$R$^3$, —N(R)—S(O)$_2$R$^8$, heteroaryl, aryl, halo, amino, formyl, heterocyclenalkenyl, heterocyclylalkyl, CH(N)OH, CH(N)OR$^8$, hydroxyalkyl, and saturated or partially unsaturated heterocyclic radical, where R$^8$, at each occurrence, is independently selected from the group consisting of hydrogen, alkyl, cycloalkyl, aryl, aralkyl, heteroaryl, heteroarylalkyl, carboalkoxyalkyl, carboalkoxy, acyloxyalkyl, acyloxyalkyl, and saturated or partially unsaturated heterocyclic radical;

R$^2$ and R$^3$ are independently selected from the group consisting of hydrogen, alkyl, cycloalkyl, aryl, aralkyl, heteroaryl, heteroarylalkyl, and saturated or partially unsaturated heterocyclic radical; or R$^2$ and R$^3$ taken together form a 5- or 6-membered heteroaromatic or saturated or partially unsaturated heterocyclic ring; or —NR$^2$R$^3$ together forms an alpha-, beta-, or gamma-amino acid, wherein R$^2$ is hydrogen or C1-C6 alkyl, and R$^3$ has a formula selected from the group consisting of acylaminoalkyl, dialkylaminoalkyl, alkoxyalkyl, hydroxyalkyl, cyano, arylsulfonyl, alkylsulfonyl, hydroxy, alkoxy, —C(R$^6$)(R$^6$)CO$_2$H, —CH$_2$CH$_2$CH(R$^6$)CO$_2$H, —CH$_2$CH(R$^6$)CO$_2$H, —CH(R$^6$)CO$_2$alkyl, —SO$_2$aralkyl, —SO$_2$fluoroalkyl, —CH(R$^6$)CONH$_2$, —CH(R$^6$)CH$_2$CO$_2$H, —CH(R$^6$)CO$_2$H, —CH(R$^6$)CH$_2$CH$_2$CO$_2$H, —CH$_2$CH(R$^6$)CH$_2$CO$_2$H, and —CH$_2$CH$_2$CH(R$^6$)CO$_2$H;

wherein R$^6$ is independently selected from the group consisting of hydrogen, alkyl, cycloalkyl, aryl, heteroaryl, saturated or partially unsaturated heterocyclic radical, aminoalkyl, alkylthioalkyl, carbamoyl, hydroxy, and —CH$_2$R$^7$, where R$^7$ is selected from the group consisting of aryl, aralkyl, cycloalkyl, heteroaryl, saturated or partially unsaturated heterocyclic radical, hydroxy, alkoxy, aryloxy, aralkoxy, thio, alkylthio, arylthio, and aralkylthio;

$G^1$ is attached to either of positions C3 or C4 of the pyrazole ring, the other position being optionally substituted with alkyl, alkenyl, alkynyl, halo, fluoroalkyl, hydroxy, alkoxy, or cyano; and $G^2$ is independently are selected from the group consisting of alkyl, cycloalkyl, aryl, heteroaryl, saturated or partially unsaturated heterocyclic radical, trifluoromethyl, carboxyalkylamino, alkylamino, carboxy, alkenyl, alkoxyalkyl, heterocyclylalkyl, cycloalkylalkyl, arylalkyl, and —W-Cy, where W is selected from the group consisting of O, N(R), S, C(O), CH(R), —O—CH(R)—, —N(R)—CH(R)—, —S—CH(R)—, —C(O)—N(R)—, —N(R)—C(O)—, —S(O)$_2$—N(R), —N(R)—S(O)$_2$—, and —N(R)—C(O)—N(R)—, where R, at each occurrence, is independently selected from the group consisting of hydrogen, alkyl, cycloalkyl, aryl, aralkyl, heteroaryl, heteroarylalkyl, and saturated or partially unsaturated heterocyclic radical, Cy is selected from the group consisting of cycloalkyl, aryl, aralkyl, heteroaryl, heteroarylalkyl, and saturated or partially unsaturated heterocyclic radical;

$G^3$ can be absent or is independently selected from the group consisting of alkyl, cycloalkyl, aryl, heteroaryl, saturated or partially unsaturated heterocyclic radical, and —W-Cy, where W is selected from the group consisting of O, N(R), S, C(O), CH(R), —O—CH(R)—, —N(R)—CH(R)—, —S—CH(R)—, —C(O)—N(R)—, —N(R)—C(O)—, —S(O)$_2$—N(R), —N(R)—S(O)$_2$—, and —N(R)—C(O)—N(R)—, where R, at each occurrence, is independently selected from the group consisting of hydrogen, alkyl, cycloalkyl, aryl, aralkyl, heteroaryl, heteroarylalkyl, and saturated or partially unsaturated heterocyclic radical, Cy is selected from the group consisting of cycloalkyl, aryl, aralkyl, heteroaryl, heteroarylalkyl, and saturated or partially unsaturated heterocyclic radical, and $G^2$ and $G^3$, collectively, are attached at any two of positions C7, C8, and C9 of the pyrimidine ring, the remaining position being optionally substituted with alkyl, alkenyl, alkynyl, halo, fluoroalkyl, hydroxy, alkoxy, or cyano;

wherein the ring portion of any of said cycloalkyl, aryl, aralkyl, heteroaryl, heteroarylalkyl, or heterocyclic radical in $G^1$, $G^2$, or $G^3$ can be optionally substituted.

In one aspect, embodiments of the invention provide novel HCV RdRp inhibitors of formula (I):

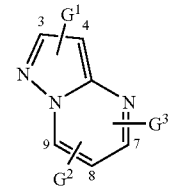

or a pharmaceutically acceptable salt thereof, wherein:

$G^1$ is selected from the group consisting of —OH, cyano, —C(O)—OH, —C(O)—OR, —C(O)—NR$^2$R$^3$, —N(R)—C(O)R, —S(O)$_2$ NR$^2$R$^3$, —N(R)—S(O)$_2$R, heteroaryl, and saturated or partially unsaturated heterocyclic radical, where R, at each occurrence, is independently selected from the group consisting of hydrogen, alkyl, cycloalkyl, aryl, aralkyl, heteroaryl, heteroarylalkyl, and saturated or partially unsaturated heterocyclic radical;

R$^2$ and R$^3$ are independently selected from the group consisting of hydrogen, alkyl, cycloalkyl, aryl, aralkyl, heteroaryl, heteroarylalkyl, and saturated or partially unsaturated heterocyclic radical; or R$^2$ and R$^3$ taken together form a 5- or 6-membered heteroaromatic or saturated or partially unsaturated heterocyclic ring; or —NR$^2$R$^3$ together forms an alpha-, beta-, or gamma-amino acid, wherein R$^2$ is hydrogen or C$_1$-C$_6$ alkyl, and R$^3$ has a formula selected from the group consisting of —CH$_2$CH(R$^6$)CO$_2$H, —CH(R$^6$)CH$_2$CO$_2$H, —CH(R$^6$)CO$_2$H, —CH(R$^6$)CH$_2$CH$_2$CO$_2$H, —CH$_2$CH(R$^6$)CH$_2$CO$_2$H, and —CH$_2$CH$_2$CH(R$^6$)CO$_2$H;

wherein R$^6$ is selected from the group consisting of hydrogen, alkyl, cycloalkyl, aryl, heteroaryl, saturated or partially unsaturated heterocyclic radical, and —CH$_2$R$^7$, where R$^7$ is selected from the group consisting of aryl, aralkyl, cycloalkyl, heteroaryl, saturated or partially unsaturated heterocyclic radical, hydroxy, alkoxy, aryloxy, aralkoxy, thio, alkylthio, arylthio, and aralkylthio;

$G^1$ is attached to either of positions C3 or C4 of the pyrazole ring, the other position being optionally substituted with alkyl, alkenyl, alkynyl, halo, fluoroalkyl, hydroxy, alkoxy, or cyano; and $G^2$ and $G^3$ independently are selected from the group consisting of alkyl, cycloalkyl, aryl, heteroaryl, saturated or partially unsaturated heterocyclic radical, and —W-Cy, where W is selected from the group consisting of O, N(R), S, C(O), CH(R), —O—CH(R)—, —N(R)—CH(R)—, —S—CH(R)—, —C(O)—N(R)—, —N(R)—C(O)—, —S(O)$_2$—N(R), —N(R)—S(O)$_2$—, and —N(R)—C(O)—N(R)—, where R, at each occurrence, is independently selected from the group consisting of hydrogen, alkyl, cycloalkyl, aryl, aralkyl, heteroaryl, heteroarylalkyl, and saturated or partially unsaturated heterocyclic radical, Cy is selected from the group consisting of cycloalkyl, aryl, aralkyl, heteroaryl, heteroarylalkyl, and saturated or partially unsaturated heterocyclic radical, and $G^2$ and $G^3$, collectively, are attached at any two of positions C7, C8, and C9 of the pyrimidine ring, the remaining position being optionally substituted with alkyl, alkenyl, alkynyl, halo, fluoroalkyl, hydroxy, alkoxy, or cyano;

wherein the ring portion of any of said cycloalkyl, aryl, aralkyl, heteroaryl, heteroarylalkyl, or heterocyclic radical in $G^1$, $G^2$, or $G^3$ can be optionally substituted.

In one aspect, the invention features a compound of formula (V)

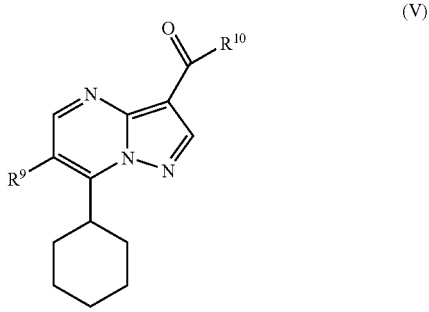

(V)

or a pharmaceutically acceptable salt thereof, wherein;

$R^9$ is aryl or heteroaryl, each of which is independently optionally substituted;

$R^{10}$ is OH, heteroaryl, NHR, or $NR^2R^3$;

R, at each occurrence, is independently selected from the group consisting of hydrogen, alkyl, cycloalkyl, aryl, aralkyl, heteroaryl, heteroarylalkyl, and saturated or partially unsaturated heterocyclic radical; and —$NR^2R^3$ together forms an alpha- or beta-amino acid, wherein $R^2$ is hydrogen or $C_1$-$C_6$ alkyl, and $R^3$ has a formula selected from the group consisting of —$CH_2CH(R^6)CO_2H$, —$CH(R^6)CH_2CO_2H$, and —$CH(R^6)CO_2H$.

In another aspect, the invention features a compound of formula (VI):

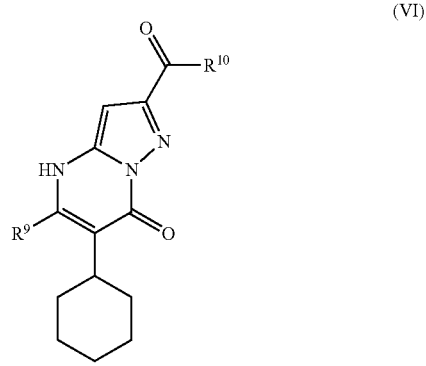

(VI)

or a pharmaceutically acceptable salt thereof, wherein;

$R^9$ is aryl or heteroaryl, each of which is independently optionally substituted;

$R^{10}$ is OH, heteroaryl, NHR, or $NR^2R^3$;

R, at each occurrence, is independently selected from the group consisting of hydrogen, alkyl, cycloalkyl, aryl, aralkyl, heteroaryl, heteroarylalkyl, and saturated or partially unsaturated heterocyclic radical; and —$NR^2R^3$ together forms an alpha- or beta-amino acid, wherein $R^2$ is hydrogen or $C_1$-$C_6$ alkyl, and $R^3$ has a formula selected from the group consisting of —$CH_2CH(R^6)CO_2H$, —$CH(R^6)CH_2CO_2H$, and —$CH(R^6)CO_2H$.

In another aspect, NR2R3 together forms an alpha- or beta-amino acid.

In another aspect, embodiments of the invention provide pharmaceutical compositions comprising At least one compound of formula (I), or a pharmaceutically acceptable salt thereof, and a pharmaceutically acceptable carrier, excipient, or diluent.

In a further aspect, embodiments of the invention provide a method for inhibiting HCV replication in a cell, comprising contacting a cell that is infected by HCV with at least one compound of formula (I) or a pharmaceutically acceptable salt thereof.

In a further aspect, embodiments of the invention provide a use of at least one compound of formula (I) for preparation of a medicament for the prophylaxis or treatment of HCV infection.

In a further aspect, embodiments of the invention provide a method for the prophylaxis or treatment of HCV infection, comprising administering to a human or animal subject a therapeutically effective amount of at least one compound of formula (I), or a pharmaceutically acceptable salt thereof.

DESCRIPTION OF THE INVENTION

The present invention provides substituted pyrazolo[1,5-a]pyrimidine compounds which are represented by structural Formulae VII and VIII, or pharmaceutically acceptable salts, solvates, esters, or prodrugs thereof, wherein the various moieties are as described above.

Embodiments of the invention also provide compounds and methods for inhibiting HCV RNA-dependent RNA polymerase enzymatic activity. The invention also provides compositions and methods for the prophylaxis or treatment of HCV infection. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

As used above and, throughout this disclosure, the following terms, unless otherwise indicated, shall be understood to have the following meanings:

"Patient" or "Subject" includes both human and animals.

"Mammal" means humans and other mammalian animals.

The terms "HCV RNA-dependent RNA polymerase inhibitor", "HCV RdRp inhibitor", "inhibitor of HCV RNA-dependent RNA polymerase", and "inhibitor of HCV RdRp" are used to identify a compound having a structure as defined herein, which is capable of interacting with HCV RNA-dependent RNA polymerase and inhibiting its enzymatic activity. Inhibiting HCV RNA-dependent RNA polymerase enzymatic activity means reducing the ability of HCV RdRp to incorporate ribonucleotides into a growing HCV RNA strand. In some preferred embodiments, such reduction of HCV RdRp activity is at least 50%, more preferably at least 75%, and still more preferably at least 90%. In other preferred embodiments, HCV RdRp activity is reduced by at least 95% and more preferably by at least 99%.

Preferably, such inhibition is specific, i.e., the HCV RdRp inhibitor reduces the ability of HCV RdRp to incorporate ribonucleotides into a growing HCV RNA strand at a concentration that is lower than the concentration of the inhibitor that is required to produce another, unrelated biological effect. Preferably, the concentration of the inhibitor required for HCV RdRp inhibitory activity is at least 2-fold lower, more preferably at least 5-fold lower, even more preferably at least 10-fold lower, and most preferably at least 20-fold lower than the concentration required to produce an unrelated biological effect.

The terms "alkyl", "alkenyl", and "alkynyl", as employed herein, refer to straight and branched chain aliphatic groups having from 1 to 12 carbon atoms, preferably 1-8 carbon atoms, and more preferably 1-6 carbon atoms, which may be optionally substituted with one, two or three substituents. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, hexyl, 2-propynyl, 2-butynyl, 3-butenyl, and 3-methyl-buten-2-yl.

Referring now to Formulae VII and VIII, "alkyl" further means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl. For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

Referring now to Formulae VII and VIII, "alkenyl" further means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

Referring now to Formulae VII and VIII, "alkynyl" further means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

Referring now to Formulae VII and VIII, "alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

The term "cycloalkyl" as employed herein includes saturated and partially unsaturated cyclic hydrocarbon groups having from 3 to about 12 carbons, preferably from 3 to about 8 carbons, and more preferably from 3 to about 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

Referring now to Formulae VII and VIII, "cycloalkyl" further means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

Referring now to Formulae VII and VIII, "cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

Referring now to Formulae VII and VIII, "ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), $Y_1Y_2N$—, $Y_1Y_2$N-alkyl-, $Y_1Y_2$NC(O)—, $Y_1Y_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are methylene dioxy, ethylenedioxy, —C(CH$_3$)$_2$— and the like which form moieties such as, for example:

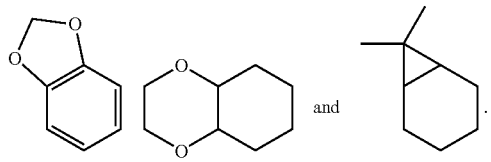

An "aryl" group is a C$_6$-C$_{14}$ aromatic moiety comprising one to three aromatic rings, which may be optionally substituted. Preferably, the aryl group is a C6-C10 aryl group. Aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is C$_6$-C10 aryl (C$_1$-C$_6$)alkyl, including, without limitation, benzyl, phenethyl, and naphthylmethyl.

Referring now to Formulae VII and VIII, "aryl" further means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

As used herein, the term "heteroaryl" refers to groups having 5 to 14 ring atoms, preferably 5, 6, 9, or 10 ring atoms; having 6, 10, or 14 p electrons shared in a cyclic array; and having, in addition to carbon atoms, from one to four heteroatoms selected from the group consisting of N, O, and S. Heteroaryl groups include, without limitation, thienyl, benzothienyl, furanyl, benzofuranyl, dibenzofuranyl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl. A "heteroaralkyl" or "heteroarylalkyl" group comprises a heteroaryl group covalently linked to an alkyl group, either of which may independently be optionally substituted or unsubstituted. Preferably, the heteroaralkyl group is C$_6$-C14 heteroaryl(C$_1$-C$_6$)alkyl, including, without limitation, pyridylmethyl, thiazolylmethyl and the like.

Referring now to Formulae VII and VIII, "heteroaryl" further means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least one of a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

Referring now to Formulae VII and VIII, "heteroarylalkyl" means a heteroaryl moiety as defined above linked via an alkyl moiety (defined above) to a parent core. Non-limiting examples of suitable heteroarylalkyls include 2-pyridinylmethyl, quinolinylmethyl and the like.

As used herein, the terms "heterocyclic radical" and "heterocyclyl" refer to a stable 5- to 7-membered monocyclic or 7- to 10-membered bicyclic heterocyclic moiety that is either saturated or partially unsaturated, and having, in addition to carbon atoms, from one to three heteroatoms selected from the group consisting of N, O, and S, wherein the nitrogen and sulfur heteroatoms optionally can be oxidized and the nitrogen atoms optionally can be quaternized, and including any bicyclic group in which any of the above-defined heterocyclic rings is fused to a benzene ring. The heterocyclic ring can be attached to its pendant group at any heteroatom or carbon atom that results in a stable structure. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, and morpholinyl.

Referring now to Formulae VII and VIII, "heterocyclyl" further means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

Referring now to Formulae VII and VIII, "heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "partially unsaturated heterocyclic radical" refers to a stable 5- to 7-membered monocyclic or 7- to 10-membered bicyclic heterocyclic ring moiety that includes at least one double bond between ring atoms. The term is intended to encompass rings having multiple sites of unsaturation, but is not intended to include aryl or heteroaryl moieties as herein defined. In addition to carbon atoms, the heterocyclic ring moiety has from one to three heteroatoms selected from the group consisting of N, O, and S, wherein the nitrogen and sulfur heteroatoms optionally can be oxidized and the nitrogen atoms optionally can be quaternized, and including any bicyclic group in which any of the above-defined heterocyclic rings is fused to a benzene ring. The heterocyclic ring can be attached to its pendant group at any heteroatom or carbon atom that results in a stable structure. Examples of such partially unsaturated heterocyclic radicals include, without limitation, tetrahydroquinolinyl, tetrahydroisoquinolinyl, tetrahydrobenzothiophene, tetrahydroindole, and tetrahydrobenzofuran.

The term "heterocyclenalkenyl" refers to a heterocyclyl group wherein a ring carbon and an exo carbon form a carbon-carbon double bond (e.g., as exemplified in compound 449 in the compound table herein), which is in turn attached to the core scaffold of interest. The designations —CH(N)OH and —CH(N)OR refer to groups wherein the carbon and nitrogen atoms are connected by a double bond, thereby forming an oxime or oxime alkyl ether, respectively.

As employed herein, a "substituted" cycloalkyl aryl, aralkyl, heteroaryl, heteroarylalkyl, or heterocyclyl group is one having from one to four, preferably from one to three, more preferably one or two, non-hydrogen substituents. Suitable substituents include, without limitation, halo, hydroxy, oxo, nitro, fluoroalkyl, alkyl, alkenyl, alkynyl, cycloalkyl, (cycloalkyl)alkyl, aryl, (aryl)alkyl, heteroaryl, (heteroaryl)alkyl, (heteroaryl)alkyloxy, (heteroaryl)alkylamino, (heteroaryl)alkylthio, heteroaryloxy, heteroarylamino, heteroarylthio, saturated or partially unsaturated heterocyclic radical, (heterocyclyl)alkyl, (heterocyclyl)oxy, (heterocyclyl)amino, (heterocyclyl)thio, (heterocyclyl)alkyloxy, (heterocyclyl)alkylthio, fluoroalkyloxy, cycloalkylalkoxy, cycloalkoxy, alkoxyalkyl, alkoxy, (aryl)alkoxy, aryloxy, amino, acylamino, carbamoyl, aminoalkyl, hydroxyalkyl, carboalkoxy, carboaryloxy, carboxy, alkylthio, arylthio, aralkylthio, alkylsulfinyl, arylsulfinyl, aralkylsulfinyl, alkylsulfonyl, arylsulfonyl, aralkylsulfonyl, alkylsulfonamido, arylsulfonamido, aralkylsulfonamido, acyl, acyloxy, cyano, and ureido groups.

The term "substituted", as used herein, means that one or more hydrogens of the designated moiety are replaced with a selection from the indicated group, provided that no atom's normal valency under the existing circumstances is exceeded, and provided that the substitution results in a stable compound. Referring now to Formulae VII and VIII, the term "optionally substituted" means optional substitution with the specified groups, radicals or moieties. Combinations of substituents and/or variables are permissible only if such combinations result in stable compounds. The terms "stable compound" and "stable structure" refer to a compound that is sufficiently robust to survive isolation to a useful degree of purity and formulation into an efficacious therapeutic agent.

The term "halogen" or "halo" as employed herein refers to chlorine, bromine, fluorine, or iodine.

As herein employed, the term "acyl" refers to an alkylcarbonyl or arylcarbonyl substituent. Referring now to Formulae VII and VIII, "acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

The terms "acylamino" and "amido" refer to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. Unless otherwise explicitly limited, the term "amino" is meant to include $NH_2$, alkylamino, dialkylamino, arylamino, aralkylamino, and cyclic amino groups.

Referring now to Formulae VII and VIII, "alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

Referring now to Formulae VII and VIII, "aroyl" means an aryl-C(O)— group in which the aryl group is as previously described. The bond to the parent moiety is through the carbonyl. Non-limiting examples of suitable groups include benzoyl and 1-naphthoyl.

Referring now to Formulae VII and VIII, "aryloxy" means an aryl-O— group in which the aryl group is as previously described. Non-limiting examples of suitable aryloxy groups include phenoxy and naphthoxy. The bond to the parent moiety is through the ether oxygen.

Referring now to Formulae VII and VIII, "aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

Referring now to Formulae VII and VIII, "alkylthio" means an alkyl-S— group in which the alkyl group is as previously described. Non-limiting examples of suitable alkylthio groups include methylthio and ethylthio. The bond to the parent moiety is through the sulfur.

Referring now to Formulae VII and VIII, "arylthio" means an aryl-S— group in which the aryl group is as previously described. Non-limiting examples of suitable arylthio groups include phenylthio and naphthylthio. The bond to the parent moiety is through the sulfur.

Referring now to Formulae VII and VIII, "aralkylthio" means an aralkyl-S— group in which the aralkyl group is as previously described. Non-limiting example of a suitable aralkylthio group is benzylthio. The bond to the parent moiety is through the sulfur.

Referring now to Formulae VII and VIII, "alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

Referring now to Formulae VII and VIII, "aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

Referring now to Formulae VII and VIII, "aralkoxycarbonyl" means an aralkyl-O—C(O)— group. Non-limiting example of a suitable aralkoxycarbonyl group is benzyloxycarbonyl. The bond to the parent moiety is through the carbonyl.

Referring now to Formulae VII and VIII, "alkylsulfonyl" means an alkyl-$S(O_2)$— group. Preferred groups are those in which the alkyl group is lower alkyl. The bond to the parent moiety is through the sulfonyl.

Referring now to Formulae VII and VIII, "arylsulfonyl" means an aryl-$S(O_2)$— group. The bond to the parent moiety is through the sulfonyl.

Referring now to Formulae VII and VIII, "hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl. The term "ureido" as employed herein refers to a substituted or unsubstituted urea moiety.

The term, "pharmaceutically acceptable" is used herein to mean a non-toxic material that is compatible with a biological system such as a cell, cell culture, tissue, or organism.

The term "purified", "in purified form", "isolated", or "in isolated and purified form" for a compound refers to the physical state of the compound after being isolated from a synthetic process or natural source or combination thereof. Thus, the term "purified", "in purified form", "isolated", or "in isolated and purified form" for a compound refers to the physical state of the compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Referring to Formula VII above, $R^2$ is selected from the group consisting of Cl, Br, F, and I.

In some embodiments, $R^3$ is is selected from the group consisting of tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, and morpholinyl.

In some embodiments, $R^4$ is H. In other embodiments, $R^4$ is selected from the group consisting of Cl, Br, —OH, —SH, alkyl, alkenyl, alkynyl, haloalkyl and cyclopropyl. In other embodiments, $R^4$ is —$NH_2$. In other embodiments, $R^4$ is —OH. In other embodiments, $R^4$ is alkoxy. In other embodiments, $R^4$ is alkylthio. Further, in other embodiments, $R^4$ is halo.

In some embodiments, n is 1.
In some embodiments, p is 1.
Non-limiting examples of compounds of Formula (VII) include:

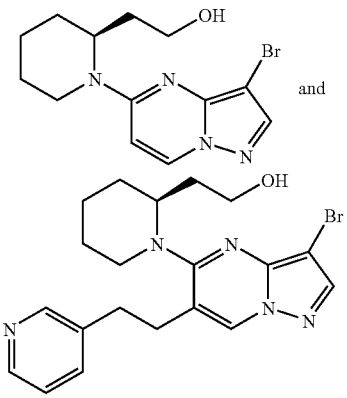

Referring to Formula VIII above, $R^2$ is selected from the group consisting of Cl, Br, F, and I.

In some embodiments, $R^3$ is methyl or ethyl.

In some embodiments $R^4$ is ethyl. In other embodiments, $R^4$ is alkoxy.

Non-limiting examples of compounds of Formula (VIII) include:

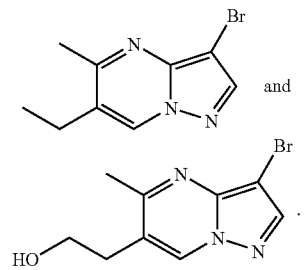

In one aspect, embodiments of the invention provide novel inhibitors of HCV RNA-dependent RNA polymerase of formula (I):

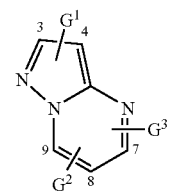

or a pharmaceutically acceptable salt thereof, wherein:

$G^1$ is selected from the group consisting of —OH, cyano, —C(O)—OH, —C(O)—OR, —C(O)—$NR^2R^3$, —N(R)—C(O)R, —$S(O)_2$ $NR^2R^3$, —N(R)—$S(O)_2R$, heteroaryl, and saturated or partially unsaturated heterocyclic radical, where R, at each occurrence, is independently selected from the group consisting of hydrogen, alkyl, cycloalkyl, aryl, aralkyl, heteroaryl, heteroarylalkyl, and saturated or partially unsaturated heterocyclic radical;

$R^2$ and $R^3$ are independently selected from the group consisting of hydrogen, alkyl, cycloalkyl, aryl, aralkyl, heteroaryl, heteroarylalkyl, and saturated or partially unsaturated heterocyclic radical; or $R^2$ and $R^3$ taken together form a 5- or 6-membered heteroaromatic or saturated or partially unsaturated heterocyclic ring; or —$NR^2R^3$ together forms an alpha-, beta-, or gamma-amino acid, wherein $R^2$ is hydrogen or $C_1$-$C_6$ alkyl, and $R^3$ has a formula selected from the group consisting of —$CH_2CH(R^6)CO_2H$, —$CH(R^6)CH_2CO_2H$, —$CH(R^6)CO_2H$, —$CH(R^6)CH_2CH_2CO_2H$, —$CH_2CH(R^6)CH_2CO_2H$, and —$CH_2CH_2CH(R^6)CO_2H$;

wherein $R^6$ is selected from the group consisting of hydrogen, alkyl, cycloalkyl, aryl, heteroaryl, saturated or partially unsaturated heterocyclic radical, and —$CH_2R^7$, where $R^7$ is selected from the group consisting of aryl, aralkyl, cycloalkyl, heteroaryl, saturated or partially unsaturated heterocyclic radical, hydroxy, alkoxy, aryloxy, aralkoxy, thio, alkylthio, arylthio, and aralkylthio;

$G^1$ is attached to either of positions C3 or C4 of the pyrazole ring, the other position being optionally substituted with alkyl, alkenyl, alkynyl, halo, fluoroalkyl, hydroxy, alkoxy, or cyano; and $G^2$ and $G^3$ independently are selected from the group consisting of alkyl, cycloalkyl, aryl, heteroaryl, saturated or partially unsaturated heterocyclic radical, and —W-Cy, where W is selected from the group consisting of O, N(R), S, C(O), CH(R), —O—CH(R), —N(R)—CH(R)—, —S—CH(R)—, —C(O)—N(R)—, —N(R)—C(O)—, —S(O)$_2$—N(R)—, —N(R)—S(O)$_2$—, and —N(R)—C(O)—N(R)—, where R, at each occurrence, is independently selected from the group consisting of hydrogen, alkyl, cycloalkyl, aryl, aralkyl, heteroaryl, heteroarylalkyl, and saturated or partially unsaturated heterocyclic radical, Cy is selected from the group consisting of cycloalkyl, aryl, aralkyl, heteroaryl, heteroarylalkyl, and saturated or partially unsaturated heterocyclic radical, and $G^2$ and $G^3$, collectively, are attached at any two of positions C7, C8, and C9 of the pyrimidine ring, the remaining position being optionally substituted with alkyl, alkenyl, alkynyl, halo, fluoroalkyl, hydroxy, alkoxy, or cyano;

wherein the ring portion of any of said cycloalkyl, aryl, aralkyl, heteroaryl, heteroarylalkyl, or heterocyclic radical in $G^1$, $G^2$, or $G^3$ can be optionally substituted.

Substituted cycloalkyl, aryl, heteroaryl, or heterocyclic groups are preferably substituted with one or more substituents selected from the group consisting of halo, preferably Cl, Br, or F; hydroxy; nitro; fluoroalkyl, preferably (fluoro)$_{1-5}$($C_1$-$C_6$)alkyl, more preferably (fluoro)$_{1-5}$($C_1$-$C_6$)alkyl, including, e.g., $CH_2F$, $CF_3$, $CH_2CH_2F$, and $CF_2CF_3$; alkyl, preferably $C_1$-$C_6$ alkyl, more preferably $C_1$-$C_4$ alkyl; alkenyl, preferably $C_2$-$C_8$ alkenyl, more preferably $C_2$-$C_6$ alkenyl; alkynyl, preferably $C_2$-$C_8$ alkynyl, more preferably $C_2$-$C_6$ alkynyl; cycloalkyl, preferably $C_3$-$C_8$ cycloalkyl, more preferably $C_3$-$C_6$ cycloalkyl; (cycloalkyl)alkyl, preferably $C_3$-$C_8$ cycloalkyl($C_1$-$C_6$)alkyl, more preferably $C_3$-$C_6$ cycloalkyl($C_1$-$C_6$)alkyl; aryl, preferably $C_6$-$C_{14}$ aryl, more preferably $C_6$-$C_{10}$ aryl, including, e.g., phenyl and naphthyl; (aryl)alkyl, preferably $C_6$-$C_{10}$ aryl($C_1$-$C_6$)alkyl, more preferably $C_6$-$C_{10}$ aryl($C_1$-$C_4$)alkyl, including, e.g., benzyl and phenethyl; heteroaryl; (heteroaryl)alkyl, preferably heteroaryl($C_1$-$C_6$)alkyl, more preferably heteroaryl($C_1$-$C_4$)alkyl; (heteroaryl)alkyloxy, (e.g., (furyl)alkoxy, (thiophenyl)alkoxy, (pyridyl)alkoxy, etc); (heteroaryl)alkylamino, (e.g., (furyl)alkylamino, (thiophenyl)alkylamino, (pyridyl)alkylamino, etc); (heteroaryl)alkylthio, (e.g., (furyl)alkylthio, (thiophenyl)alkylthio, (pyridyl)alkylthio, etc); alkylamino (e.g., ($C_1$-$C_6$) alkylamino); heteroaryloxy (e.g., furyloxy, thiophenyloxy, pyridyloxy, etc); heteroarylamino (e.g., furylamino, thiophenylamino, pyridylamino, etc); heteroarylthio (e.g., furylthio, thiophenylthio, pyridylthio, etc); saturated or partially unsaturated heterocyclic radical; (heterocyclyl)alkyl; (heterocyclyl)oxy; (heterocyclyl)amino; (heterocyclyl)thio; (heterocyclyl)alkyloxy; (heterocyclyl)alkylthio; alkoxy, preferably $C_1$-$C_6$ alkoxy, including, e.g., methoxy and ethoxy; (aryl)alkoxy, preferably $C_6$-$C_{10}$ aryl($C_1$-$C_6$)alkoxy, more preferably $C_6$-$C_{10}$ aryl($C_1$-$C_4$)alkoxy, including, e.g., benzyloxy; aryloxy, preferably $C_6$-$C_{10}$aryloxy, including, e.g., phenoxy; amino, including: $NH_2$; alkylamino, preferably $C_1$-$C_6$ alkylamino, more preferably $C_1$-$C_4$ alkylamino, including, e.g., methylamino, ethylamino, and propylamino; dialkylamino, preferably di($C_1$-$C_6$)alkylamino, more preferably di($C_1$-$C_4$) alkylamino, including, e.g., dimethylamino and diethylamino; arylamino, preferably $C_6$-$C_{14}$ arylamino, more preferably $C_6$-$C_{10}$ arylamino, including, e.g., phenylamino; diarylamino, preferably di($C_6$-$C_{14}$)arylamino, more preferably di($C_6$-$C_{10}$)arylamino, including, e.g., diphenylamino; (aryl)alkylamino, preferably $C_6$-$C_{10}$ aryl($C_1$-$C_6$)alkylamino, more preferably $C_6$-$C_{10}$ aryl($C_1$-$C_4$)alkylamino, including, e.g., benzylamino; and di(aryl)alkylamino, preferably di($C_6$-$C_{10}$)aryl($C_1$-$C_6$)alkylamino, more preferably di($C_6$-$C_{10}$)aryl($C_1$-$C_4$)alkylamino, including, e.g., dibenzylamino; acylamino, including: alkaneacylamino, preferably $C_1$-$C_6$ alkaneacylamino, more preferably $C_1$-$C_4$ alkaneacylamino, including, e.g., acetamido and propionamido; areneacylamino, preferably $C_6$-$C_{14}$ areneacylamino, more preferably $C_6$-$C_{10}$ areneacylamino, including, e.g., benzamido; and arylalkaneacylamino, preferably $C_6$-$C_{10}$ aryl($C_1$-$C_6$)alkaneacylamino, more preferably $C_6$-$C_{10}$ aryl($C_1$-$C_4$)alkaneacylamino, including, e.g., phenylacetamido; carbamoyl, including: —C(O)$NH_2$; alkylcarbamoyl, preferably $C_1$-$C_6$ alkylcarbamoyl or di($C_1$-$C_6$)alkylcarbamoyl, including, e.g., methylcarbamoyl and dimethylcarbamoyl; arylcarbamoyl, preferably ($C_6$-$C_{10}$)arylcarbamoyl or di($C_6$-$C_{10}$)arylcarbamoyl, including, e.g., phenylcarbamoyl and diphenylcarbamoyl; and arylalkylcarbamoyl, preferably $C_6$-$C_{10}$ aryl($C_1$-$C_6$)alkylcarbamoyl or di($C_6$-$C_{10}$)aryl($C_1$-$C_6$)alkylcarbamoyl, including, e.g., benzylcarbamoyl and dibenzylcarbamoyl; aminoalkyl, preferably amino($C_1$-$C_6$)alkyl; hydroxyalkyl, preferably hydroxy($C_1$-$C_6$)alkyl; carboalkoxy, preferably carbo($C_1$-$C_6$)alkoxy, including, e.g., carbomethoxy and carboethoxy; carboaryloxy, preferably carbo($C_6$-$C_{10}$)aryloxy, including, e.g., carbophenoxy; carboaralkoxy, preferably carbo($C_6$-$C_{10}$)ar($C_1$-$C_6$)alkoxy, including, e.g., carbobenzyloxy; carboxy; alkylthio, preferably $C_1$-$C_6$ alkylthio, more preferably $C_1$-$C_4$ alkylthio, including, e.g., methylthio; arylthio, preferably $C_6$-$C_{10}$ arylthio, including, e.g., phenylthio and tolylthio; aralkylthio, preferably $C_6$-$C_{10}$ ar($C_1$-$C_6$)alkylthio, including, e.g., benzylthio; alkylsulfinyl, preferably $C_1$-$C_6$ alkylsulfinyl, more preferably $C_1$-$C_4$ alkylsulfinyl, including, e.g., methylsulfinyl; arylsulfinyl, preferably $C_6$-$C_{10}$ arylsulfinyl, including, e.g., phenylsulfinyl and tolylsulfinyl; aralkylsulfinyl, preferably $C_6$-$C_{10}$ ar($C_1$-$C_6$)alkylsulfinyl, including, e.g., benzylsulfinyl; alkylsulfonyl, preferably $C_1$-$C_6$ alkylsulfonyl, more preferably $C_1$-$C_4$ alkylsulfonyl, including, e.g., methylsulfonyl; arylsulfonyl, preferably $C_6$-$C_{10}$ arylsulfonyl, including, e.g., phenylsulfonyl and tolylsulfonyl; aralkylsulfonyl, preferably $C_6$-$C_{10}$ ar($C_1$-$C_6$)alkylsulfonyl, including, e.g., benzylsulfonyl; alkylsulfonamido, preferably $C_1$-$C_6$ alkylsulfonamido, more preferably $C_1$-$C_4$ alkylsulfonamido, including, e.g., methylsulfonamido; arylsulfonamido, preferably $C_6$-$C_{10}$ arylsulfonamido, including, e.g., phenylsulfonamido and tolylsulfonamido; aralkylsulfonamido, preferably $C_6$-$C_{10}$ ar($C_1$-$C_6$)

alkylsulfonamido, including, e.g., benzylsulfonamido; acyl, including: alkanoyl, preferably $C_1$-$C_6$ alkanoyl, including, e.g., acetyl; aroyl, preferably $C_6$-$C_{10}$ aroyl, including, e.g., benzoyl; and aralkanoyl, preferably $C_6$-$C_{10}$ ar($C_1$-$C_6$)alkanoyl, including, e.g., phenylacetyl; acyloxy, including, e.g., acetoxy; cyano; and ureido groups. One or more carbon atoms of a cycloalkyl group and one or more carbon atoms or heteroatoms of a heterocyclic radical also may be optionally substituted with an oxo group. The prefix or suffix "ar" refers to aryl.

In some embodiments, at least one of $G^2$ and $G^3$ is aryl or heteroaryl, optionally substituted as described above. In some embodiments, at least one of $G^2$ and $G^3$ is substituted phenyl. In some embodiments, at least one of $G^2$ and $G^3$ is phenyl substituted with one or two substituents selected from the group consisting of $C_1$-$C_6$ alkyl, $C_6$-$C_{10}$ aryl, $C_6$-$C_{10}$ ar($C_1$-$C_6$)alkyl, heterocyclic radical, halo, (fluoro)$_{1-5}$($C_1$-$C_6$)alkyl, $C_1$-$C_6$ alkoxy, $C_6$-$C_{10}$ aryloxy, and $C_6$-$C_{10}$ ar($C_1$-$C_6$)alkoxy. In certain preferred embodiments, each of $G^2$ and $G^3$ is aryl or heteroaryl, optionally substituted as described above. In some embodiments, $G^2$ and $G^3$ preferably are not both unsubstituted phenyl when $G^2$ and $G^3$ are at positions C7 and C9. In other embodiments, one of $G^2$ or $G^3$ is substituted phenyl when $G^2$ and $G^3$ are at positions C7 and C9. In other embodiments, both $G^2$ and $G^3$ are independently substituted phenyl when $G^2$ and $G^3$ are at positions C7 and C9.

In some embodiments, at least one of $G^2$ and $G^3$ is —W-Cy, where Cy is selected from the group consisting of cycloalkyl, aryl, aralkyl, heteroaryl, heteroarylalkyl, and saturated or partially unsaturated heterocyclic radical, any of which optionally can be substituted as described above. In certain embodiments, Cy is aryl, preferably $C_6$-$C_{10}$ aryl, which can be unsubstituted or optionally substituted. In some preferred embodiments, Cy is unsubstituted phenyl or phenyl substituted with one or two substituents selected from the group consisting of $C_1$-$C_6$ alkyl, $C_6$-$C_{10}$ aryl, $C_6$-$C_{10}$ ar($C_1$-$C_6$) alkyl, heterocyclic radical, halo, (fluoro)$_{1-5}$($C_1$-$C_6$)alkyl, $C_1$-$C_6$ alkoxy, $C_6$-$C_{10}$ aryloxy, and $C_6$-$C_{10}$ ar($C_1$-$C_6$)alkoxy.

In certain other embodiments, Cy is cycloalkyl, preferably $C_5$-$C_6$ cycloalkyl, where the cycloalkyl can be unsubstituted or optionally substituted. In some preferred embodiments, Cy is unsubstituted $C_5$-$C_6$ cycloalkyl, or $C_5$-$C_6$ cycloalkyl substituted with one or two substituents selected from the group consisting of $C_1$-$C_6$ alkyl, $C_6$-$C_{10}$ aryl, $C_6$-$C_{10}$ ar($C_1$-$C_6$) alkyl, heterocyclic radical, halo, (fluoro)$_{1-5}$($C_1$-$C_6$)alkyl, $C_1$-$C_6$ alkoxy, $C_6$-$C_{10}$ aryloxy, and $C_6$-$C_{10}$ ar($C_1$-$C_6$)alkoxy.

In some embodiments, the heterocyclyl in $G^1$ is optionally substituted as described above. In some embodiments, the heterocyclyl in $G^2$ or $G^3$ is optionally substituted as described above.

In yet other embodiments, Cy is aralkyl, preferably $C_6$-$C_{10}$ ar($C_1$-$C_6$)alkyl, wherein the aryl portion of the aralkyl can be optionally substituted as described above. In some preferred embodiments, Cy is benzyl or phenethyl, or a substituted benzyl or phenethyl, wherein the phenyl ring is substituted with one or two substituents selected from the group consisting of $C_1$-$C_6$ alkyl, $C_6$-$C_{10}$ aryl, $C_6$-$C_{10}$ ar($C_1$-$C_6$)alkyl, heterocyclic radical, halo, (fluoro)$_{1-5}$($C_1$-$C_6$)alkyl, $C_1$-$C_6$ alkoxy, $C_6$-$C_{10}$ aryloxy, and $C_6$-$C_{10}$ ar($C_1$-$C_6$)alkoxy.

In each of the embodiments described above for Cy, W is selected from the group consisting of O, N(R), S, C(O), CH(R), —O—CH(R)—, —N(R)—CH(R)—, —S—CH(R)—, —C(O)—N(R)—, —N(R)—C(O)—, —S(O)$_2$—N(R)—, —N(R)—S(O)$_2$—, and —N(R)—C(O)—N(R)—, where R, at each occurrence, is independently selected from the group consisting of hydrogen, alkyl, cycloalkyl, aryl, aralkyl, heteroaryl, heteroarylalkyl, and saturated or partially unsaturated heterocyclic radical. In some preferred embodiments, W is N(R), wherein R is hydrogen or $C_1$-$C_6$ alkyl. In some preferred embodiments, W is NH or NCH$_3$.

In some embodiments, $G^1$ is selected from the group consisting of OH, —C(O)OH, and heteroaryl. The heteroaryl preferably is an acidic heteroaryl, including, e.g., tetrazolyl.

In some other embodiments, $G^1$ is —C(O)NR$^2$R$^3$, wherein —NR$^2$R$^3$ together forms an alpha-, beta-, or gamma-amino acid. In these embodiments, R$^2$ is hydrogen or $C_1$-$C_6$ alkyl, and R$^3$ has a formula selected from the group consisting of —CH$_2$CH(R$^6$)CO$_2$H, —CH(R$^6$)CH$_2$CO$_2$H, —CH(R$^6$)CO$_2$H, —CH(R$^6$)CH$_2$CH$_2$CO$_2$H, —CH$_2$CH(R$^6$)CH$_2$CO$_2$H, and —CH$_2$CH$_2$CH(R$^6$)CO$_2$H wherein R$^6$ is selected from the group consisting of hydrogen, alkyl, cycloalkyl, aryl, heteroaryl, saturated or partially unsaturated heterocyclic radical, and —CH$_2$R$^7$, and R$^7$ is selected from the group consisting of aryl, aralkyl, cycloalkyl, heteroaryl, saturated or partially unsaturated heterocyclic radical, hydroxy, alkoxy, aryloxy, aralkoxy, thio, alkylthio, arylthio, and aralkylthio. The substituent R$^6$ can be in either the (R) or (S) configuration. In some embodiments, —NR$^2$R$^3$ together forms a naturally occurring amino acid. In some other embodiments, —NR$^2$R$^3$ together forms a non-naturally occurring amino acid.

It will be appreciated that heteroaromatic rings bearing a hydroxy substituent at a position adjacent to a ring nitrogen atom may exist in either the hydroxy or the keto tautomeric form, or may exist as a mixture of the two. For example, compounds of formula (I) having a hydroxy substituent at C3 may exist as the hydroxy tautomer (1) or as the keto tautomer (2):

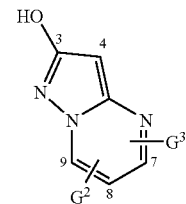

1

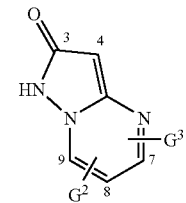

2

Similarly, compounds of formula (I) having a hydroxy substituent at C7 may exist as the hydroxy tautomer (3) or the keto tautomer (4):

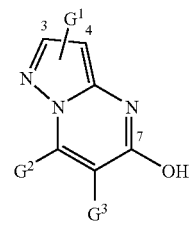

3

-continued

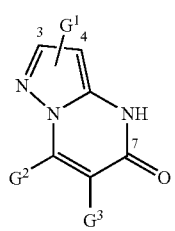
4

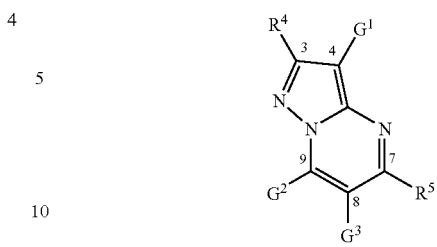
5

It is to be understood that all tautomeric forms of the compounds of formula (I), as well as all possible mixtures thereof in any proportion, are included within the scope of the invention, as also stated later.

Additionally, it is to be understood that the invention also encompasses all hydrated, dehydrated, and solvated forms of the compounds of formula (I).

In some embodiments, $G^1$ is attached at C3, and $G^2$ and $G^3$ are attached at C9 and C7, respectively. Thus, the compounds of these embodiments have the formula (II):

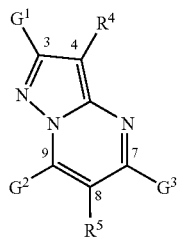

wherein $G^1$, $G^2$ and $G^3$ are as described above, and $R^4$ and $R^5$ independently are selected from the group consisting of hydrogen, alkyl, halo, fluoroalkyl, hydroxy, alkoxy, and cyano. In some preferred embodiments, $R^4$ and $R^5$ are both hydrogen.

In some other embodiments, $G^1$ is attached at C3, and $G^2$ and $G^3$ are attached at C8 and C7, respectively. Thus, the compounds of these embodiments have the formula (III):

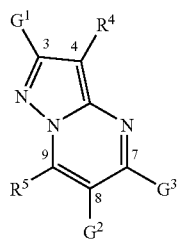

wherein $G^1$, $G^2$ and $G^3$ are as described above, and $R^4$ and $R^5$ independently are selected from the group consisting of hydrogen, alkyl, halo, fluoroalkyl, hydroxy, alkoxy, and cyano. In some preferred embodiments, $R^4$ and $R^5$ are both hydrogen.

In yet other embodiments, $G^1$ is attached at C4, and $G^2$ and $G^3$ are attached at C9 and C8, respectively. Thus, the compounds of these embodiments have the formula (IV):

wherein $G^1$, $G^2$ and $G^3$ are as described above, and $R^4$ and $R^5$ independently are selected from the group consisting of hydrogen, alkyl, halo, fluoroalkyl, hydroxy, alkoxy, and cyano. In some preferred embodiments, $R^4$ and $R^5$ are both hydrogen.

Formulae (I)-(IV) illustrate certain preferred embodiments. However, other regioisomers are also possible and are included within the scope of the invention.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formulae I-VIII may exist in unsolvated as well as solvated forms with pharmaceutically acceptable solvents such as water, ethanol, and the like, and it is intended that the invention embrace both solvated and unsolvated forms. One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formulae I-VIII form salts (e.g., pharmaceutically acceptable salts) which are also within the scope of this invention. Reference to a compound of Formulae I-VIII herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulae I-VIII contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulae I-VIII may be formed, for example, by reacting a compound of Formulae I-VIII with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pamoates (i.e., 1,1-methylene-bis-(2-hydroxy-3-naphthoates)), pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website) and *Remington: The Science and Practice of Pharmacy*, 20th Ed., ed. A. Gennaro, Lippincott Williams & Wilkins, 2000. These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formulae I-VIII, and salts, solvates and prodrugs thereof, may exist in their tautomeric form (for example, as an amide or imino ether). All such tautomeric forms are contemplated herein as part of the present invention. Also, for example, all keto-enol and imine-enamine forms of the compounds are included in the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formulae I-VIII or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of Formulae I-VIII contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formulae I-VIII incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N- or di-N,N-$(C_1-C_6)$alkylaminoalkyl, —C(Y$^4$)Y$^5$ wherein Y$^4$ is H or methyl and Y$^5$ is mono-N- or di-N,N-$(C_1-C_6)$alkylamino morpholino, piperidin-1-yl or pyrrolidin-1-yl, and the like.

The compounds of Formulae I-VIII may contain asymmetric or chiral centers, and, therefore, exist in different stereoisomeric forms. It is intended that all stereoisomeric forms of the compounds of Formulae I-VIII as well as mixtures thereof, including racemic mixtures, form part of the present invention. In addition, the present invention embraces all geometric and positional isomers. For example, if a compound of Formulae I-VIII incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formulae I-VIII may be atropisomers (e.g., substituted biaryls) and are considered as part of this invention. Enantiomers can also be separated by use of chiral HPLC column.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formulae I-VIII (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of Formulae I-VIII can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formulae I-VIII, and of the salts, solvates, esters and prodrugs of the compounds of Formulae I-VIII, are intended to be included in the present invention.

In other embodiments, the compounds (including salts, prodrugs, compositions and methods thereof) are of the following formulae, wherein the variables are as defined herein:

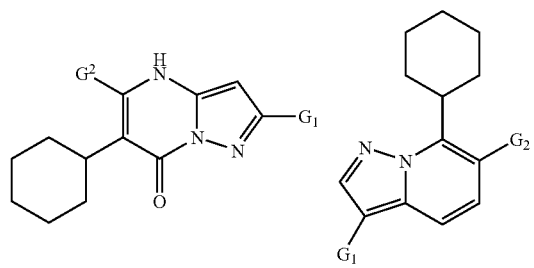

In another aspect, embodiments of the invention provide pharmaceutical compositions comprising an inhibitor of HCV RNA-dependent RNA polymerase according to any one of formulae (I)-(IV) and a pharmaceutically acceptable carrier, excipient, or diluent.

Preferred values for G$^1$, G$^2$, G$^3$, W, Cy, R, R$^2$, R$^3$, R$^4$, and R$^5$ are as set forth above for the first aspect of the invention. Compounds of the invention may be formulated by any method well known in the art and may be prepared for administration by any route, including, without limitation, parenteral, oral, sublingual, transdermal, topical, or intrarectal. In some embodiments, oral administration is preferred.

The characteristics of the carrier will depend on the route of administration. The compositions according to the invention may contain, in addition to the HCV RdRp inhibitor, diluents, fillers, salts buffers, stabilizers, solubilizers, and other materials well known in the art, provided that such materials do not interfere with the effectiveness of the biological activity of the active ingredient(s). The composition may be in any suitable form, depending on the intended route of administration, including, e.g., tablet, capsule, or liquid forms for oral administration, or solution or suspension forms for parenteral administration. The preparation of pharmaceutically acceptable formulations is described in, e.g., *Remington: The Science and Practice of Pharmacy*, 20th Ed., ed. A. Gennaro, Lippincott Williams & Wilkins, 2000.

In some embodiments, the pharmaceutical compositions of the invention also include one or more other agents for the treatment of viral infections, including e.g., antiviral agents or immunomodulatory agents. In certain embodiments, the other agent is an inhibitor of HCV RdRp, HCV helicase, HCV protease, or another HCV target protein. In certain other embodiments, the other agent is a broad-spectrum antiviral or immunomodulatory agent, e.g., ribavirin, interferon, or a derivative thereof.

In a further aspect, embodiments of the invention provide methods for inhibiting HCV replication in a cell. The methods comprise contacting a cell that is infected by HCV with a compound or composition according to the invention. In some embodiments, the cell is a hepatocyte. However, HCV is capable of replication in cell types other than hepatocytes, and the methods of the invention are also effective in such other cell types.

In certain embodiments, the cell is a cultured cell that is capable of supporting replication of HCV. Cell culture systems that support HCV replication can be prepared by infection of primary cell cultures or cell lines, or by cultivation of primary cells from a chronically infected mammal. Examples of such HCV replication systems can be found described, e.g., in Lohmann et al., *Science* 285: 110-113 (1999), Blight et al., *Science* 290: 1972 (2000), and Barenschlager and Lohmann, *J. Gen. Virology* 81: 8631-1648 (2000). In certain other embodiments, the cell is located in a human or animal subject. Preferably, the animal is a mammal. In some embodiments, the animal is a primate.

In a further aspect, embodiments of the invention provide a use of at least one compound of formula (I) for preparation of a medicament for use in prophylaxis or treatment of HCV infection.

In a further aspect, embodiments of the invention provide methods for treating or preventing an illness or condition associated with HCV infection, the methods comprising administering to a human or animal subject infected with HCV a therapeutically or prophylactically effective amount of at least one compound or composition according to the invention. By "illness or condition associated with HCV infection" is meant any illness or condition caused directly or indirectly by infection with HCV. Preferably, the animal is a mammal. In some embodiments, the animal is a primate.

HCV is characterized by pronounced genomic variability, and HCV replication leads to the rapid generation of virus variants. Holland et al., *Current Topics in Microbiology and Immunology* 176: 1-20 (1992) teaches that HCV exists, even within an individual patient, as a swarm of microvariants, a phenomenon the authors refer to as quasispecies. Therefore, the terms "hepatitis C virus" and "HCV", as used herein, are intended to refer to any of such virus variants, or mixtures thereof.

The term "therapeutically effective amount", as used herein, refers to an amount sufficient to cause a benefit to the subject or sufficient to cause any beneficial change in any symptom or marker associated with HCV infection. By "marker associated with HCV infection" is meant any biological measure that correlates with HCV infection and/or is predictive of clinical prognosis. Such markers include, without limitation, active virus and viral antigens.

The term "prophylactically effective amount", as used herein, refers to an amount sufficient to prevent or reduce the severity of HCV symptoms in a human or animal subject exposed to or infected by HCV. In some embodiments, prophylactic treatment includes administering a compound or composition according to the invention to a human or animal subject found to carry HCV, but which does not exhibit symptoms of hepatitis C disease. Prophylactic treatment also includes administering a compound or composition according to the invention to a human or animal subject which shows an improved disease state, but which still carries HCV and is at risk of recurrence of symptomatic disease.

The effective (e.g., therapeutically or prophylactically) amount of the HCV RdRp inhibitor administered will be determined empirically, and will be based on such considerations as the particular inhibitor used, the age, body weight, and condition of the individual, the treatment effect desired, administration route, and the like. It is expected that the typical dose range will be from about 0.1 mg/kg to about 100 mg/kg per dose, which can be given one to several times per day.

In some embodiments, the methods according to this aspect of the invention further include administration of one or more other agents for treating viral infections, e.g., antiviral agents or immunomodulatory agents. In certain embodiments, the other agent is an inhibitor of HCV RdRp, HCV helicase, HCV protease, or another HCV target protein. In certain other embodiments, the other agent is a broad-spectrum antiviral or immunomodulatory agent, e.g., ribavirin, interferon, or a derivative thereof.

The other agent or agents can be administered at the same time as the HCV RdRp inhibitor, or can be administered at a different time. Sequential or alternating therapy regimens are also contemplated within the scope of the invention.

The compounds according to the invention can have pharmacological properties; in particular, the compounds of Formulae VII-VIII can be inhibitors, regulators or modulators of protein kinases. Non-limiting examples of protein kinases that can be inhibited, regulated or modulated include cyclin-dependent kinases (CDKs), such as, CDK1, CDK2, CDK3, CDK4, CDK5, CDK6, CDK7, and CDK8, mitogen activated protein kinase (MAPK/ERK), glycogen synthase kinase 3 (GSK3beta), Chk kinases, such as Chk1 and Chk2, Pim-1 kinase, tyrosine kinases, such as the HER subfamily (including, for example, EGFR (HER1), HER2, HER3 and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase-4 (FLK-4) and the fms-like tyrosine kinase-1 (flt-1)), non-receptor protein tyrosine kinases, for example LCK, Src, Frk, Btk, Csk, Abl, Zap70, Fes/Fps, Fak, Jak, Ack, and LIMK, growth factor receptor tyrosine kinases such as VEGF-R2, FGF-R, TEK, Akt kinases and the like.

The compounds of Formulae VII-VIII can be inhibitors of protein kinases such as, for example, the inhibitors of the checkpoint kinases such as Chk1, Chk2 and the like. Preferred compounds can exhibit $IC_{50}$ values of less than about 25 μm, preferably about 0.001 to about 1.0 μm, and more preferably about 0.001 to about 0.1 μm. The assay methods are described in the Examples set forth below.

The compounds of Formulae VII-VIII can be inhibitors of protein kinases such as, for example, the inhibitors of the cyclin-dependent kinases such as CDK1, CDK2, CDK3, CDK4, CDK5, CDK6, CDK7, and CDK8, and the like. The compounds shown in Table 1 below exhibited CDK2 inhibitory activity ($IC_{50}$) of about 0.0001 μM to > about 5 μM. The assay methods are described in the examples below.

TABLE 1

| Structure | CDK2 $IC_{50}$ (μM) |
|---|---|
| [structure] | 0.1 |
| [structure] | 0.3 |
| [structure] | 0.03 |

The compounds of Formulae VII-VIII can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, incorporated by reference herein.

More specifically, the compounds of Formulae VII-VIII can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formulae VII-VIII may also be useful in the treatment of Alzheimer's disease, as suggested by the recent finding that CDK5 is involved in the phosphorylation of tau protein (*J. Biochem*, (1995) 117, 741-749).

Compounds of Formulae VII-VIII may induce or inhibit apoptosis. The apoptotic response is aberrant in a variety of human diseases. Compounds of Formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulae VII-VIII as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formulae VII-VIII may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulae VII-VIII may also be useful in inhibiting tumor angiogenesis and metastasis.

Compounds of Formulae VII-VIII may also act as inhibitors of other protein kinases, e.g., protein kinase C, her2, raf 1, MEK1, MAP kinase, EGF receptor, PDGF receptor, IGF receptor, P13 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formulae VII-VIII, or a pharmaceutically acceptable salt, solvate, ester, or prodrug of the compound to the mammal.

A preferred dosage is about 0.001 to 500 mg/kg of body weight/day of the compound of Formulae VII-VIII. An especially preferred dosage is about 0.01 to 25 mg/kg of body weight/day of a compound of Formulae VII-VIII, or a pharmaceutically acceptable salt, solvate, ester, or prodrug of the compound.

The compounds of this invention may also be useful in combination (administered together or sequentially) with one or more of anti-cancer treatments such as radiation therapy, and/or one or more anti-cancer agents different from the compound of Formulae VII-VIII. The compounds of the present invention can be present in the same dosage unit as the anti-cancer agent or in separate dosage units.

Another aspect of the present invention is a method of treating one or more diseases associated with cyclin dependent kinase, comprising administering to a mammal in need of such treatment an amount of a first compound, which is a compound of Formulae VII-VIII, or a pharmaceutically acceptable salt, solvate, ester, or prodrug thereof; and an amount of at least one second compound, the second compound being an anti-cancer agent different from the compound of Formulae VII-VIII, wherein the amounts of the first compound and the second compound result in a therapeutic effect.

Non-limiting examples of suitable anti-cancer agents include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formulae VII-VIII may also be administered sequentially with known anticancer or cytotoxic agents when a combination formulation is inappropriate. The invention is not limited in the sequence of administration; compounds of Formulae VII-VIII may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in one aspect, this invention includes combinations comprising an amount of at least one compound of Formulae VII-VIII, or a pharmaceutically acceptable salt, solvate, ester, or prodrug thereof, and an amount of one or more anti-cancer treatments and anti-cancer agents listed above wherein the amounts of the compounds/treatments result in desired therapeutic effect.

Another aspect of the present invention is a method of inhibiting one or more Checkpoint kinases in a patient in need thereof, comprising administering to the patient a therapeutically effective amount of at least one compound of Formulae VII-VIII or a pharmaceutically acceptable salt, solvate, ester, or prodrug thereof.

Another aspect of the present invention is a method of treating, or slowing the progression of, a disease associated with one or more Checkpoint kinases in a patient in need thereof, comprising administering a therapeutically effective amount of at least one compound of Formulae VII-VIII or a pharmaceutically acceptable salt, solvate, ester, or prodrug thereof.

Yet another aspect of the present invention is a method of treating one or more diseases associated with Checkpoint kinase, comprising administering to a mammal in need of such treatment an amount of a first compound, which is a compound of Formulae VII-VIII, or a pharmaceutically acceptable salt, solvate, ester, or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one compound according to Formulae VII-VIII, or a pharmaceutically acceptable salt, solvate, ester, or prodrug thereof.

In the above methods, the checkpoint kinase to be inhibited can be Chk1 and/or Chk2.

Another aspect of the present invention is a method of inhibiting one or more tyrosine kinases in a patient in need thereof, comprising administering to the patient a therapeutically effective amount of at least one compound of Formulae VII-VIII or a pharmaceutically acceptable salt, solvate, ester, or prodrug thereof.

Yet another aspect of the present invention is a method of treating, or slowing the progression of, a disease associated with one or more of Akt kinase, Aurora kinase, and tyrosine kinases in a patient in need thereof, comprising administering a therapeutically effective amount of at least one compound of Formulae VII-VIII or a pharmaceutically acceptable salt, solvate, ester, or prodrug thereof.

Another aspect of the present invention is a method of treating one or more diseases associated with Akt kinase, Aurora kinase and/or tyrosine kinase, comprising administering to a mammal in need of such treatment an amount of a first compound, which is a compound of Formulae VII-VIII, or a pharmaceutically acceptable salt, solvate, ester, or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with one or more of Akt kinase, Aurora kinase and tyrosine kinases in a patient in need thereof, comprising administering a therapeutically effective amount of a pharmaceutical composition comprising in combination at least one pharmaceutically acceptable carrier and at least one compound of Formulae VII-VIII or a pharmaceutically acceptable salt, solvate, ester, or prodrug thereof.

In the above methods, the tyrosine kinase can be VEGFR, EGFR, HER2, SRC, JAK and/or TEK.

Yet another aspect of the present invention is a method of treating, or slowing the progression of, a disease associated with Pim-1 kinase in a patient in need thereof, comprising administering a therapeutically effective amount of at least one compound of Formulae VII-VIII or a pharmaceutically acceptable salt, solvate, ester, or prodrug thereof.

Another aspect of the present invention is a method of treating one or more diseases associated with Pim-1 kinase, comprising administering to a mammal in need of such treatment an amount of a first compound, which is a compound of Formulae VII-VIII, or a pharmaceutically acceptable salt, solvate, ester, or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with Pim-1 kinase in a patient in need thereof, comprising administering a therapeutically effective amount of a pharmaceutical composition comprising in combination at least one pharmaceutically acceptable carrier and at least one compound of Formulae VII-VIII or a pharmaceutically acceptable salt, solvate, ester, or prodrug thereof.

The pharmacological properties of the compounds of this invention may be confirmed by a number of pharmacological assays. The exemplified pharmacological assays which are described herein below have been carried out with compounds according to the invention and their salts.

This invention is also directed to pharmaceutical compositions which comprise at least one compound of Formulae VII-VIII, or a pharmaceutically acceptable salt, solvate, ester, or prodrug of the compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formulae VII-VIII, or a pharmaceutically acceptable salt, solvate, ester, or prodrug of the compound and a pharmaceutically acceptable carrier, vehicle or diluent.

Yet another aspect of this invention is a kit comprising an amount of at least one compound of Formulae VII-VIII, or a pharmaceutically acceptable salt, solvate, ester, or prodrug of the compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The retention time and observed parent ion are given.

The following solvents and reagents may be referred to by their abbreviations in parenthesis:

Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: µl
grams: g
milligrams: mg
room temperature or rt (ambient): about 25° C.
dimethoxyethane: DME In general, the compounds of this invention can be prepared through the general routes described below in Schemes 1a and 2a shown below.

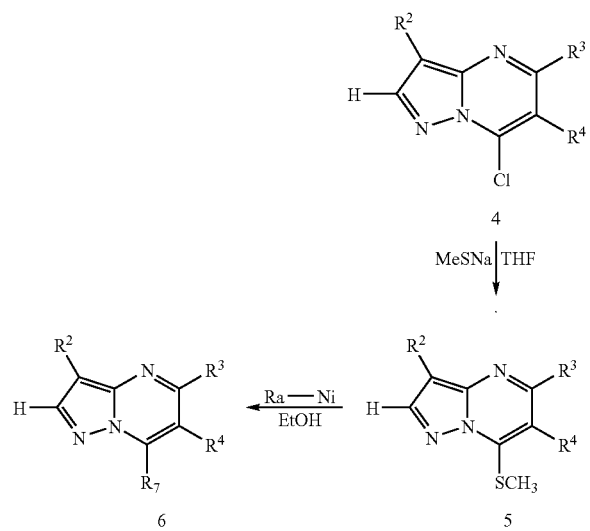

Alternatively, when R$^3$ is amino substituted, the process shown in Scheme 2a can be utilized starting with the malonate 7. Condensation and dichlorination give compounds of type 9. Sequential displacement of the 3- and 7-position chlorides followed by Ra—Ni reduction give compounds of type 11.

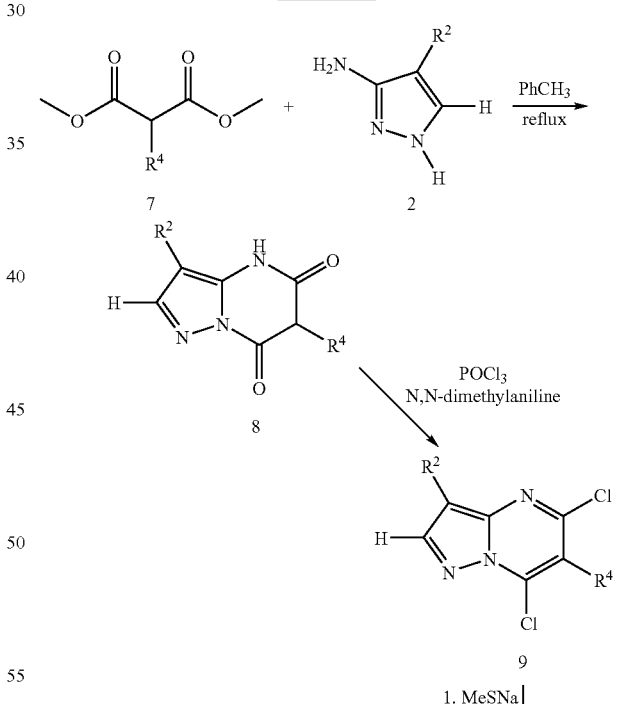

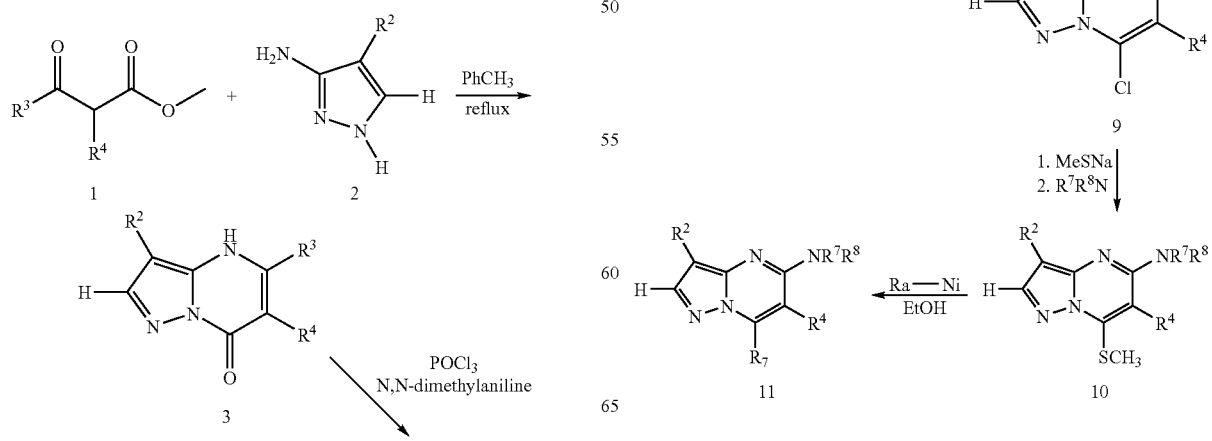

PREPARATIVE EXAMPLES AND EXAMPLES—SET A

Preparative Example 1

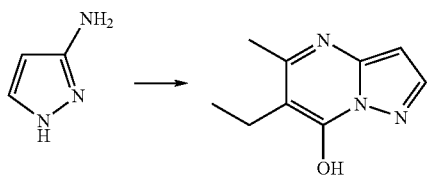

A mixture of 3-aminopyrazole (4.80 g, 57.8 mmol) and ethyl 2-ethylacetoacetate (10.96 g, 69.4 mmol) in ACOH (25 mL) was stirred and refluxed under $N_2$ for 18 hr. The mixture was cooled to 25° C., the solid was filtered off, washed on filter with ACOH (20 mL), $Et_2O$ (50 mL), and dried in a vacuum. White solid (7.70 g, 35%) was obtained.

Preparative Example 1.5

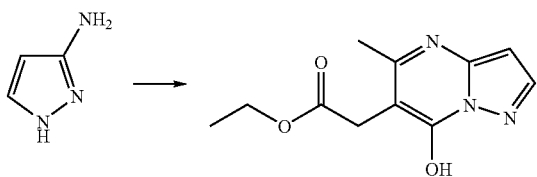

A mixture of 3-aminopyrazole (8.30 g, 0.100 mol) and diethyl acetylsuccinate (23.0 g, 0.101 mol) in $PhCH_3$ (100 mL) was stirred and refluxed under $N_2$ for 18 hr. The mixture was cooled to 25° C., the solid was filtered off, washed on filter with $PhCH_3$ (2×100 mL), $Et_2O$ (2×100 mL), and dried in a vacuum. Pale yellow crystalline solid (18.3 g, 78%) was obtained. LC-MS: 236 [M+H].

Preparative Example 2

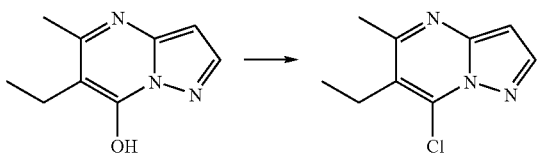

A mixture of the product from Preparative Example 1 (5.95 g, 33.6 mmol), N,N-dimethylaniline (6.09 g, 50.0 mmol), and $POCl_3$ (30.0 mL) was refluxed under $N_2$ for 3 hr. The mixture was cooled to 25° C., poured onto 500 g of crushed ice, and extracted with 20:1 $EtOAc/CH_2Cl_2$ (3×100 mL). The extracts were washed with $H_2O$ (2×200 mL), brine (100 mL), dried over $Na_2SO_4$, filtered, and the solvent was evaporated. The residue was purified by column chromatography on silicagel with 10:1 $CH_2Cl_2/EtOAc$ as eluent. Pale yellow oil (2.51 g, 38%) was obtained.

Preparative Example 2.5

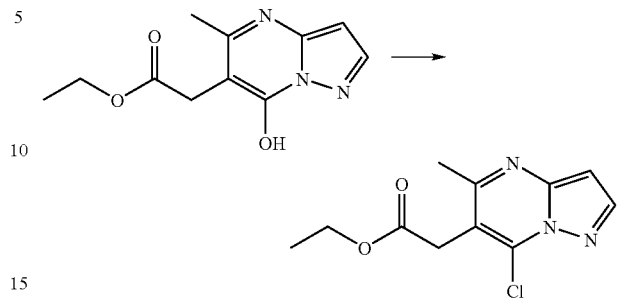

A mixture of the product from Preparative Example 1.5 (12.0 g, 51.0 mmol), N,N-dimethylaniline (10.0 mL), and $POCl_3$ (46 mL) was stirred at 25° C. for 3 d. Excess of $POCl_3$ was evaporated and the residue was poured into saturated aqueous $NaHCO_3$ (500 mL). The mixture was extracted with $CH_2Cl_2$ (3×200 mL), the combined extracts were dried over $Na_2SO_4$, filtered, and the solvent was evaporated. The residue was purified by column chromatography on silicagel with 4:1 $CH_2Cl_2/EtOAc$ as eluent. Pale yellow oil (slowly solidifies) (10.2 g, 79%) was obtained.

Preparative Example 3

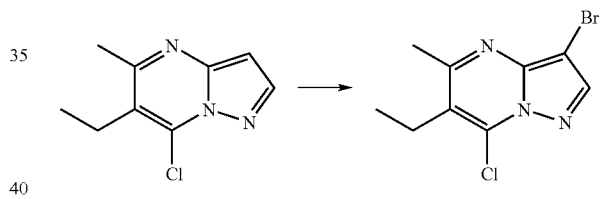

A solution of NBS (1.82 g, 10.2 mmol) in anhydrous $CH_3CN$ (20 mL) was added under $N_2$ to a stirred solution of the product from Preparative Example 2 (2.00 g, 10.2 mmol) in anhydrous $CH_3CN$ (10 mL). The mixture was stirred for 18 hr, the solvents were evaporated, and the residue was purified by column chromatography on silicagel with 30:1 $CH_2Cl_2/$ EtOAc as eluent. Pale yellow solid (2.71 g, 96%) was obtained. LC-MS: 254 [M+].

Preparative Example 3.5

By essentially same method set forth in Preparative Example 3, the compound below was prepared (starting from the compound from Preparative Example 2.5)

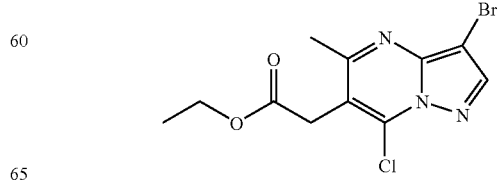

Preparative Example 4

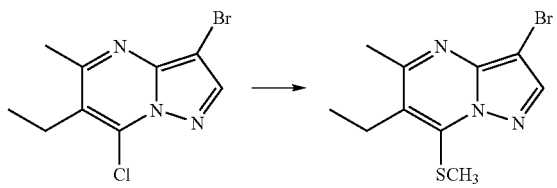

A mixture of the product from Preparative Example 3 (1.00 g, 3.64 mmol) and sodium thiomethoxide (308 mg, 4.40 mmol) in THF (10 mL) was stirred at 25° C. under $N_2$ for 24 h. The solvent was evaporated and the residue was purified by column chromatography on silicagel with 10:1 hexane/EtOAc as eluent. Pale yellow solid (890 mg, 85%) was obtained. LC-MS: 286 [M+].

Preparative Example 4.5

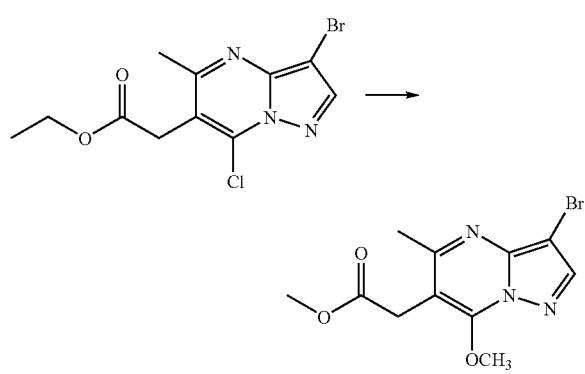

A mixture of the product from Preparative Example 3.5 (3.32 g, 10.0 mmol) and sodium methoxide (800 mg, 14.8 mmol) in MeOH (60 mL) was stirred at 25° C. under $N_2$ for 3 h. The solvent was evaporated and the residue was purified by column chromatography on silicagel with 20:1 hexane/EtOAc as eluent. White solid (1.95 g, 62%) was obtained. LC-MS: 314 [M+].

Example 1

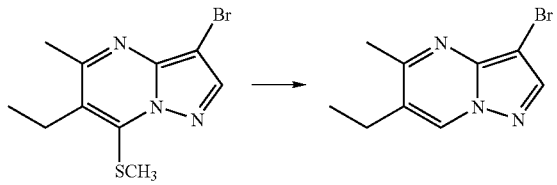

A mixture of the product from Preparative Example 4 (600 mg, 2.10 mmol) and 50% slurry of Raney Ni in $H_2O$ (2.0 g) in EtOH (10 mL) was stirred at 50° C. under $N_2$ for 24 h. Additional Raney Ni (2.0 g) was then added and the mixture was stirred at 50° C. under $N_2$ for additional 24 h. $CH_2Cl_2$ (20 mL) was added, the mixture was filtered through Celite, and the solvent was evaporated. The residue was purified by column chromatography on silicagel with 6:1 hexane/EtOAc as eluent. White solid (36 mg, 7%) was obtained. LC-MS: 240 [M+]. Mp=120-122° C.

Examples 2-3

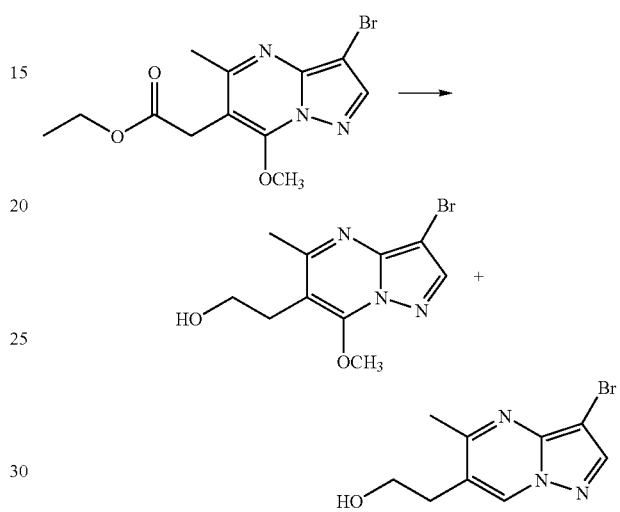

1.0 M $LiAlH_4$ in THF (1.60 mL, 1.60 mmol) was added under $N_2$ at 0° C. to a stirred solution of the product from Preparative Example 4.5 (1.00 g, 3.20 mmol) in anhydrous THF (20 mL). The reaction was stirred at 0° C. for 45 min and then it was quenched with MeOH (4 mL). The residue was purified by preparative TLC on silicagel with EtOAc as eluent. Two products were isolated: The first product was obtained as a pale yellow solid (54 mg, 6%). LC-MS: 286 [M+]. Mp=118-120° C. and the second product was obtained as a pale yellow solid (55 mg, 7%). LC-MS: 256 [M+]. Mp=131-133° C.

Preparative Example 6

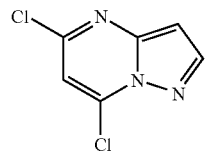

The title compound was prepared according to the method of Shiota as outlined in *Chem. Pharm. Bull.* 1999, 47(7), 928-938.

Preparative Examples 6.1-6.3

By a similar procedure as described in Preparative Example 6, only substituting the appropriate malonate the compounds shown in Table 6.1 can be prepared.

TABLE 6.1

| Prep. Ex. | CMPD |
|---|---|
| 6.1 | 5-Cl, 6-methyl, 7-Cl pyrazolo[1,5-a]pyrimidine |
| 6.2 | 5-Cl, 6-(2-(pyridin-3-yl)ethyl), 7-Cl pyrazolo[1,5-a]pyrimidine |
| 6.3 | 5-Cl, 6-(3-carbamoyl-3-methylbutyl), 7-Cl pyrazolo[1,5-a]pyrimidine |

Preparative Example 7

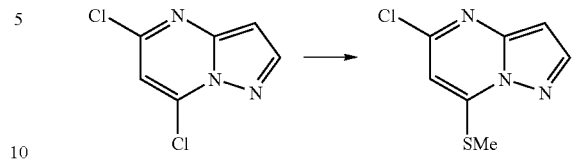

To a solution of dichloride (3.0 g, 16.0 mmol) from Preparative Example 6 in THF (25 mL) was added NaSMe (1.1 g, 16.0 mmol) in one portion. The resulting mixture was stirred for 12 h at rt and was concentrated under reduced pressure. The crude product was partitioned between EtOAc (150 mL) and $H_2O$ (30 mL) and the layers were separated. The organic layer was washed sequentially with $H_2O$ (2×30 mL) and brine (1×30 mL). The organic layer was dried ($Na_2SO_4$), filtered, and concentrated under reduced pressure to afford 3.0 g (94% yield) of a tan solid. LC-MS: 200.1 [M+H], purity 99%.

Preparative Examples 7.1-7.3

By a similar procedure as described in Preparative Example 7 only substituting the compounds shown in Column 2 of Table 7.1, the compounds shown in Column 3 of Table 7.1 can be prepared.

TABLE 7.1

| Prep. Ex. | Column 2 | Column 3 |
|---|---|---|
| 7.1 | 5-Cl, 6-methyl, 7-Cl pyrazolo[1,5-a]pyrimidine | 5-Cl, 6-methyl, 7-SCH3 pyrazolo[1,5-a]pyrimidine |
| 7.2 | 5-Cl, 6-(2-(pyridin-3-yl)ethyl), 7-Cl pyrazolo[1,5-a]pyrimidine | 5-Cl, 6-(2-(pyridin-3-yl)ethyl), 7-SCH3 pyrazolo[1,5-a]pyrimidine |
| 7.3 | 5-Cl, 6-(3-carbamoyl-3-methylbutyl), 7-Cl pyrazolo[1,5-a]pyrimidine | 5-Cl, 6-(3-carbamoyl-3-methylbutyl), 7-SCH3 pyrazolo[1,5-a]pyrimidine |

Preparative Example 7.5

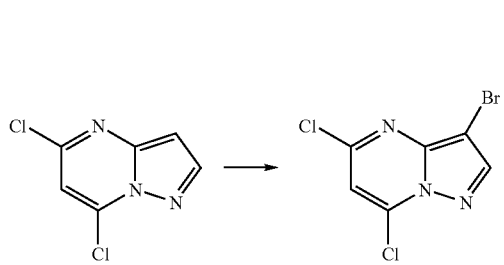

A solution of NBS (3.56 g, 20.0 mmol) in anhydrous CH₃CN (40 mL) was added under N₂ to a stirred solution of the product from Preparative Example 6 (3.74 g, 20.0 mmol) in anhydrous CH₃CN (30 mL). The mixture was stirred for 20 hr, the solvents were evaporated, and the residue was purified by column chromatography on silicagel with CH₂Cl₂ as eluent. Pale yellow solid (5.10 g, 96%) was obtained. LC-MS: 267 [M+].

Preparative Examples 7.6-7.8

By a similar procedure as described in Preparative Example 7.5 only substituting the compounds shown in Column 2 of Table 7.6, the compounds shown in Column 3 of Table 7.6 can be prepared.

Preparative Example 8

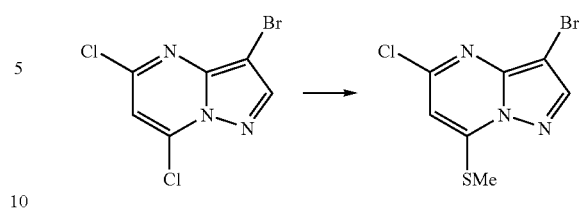

Prepared the procedure outlined in Preparative Example 7 except starting with dichloride (7.4 g, 27.7 mmol) from Preparative Example 7.5 and NaSMe (2.1 g, 30.5 mmol) afforded 7.4 g (96% yield) of the title compound as a light orange solid. LC-MS: 278.1 [M+H], purity 95%.

Preparative Example 9

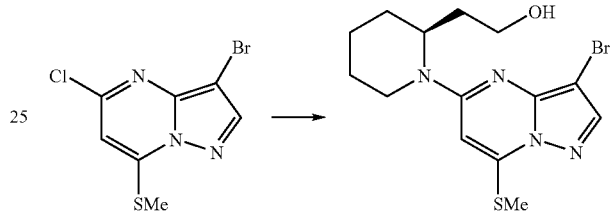

TABLE 7.6

| Prep. Ex. | Column 2 | Column 3 |
|---|---|---|
| 7.6 | ![structure] Cl-pyrazolopyrimidine with CH₃ and SCH₃ | ![structure] Cl-pyrazolopyrimidine with Br, CH₃ and SCH₃ |
| 7.7 | ![structure] Cl-pyrazolopyrimidine with pyridyl-ethyl and SCH₃ | ![structure] Cl-pyrazolopyrimidine with Br, pyridyl-ethyl and SCH₃ |
| 7.8 | ![structure] Cl-pyrazolopyrimidine with dimethyl amide side chain and SCH₃ | ![structure] Cl-pyrazolopyrimidine with Br, dimethyl amide side chain and SCH₃ |

A mixture of the product from Preparative Example 8 (2.00 g, 7.18 mmol), the aminoalcohol (1.21 g, 9.34 mmol), and DIPEA (5.88 mL, 35.9 mmol) in dioxane (30 mL) was stirred at 100° C. under N₂ for 3 d. The solvent was evaporated and the residue was purified by column chromatography on silicagel with 1:4 hexane/EtOAc as eluent. Pale yellow solid (0.90 g, 34%) was obtained. LC-MS: 371 [M+].

Preparative Examples 9.1-9.5

By a similar procedure as described in Preparative Example 9 only substituting the compounds shown in Column 2 of Table 9, the compounds shown in Column 3 of Table 9 can be prepared.

Example 4

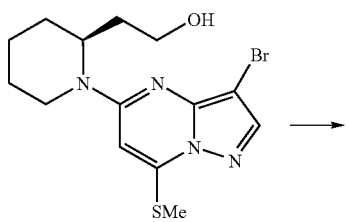

TABLE 9

| Prep. Ex. | Column 2 | Column 3 |
|---|---|---|
| 9.1 | 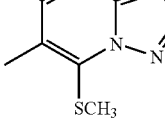 | 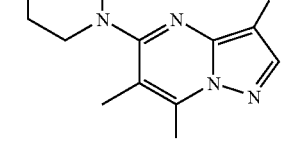 |
| 9.2 | 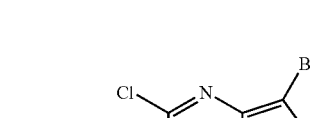 | 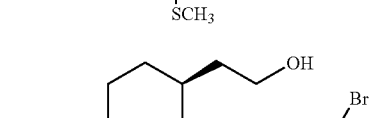 |
| 9.3 | 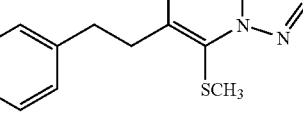 | 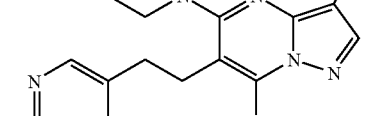 |
| 9.4 | 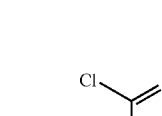 | 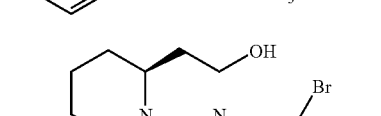 |
| 9.5 | 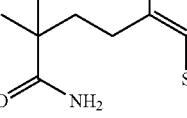 | 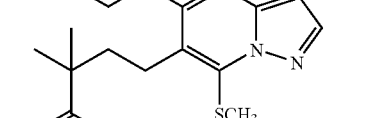 |

-continued

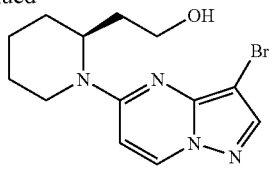

A mixture of the product from Preparative Example 9 (80 mg, 0.22 mmol) and 50% slurry of Raney Ni in $H_2O$ (0.20 g) in EtOH (3 mL) was stirred at 25° C. under $N_2$ for 24 h. $CH_2Cl_2$ (10 mL) was added, the mixture was filtered through Celite, and the solvent was evaporated. The residue was purified by preparative TLC on silicagel with 20:1 $CH_2Cl_2$/ MeOH as eluent. Colorless solid (19 mg, 27%) was obtained. LC-MS: 325 [M+]. Mp=81-84° C.

Examples 5-9

By a similar procedure as described in Example 4 only substituting the compounds shown in Column 2 of Table 10, the compounds shown in Column 3 of Table 10 can be prepared.

TABLE 10

| Ex. | Column 2 | Column 3 |
|---|---|---|
| 5 | | |
| 6 | | |
| 7 | | |
| 8 | | |
| 9 | | |

Assays:

CHK1 SPA Assay

An in vitro assay has been developed that utilizes recombinant His-CHK1 expressed in the baculovirus expression system as an enzyme source and a biotinylated peptide based on CDC25C as substrate (biotin-RSGLYRSPSMPENLNRPR).

Materials and Reagents:
1) CDC25C Ser 216 C-term Biotinylated peptide substrate (25 mg), stored at −20° C., Custom Synthesis by Research Genetics: biotin-RSGLYRSPSMPENLNRPR 2595.4 MW
2) His-CHK1 In House lot P976, 235 ug/mL, stored at −80° C.
3) D-PBS (without CaCl and MgCl): GIBCO, Cat.# 14190-144
4) SPA beads: Amersham, Cat.# SPQ0032: 500 mg/vial
   Add 10 mls of D-PBS to 500 mg of SPA beads to make a working concentration of 50 mg/ml. Store at 4° C. Use within 2 week after hydration.
5) 96-Well White Microplate with Bonded GF/B filter: Packard, Cat.# 6005177
6) Top seal-A 96 well Adhesive Film: Perkin Elmer, Cat.# 6005185
7) 96-well Non-Binding White Polystyrene Plate: Corning, Cat. # 6005177
8) MgCl$_2$: Sigma, Cat.# M-8266
9) DTT: Promega, Cat.# V3155
10) ATP, stored at 4° C.: Sigma, Cat.# A-5394
11) $\gamma^{33}$P-ATP, 1000-3000 Ci/mMol: Amersham, Cat.# AH9968
12) NaCl: Fisher Scientific, Cat.# BP358-212
13) H$_3$PO$_4$ 85% Fisher, Cat.# A242-500
14) Tris-HCL pH 8.0: Bio-Whittaker, Cat. # 16-015V
15) Staurosporine, 100 ug: CALBIOCHEM, Cat. # 569397
16) Hypure Cell Culture Grade Water, 500 mL: HyClone, Cat.# SH30529.02

Reaction Mixtures:
1) Kinase Buffer: 50 mM Tris pH 8.0; 10 mM MgCl$_2$; 1 mM DTT
2) His-CHK1, In House Lot P976, MW ~30 KDa, stored at −80° C.
   6 nM is required to yield positive controls of ~5,000 CPM. For 1 plate (100 rxn): dilute 8 uL of 235 ug/mL (7.83 uM) stock in 2 mL Kinase Buffer. This makes a 31 nM mixture. Add 20 uL/well. This makes a final reaction concentration of 6 nM.
3) CDC25C Biotinylated peptide.
   Dilute CDC25C to 1 mg/mL (385 uM) stock and store at −20° C. For 1 plate (100 rxn): dilute 10 uL of 1 mg/mL peptide stock in 2 ml Kinase Buffer. This gives a 1.925 uM mix. Add 20 uL/rxn. This makes a final reaction concentration of 385 nM.
4) ATP Mix.
   For 1 plate (100 rxn): dilute 10 uL of 1 mM ATP (cold) stock and 2 uL fresh P33-ATP (20 uCi) in 5 ml Kinase Buffer. This gives a 2 uM ATP (cold) solution; add 50 ul/well to start the reaction. Final volume is 100 ul/rxn so the final reaction concentrations will be 1 uM ATP (cold)- and 0.2 uCi/rxn.
5) Stop Solution:
   For 1 plate add: To 10 mL Wash Buffer 2 (2M NaCl 1% H$_3$PO$_4$): 1 mL SPA bead slurry (50 mg); Add 100 uL/well.
6) Wash buffer 1: 2 M NaCl
7) Wash buffer 2: 2 M NaCl, 1% H$_3$PO$_4$ Assay Procedure:

| Assay Component | Final Concentration | Volume |
|---|---|---|
| CHK1 | 6 nM | 20 μl/rxn |
| Compound (10% DMSO) | — | 10 μl/rxn |
| CDC25C | 0.385 μM | 20 μl/rxn |
| $\gamma^{33}$P-ATP | 0.2 μCi/rxn | 50 μl/rxn |
| Cold ATP | 1 μM | |
| Stop solution | 0.5 mg/rxn | 100 μl/rxn* |
| SPA beads | | 200 μl/rxn** |

*Total reaction volume for assay.
**Final reaction volume at termination of reaction (after addition of stop solution).

1) Dilute compounds to desired concentrations in water/10% DMSO-this will give a final DMSO concentration of 1% in the rxn. Dispense 10 μl/rxn to appropriate wells. Add 10 μL 10% DMSO to positive (CHK1+CDC25C+ATP) and negative (CHK1+ATP only) control wells.
2) Thaw enzyme on ice—dilute enzyme to proper concentration i kinase buffer (see Reaction Mixtures) and dispense 20 μl to each well.
3) Thaw the Biotinylated substrate on ice and dilute in kinase buffer (see Reaction Mixtures). Add 20 uL/well except to negative control wells. Instead, add 20 uL Kinase Buffer to these wells.
4) Dilute ATP (cold) and P33-ATP in kinase buffer (see Reaction Mixtures). Add 50 uL/well to start the reaction.
5) Allow the reaction to run for 2 hours at room temperature.
6) Stop reaction by adding 100 uL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 ml each wash; 1X with 2M NaCl; 1X with 2M NaCl/1% H$_3$PO$_4$
11) Allow filter plate to dry 15 min.
12) Put TopSeal-A adhesive on top of filter plate.
13) Run filter plate in Top Count
   Settings:
      Data mode: CPM
      Radio nuclide: Manual SPA:P33
      Scintillator: Liq/plast
      Energy Range: Low CDK2 Assay:

BACULOVIRUS CONSTRUCTIONS: Cyclins A and E were cloned into pFASTBAC (Invitrogen) by PCR, with the addition of a GluTAG sequence (EYMPME) at the amino-terminal end to allow purification on anti-GluTAG affinity columns. The expressed proteins were approximately 46 kDa (cyclin E) and 50 kDa (cyclin A) in size. CDK2 was also cloned into PFASTBAC by PCR, with the addition of a haemaglutinin epitope tag at the carboxy-terminal end (YD-VPDYAS). The expressed protein was approximately 34 kDa in size.

ENZYME PRODUCTION: Recombinant baculoviruses expressing cyclins A, E and CDK2 were infected into SF9 cells at a multiplicity of infection (MOI) of 5, for 48 hrs. Cells were harvested by centrifugation at 1000 RPM for 10 minutes. Cyclin-containing (E or A) pellets were combined with CDK2 containing cell pellets and lysed on ice for 30 minutes in five times the pellet volume of lysis buffer containing 50 mM Tris pH 8.0, 0.5% NP40, 1 mM DTT and protease/phosphatase inhibitors (Roche Diagnostics GmbH, Mannheim, Germany). Mixtures were stirred for 30-60 minutes to promote cyclin-CDK2 complex formation. Mixed lysates were then spun down at 15000 RPM for 10 minutes and the supernatant retained. 5 ml of anti-GluTAG beads (for one liter of SF9 cells) were then used to capture cyclin-CDK2 complexes. Bound beads were washed three times in lysis buffer. Proteins were competitively eluted with lysis buffer containing 100-200 ug/mL of the GluTAG peptide. Eluate was dialyzed overnight in 2 liters of kinase buffer containing 50 mM Tris pH 8.0, 1 mM DTT, 10 mM MgCl2, 100 uM sodium orthovanadate and 20% glycerol. Enzyme was stored in aliquots at −70° C.

IN VITRO KINASE ASSAY: CDK2 kinase assays (either cyclin A or E-dependent) were performed in low protein binding 96-well plates (Corning Inc, Corning, N.Y.). Enzyme was diluted to a final concentration of 50 µg/ml in kinase buffer containing 50 mM Tris pH 8.0, 10 mM $MgCl_2$, mM DTT, and 0.1 mM sodium orthovanadate. The substrate used in these reactions was a biotinylated peptide derived from Histone H1 (from Amersham, UK). The substrate was thawed on ice and diluted to 2 µM in kinase buffer. Compounds were diluted in 10% DMSO to desirable concentrations. For each kinase reaction, 20 µl of the 50 µg/ml enzyme solution (1 µg of enzyme) and 20 µl of the 1 µM substrate solution were mixed, then combined with 10 µl of diluted compound in each well for testing. The kinase reaction was started by addition of 50 µl of 4 µM ATP and 1 µCi of 33P-ATP (from Amersham, UK). The reaction was allowed to run for 1 hour at room temperature. The reaction was stopped by adding 200 µl of stop buffer containing 0.1% Triton X-100, 1 mM ATP, 5 mM EDTA, and 5 mg/ml streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ DETERMINATION: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis. The thus-obtained $IC_{50}$ values for selected compounds of the invention are shown in Table 1 above. These kinase activities were generated by using the above-described assay.

As demonstrated above by the assay values, the compounds of the present invention can exhibit good Chk1 inhibitory properties.

EXAMPLES—SET B

Chemical Synthesis

NMR spectra were acquired on a Mercuryplus 400 MHz NMR Spectrometer (Varian), using CDCl3 or DMSO-d6 as solvents. LC-MS data was obtained using an Agilent 1100 Series LC/MSD (quadrupole, API-ES (Atmospheric Pressure Interface Electrospray)) with a capillary voltage set to 3500 V and running in positive mode. Purification via reverse phase chromatography was accomplished using a C18 reverse phase column with a gradient of 0.1% trifluoroacetic acid in water to 95:5 acetonitrile: water at a flow rate of 20 mL/min. Samples were collected using a UV (Gilson, 254 nm) or mass spectra (Agilent 1100 Series LC/MSD model SL) signal. Normal phase silica gel chromatography on a Biotage instrument was accomplished using a Quad UV System (P/N 07052) utilizing KP-SIL 32-63 um columns, 60 A with flash cartridges 12+M or 25+M.

Abbreviations Used in the Examples

| AcOH | Acetic acid |
|---|---|
| DCM | Dichloromethane |
| DIAD | Diisopropylazodicarboxylate |
| DIEA | Diisopropylethylamine |
| DMAP | 4-Dimethylaminopyridine |
| DME | Dimethoxyethane |
| DMF | Dimethylformamide |
| DMFDMA | N,N-Dimethylformamide dimethylacetal |
| DMSO | Dimethyl sulfoxide |
| EtOAc | Ethyl acetate |
| EtOH | Ethanol |
| HATU | N,N,N',N'-Tetramethyl-O-(7-Azabenzotriazol-1-yl)Uronium hexafluorophosphate |
| Hex | hexanes |
| HPLC | High pressure liquid chromatography |
| mCPBA | meta-Chloroperoxybenzoic acid |
| MeOH | Methanol |
| Pyr | Pyridine |
| RT | Room temperature |
| THF | Tetrahydrofuran |
| TLC | Thin layer chromatography |

Representative compounds of formula (I), wherein $G^1$ is —C(O)—OH, were prepared according the synthetic route outlined in Scheme 1.

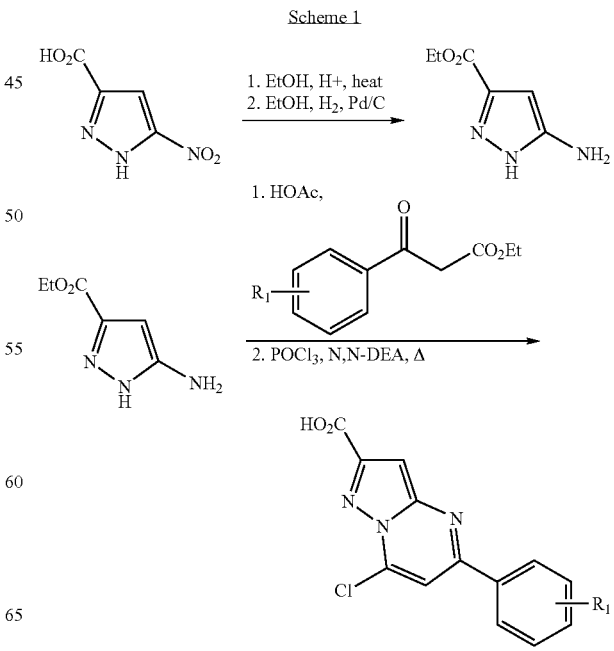

-continued

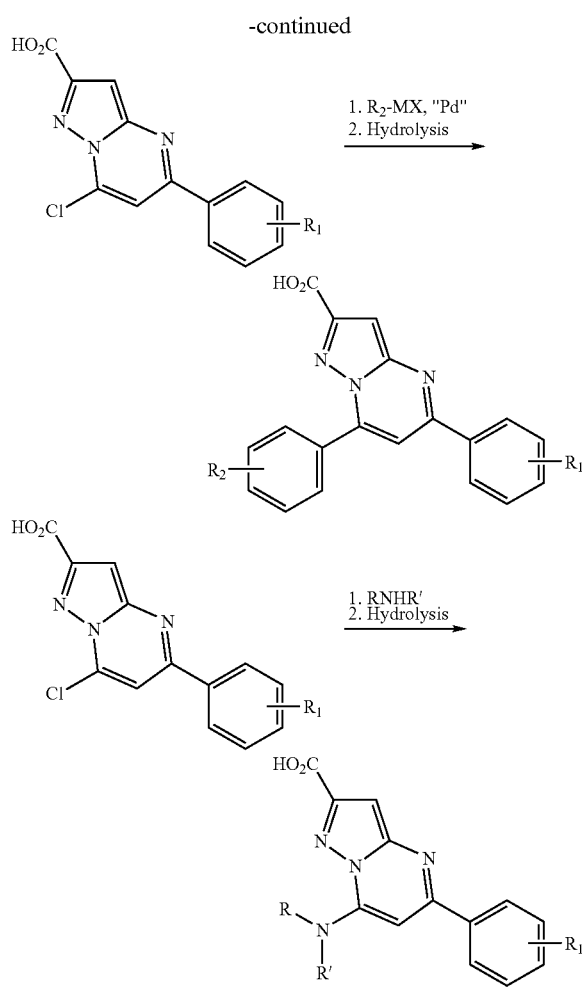

Example 1

7-Biphenyl-4-yl-5-(4-chlorophenyl)pyrazole[1,5a]pyrimidine-2-carbocylic acid ethyl ester Step 1: 5-(4-chlorophenyl)-7-oxo-4,7-dihydropyrazolo[1,5a]pyrimidine-2-carboxylic acid ethyl ester

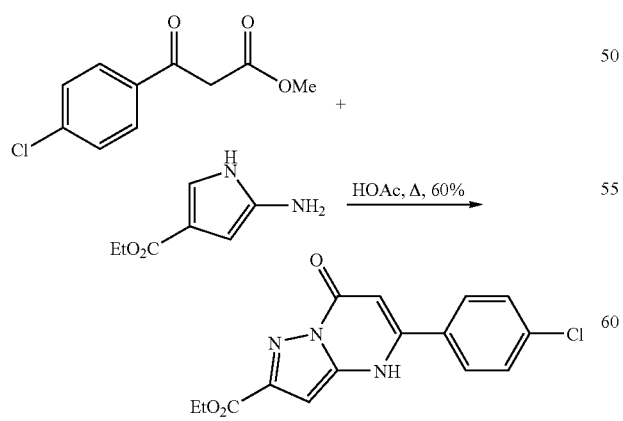

A mixture of methyl 4-chlorobenzoylacetate (2.13 g, 10 mmol) and ethyl 5-amino-3-pyrazole carboxylate (1.55 g, 10 mmol) in glacial acetic acid were heated to reflux for 20 hours. A shiny precipitate formed during the reaction. The reaction mixture was cooled, diluted with ethyl acetate and filtered. The precipitate was washed with ethyl acetate to afford an off-white shiny solid (1.92 g, 60%). $^1$H NMR (400 MHz, DMSO-$d_6$) δ 12.8 (bs, 1H), 7.87 (d, 2H, J=6.4 Hz), 7.67 (d, 2H, J=6.4 Hz), 6.55 (s, 1H), 6.21 (s, 1H), 4.34 (q, 2H, J=6.8 Hz), 1.35 (t, 3H, J=6.8 Hz). MS calcd for $C_{15}H_{13}ClN_3O_3$ [M+H]$^+$ 318.057, found 318.0.

Step 2: 7-Chloro-5-(4-chlorophenyl)pyrazolo[1,5a]pyrimidine-2-carboxylic acid ethyl ester

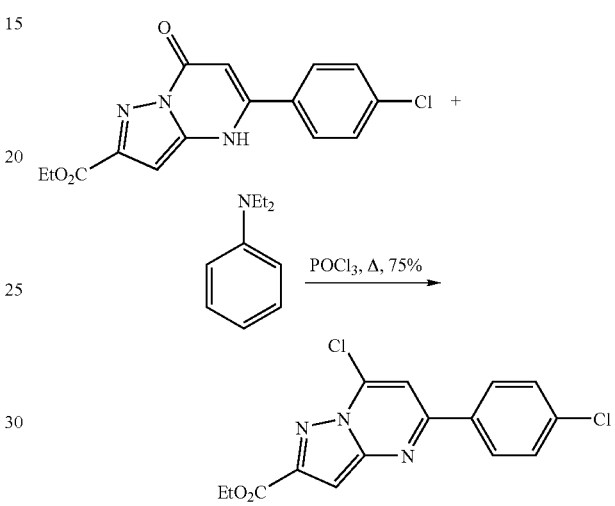

To suspension of 5-(4-chloro-phenyl)-7-oxo-4,7-dihydropyrazolo[1,5a]-pyrimidine-2-carboxylic acid ethyl ester (1.92 g, 6.04 mmol) and N,N-diethylaniline (2.4 mL, 15.1 mmol) was added phosphorous oxychloride (6 mL). The reaction mixture was heated to reflux for 3 hours. The reaction mixture solidified upon cooling. The reaction mixture was dissolved in dichloromethane and concentrated. The solid was dissolved in dichloromethane and washed with successively with cold water (3×100 mL), saturated sodium bicarbonate solution (1×100 mL) and brine. The organic layer was dried over sodium sulfate and concentrated. Purification by column chromatography (SiO$_2$, 1% ethyl acetate/dichloromethane) afforded a yellow solid (1.53 g, 75%). $^1$H NMR (400 MHz, CDCl$_3$) δ 8.04 (d, 2H, J=8.8 Hz), 7.52 (s, 1H), 7.51 (d, 2H, J=8.8 Hz), 7.33 (s, 1H), 4.53 (q, 2H, J=7.2 Hz), 1.49 (t, 3H, J=6.8 Hz). MS calcd for $C_{15}H_{12}Cl_2N_3O_2$ [M+H]$^+$ 336.023, found 336.0.

Step 3: 7-Biphenyl-4-yl-5-(4-chlorophenyl prazolo[1,5a]pyrimidine-2-carboxylic acid ethyl ester

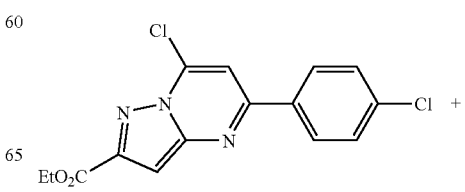

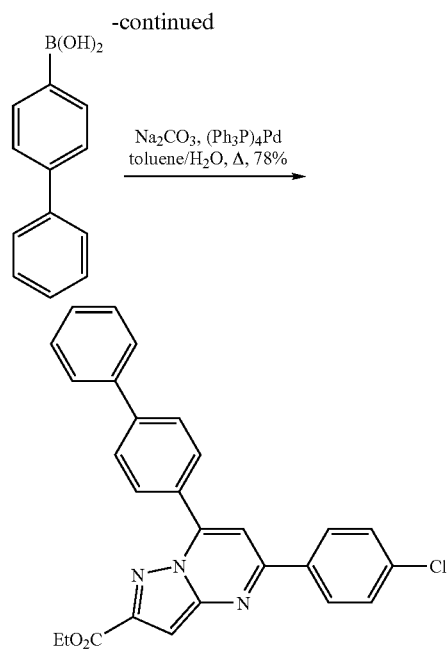

To a reaction tube containing 7-chloro-5-(4-chloro-phenyl)-pyrazolo[1,5a]-pyrimidine-2-carboxylic acid ethyl ester (50 mg, 0.15 mmol), 4-(phenyl)phenyl boronic acid (36 mg, 0.18 mmol), sodium carbonate (35 mg, 0.33 mmol) and tetrakis(triphenylphosphine) palladium(0) (17 mg, 0.015 mmol) was added toluene (5 mL) and water (1 mL). The reaction tube was evacuated and flushed with argon. The reaction mixture was heated to reflux overnight. After cooling the reaction mixture was diluted with ethyl acetate (10 mL) and water (15 mL). The organic layer was separated, washed with saturated sodium chloride solution, dried over sodium sulfate and concentrated. Purification by column chromatography (SiO₂, dichloromethane) afforded a pale yellow solid (53 mg, 78%). ¹H NMR (400 MHz, CDCl₃) δ 8.23 (d, 2H, J=6.4 Hz), 8.12 (d, 2H, J=6.8 Hz), 7.81 (d, 2H, J=6.4 Hz), 7.68 (d, 2H, J=7.2 Hz), 7.55-7.40 (m, 8H), 7.31 (s, 1H), 6.90 (d, 1H, J=8.8 Hz), 4.49 (q, 2H, J=7.2 Hz), 1.47 (t, 3H, J=6.8 Hz). MS calcd for $C_{27}H_{21}ClN_3O_2$ [M+H]⁺ 454.12, found 454.0.

Example 2

5-(4-Chlorophenyl-7-(2-chlorophenyl)pyrazole[1,5a] pyrimidine-2-carboxylic acid ethyl ester

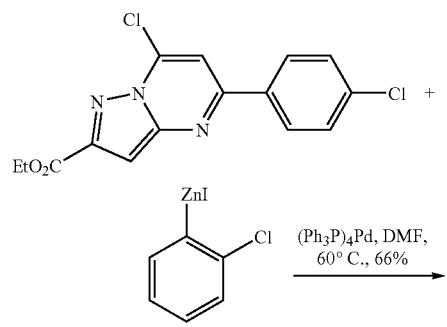

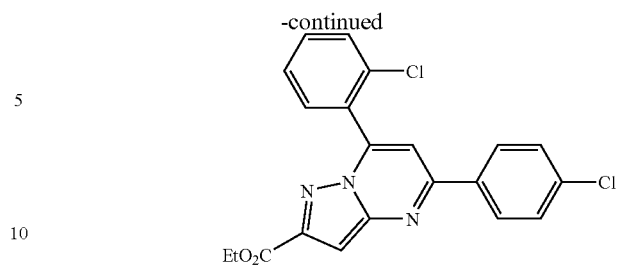

To a reaction tube containing 7-chloro-5-(4-chloro-phenyl)-pyrazolo[1,5a]pyrimidine-2-carboxylic acid ethyl ester 50 mg, 0.15 mmol), and tetrakis(triphenylphosphine) palladium(0) (17 mg, 0.015 mmol) in dimethylformamide (2 mL) was added 0.5 M 2-chlorophenyl zinc iodide in THF (0.38 mL, 0.19 mmol). The reaction tube was evacuated and flushed with argon. The reaction mixture was heated to 60° C. overnight. After cooling the reaction mixture was diluted with ethyl acetate (10 mL) and saturated ammonium chloride solution (10 mL). The organic layer was separated, washed with water and saturated sodium chloride solution, dried over sodium sulfate and concentrated. Purification by column chromatography (SiO₂, dichloromethane) afforded a pale yellow solid (51 mg, 66%) with a purity of 80%. ¹H NMR (400 MHz, CDCl₃) δ 8.08 (d, 2H, J=8.8 Hz), 7.70-7.45 (m, 6H), 7.40 (s, 1H), 7.30 (s, 1H), 4.45 (q, 2H, J=6.8 Hz), 1.43 (t, 3H, J=6.8 Hz). MS calcd for $C_{21}H_{16}Cl_2N_3O_2$ [M+H]⁺ 412.05, found 412.0.

Example 3

5-(4-Chlorophenyl-7-(2-chlorophenyl)pyrazole[1,5a] pyrimidine-2-carboxylic acid

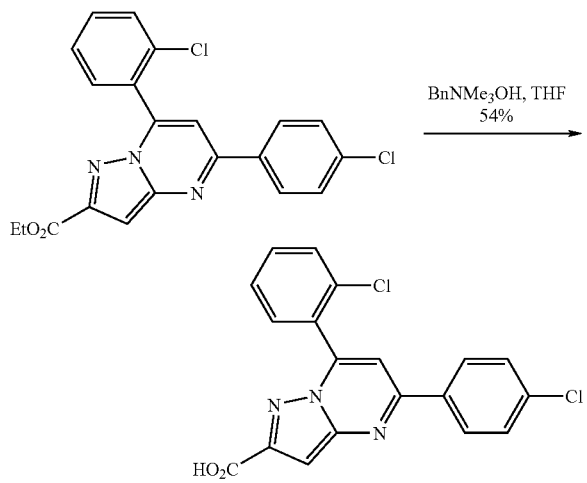

To 5-(4-chloro-phenyl-7-(2-chloro-phenyl)-pyrazolo[1,5a]pyrimidine-2-carboxylic acid ethyl ester (50 mg, 0.12 mmol) in tetrahydrofuran (3 mL) was added benzyltrimethylammonium hydroxide (2.2 M in methanol, 222 μL, 0.49 mmol) at room temperature. The reaction was stirred for 1.5 hours before p-toluenesulphonic acid resin (275 mg, ~4.5 equivalents) was added. The reaction mixture stirred for 1 hour. The mixture was filtered and concentrated. Purification by HPLC preparative chromatography afforded an off-white solid (25 mg, 54%). This compound corresponds to entry 106 in the Table 1. $^1$H NMR (400 MHz, DMSO-d$_6$) δ 13.45 (bs, 1H), 8.33 (d, 2H, J=6.4 Hz), 7.99 (s, 1H), 7.80-7.6 (m, 6H), 7.25 (s, 1H). MS calcd for $C_{19}H_{12}Cl_2N_3O_2$ [M+H]$^+$ 384.02, found 384.0.

Example 4

Synthesis of pyrazolo[1,5a]pyrimidinyl amino derivatives

Step 1

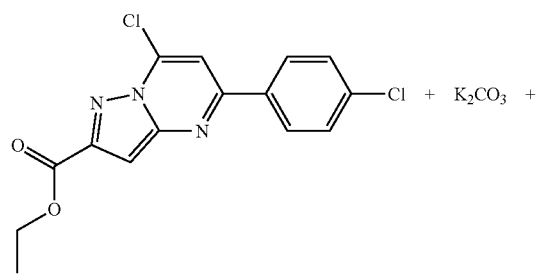

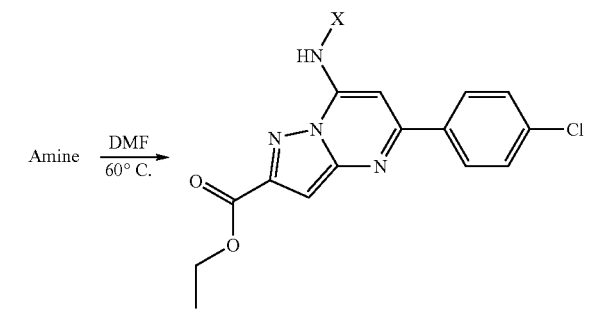

X = benzyl, cyclohexyl, morpholine, etc

A mixture of the 7-chloropyrazolo[1,5a]pyrimidine (0.05 mmol), amine (0.05 mmol) and potassium carbonate (0.1 mmol) in DMF (1.5 mL) was stirred for 16 h at 60° C.

The reaction was allowed to cool to room temperature and then diluted with ethyl acetate (10 mL). The resultant mixture was extracted with water (×2) and saturated brine. The ethyl acetate layer was dried over anhydrous sodium sulfate and concentrated. MS(+, 30V) calcd for $C_{23}H_{21}ClN_4O_2$ [M+H]$^+$ 421.14, found 421.2.

Step 2

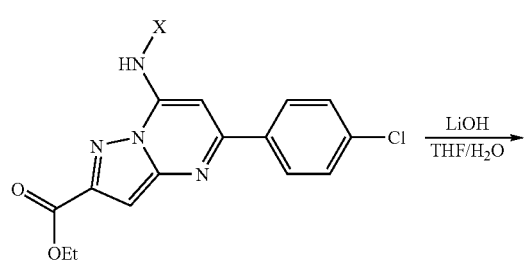

X = benzyl, cyclohexyly, morpholine, etc

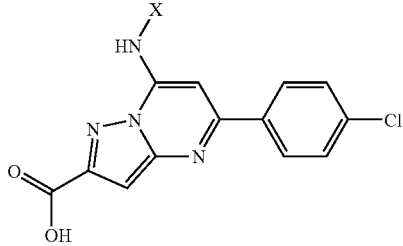

X = benzyl, cyclohexyly, morpholine, etc

To the pyrazolo[1,5a]pyrimidine amino compound (0.05 mmol) in THF (1.5 mL) and water (0.5 mL) was added 1M LiOH (200 μl, 0.2 mmol) and stirred at RT for 16 h. The reaction was diluted with ethyl acetate (10 mL) and acidified to pH 2, transferred to a separatory funnel and the layers separated. The organic layer was washed with saturated brine, dried over anhydrous sodium sulfate and concentrated.

For the above case where the amino group was DL-alpha-methylbenzylamine (Entry 78): MS(+, 30V) calcd for $C_{21}H_{17}ClN_4O_2$ [M+H]$^+$ 393.10, found 393.0.

Example 5

Synthesis of Amino and Anilino Pyrazolo[1,5a]pyrimidine Derivatives

Step 1

X = 3-chloro, 2-phenoxy, etc

A mixture of the 7-chloropyrazolo[1,5a]pyrimidine (0.05 mmol), aniline (0.05 mmol) and potassium carbonate (0.1 mmol) in DMF (1.5 mL) was stirred for 16 h at 60° C.

The reaction was allowed to cool to room temperature and then diluted with ethyl acetate (10 mL). The resultant mixture was extracted with water (×2) and saturated brine. The ethyl acetate layer was dried over anhydrous sodium sulfate and concentrated. MS (+, 30V) calcd for $C_{21}H_{17}ClN_4O_2$ [M+H]$^+$ 393.10, found 393.0.

Step 2

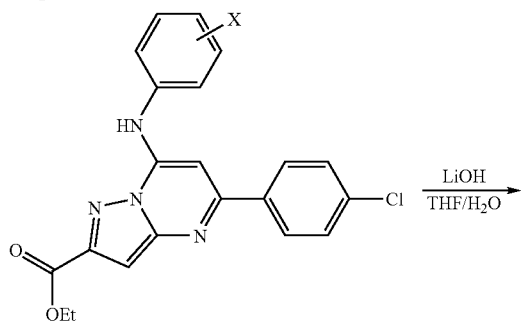

X = 3-chloro, 2-phenoxy, etc

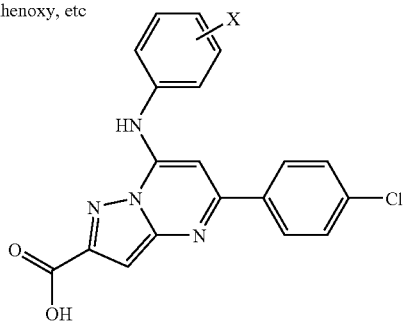

X = 3-chloro, 2-phenoxy, etc

For X=H (entry 76): MS (+, 30V) calcd for $C_{19}H_{13}ClN_4O_2$ [M+H]$^+$ 365.07, found 365.0.

Example 6

Synthesis of 6,7-Diarylpyrazolo[1,5a]pyrimidine carboxylates

Step 1

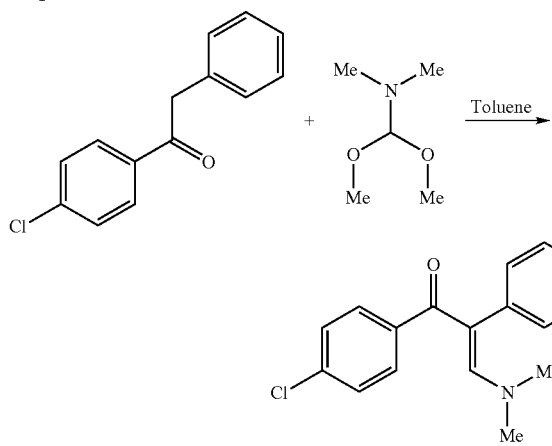

To a solution of benzyl 4-chlorophenyl ketone (230 mg, 1 mmol) in dry toluene (10 mL) under argon was added N,N-Dimethylformamide dimethylacetal (DMFDMA) (159 µl, 1.2 mmol) dropwise at RT. After 12 h DMFDMA (4 µl, 0.03 mmol) was added and the mixture heated to 50° C. for another 24 h. Then, during 5 days, DMFDMA (4 µl, 0.03 mmol) was added each day and the temperature increased about 15° C. everyday. The fifth day, as the reaction finished (TLC monitoring), the solvent was removed to yield the enaminoketone (285 mg, 100%) as a red/brown oil. $^1$H NMR (CDCl$_3$, 400 MHz): δ 7.35(s, 1H), 7.38 (m, 2H), 7.25 (m, 6H), 7.16 (m, 2H), 2.8 (s, 6H). MS (+, 30V) calcd for $C_{17}H_{16}ClNO$ [M+H]$^+$ 286.09, found 286.05.

Step 2

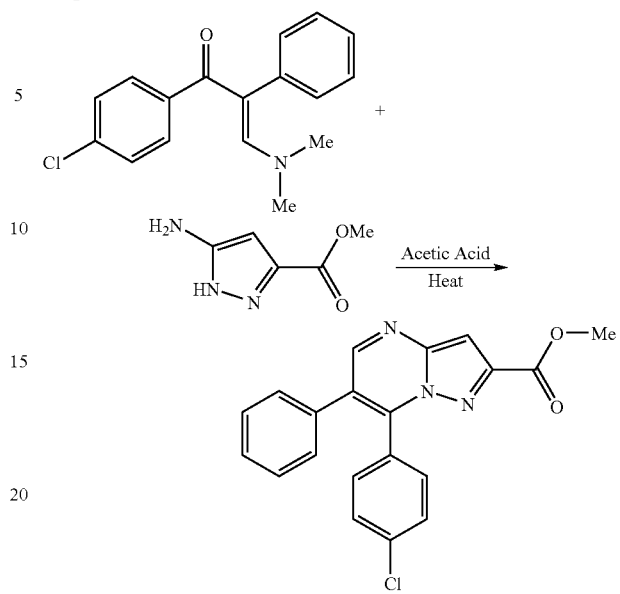

To the enaminoketone compound (285 mg, 1 mmol) in acetic acid (10 mL) was added 3-amino-5-carbemethoxy-pyrazole (141 mg, 1 mmol). The reaction was heated to 118° C. and stirred at 118° C. for 16 h. The reaction mixture was concentrated. The pyrazolopyrimidine product was purified by column chromatography (SiO2, 5% ethyl acetate/DCM) yielding a white solid (335 mg, 89%). $^1$H NMR (CDCl$_3$, 400 MHz): δ 8.66 (s broad, 1H), 7.44 (m, 2H), 7.35 (m, 6H), 7.17 (m, 2H), 3.98 (s, 3H). MS (+, 30V) calcd for $C_{20}H_{14}ClN_3O_2$ [M+H]$^+$ 364.08, found 364.05.

Step 3

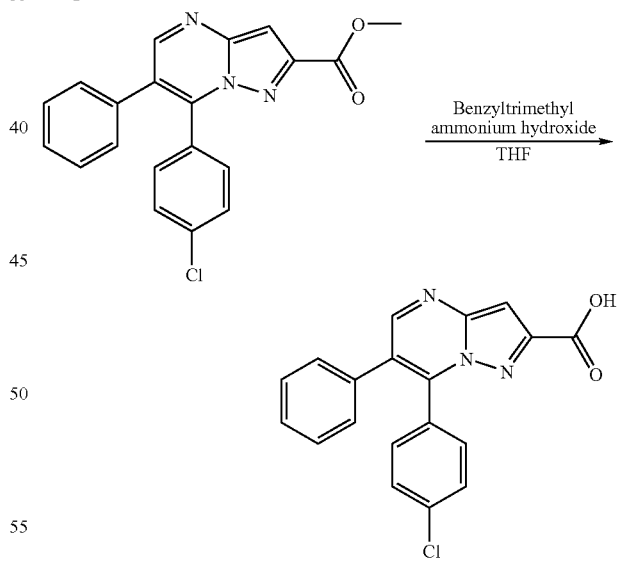

To the 7-(4-chloro-phenyl)-6-phenyl-pyrazolo[1,5]pyrimidine-2-carboxylic acid methyl ester (98 mg, 0.27 mmol) in THF (5 mL) was added benzyltrimethyl ammonium hydroxide (40 wt. % solution in methanol)(491 µl, 1.1 mmol) and the mixture stirred at room temperature for 16 h. TLC (DCM/MeOH/AcOH 90:10:1) indicated that the reaction was complete. The reaction mixture was diluted with ethyl acetate (10 mL) and acidified to pH 2 with 1N HCl. Transferred to a separatory funnel and separated the layers, the organic layer was washed with brine (×1), dried over sodium sulfate and concentrated. The pyrazolopyrimidine product was purified by PREP-LC yielding a pale yellow solid (46 mg, 49%). This corresponds to entry 236 in the Table 1. ¹H NMR (DMSO, 400 MHz): δ 8.74(s, 1H), 7.49 (s, 4H), 7.28 (m, 6H). MS (+, 30V) calcd for $C_{19}H_{11}ClN_3O_2$ [M+H]⁺ 350.08, found 350.05.

Example 7

Synthesis of 6,7-Diarylpyrazolo[1,5a]pyrimidine tetrazoles

Step 1

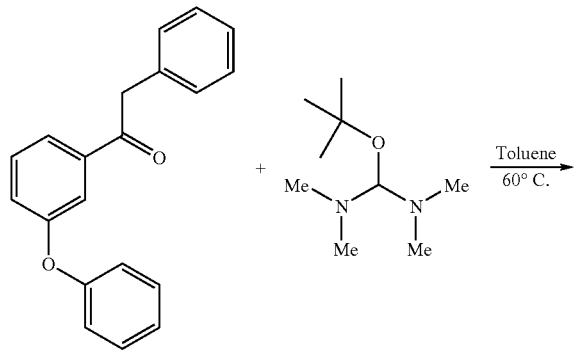

To a solution of benzyl 3-phenoxyphenyl ketone (523 mg, 1.8 mmol) in dry toluene (5 mL) under argon was added tert-butoxy bis(dimethylamino)methane (524 µl, 2.54 mmol) dropwise at RT. The reaction mixture was heated to 60° C. for 16 h. TLC indicated the reaction was complete. The solvent was removed to yield the enaminoketone (617 mg, 100%) as a red/brown oil. ¹H NMR (CDCl₃, 400 MHz): δ 7.39(s, 1H), 7.25 (m, 12H), 6.99 (dd, 2H), 2.75 (s broad, 6H). MS (+, 30V) calcd for $C_{23}H_{21}NO_2$ [M+H]⁺ 344.16, found 344.05.

Step 2

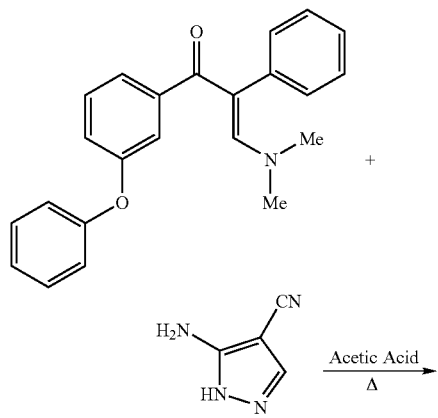

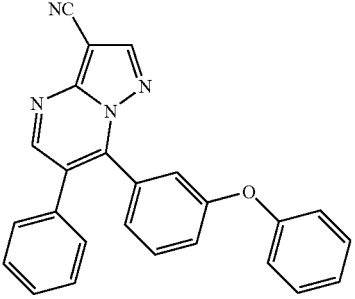

To the enaminoketone compound (150 mg, 0.44 mmol) in acetic acid (5 mL) was added 3-aminopyrazole-4-carbonitrile (48 mgs, 0.44 mmol). The reaction was heated to 118° C. and stirred at 118° C. for 16 h. The reaction mixture was concentrated. The pyrazolopyrimidine product was purified by column chromatography (SiO2, 5% ethyl acetate/DCM) yielding a white solid (117 mg, 68%). ¹H NMR (CDCl₃, 400 MHz): δ 8.82 (s, 1H), 8.38 (s, 1H), 7.45 (m, 4H), 7.31 (m, 3H), 7.15 (m, 4H), 6.85 (t, 1H), 6.78 (dd, 2H). MS (+, 30V) calcd for $C_{25}H_{16}N_4O$ [M+H]⁺ 389.13, found 389.05.

Step 3

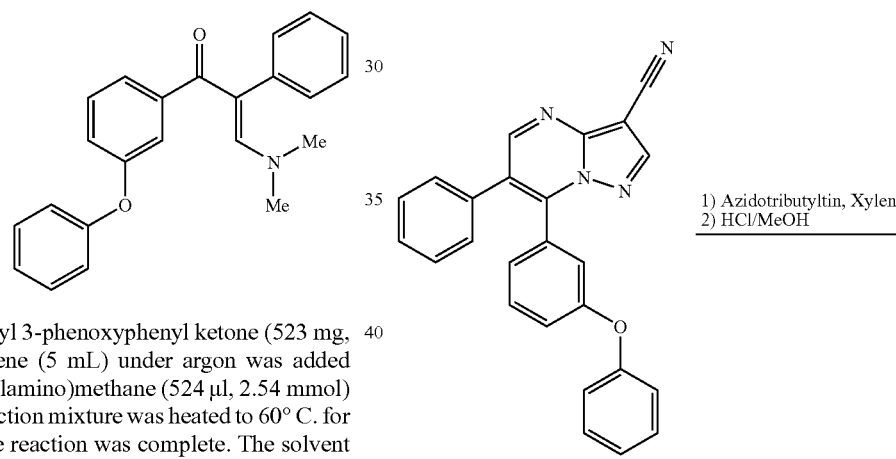

To the pyrazolopyrimidine nitrile (102 mg, 0.26 mmol) in xylenes (5 mL) was added azidotributyltin (144 µl, 0.52 mmol). The resulting mixture was heated to 110° C. under argon for 60 h. After 60 h the solvent was evaporated off, acetonitrile (10 mL) was added and the solution was washed with hexanes (8×10 mL). The acetonitrile phase was dried over anhydrous sodium sulfate and concentrated to yield the desired pyrazole pyrimidine tin protected tetrazole as a yellow gum (187 mg, 98%).

This yellow gum was taken up in methanol (5 mL). To the resulting solution was added hydrogen chloride (1.0M solution in diethyl ether) (1 mL, 1 mmol) and stirred at RT for 3 h. The reaction mixture was diluted with ethyl acetate (10 mL) and washed with aq. saturated sodium bicarbonate (×2) and brine (×1). The organic layer was dried over sodium sulfate and concentrated. The residue was triturated with hexane to give the free tetrazole product as a yellow solid (10.7 mg, 10%). This corresponds to entry 250 in the Table 1. $^1$H NMR (CDCl$_3$, 400 MHz): δ 8.85(s, 1H), 8.75 (s, 1H), 7.4 (m, 6H), 7.28 (m, 1H), 7.15 (m, 5H), 6.95 (t, 1H), 6.82 (dd, 2H). MS (+, 30V) calcd for C$_{23}$H$_{17}$N$_7$O [M+H]$^+$ 432.15, found 432.05.

Example 8

Synthesis of 5-amino-1H-pyrazole-3-carboxylic acid methyl ester

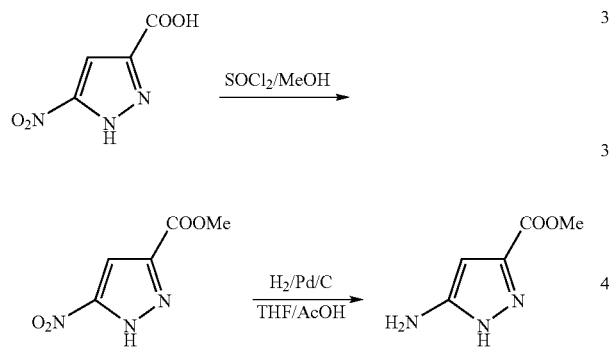

To a solution of 25.8 g (164 mmol) of 5-nitro-1H-pyrazole-3-carboxylic acid in 250 mL of anhydrous methanol (MeOH) was added dropwise 10.3 mL (141 mmol) of thionyl chloride, and the resulting mixture was heated at reflux overnight, then cooled to rt and concentrated to give 27.6 g (98% yield) of 5-nitro-1H-pyrazole-3-carboxylic acid methyl ester as a solid. $^1$H NMR (CDCl$_3$) δ 6.08s, 1H), 3.91 (s, 3H).

10.25 g (60 mmol) of 5-nitro-1H-pyrazole-3-carboxylic acid methyl ester was dissolved in 75 mL of acetic acid (AcOH) and 75 mL of tetrahydrofuran (THF). After a vacuum and argon cycle, 2.05 g (20% weight) of palladium on carbon (Pd/C 10 wt %) was added, the mixture was degassed again and filled with hydrogen from a balloon. The reaction mixture was stirred at rt under hydrogen atmosphere for 2 days. Analysis by thin layer chromatography (TLC) showed complete conversion of starting material to product. The mixture was then concentrated, the resulting purple colored oil was taken in 300 mL of ether, the finely dispersed purple impurity was filtered off, and the ether filtrate was evaporated to give 7.23 g (85% yield) of 5-amino-1H-pyrazole-3-carboxylic acid methyl ester as an off-white solid as indicated by $^1$H NMR; whose structure was confirmed using $^1$H NMR.

Example 9

Synthesis of 2-{[5-(4-chloro-phenyl)-7-(4-phenoxy-phenyl)-pyrazolo[1,5-a]pyrimidine-2-carbonyl]-amino}-3-hydroxy-propionic acid

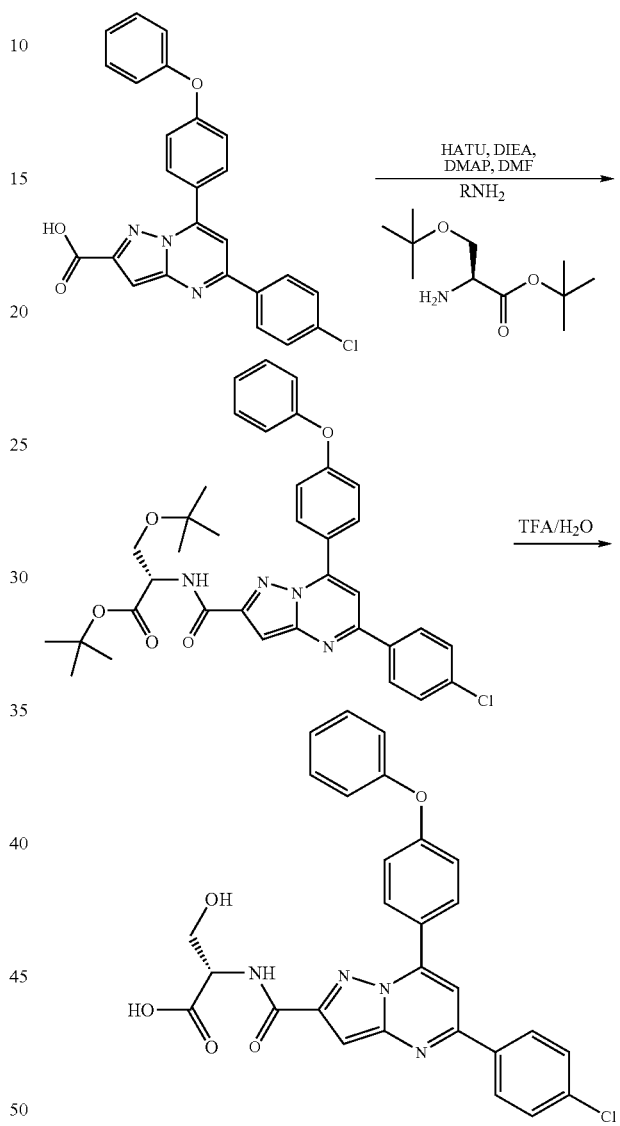

To a solution of 10 mg (0.023 mmol) of 5-(4-chloro-phenyl)-7-(4-phenoxy-phenyl)-pyrazolo[1,5-☐]pyrimidine-2-carboxylic acid in 1 mL of dimethylformamide (DMF) was added 0.016 mL (0.068 mmol) of diisopropylethylamine (DIEA), 6.3 mg (0.025 mmol) of L-serine-(tBu)OtBu hydrochloride, a few crystals of dimethylaminopyridine (DMAP cat), followed by 10.3 mg (0.027 mmol) of HATU, and the resulting mixture was stirred at rt for 3 h. The reaction mixture was then diluted with ethyl acetate, washed with 0.1 N sodium hydroxide solution, water and brine. The organic layer was dried over sodium sulfate and concentrated to afford 3-tert-butoxy-2-{[5-(4-chloro-phenyl)-7-(4-phenoxy-phenyl)-pyrazolo[1,5-☐]pyrimidine-2-carbonyl]-amino}-propionic acid tert-butyl ester which was used without any further purification in the next step.

A sample of 3-tert-butoxy-2-{[5-(4-chloro-phenyl)-7-(4-phenoxy-phenyl)-pyrazolo[1,5-☐]pyrimidine-2-carbonyl]-amino}-propionic acid tert-butyl ester was treated with 1 mL of 95:5 trifluoroacetic acid (TFA):H$_2$O, and the resulting solution was stirred at rt for 1.5 h, after which time it was quenched by the addition of 2 mL of 1:1 acetonitrile:water. The mixture was then concentrated and lyophilized to afford 11.2 mg (93% yield over 2 steps) of desired 2-{[5-(4-chloro-phenyl)-7-(4-phenoxy-phenyl)-pyrazolo[1,5-☐]pyrimidine-2-carbonyl]-amino}-3-hydroxy-propionic acid, as a solid whose $^1$H NMR spectrum was consistent with its structure. For entry 260: LC-MS calcd. for C$_{28}$H$_{21}$ClN$_4$O$_5$ [M+H]$^+$: 529.12; found: 529.1.

Example 10

Synthesis of 7-oxo-5-phenyl-4,7-dihydro-pyrazolo[1,5-a]pyrimidine-2-carboxylic acid and 5-(2-Chloro-phenyl)-7-oxo-4,7-dihydro-pyrazolo[1,5-a]pyrimidine-3-carboxylic acid

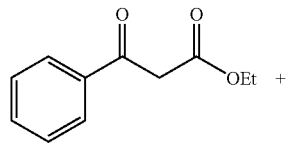

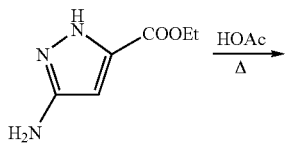

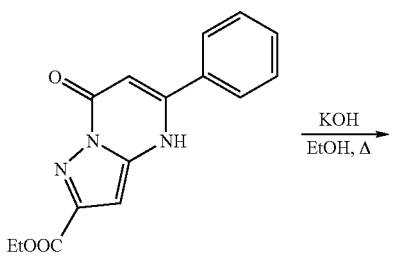

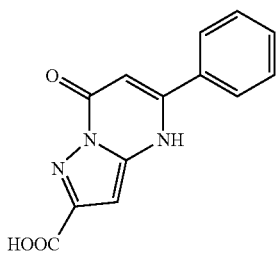

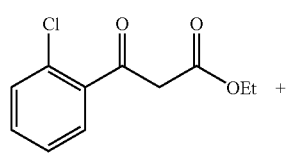

-continued

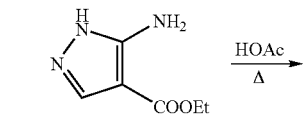

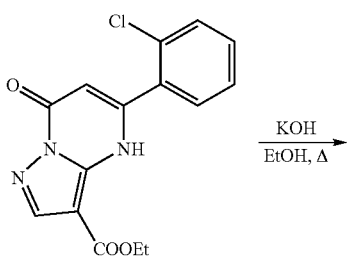

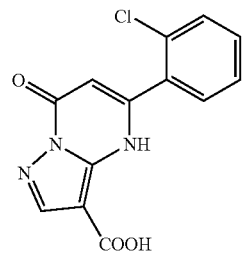

A solution of 0.56 mL (3.22 mmol) of 3-oxo-3-phenyl-propionic acid ethyl ester and 0.50 g (3.22 mmol) 5-amino-2H-pyrazole-3-carboxylic acid ethyl ester in 4 mL of acetic acid (HOAc) was heated at reflux for 4 h, during which time a precipitate formed. The precipitate was filtered off, washed with ethyl acetate and dried to give 0.51 g (56% yield) of 7-oxo-5-phenyl-4,7-dihydro-pyrazolo[1,5-a]pyrimidine-2-carboxylic acid ethyl ester as a solid as indicated by $^1$H NMR; LC-MS—calcd for C$_{15}$H$_{13}$N$_3$O$_3$ [M$^+$+H]$^+$: 284.1, found: 284.1.

To a solution of 50 mg (0.18 mmol) of 7-oxo-5-phenyl-4,7-dihydro-pyrazolo[1,5-a]pyrimidine-2-carboxylic acid ethyl ester in 4 mL of ethanol (EtOH) was added 26 mg (0.40 mmol) of potassium hydroxide (KOH) and the resulting mixture was heated at reflux for 60 h. The reaction mixture was then acidified with 4 M HCl in dioxane solution, and diluted with ethyl acetate. The organic extract was washed with water and brine, dried over sodium sulfate, and concentrated to give desired 7-oxo-5-phenyl-4,7-dihydro-pyrazolo[1,5-a]pyrimidine-2-carboxylic acid as indicated by $^1$H NMR; LC-MS—calcd for C$_{13}$H$_9$N$_3$O$_3$ [M$^+$+H]$^+$: 256.06, found: 256.1. This corresponds to entry 619.

5-(2-Chloro-phenyl)-7-oxo-4,7-dihydro-pyrazolo[1,5-a]pyrimidine-3-carboxylic acid (entry 620) was synthesized following the same synthetic sequence, starting from 3-(2-chloro-phenyl)-3-oxo-propionic acid ethyl ester, and performing the cyclization with 5-amino-1H-pyrazole-4-carboxylic acid ethyl ester.

Example 11

Synthesis of 6-(4-benzyloxy-phenyl)-7-isobutyl-3-(1H-tetrazol-5-yl)-pyrazolo[1,5-a]pyrimidine

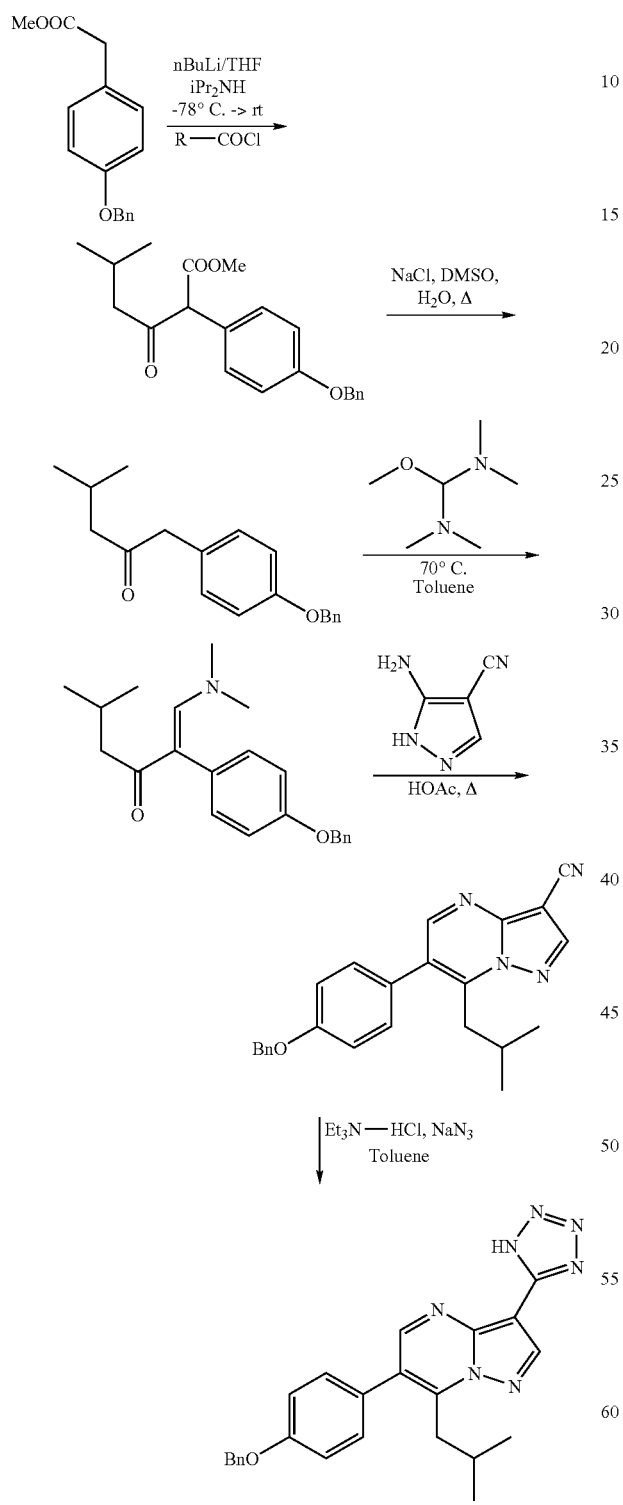

Synthesis of 6-(4-benzyloxy-phenyl)-7-isobutyl-3-(1H-tetrazol-5-yl)-pyrazolo[1,5-a]pyrimidine (410) was accomplished as depicted above, via transformations that are described elsewhere in this document for structurally similar compounds. Other compounds with modifications at the 7 position were synthesized in a similar manner.

Example 12

Synthesis of 7-isopropyl-6-methyl-3-(1H-tetrazol-5-yl)-pyrazolo[1,5-a]pyrimidine

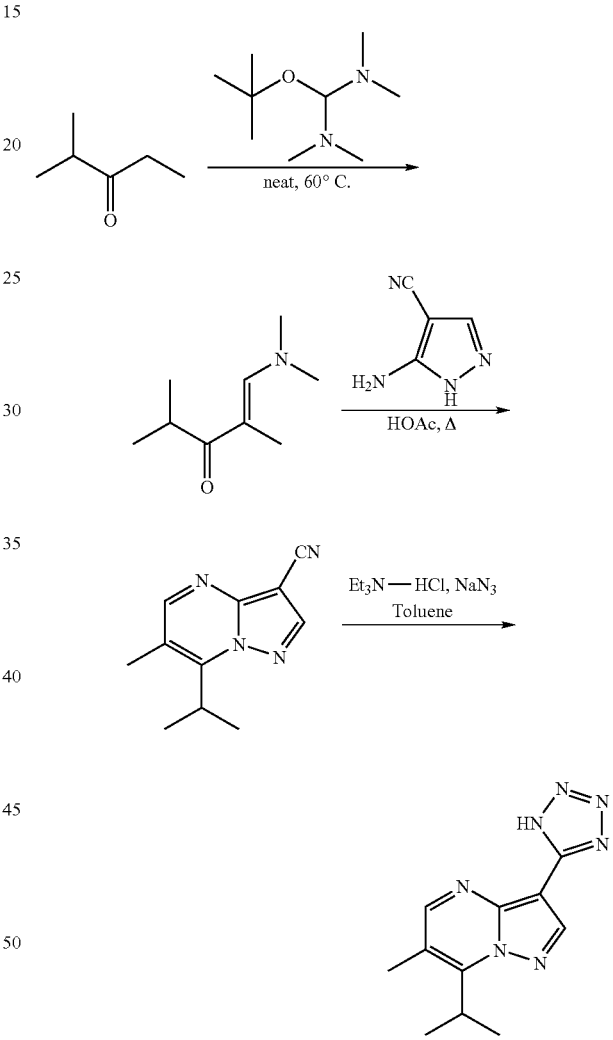

Synthesis of 7-isopropyl-6-methyl-3-(1H-tetrazol-5-yl)-pyrazolo[1,5-a]pyrimidine (390) was accomplished as depicted above, starting from the commercially available 2-methyl-pentan-3-one, via known transformations that were previously described for structurally similar compounds. 7-Ethyl-3-(1H-tetrazol-5-yl)-pyrazolo[1,5-a]pyrimidine (392), 7-cyclohexyl-6-methyl-3-(1H-tetrazol-5-yl)-pyrazolo[1,5-a]pyrimidine (391), and 7-cyclohexyl-6-methyl-pyrazolo[1,5-a]pyrimidine-3-carboxylic acid (394) were prepared following the same synthetic sequence.

Example 13

Synthesis of 6-(4-Benzyloxy-phenyl)-7-(tetrahydro-thiopyran-4-yl)-3-(1H-tetrazol-5-yl)-pyrazolo[1,5-a]pyrimidine

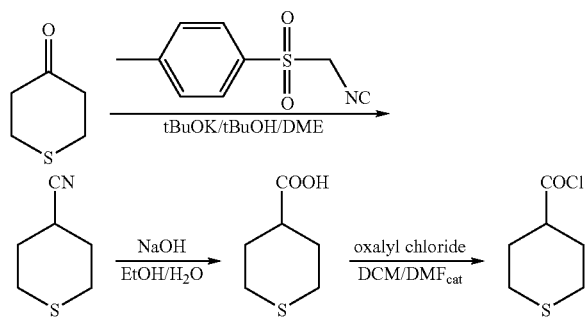

According to a modification of a literature procedure (*Helv. Chim. Acta* 1997, 80, 1528) to an ice cold solution of 2.0 g (17.2 mmol) of tetrahydro-thiopyran-4-one, and 3.69 g (18.9 mmol) of 1-isocyanomethanesulfonyl-4-methyl-benzene in 100 mL of 1,2-dimethoxyethane (DME) was added 34.4 mL (34.4 mmol) of potassium t-butoxide (1 M solution in t-butanol), and the resulting mixture was stirred at rt for 3 h. The reaction mixture was diluted with diethyl ether, washed with saturated sodium bicarbonate solution, dried over sodium sulfate and concentrated to give 2.05 g (93% yield) of desired tetrahydro-thiopyran-4-carbonitrile as indicated by $^1$H NMR.

A solution of 1.97 g (15.5 mmol) of tetrahydro-thiopyran-4-carbonitrile in 5 mL of ethanol (EtOH) was added to a solution of 6.2 g (155 mmol) of sodium hydroxide (NaOH) in 30 mL of EtOH and 15 mL of water, and the resulting mixture was heated at reflux for 4 h. The reaction mixture was cooled in an ice bath, acidified with concentrated hydrochloric acid to pH=2, and then concentrated to give a precipitate which was filtered to afford 1.36 g (60%) of desired tetrahydro-thiopyran-4-carboxylic acid as a brown crystalline solid as indicated by $^1$H NMR.

To an ice cold solution of 1.36 g (9.32 mmol) tetrahydro-thiopyran-4-carboxylic acid in 25 mL of dichloromethane (DCM) was added dropwise 1.1 mL (12.6 mmol) of oxalyl chloride, and the resulting mixture was stirred at 0° C. for 2 h. Then 2 μL of dimethylformamide (DMF cat) was added, and the reaction mixture was stirred at rt for 2 h, and concentrated to give 1.43 g (93%) of desired tetrahydro-thiopyran-4-carbonyl chloride as a brown oil as indicated by $^1$H NMR. The product was used without any further purification in the next step toward the preparation of 6-(4-Benzyloxy-phenyl)-7-(tetrahydro-thiopyran-4-yl)-3-(1H-tetrazol-5-yl)-pyrazolo[1,5-a]pyrimidine (below, entry 375).

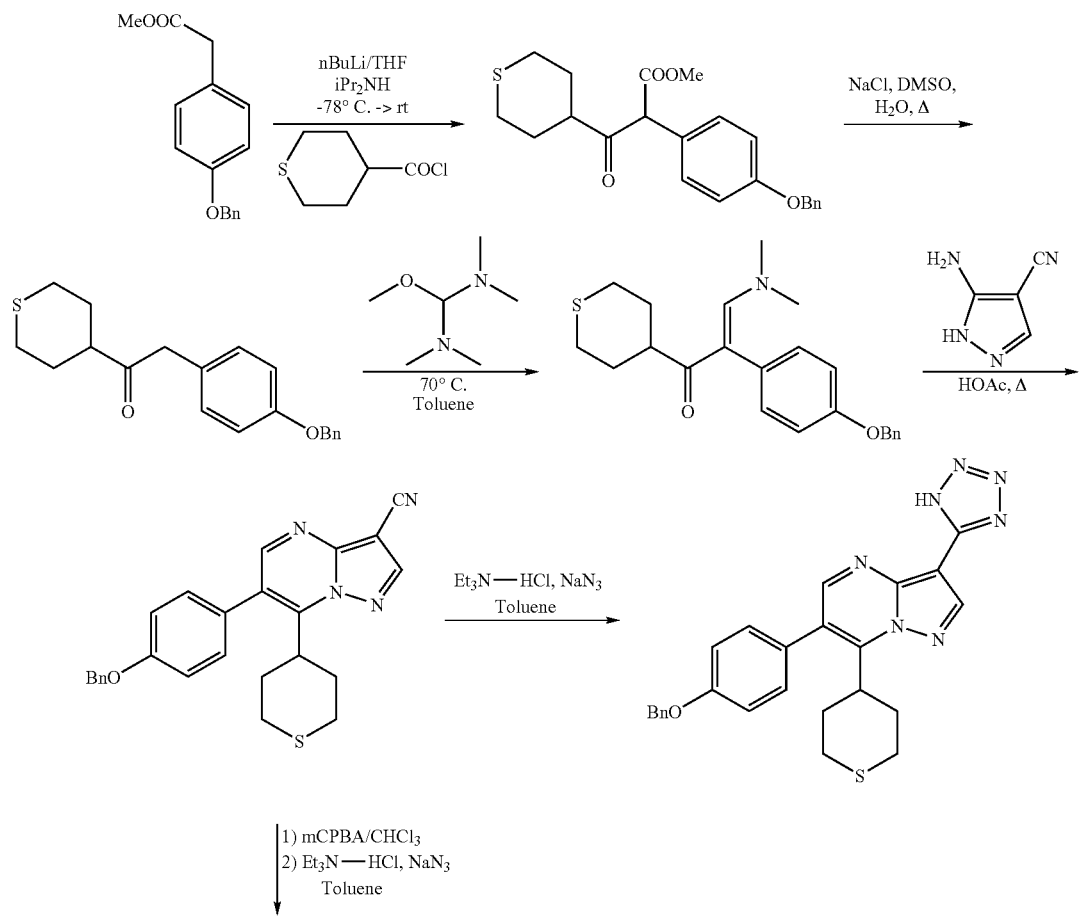

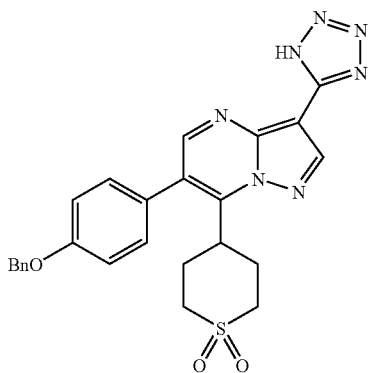

Example 14

Synthesis of 6-(4-Benzyloxy-phenyl)-7-(tetrahydro-pyran-4-yl)-3-(1H-tetrazol-5-yl)-pyrazolo[1,5-a]pyrimidine 6-(4-Benzyloxy-phenyl)-7-(tetrahydro-pyran-4-yl)-3-(1H-tetrazol-5-yl)-pyrazolo[1,5-a]pyrimidine was synthesized using the same experimental scheme.

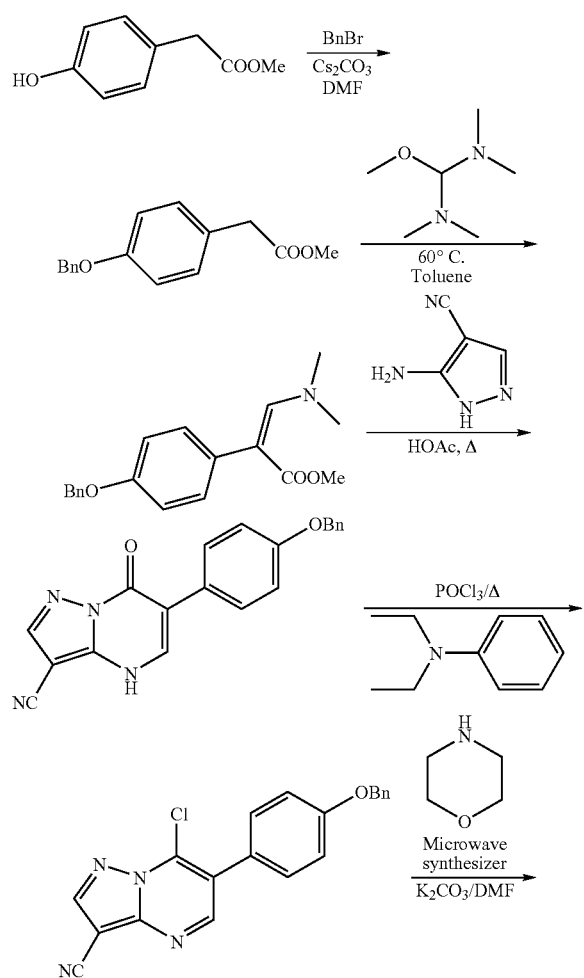

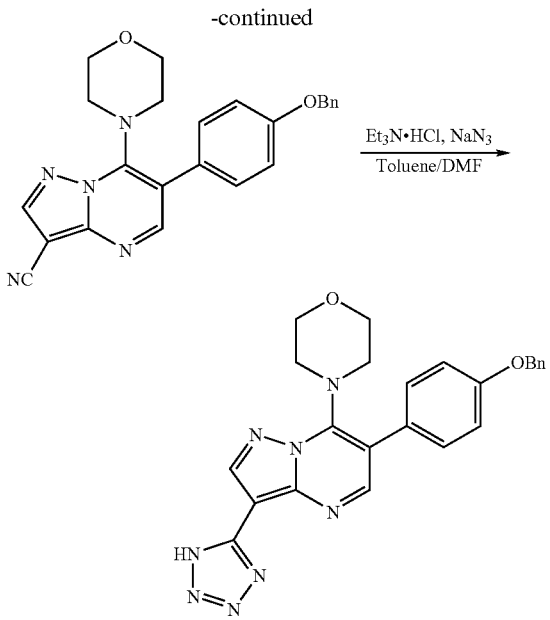

Example 15

Synthesis of 6-(4-benzyloxy-phenyl)-7-morpholin-4-yl-3-(1H-tetrazol-5-yl)-pyrazolo[1,5-a]pyrimidine A solution of 15 g (90.3 mmol) of methyl 4-hydroxyphenylacetate in 25 mL of dimethylformamide (DMF) was added 32.4 g (99.3 mmol) of cesium carbonate, followed by 13.4 mL (112.9 mmol) of benzyl bromide (BnBr), and the resulting heterogeneous mixture was stirred at rt for 72 h. The reaction mixture was filtered, the solids were washed with ethyl acetate, and the combined organic extracts were concentrated to give a residue which was chromatographed on silica gel (25% hexane in dichloromethane) to afford 19.1 g (83% yield) of desired (4-benzyloxy-phenyl)-acetic acid methyl ester as indicated by $^1$H NMR; LC-MS—calcd for $C_{16}H_{16}O_3$ [M$^+$+H]$^+$: 257.11, found: 257.2.

According to a modified literature procedure (Wasserman, H. H.; Ives, J. L. *J. Org. Chem.* 1985, 50, 3573-3580) a solution of 1.0 g (3.9 mmol) of (4-benzyloxy-phenyl)-acetic acid methyl ester in 4 mL of toluene was flushed with argon. To this solution was added 0.842 mL g (5.5 mmol) of methoxy bis(dimethylamino)methane, and the resulting mixture was stirred at 65° C. under argon overnight. The reaction mixture was concentrated to give 1.21 g of desired 2-(4-benzyloxy-phenyl)-3-dimethylamino-acrylic acid methyl ester as indicated by $^1$H NMR (containing traces of starting material). The product was used without any further purification in the next step.

A solution of 1.21 g (3.9 mmol) of 2-(4-benzyloxy-phenyl)-3-dimethylamino-acrylic acid methyl ester and 0.422 g (3.9 mmol) of 5-amino-1H-pyrazole-4-carbonitrile in 5 mL of acetic acid (HOAc) was heated at reflux overnight, during which time a precipitate formed. The reaction mixture was cooled to rt, diluted with 20% ethyl acetate in hexane solution, and filtered to give 0.86 g (65% over 2 steps) of 6-(4-benzyloxy-phenyl)-7-oxo-4,7-dihydro-pyrazolo[1,5-a]pyrimidine-3-carbonitrile as a tan colored solid as indicated by $^1$H NMR; LC-MS—calcd for $C_{20}H_{14}N_4O_2$ $[M^++H]^+$: 343.11, found: 343.1.

A slurry of 0.86 g (2.5 mmol) of 6-(4-benzyloxy-phenyl)-7-oxo-4,7-dihydro-pyrazolo[1,5-a]pyrimidine-3-carbonitrile, 1.0 mL (6.3 mmol) of N,N-diethylaniline, and 2 mL (21.5 mmol) of phosphorus oxychloride ($POCl_3$) was heated at reflux for 7 h, during which time the reaction mixture became olive in color. The mixture was cooled to rt, poured over ice, and extracted with dichloromethane/chloroform. The combined extracts were washed with water (3 times), saturated sodium bicarbonate solution (2 times), brine, dried over sodium sulfate and evaporated to give a residue which was chromatographed on silica gel (dichloromethane) to afford 0.637 (70% yield) of 6-(4-benzyloxy-phenyl)-7-chloro-pyrazolo[1,5-a]pyrimidine-3-carbonitrile as indicated by $^1$H NMR; LC-MS—calcd for $C_{20}H_{13}ClN_4O$ $[M^++H]^+$: 361.07, found: 361.1.

A solution of 50 mg (0.138 mmol) of 6-(4-benzyloxy-phenyl)-7-chloro-pyrazolo[1,5-a]pyrimidine-3-carbonitrile in 2 mL of dimethylformamide in a 5 mL microwave vessel, was added 25 mg (0.18 mmol) of potassium carbonate, followed by 15 mg (0.166 mmol) of morpholine, and the mixture was heated in a microwave synthesizer (Emrys system from Personal Chemistry, 300 W) at 160° C. for 5 min. Since analysis by LC-MS indicated product formation, the reaction mixture was diluted with ethyl acetate, washed with brine (2 times), dried over sodium sulfate and concentrated to give a residue which was purified via reverse-phase chromatography using Gilson to afford (after lyophilization) desired 6-(4-benzyloxy-phenyl)-7-morpholin-4-yl-pyrazolo[1,5-a]pyrimidine-3-carbonitrile (90% purity) as indicated by $^1$H NMR; LC-MS—calcd for $C_{24}H_{21}N_5O_2$ $[M^++H]^+$: 412.17, found: 412.1.

According to a modification of a literature procedure (Herr, R. J. Bioorg. Med. Chem. 2002, 10, 3379-3393) a solution of 35 mg (0.085 mmol) of 6-(4-benzyloxy-phenyl)-7-morpholin-4-yl-pyrazolo[1,5-a]pyrimidine-3-carbonitrile in 1.5 mL of toluene and 0.5 mL of dimethylformamide was added 71 mg (0.513 mmol) of triethylamine hydrochloride ($Et_3N$—HCl), and 33 mg (0.513 mmol) of sodium azide and the resulting heterogeneous mixture was heated at reflux for 72 h, during which time 71 mg (0.513 mmol) of triethylamine hydrochloride ($Et_3N$—HCl), and 33 mg (0.513 mmol) of sodium azide was added to the reaction mixture after every 24 h. The mixture was then cooled to rt, filtered and concentrated to a residue which was purified via reverse-phase chromatography to afford (after lyophilization) 15 mg (38% yield) of 6-(4-benzyloxy-phenyl)-7-morpholin-4-yl-3-(1H-tetrazol-5-yl)-pyrazolo[1,5-a]pyrimidine (370) as a solid as indicated by $^1$H-NMR. (LC-MS calcd for $C_{24}H_{22}N_8O_2$ $[M+H]^+$ 455.18; found 455.2.

Example 16

Synthesis of 7-cyclohexyl-6-(4-iodo-phenyl)-pyrazolo[1,5-a]pyrimidine-3-carbonitrile

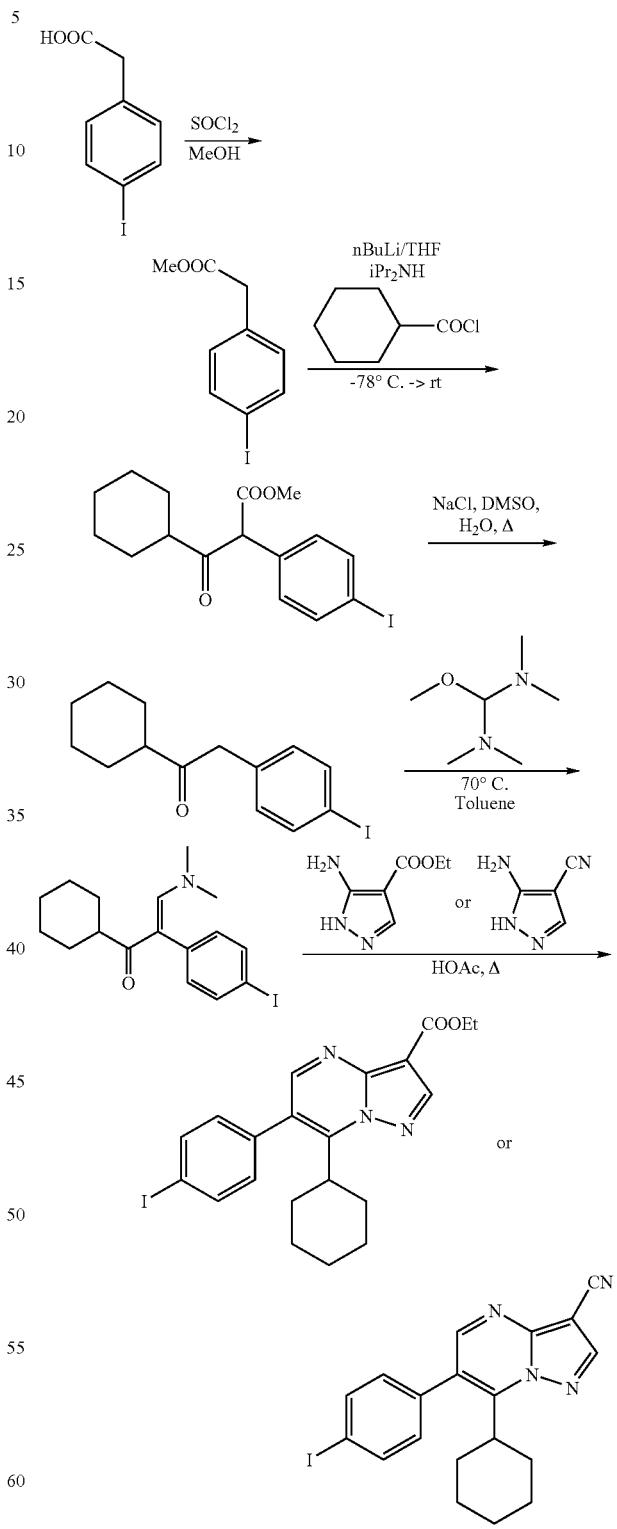

A solution of 5 g (19 mmol) of (4-iodo-phenyl)-acetic acid in 50 mL of methanol (MeOH) was added dropwise 3.5 mL (48 mmol) of thionyl chloride ($SOCl_2$), and the resulting mixture was stirred at rt for 36 h, after which time analysis by thin layer chromatography (TLC) indicated product formation. The mixture was concentrated to give 4.5 g (86% yield) of (4-iodo-phenyl)-acetic acid methyl ester as a pale beige oil as indicated by $^1$H NMR.

A solution of 2.88 mL (20.5 mmol) of diisopropylamine (iPr$_2$NH) in 50 mL of tetrahydrofuran (THF) was flushed with argon and cooled to −78° C. To this solution was added dropwise 8.2 mL (20.5 mmol) of n-butyllithium (nBuLi) 2.5 M solution in hexane, and the resulting mixture was stirred at −78° C. for 20 min, after which time a solution of 4.5 g (16.3 mmol) of (4-iodo-phenyl)-acetic acid methyl ester in 25 mL of THF was added dropwise. The mixture was allowed to warm up to rt for 40 min, then it was cooled again to −78° C., and 2.62 mL (19.6 mmol) of cyclohexanecarbonyl chloride was added dropwise, and the resulting mixture was allowed to warm up to rt, and stirred at rt overnight under argon. The reaction mixture was quenched on ice by the addition of saturated ammonium chloride solution, and extracted with ethyl acetate. The combined organic extracts were washed with water, brine, dried over sodium sulfate and concentrated to give 7 g of a burgundy oil which was chromatographed on silica gel (Biotage; 10% ethyl acetate in hexane) to afford 5.06 g (80% yield) of desired 3-cyclohexyl-2-(4-iodo-phenyl)-3-oxo-propionic acid methyl ester as a pale yellow solid as indicated by $^1$H NMR (1:2.6 keto: enol ratio). LC-MS—calcd for C$_{16}$H$_{19}$IO$_3$ [M$^+$+H]$^+$: 387.04, found: 387.0.

According to a modified literature procedure (Collins, I. et al J. Med. Chem. 2002, 45, 1887-1900) a solution of 5.06 g (13.1 mmol) of 3-cyclohexyl-2-(4-iodo-phenyl)-3-oxo-propionic acid methyl ester in 80 mL of dimethylsulfoxide (DMSO) was added a solution of 1.53 g (26.2 mmol) of sodium chloride (NaCl) in 5.8 mL of water (H$_2$O), and the resulting mixture was heated at 150° C. for 3 h during which time a white solid formed. The reaction mixture was cooled to rt, poured into 500 mL of water, and extracted thoroughly with ethyl acetate. The combined organic extracts were washed with water (3 times), brine, dried over sodium sulfate and concentrated to give 4.13 g (96% yield) of desired 1-cyclohexyl-2-(4-iodo-phenyl)-ethanone as a yellow solid as indicated by $^1$H NMR (containing small traces of impurities). The product was used without any further purification in the next step.

According to a modified literature procedure (Wasserman, H. H.; Ives, J. L. J. Org. Chem. 1985, 50, 3573-3580) a solution of 4.13 g (12.6 mmol) of 1-cyclohexyl-2-(4-iodo-phenyl)-ethanone in 20 mL of toluene was flushed with argon. To this solution was added 2.7 mL (17.6 mmol) of methoxy bis(dimethylamino)methane, and the resulting mixture was stirred at 70° C. under argon overnight. The reaction mixture was concentrated to give 5.07 g of crude 1-cyclohexyl-3-dimethylamino-2-(4-iodo-phenyl)-propenone as indicated by $^1$H NMR (containing traces of starting material). The product was used without any further purification in the next step.

A solution of 2.55 g (6.32 mmol max) of crude 1-cyclohexyl-3-dimethylamino-2-(4-iodo-phenyl)-propenone, and 0.98 g (6.32 mmol) of 5-amino-1H-pyrazole-4-carboxylic acid ethyl ester in 30 mL of acetic acid (HOAc) was heated at reflux for 66 h, during which time a precipitate formed. The precipitate was filtered off and discarded, and the acetic acid filtrate was concentrated to a solid residue, which was washed with 1:1 ethyl acetate:hexane and dried to give 1.67 g (55% yield) of 7-cyclohexyl-6-(4-iodo-phenyl)-pyrazolo[1,5-a]pyrimidine-3-carboxylic acid ethyl ester as a pale yellow solid. $^1$H NMR (CDCl$_3$) δ8.57s, 1H), 8.53s, 1H), 7.86-7.83 (d, J=8.4 Hz, 2H), 7.1-7.06 (d, J=8.4 Hz, 2H), 4.46 (q, 2H, J=7.2 Hz), 3.31-3.21 (m, 1H), 2.62-2.41 (m, 2H), 1.87-1.82 (m, 2H), 1.74-1.66 (m, 3H), 1.44 (t, 3H, J=7.2 Hz), 1.41-1.21 (m, 3H).

A solution of 1.66 g (4.1 mmol max) of crude 1-cyclohexyl-3-dimethylamino-2-(4-iodo-phenyl)-propenone, and 0.44 g (4.1 mmol) of 5-amino-1H-pyrazole-4-carbonitrile in 20 mL of acetic acid (HOAc) was heated at reflux for 66 h, during which time a finely dispersed precipitate formed. Since all attempts to filter off the precipitate were unsuccessful, the reaction mixture was concentrated to give a brown residue which was chromatographed on silica gel (Biotage; 2% ethyl acetate in dichloromethane) to afford 1.09 g (62% yield) of 7-cyclohexyl-6-(4-iodo-phenyl)-pyrazolo[1,5-a]pyrimidine-3-carbonitrile as a yellow solid. $^1$H NMR (CDCl$_3$) δ8.49s 1H), 8.39s, 1H), 7.88-7.86 (d, J=8.4 Hz, 2H), 7.07-7.05 (d, J=8.4 Hz, 2H), 4.13 (q, 2H, J=7.2 Hz), 3.28-3.21 (m, 1H), 2.59-2.47 (m, 2H), 1.87-1.84 (m, 2H), 1.75-1.65 (m, 3H), 1.28 (t, 3H, J=7.2 Hz), 1.39-1.20 (m, 3H).

Example 17

Synthesis of 7-cyclohexyl-6-(3'-methoxy-biphenyl-4-yl)-pyrazolo[1,5-a]pyrimidine-3-carboxylic acid, 7-cyclohexyl-6-(4'-methanesulfonyl-biphenyl-4-yl)-3-(1H-tetrazol-5-yl)-pyrazolo[1,5-a]pyrimidine, and 6-(4-benzyl-phenyl)-7-cyclohexyl-pyrazolo[1,5-a]pyrimidine-3-carboxylic acid

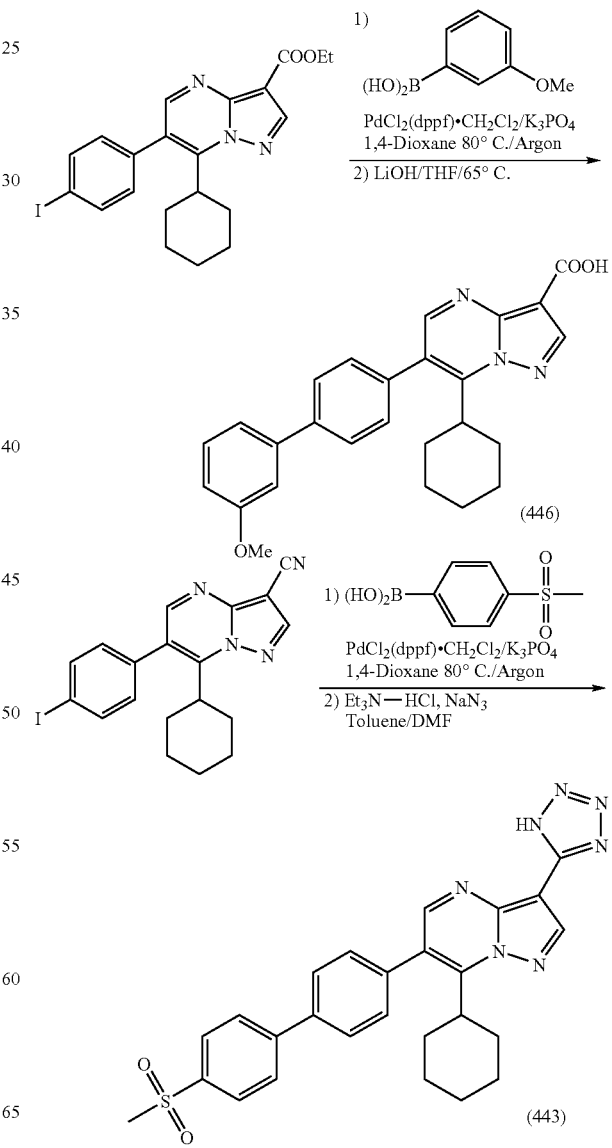

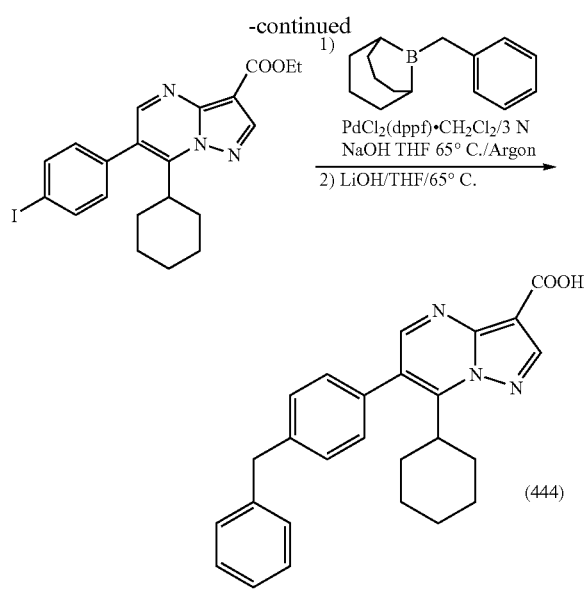

A mixture of 60 mg (0.126 mmol) of 7-cyclohexyl-6-(4-iodo-phenyl)-pyrazolo[1,5-a]pyrimidine-3-carboxylic acid ethyl ester, 29 mg (0.19 mmol, 1.5 equiv) of 3-methoxyphenylboronic acid, 5 mg (0.0063 mmol, 5 mol %) of Pd catalyst, and 80 mg (0.378 mmol, 3 equiv) of potassium phosphate was placed into a carousel tube. After a vacuum and argon cycle, 1,4-dioxane (3 mL) was added, and the resulting mixture was heated at 80° C. under argon for 14 h. Since analysis by LC-MS revealed unreacted starting material still present, 29 mg (0.19 mmol, 1.5 equiv) of 3-methoxyphenylboronic acid, 10 mg (0.012 mmol, 10 mol %) of Pd catalyst, and 80 mg (0.378 mmol, 3 equiv) of potassium phosphate was added and heating was continued for 24 h. The reaction mixture was then diluted with ethyl acetate, filtered through a small pad of Celite, dried over sodium sulfate and evaporated to give a brown residue (crude coupling product), which was chromatographed on silica gel (Biotage; gradient elution 2% to 5% ethyl acetate in dichloromethane) to afford 47 mg (82% yield) of desired 7-cyclohexyl-6-(3'-methoxy-biphenyl-4-yl)-pyrazolo[1,5-a]pyrimidine-3-carboxylic acid ethyl ester as indicated by $^1$H NMR; LC-MS—calcd for $C_{28}H_{29}N_3O_3$ [M$^+$+H]$^+$: 456.22, found: 456.2.

To a solution of 47 mg (0.103 mmol) of 7-cyclohexyl-6-(3'-methoxy-biphenyl-4-yl)-pyrazolo[1,5-a]pyrimidine-3-carboxylic acid ethyl ester in 3 mL of tetrahydrofuran was added 0.62 mL (0.62 mmol) of 1 M LiOH solution, and the resulting mixture was heated at reflux overnight. The reaction mixture was then acidified with 1 M HCl solution to pH=2, and extracted with ethyl acetate. The combined organic extracts were dried over sodium sulfate, and concentrated to give a residue which was purified via reverse-phase chromatography to afford (after lyophilization) 15 mg (34% yield) of 7-cyclohexyl-6-(3'-methoxy-biphenyl-4-yl)-pyrazolo[1,5-a]pyrimidine-3-carboxylic acid (446) as a solid (90% purity) as indicated by $^1$H NMR; LC-MS—calcd for $C_{26}H_{25}N_3O_3$ [M$^+$+H]$^+$: 428.19, found: 428.2.

A mixture of 65 mg (0.15 mmol) of 7-cyclohexyl-6-(4-iodo-phenyl)-pyrazolo[1,5-a]pyrimidine-3-carbonitrile, 45 mg (0.225 mmol, 1.5 equiv) of 4-(methanesulfonyl)phenylboronic acid, 6 mg (0.0075 mmol, 5 mol %) of Pd catalyst, and 95 mg (0.45 mmol, 3 equiv) of potassium phosphate was placed into a carousel tube. After a vacuum and argon cycle, 1,4-dioxane (3 mL) was added, and the resulting mixture was heated at 80° C. under argon for 14 h. Since analysis by LC-MS revealed unreacted starting material still present, 45 mg (0.225 mmol, 1.5 equiv) of 4-(methanesulfonyl)phenylboronic acid, 12 mg (0.015 mmol, 10 mol %) of Pd catalyst, and 95 mg (0.45 mmol, 3 equiv) of potassium phosphate was added and heating was continued for 24 h. The reaction mixture was then diluted with ethyl acetate, filtered through a small pad of Celite, dried over sodium sulfate and evaporated to give a brown residue (crude coupling product), which was chromatographed on silica gel (Biotage; gradient elution 2% to 10% ethyl acetate in dichloromethane) to afford 42 mg (62% yield) of desired 7-cyclohexyl-6-(4'-methanesulfonyl-biphenyl-4-yl)-pyrazolo[1,5-a]pyrimidine-3-carbonitrile as indicated by $^1$H NMR; LC-MS—calcd for $C_{26}H_{24}N_4O_2S$ [M$^+$+H]$^+$: 457.16, found: 457.1.

To a solution of 42 mg (0.092 mmol) of 7-cyclohexyl-6-(4'-methanesulfonyl-biphenyl-4-yl)-pyrazolo[1,5-a]pyrimidine-3-carbonitrile in 1 mL of toluene and 1.2 mL of dimethylformamide (DMF) was added 76 mg (0.55 mmol) of triethylamine hydrochloride (Et$_3$N—HCl), and 36 mg (0.55 mmol) of sodium azide and the resulting heterogeneous mixture was heated at 120° C. for 72 h, during which time 76 mg (0.55 mmol) of triethylamine hydrochloride (Et$_3$N—HCl), and 36 mg (0.55 mmol) of sodium azide was added to the reaction mixture after every 24 h. The mixture was then cooled to rt, filtered and concentrated to a residue which was purified via reverse-phase chromatography to afford (after lyophilization) 7 mg (15% yield) of 7-cyclohexyl-6-(4'-methanesulfonyl-biphenyl-4-yl)-3-(1H-tetrazol-5-yl)-pyrazolo[1,5-a]pyrimidine as a white solid (90% purity, entry 443) as indicated by $^1$H-NMR; LC-MS calcd for $C_{26}H_{25}N_7O_2S$ [M$^+$+H]$^+$ 500.18; found 500.2.

According to a modification of a literature procedure (Suzuki, A. et al *Tetrahedron Lett.* 1986, 27, 6369-6372) a mixture of 57 mg (0.12 mmol) of 7-cyclohexyl-6-(4-iodo-phenyl)-pyrazolo[1,5-a]pyrimidine-3-carboxylic acid ethyl ester and 5 mg (0.006 mmol, 5 mol %) of Pd catalyst was placed into a carousel tube. After a vacuum and argon cycle, tetrahydrofuran (THF) (2 mL) was added, followed by 0.29 mL (0.144 mmol, 1.2 equiv) of B-Benzyl-9-BBN 0.5 M solution in THF, and 0.12 mL (0.36 mmol, 3 equiv) of 3 N NaOH solution, and the resulting mixture was heated reflux under argon overnight. Since analysis by LC-MS revealed unreacted starting material still present, 0.12 mL (0.06 mmol) of B-Benzyl-9-BBN, 5 mg (0.006 mmol, 5 mol %) of Pd catalyst, and 0.12 mL (0.36 mmol) of 3 N NaOH solution was added and heating was continued for 24 h. The reaction mixture was then diluted with ethyl acetate, washed with water, dried over sodium sulfate, passed through a small pad of Celite, and evaporated to give a brown residue (crude coupling product), which was chromatographed on silica gel (Biotage; 2% ethyl acetate in dichloromethane) to afford 36 mg (68% yield) of desired 6-(4-benzyl-phenyl)-7-cyclohexyl-pyrazolo[1,5-a]pyrimidine-3-carboxylic acid ethyl ester as indicated by $^1$H NMR (containing traces of impurities); LC-MS—calcd for $C_{28}H_{29}N_3O_2$ [M$^+$+H]$^+$: 440.23, found: 440.2.

To a solution of 36 mg (0.082 mmol) of 6-(4-benzyl-phenyl)-7-cyclohexyl-pyrazolo[1,5-a]pyrimidine-3-carboxylic acid ethyl ester in 3 mL of tetrahydrofuran was added 0.5 mL (0.5 mmol) of 1 M LiOH solution, and the resulting mixture was heated at reflux overnight. The reaction mixture was then acidified with 1 M HCl solution to pH=2, and extracted with ethyl acetate. The combined organic extracts were dried over sodium sulfate, and concentrated to give a residue which was purified via reverse-phase chromatography to afford (after lyophilization) 7 mg (21% yield) of 6-(4-benzyl-phenyl)-7-cyclohexyl-pyrazolo[1,5-a]pyrimidine-3-carboxylic acid as a solid (90% purity, entry 444) as indicated by $^1$H NMR; LC-MS—calcd for $C_{26}H_{25}N_3O_2$ [M$^+$+H]$^+$: 412.19, found: 412.3.

Example 18

Synthesis of 7-cyclohexyl-6-(4-furan-3-yl-phenyl)-pyrazolo[1,5-a]pyrimidine-3-carboxylic acid

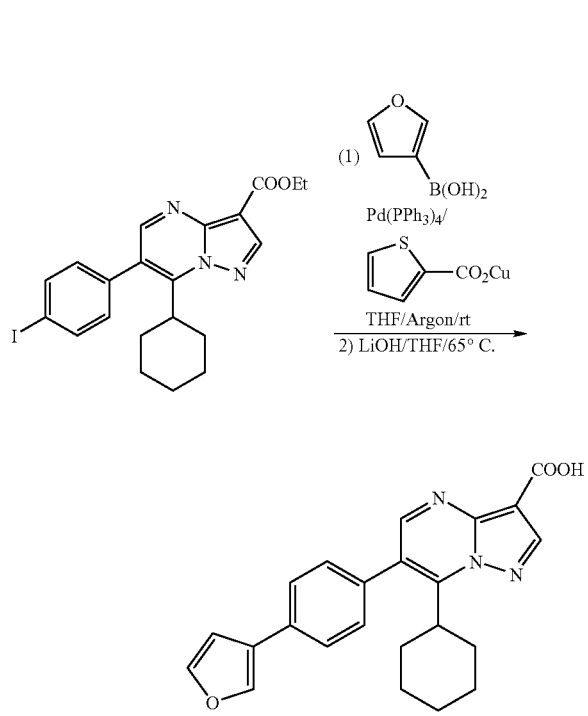

According to a modification of a literature procedure (Savarin C.; Liebeskind, L. S. *Org. Lett.* 2001, 3, 2149-2152) a mixture of 24 mg (0.05 mmol) of 7-cyclohexyl-6-(4-iodophenyl)-pyrazolo[1,5-a]pyrimidine-3-carboxylic acid ethyl ester, 7 mg (0.06 mmol, 1.2 equiv) of 3-furylboronic acid, 3 mg (0.0025 mmol, 5 mol %) of Pd(PPh$_3$)$_4$, and 12 mg (0.06 mmol, 1.2 equiv) of copper(I) thiophene-2-carboxylate (CuTC) was placed into a Schlenk flask. After a vacuum and argon cycle, tetrahydrofuran (1.2 mL) was added, and the resulting mixture was stirred at rt under argon overnight. The reaction mixture was diluted with water and extracted with ethyl acetate. The combined ethyl acetate extracts were washed with brine, filtered through a small pad of Celite, dried over sodium sulfate and evaporated to give 28 mg of a yellow oil (crude coupling product) which was used in the next reaction without any further purification; LC-MS—calcd for C$_{25}$H$_{25}$N$_3$O$_3$ [M$^+$+H]$^+$: 416.19, found: 416.2.

The above residue was taken in tetrahydrofuran (2 mL) and 0.3 mL (0.3 mmol, 5 equiv) of 1 M LiOH solution was added, and the resulting mixture was heated at reflux overnight. The reaction mixture was then diluted with ethyl acetate, and acidified with 1N HCl solution to pH 2. The organic extract was washed with brine, dried over sodium sulfate and evaporated to give a residue which was purified via reverse-phase chromatography to afford (after lyophilization) 4 mg (20% yield) of 7-cyclohexyl-6-(4-furan-3-yl-phenyl)-pyrazolo[1,5-a]pyrimidine-3-carboxylic acid (445) as a white solid (90% purity), as indicated by $^1$H-NMR; LC-MS calcd for C$_{23}$H$_{21}$N$_3$O$_3$ [M$^+$+H]$^+$: 388.16, found: 388.1.

Example 19

Synthesis of 7-cyclohexyl-6-[4-(3-methoxy-phenoxy)-phenyl]-3-(1H-tetrazol-5-yl)-pyrazolo[1,5-a]pyrimidine

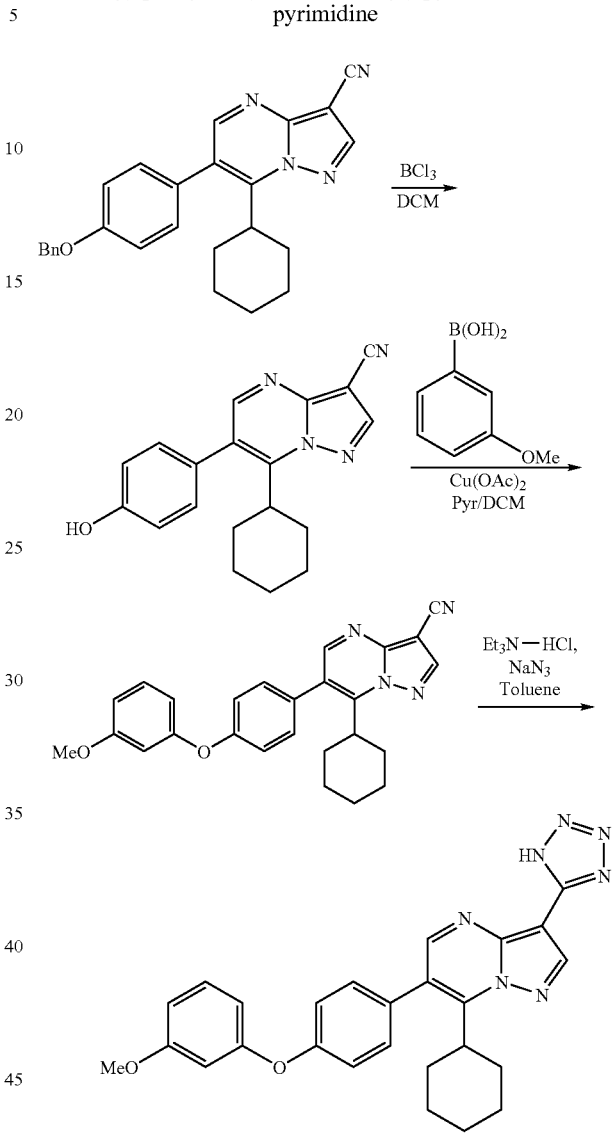

The starting material in this sequence was synthesized following the same experimental procedure that was used to prepare a related intermediate where the benzyloxy group (OBn) was replaced by iodine (I).

A solution of 800 mg (1.95 mmol) of 6-(4-benzyloxy-phenyl)-7-cyclohexyl-pyrazolo[1,5-a]pyrimidine-3-carbonitrile in 5 mL of dichloromethane (DCM) was cooled to −78° C. To the above cold solution was added 2.93 mL (2.93 mmol) of boron trichloride (BCl$_3$) 1 M solution in DCM and the resulting mixture was stirred at −78° C. for 90 min. Since analysis by thin layer chromatography (TLC) revealed that starting material was still present, excess boron trichloride (BCl$_3$) (3 equiv) was added, and the reaction was quenched at −78° C. with 5 mL of methanol. The mixture was allowed to warm up to rt, saturated sodium bicarbonate solution was added, and the mixture was extracted with DCM. The combined organic extracts were washed with water, brine, dried over sodium sulfate and evaporated to give 754 mg of an off-white solid which was chromatographed on silica gel (5% ethyl acetate in DCM) to give 560 mg (90% yield) of desired 7-cyclohexyl-6-(4-hydroxy-phenyl)-pyrazolo[1,5-a]pyrimidine-3-carbonitrile as a white solid. LC-MS—calcd for $C_{19}H_{18}N_4O$ $[M^++H]^+$: 319.15, found: 319.1. $^1H$ NMR (CDCl$_3$) δ8.53s, 1H), 8.38s, 1H), 7.20-7.18 (d, J=8.4 Hz, 2H), 7.00-6.98 (d, J=8.4 Hz, 2H), 5.43 (s, 1H, OH), 3.34-3.28 (m, 1H), 2.58-2.44 (m, 2H), 1.86-1.82 (m, 2H), 1.74-1.68 (m, 3H), 1.41-1.18 (m, 3H).

An aqua-green mixture of 50 mg (0.157 mmol) of 7-cyclohexyl-6-(4-hydroxy-phenyl)-pyrazolo[1,5-a]pyrimidine-3-carbonitrile, 43 mg (0.235 mmol) of copper (II) acetate (Cu(OAc)$_2$), 48 mg (0.314 mmol) of 3-methoxyphenylboronic acid, 0.025 mL (0.31 mmol) of pyridine (pyr), and 5 mL of DCM was stirred at rt for 68 h while opened to air. The reaction mixture was filtered through Celite, while rinsing the Celite pad with ethyl acetate and chloroform. The combined organic filtrates were concentrated to a green solid residue which was partitioned between ethyl acetate and water and extracted with ethyl acetate. The combined organic extracts were washed with water (3 times), brine, dried over sodium sulfate and evaporated to give 74 mg of a brown residue which was chromatographed on silica gel (Biotage; DCM) to give 38 mg (58% yield) of desired 7-cyclohexyl-6-[4-(3-methoxyphenoxy)-phenyl]-pyrazolo[1,5-a]pyrimidine-3-carbonitrile as a colorless oil as indicated by $^1$H-NMR; LC-MS—calcd for $C_{26}H_{24}N_4O_2$ $[M^++H]^+$: 425.19, found: 425.1.

Conversion of 7-cyclohexyl-6-[4-(3-methoxy-phenoxy)-phenyl]-pyrazolo[1,5-a]pyrimidine-3-carbonitrile to the corresponding tetrazole 7-cyclohexyl-6-[4-(3-methoxy-phenoxy)-phenyl]-3-(1H-tetrazol-5-yl)-pyrazolo[1,5-a]pyrimidine (301) was accomplished via a described experimental described elsewhere in this document.

Example 20

Synthesis of 7-cyclohexyl-6-[4-(2,4-dimethyl-thiazol-5-ylmethoxy)-phenyl]-3-(1H-tetrazol-5-yl)-pyrazolo[1,5-a]pyrimidine

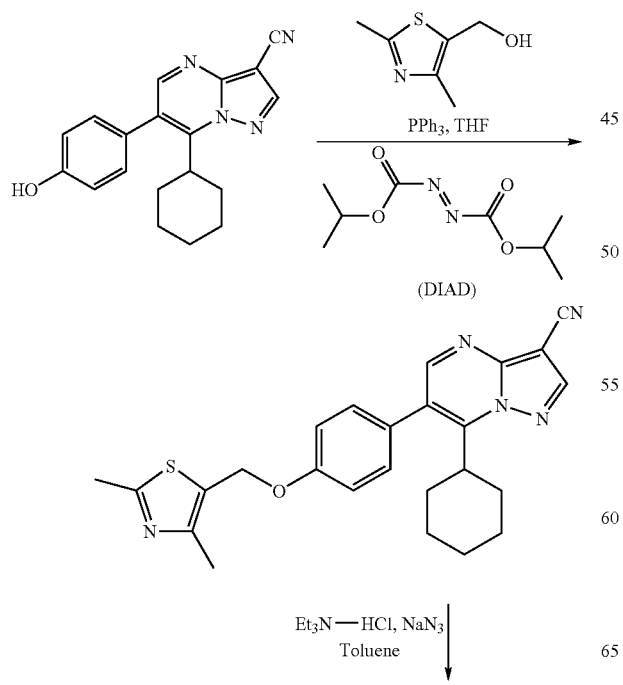

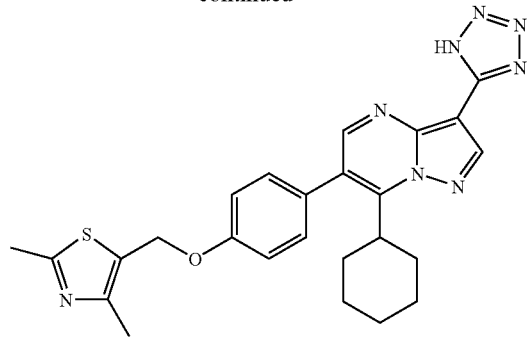

To an ice cold mixture of 40 mg (0.13 mmol) of 7-cyclohexyl-6-(4-hydroxy-phenyl)-pyrazolo[1,5-a]pyrimidine-3-carbonitrile in 3 mL of tetrahydrofuran (THF) was added 74 mg (0.52 mmol) of (2,4-dimethyl-thiazol-5-yl)-methanol, 136 mg (0.52 mmol) of triphenylphosphine (PPh$_3$), followed by 0.102 mL (0.52 mmol) of diisopropyl azodicarboxylate (DIAD) and the mixture was allowed to warm up to rt and stirred at rt overnight. The reaction mixture was then concentrated and the residue was chromatographed on silica gel (Biotage; 10% ethyl acetate in DCM) to give desired 7-cyclohexyl-6-[4-(2,4-dimethyl-thiazol-5-ylmethoxy)-phenyl]-pyrazolo[1,5-a]pyrimidine-3-carbonitrile as indicated by $^1$H-NMR; LC-MS—calcd for $C_{25}H_{25}N_5OS$ $[M^++H]^+$: 444.18, found: 444.2.

Conversion of 7-cyclohexyl-6-[4-(2,4-dimethyl-thiazol-5-ylmethoxy)-phenyl]-pyrazolo[1,5-a]pyrimidine-3-carbonitrile to the corresponding tetrazole 7-cyclohexyl-6-[4-(2,4-dimethyl-thiazol-5-ylmethoxy)-phenyl]-3-(1H-tetrazol-5-yl)-pyrazolo[1,5-a]pyrimidine (358) was accomplished via a procedure described elsewhere.

Example 21

Synthesis of 7-cyclohexyl-3-(1H-tetrazol-5-yl)-6-[4-(3-trifluoromethyl-benzyloxy)-phenyl]-pyrazolo[1,5-a]pyrimidine

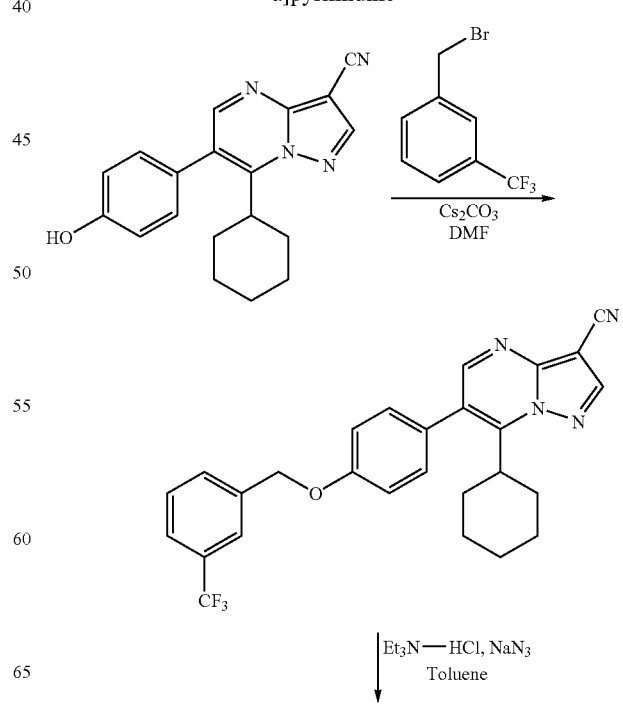

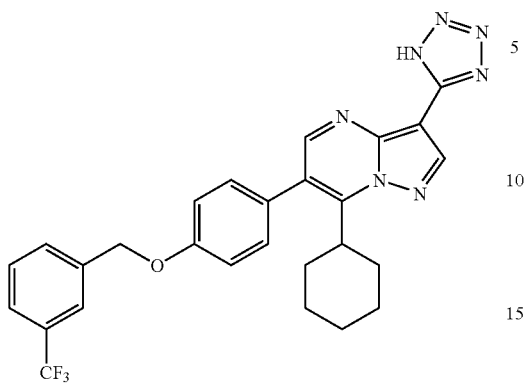

To a solution of 53 mg (0.17 mmol) of 7-cyclohexyl-6-(4-hydroxy-phenyl)-pyrazolo[1,5-a]pyrimidine-3-carbonitrile in 3 mL of dimethylformamide (DMF) was added 72 mg (0.22 mmol) of cesium carbonate (Cs$_2$CO$_3$), followed by 0.034 mL (0.22 mmol) of 3-(trifluoromethyl)-benzyl bromide, and the resulting heterogeneous mixture was stirred at rt overnight. The reaction mixture was diluted with water and extracted with ethyl acetate, and the combined organic extracts were concentrated to give a residue which was chromatographed on silica gel (Biotage; DCM) to afford 65 mg (80% yield) of desired 7-cyclohexyl-6-[4-(3-trifluoromethyl-benzyloxy)-phenyl]-pyrazolo[1,5-a]pyrimidine-3-carbonitrile as indicated by $^1$H NMR; LC-MS—calcd for C$_{27}$H$_{23}$F$_3$N$_4$O [M$^+$+H]$^+$: 477.18, found: 477.1.

Conversion of 7-cyclohexyl-6-[4-(3-trifluoromethyl-benzyloxy)-phenyl]-pyrazolo[1,5-a]pyrimidine-3-carbonitrile to the corresponding tetrazole 7-cyclohexyl-3-(1H-tetrazol-5-yl)-6-[4-(3-trifluoromethyl-benzyloxy)-phenyl]-pyrazolo[1,5-a]pyrimidine (331) was accomplished via a procedure described elsewhere in this document.

Example 22

Synthesis of 6-bromo-7-cyclohexyl-pyrazolo[1,5-a]pyrimidine-3-carboxylic acid ethyl ester

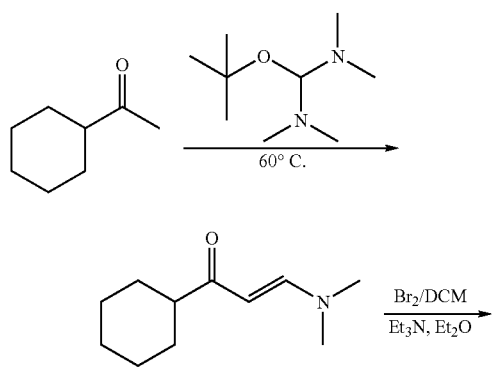

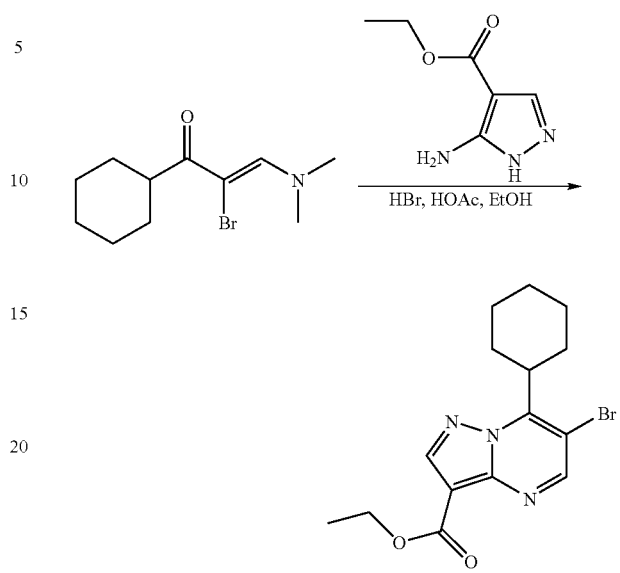

A mixture of 3.0 g (23.8 mmol) of cyclohexyl methyl ketone and 4.56 g (26.2 mmol) of t-butoxybis(dimethylamino)methane (Bredereck's reagent) was stirred at 60°C overnight. The reaction mixture was then concentrated to give 4.0 g (93% yield) of 1-cyclohexyl-3-dimethylamino-propenone as an orange oil as indicated by $^1$H NMR. This product was used in the next reaction without any further purification.

To an ice cold solution of 1.18 g (6.51 mmol) of 1-cyclohexyl-3-dimethylamino-propenone in 8 mL of dichloromethane was added dropwise 1.04 g (6.51 mmol) of bromine via an addition funnel. The reaction mixture was stirred at 0°C. for 0.5 h and then 0.9 mL (6.51 mmol) of triethylamine in 10 mL of ether was added dropwise. The mixture was stirred at 0°C. for 1 h and allowed to warm up to rt. A light yellow solid precipitated from the solution, and it was separated by filtration. The filtrate was then concentrated to give 1.69 g of 2-bromo-1-cyclohexyl-3-dimethylamino-propenone as a brown solid as indicated by $^1$H NMR. The product was used in the next reaction without any further purification.

To a mixture of 1.69 g (6.50 mmol) of 2-bromo-1-cyclohexyl-3-dimethylamino-propenone and 1.01 g (6.50 mmol) of 3-amino-1H-pyrazole-4-carboxylic acid ethyl ester in 6 mL of ethanol was added 1.0 mL of 30% hydrogen bromide in acetic acid solution, and the resulting mixture was heated at reflux for 1 h. Then the reaction mixture was cooled to rt and concentrated to give a residue which was chromatographed on silica gel (gradient elution with dichloromethane to 25% ethyl acetate in dichloromethane) to give 620 mg (27% over 2 steps) of 6-bromo-7-cyclohexyl-pyrazolo[1,5-α]pyrimidine-3-carboxylic acid ethyl ester as indicated by $^1$H NMR (δ8.70s, 1H8.49s, 1H), 4.44 (q, J=6.8 Hz, 2H), 2.70-2.57 (b, 1H), 1.98-1.90 (m, 2H), 1.87-1.78 (m, 2H), 1.78-1.69 (m, 2H), 1.59-1.42 (m, 4H), 1.43 (t, J=6.8 Hz, 3H)); LC-MS—calcd for C$_{15}$H$_{18}$BrN$_3$O$_2$ [M$^+$+H]$^+$: 352.06, found: 352.0.

Example 23

Synthesis of 7-cyclohexyl-6-(4-methanesulfanyl-phenyl)-pyrazolo[1,5-a]pyrimidine-3-carboxylic acid and 7-cyclohexyl-6-furan-3-yl-pyrazolo[1,5-a]pyrimidine-3-carboxylic acid

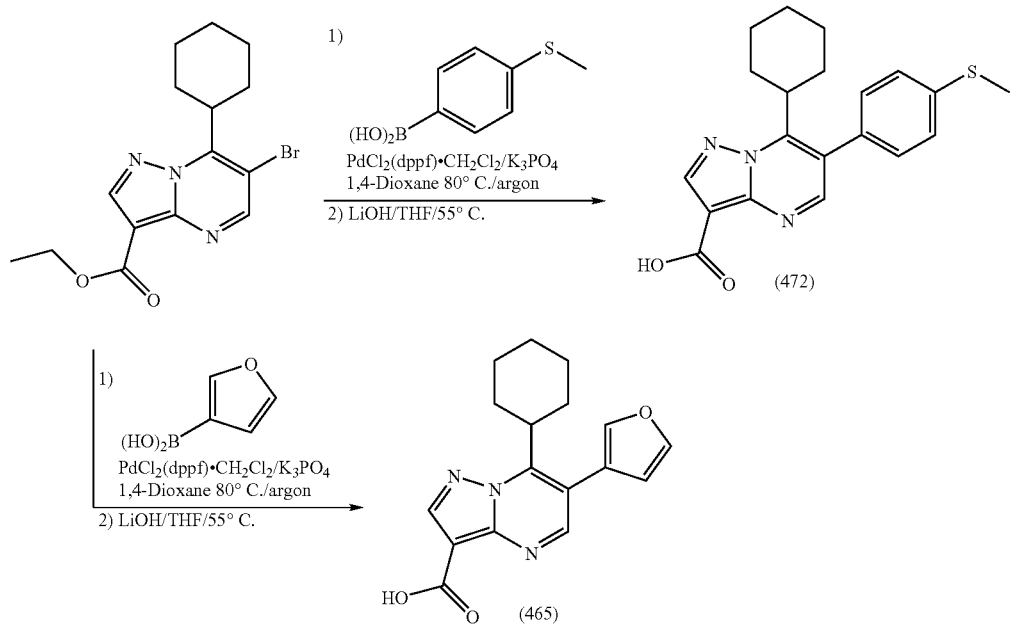

A mixture of 14 mg (0.085 mmol) of 4-methylsulfanyl-phenylboronic acid, 2 mg (0.0028 mmol) of Pd catalyst, and 45 mg (0.213 mmol) of potassium phosphate was placed into a 4 mL vial. To this mixture 25 mg (0.077 mmol) of 6-bromo-7-cyclohexyl-pyrazolo[1,5-α]pyrimidine-3-carboxylic acid ethyl ester in 1.5 mL of 1,4-dioxane was added, the resulting mixture was flushed with argon and stirred at 80° C. (oil bath) overnight. The reaction mixture was then diluted with ethyl acetate, filtered through a small pad of Celite, and evaporated (savant) to give a residue (crude coupling product). This residue was dissolved in 1 mL of tetrahydrofuran (THF) and treated with 0.5 mL (0.5 mmol) of 1 M LiOH solution, and the resulting mixture was stirred at rt overnight. Since analysis by thin layer chromatography (TLC) revealed that the reaction was not complete, the mixture was then shaken at 55° C. (sand bath) for 15 h. The reaction mixture was diluted with ethyl acetate, and acidified with 1 M HCl solution to pH=2. The organic layer was separated and concentrated (savant) to give a residue which was purified via reverse-phase chromatography (using Gilson) to afford (after lyophilization) 14 mg (56% overall yield) of 7-cyclohexyl-6-(4-methylsulfanyl-phenyl)-pyrazolo[1,5-a]pyrimidine-3-carboxylic acid (472) as a solid as indicated by $^1$H NMR; LC-MS—calcd for $C_{20}H_{21}N_3O_2S$ [M$^+$+H]$^+$: 368.14, found: 368.2.

The same experimental procedure was used for the synthesis of 7-cyclohexyl-6-furan-3-yl-pyrazolo[1,5-a]pyrimidine-3-carboxylic acid (465) which was obtained as a solid as indicated by $^1$H NMR; LC-MS—calcd for $C_{17}H_{17}N_3O_3$ [M$^+$+H]$^+$: 312.13, found: 312.1.

Example 24

Synthesis of 7-Cyclohexyl-6-(4-methanesulfonyl-phenyl)-pyrazolo[1,5-a]pyrimidine-3-carboxylic acid and 7-Cyclohexyl-6-(4-methanesulfinyl-phenyl)-pyrazolo[1,5-a]pyrimidine-3-carboxylic acid -continued

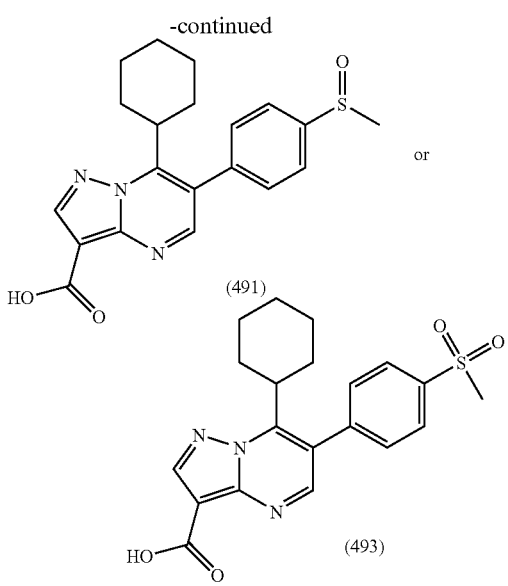

To a cloudy solution of 14 mg (0.038 mmol) of 7-cyclohexyl-6-(4-methylsulfanyl-phenyl)-pyrazolo[1,5-a]pyrimidine-3-carboxylic acid in 2 mL of chloroform was added 9 mg (1.5 equiv) of m-chloroperoxybenzoic acid (mCPBA) and the cloudy solution became clear. Since after 5 min of stirring at rt TLC indicated disappearance of starting material, the mixture was concentrated to a residue which was purified via reverse-phase chromatography (using Gilson) to afford (after lyophilization) 10 mg (69% yield) of 7-cyclohexyl-6-(4-methanesulfinyl-phenyl)-pyrazolo[1,5-a]pyrimidine-3-carboxylic acid (491) as a solid as indicated by LC-MS—calcd for $C_{20}H_{21}N_3O_3S$ $[M^++H]^+$: 384.13, found: 384.2.

Note that when the same experimental procedure was carried out with 2.2 equiv of mCPBA, 7-Cyclohexyl-6-(4-methanesulfonyl-phenyl)-pyrazolo[1,5-a]pyrimidine-3-carboxylic acid (493) was obtained.

Example 25

2-{[7-cyclohexyl-6-(4-fluoro-phenyl)-pyrazolo[1,5-a]pyrimidine-3-carbonyl]-amino}-3-(4-hydroxyphenyl)-propionic acid

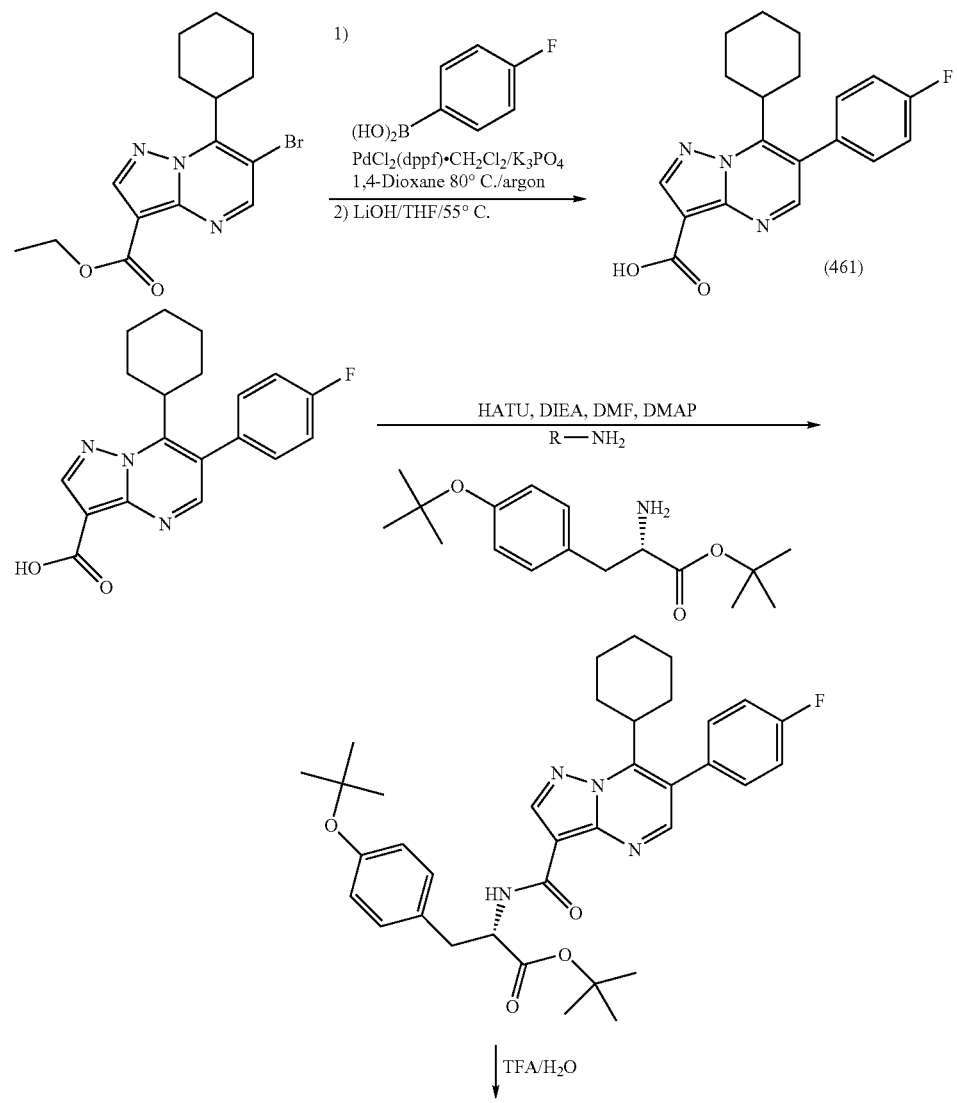

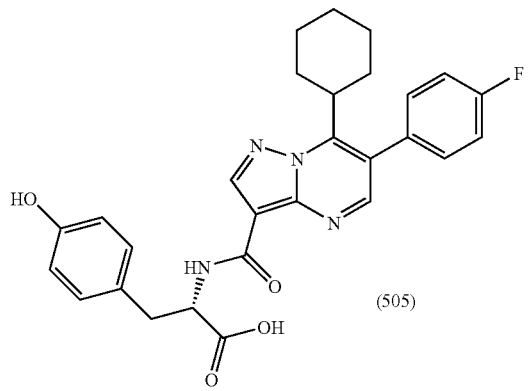

(505)

7-cyclohexyl-6-(4-fluoro-phenyl)-pyrazolo[1,5-☐]pyrimidine-3-carboxylic acid (461) was obtained via a Suzuki reaction that was previously described in another section. The analytical data for this compound is given below. δCDCl₃ 8.66 (s, 1H), 8.51 (s, 1H), 7.30-7.27 (m, 2H), 7.26-7.21 (m, 2H), 3.26 (m, 1H), 2.59-2.53 (m, 2H), 1.87-1.84 (m, 2H), 1.75-1.68 (m, 3H), 1.40-1.22 (m, 3H). LC-MS calcd. for $C_{19}H_{18}FN_3O_2$ [M⁺+H]⁺: 340.15; found: 340.1.

To a solution of 15.0 mg (0.044 mmol) of 7-cyclohexyl-6-(4-fluoro-phenyl)-pyrazolo[1,5-α]pyrimidine-3-carboxylic acid in 2 mL of dimethylformamide (DMF) was added 0.019 mL (0.132 mmol) of diisopropylethylamine (DIEA), a few crystals of dimethylaminopyridine (DMAP cat), 17.4 mg (0.053 mmol) of H-Tyr(tBu)-OtBu.HCl, followed by 20 mg (0.053 mmol) of HATU, and the resulting mixture was stirred at rt overnight. The reaction mixture was diluted with ethyl acetate, washed with 0.1 N sodium hydroxide solution (2 times) and brine. The separated organic layer was dried over sodium sulfate and concentrated to give 3-(4-tert-butoxy-phenyl)-2-{[7-cyclohexyl-6-(4-fluoro-phenyl)-pyrazolo[1,5-☐]pyrimidine-3-carbonyl]-amino}-propionic acid tert-butyl ester, which was used without any further purification in the next step.

A sample of crude 3-(4-tert-butoxy-phenyl)-2-{[7-cyclohexyl-6-(4-fluoro-phenyl)-pyrazolo[1,5-α]pyrimidine-3-carbonyl]-amino}-propionic acid tert-butyl ester was treated with 1 mL of 95:5 trifluoroacetic acid (TFA):H₂O and the resulting solution was stirred at rt for 1 h. Then the reaction mixture was quenched with 2 mL of 1:1 acetonitrile:water, concentrated, and the residue was purified via reverse-phase chromatography to afford (after lyophilization) 10 mg (45% yield over two steps) of desired 2-{[7-cyclohexyl-6-(4-fluoro-phenyl)-pyrazolo[1,5-a]pyrimidine-3-carbonyl]-amino}-3-(4-hydroxy-phenyl)-propionic acid (505) as a solid as indicated by ¹H NMR; LC-MS calcd. for $C_{28}H_{27}FN_4O_4$ [M⁺+H]⁺: 503.2; found: 503.2.

Note that in the cases where methyl or ethyl esters were utilized a second deprotection step, a typical aqueous LiOH mediated saponification, was employed to generate the requisite carboxylic acid.

Example 26

Synthesis of N-[7-cyclohexyl-6-(4-fluoro-phenyl)-pyrazolo[1,5-a]pyrimidine-3-carbonyl]-C-phenyl-methanesulfonamide

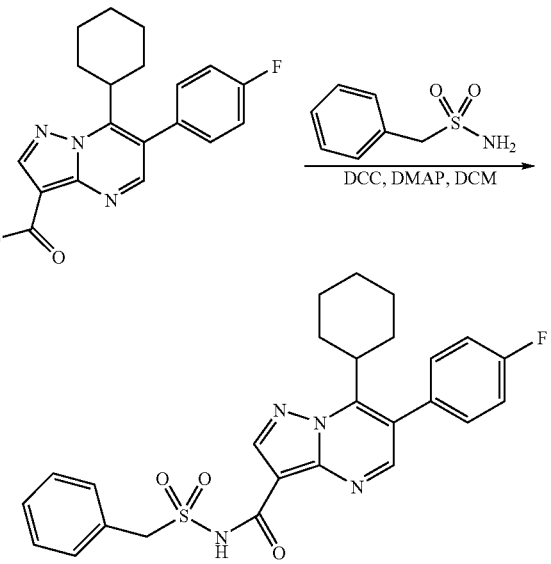

To a solution of 20 mg (0.059 mmol) of 7-cyclohexyl-6-(4-fluoro-phenyl)-pyrazolo[1,5-α]pyrimidine-3-carboxylic acid in 2 mL of dichloromethane (DCM) was a few crystals of DMAP (cat), 12 mg (0.071 mmol) of toluenesulfonamide, followed by 0.071 mL (0.071 mmol) of 1 M dicyclohexylcarbodiimide (DCC) solution in DCM. The reaction mixture was stirred at rt overnight, concentrated, and the resulting residue was purified by reverse-phase chromatography (Gilson) to afford (after lyophilization) 15 mg (51% yield) of desired N-[7-cyclohexyl-6-(4-fluoro-phenyl)-pyrazolo[1,5-α]pyrimidine-3-carbonyl]-C-phenyl-methanesulfonamide (533) as a solid as indicated by ¹H NMR; LC-MS calcd. for $C_{26}H_{25}FN_4O_3S$ [M⁺+H]⁺: 493.16; found: 493.1.

Example 27

Synthesis of 6-(4-benzyloxy-phenyl)-3-bromo-7-cyclohexyl-pyrazolo[1,5-a]pyrimidine-2-carboxylic acid

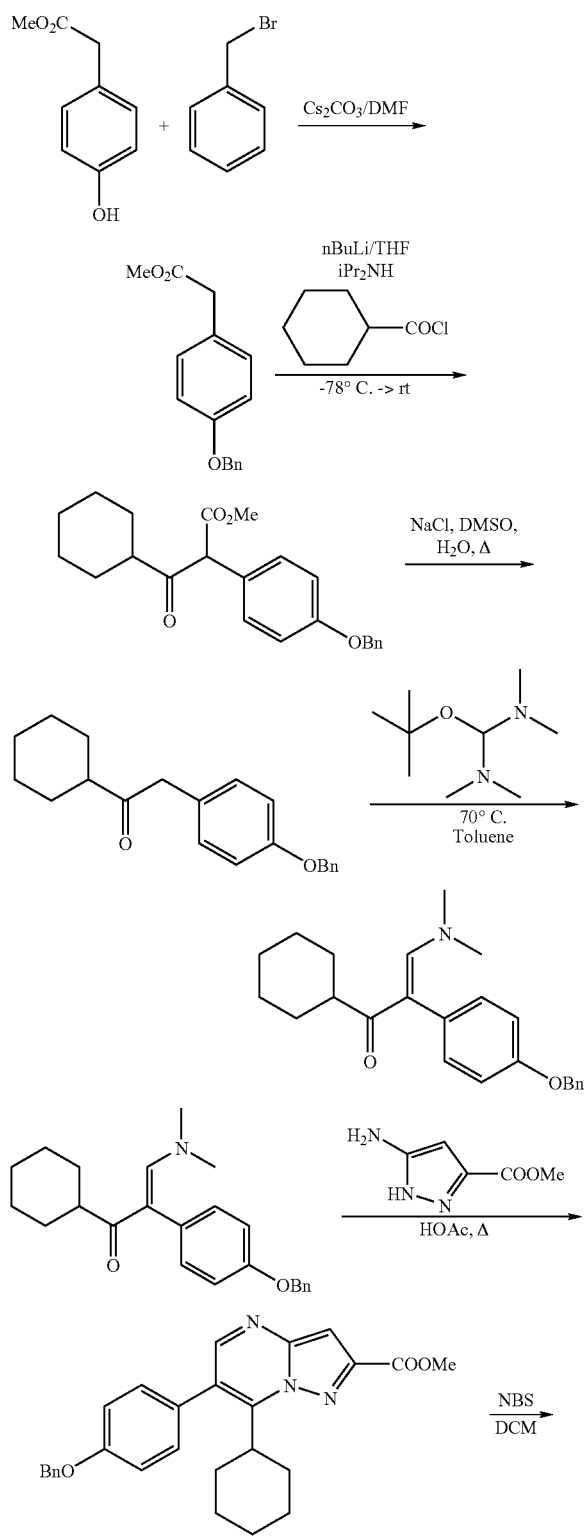

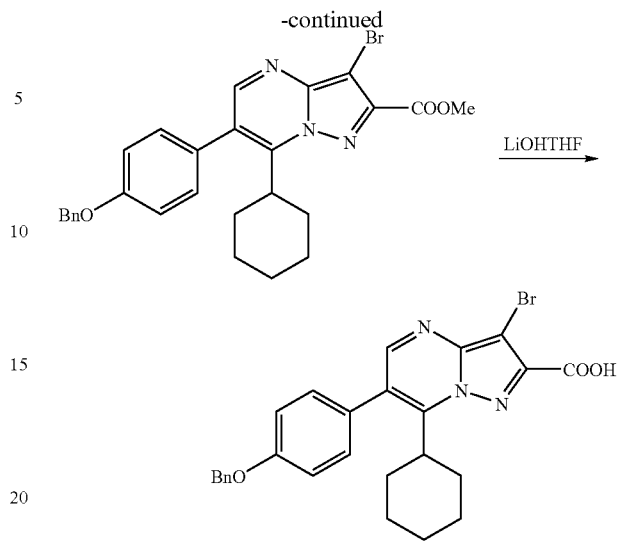

A solution of 0.718 g (1.97 mmol) of 2-(4-benzyloxy-phenyl)-1-cyclohexyl-3-dimethylamino-propenone and 0.28 g (1.97 mmol) of 5-amino-1H-pyrazole-3-carboxylic acid methyl ester in 20 mL of acetic acid (HOAc) was heated at reflux overnight. The reaction mixture was cooled to rt and concentrated to give a residue which was chromatographed on silica gel (5% ethyl acetate in dichloromethane) to afford 0.643 g (74% yield) of 6-(4-benzyloxy-phenyl)-7-cyclohexyl-pyrazolo[1,5-a]pyrimidine-2-carboxylic acid methyl ester as a beige solid as indicated by $^1$H NMR.

To an ice cold solution of 50 mg (0.113 mmol) of 6-(4-benzyloxy-phenyl)-7-cyclohexyl-pyrazolo[1,5-a]pyrimidine-2-carboxylic acid methyl ester in 2 mL of dichloromethane (DCM) was added a solution of 21 mg (0.118 mmol) of N-bromosuccinimide (NBS) in 1 mL of DCM and the resulting mixture was allowed to warm up to rt and stirred at rt overnight. The reaction mixture was concentrated to give a residue which was chromatographed on silica gel (5% ethyl acetate in dichloromethane) to afford 7 mg (11% yield) of 6-(4-benzyloxy-phenyl)-3-bromo-7-cyclohexyl-pyrazolo[1,5-a]pyrimidine-2-carboxylic acid methyl ester as a colorless oil as indicated by $^1$H NMR (90% purity); LC-MS—calcd for $C_{27}H_{26}BrN_3O_3$ $[M^++H]^+$: 520.12, found: 520.0.

Saponification of 6-(4-benzyloxy-phenyl)-3-bromo-7-cyclohexyl-pyrazolo[1,5-a]pyrimidine-2-carboxylic acid methyl ester to the carboxylic acid (477) was carried out utilizing a previously described procedure.

Example 28

Synthesis of [6-(4-benzyloxy-phenyl)-7-cyclohexyl-pyrazolo[1,5-a]pyrimidin-3-yl]-methanol

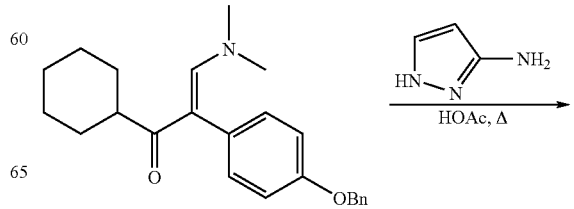

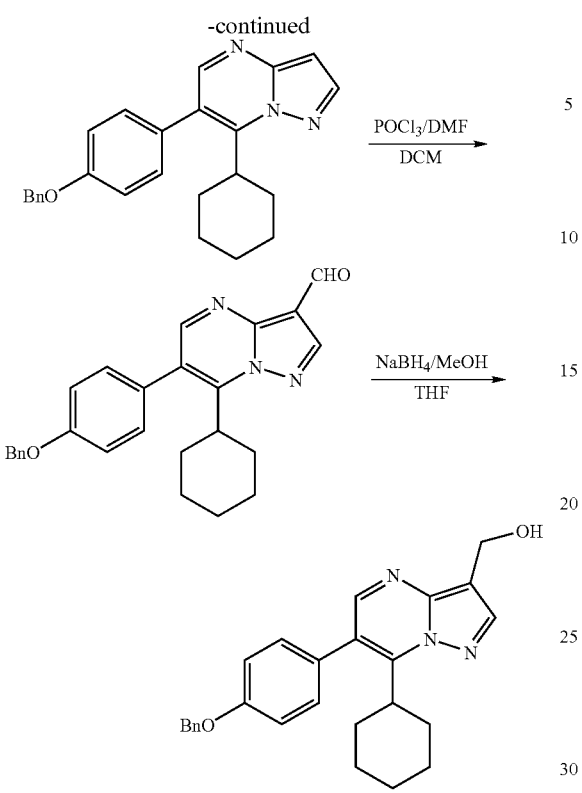

A solution of 4.37 g (12 mmol) of 2-(4-benzyloxy-phenyl)-1-cyclohexyl-3-dimethylamino-propenone and 1.0 g (12 mmol) of 1H-pyrazol-3-ylamine in 40 mL of acetic acid (HOAc) was heated at reflux overnight. The reaction mixture was cooled to rt and concentrated to give a beige solid residue which was chromatographed on silica gel (2% ethyl acetate in dichloromethane) to afford 3.38 g (74% yield) of 6-(4-benzyloxy-phenyl)-7-cyclohexyl-pyrazolo[1,5-a]pyrimidine as a white solid as indicated by $^1$H NMR.

To an ice cold solution of 300 mg (0.78 mmol) of 6-(4-benzyloxy-phenyl)-7-cyclohexyl-pyrazolo[1,5-a]pyrimidine in 2 mL of dimethylformamide (DMF) and 1 mL of dichloromethane (DCM) was added 0.085 mL (0.9 mmol) of phosphorus oxychloride (POCl$_3$) and the resulting mixture was allowed to warm up to rt and stirred at rt for 4 h when analysis by thin layer chromatography (TLC) indicated complete conversion of starting material to product. The reaction mixture poured into ice-water, and extracted with ethyl acetate. The combined organic extracts were washed with brine, dried over sodium sulfate and evaporated to give 335 mg of 6-(4-benzyloxy-phenyl)-7-cyclohexyl-pyrazolo[1,5-a]pyrimidine-3-carbaldehyde (436) as a beige solid as indicated by $^1$H NMR; LC-MS—calcd for C$_{26}$H$_{25}$N$_3$O$_2$ [M$^+$+H]$^+$: 412.19, found: 412.1.

To a stirred solution of 4.4 mg (0.115 mmol) of sodium borohydride (NaBH$_4$) in 2 mL of methanol (MeOH) was added a solution of 35 mg (0.104 mmol) of 6-(4-benzyloxy-phenyl)-7-cyclohexyl-pyrazolo[1,5-a]pyrimidine-3-carbaldehyde in 3 mL of tetrahydrofuran (THF) and the resulting mixture was stirred at rt for 30 min when analysis by TLC indicated complete conversion of starting material to product. The reaction mixture was quenched by the addition of saturated ammonium chloride solution, and extracted with ethyl acetate. The combined organic extracts were washed with brine, dried over sodium sulfate and evaporated to give (after lyophilization) 20 mg (47% yield) of [6-(4-benzyloxy-phenyl)-7-cyclohexyl-pyrazolo[1,5-a]pyrimidin-3-yl]-methanol (479) as a white solid (85% purity) as indicated by $^1$H NMR (containing small traces of starting material); LC-MS—calcd for C$_{26}$H$_{27}$N$_3$O$_2$ [M$^+$+H]$^+$: 414.21, found: 414.2.

Example 29

Synthesis of cyclopropanecarboxylic acid [6-(4-benzyloxy-phenyl)-7-cyclohexyl-pyrazolo[1,5-a]pyrimidin-3-yl]-amide and ethanesulfonic acid [6-(4-benzyloxy-phenyl)-7-cyclohexyl-pyrazolo[1,5-a]pyrimidin-3-yl]-amide

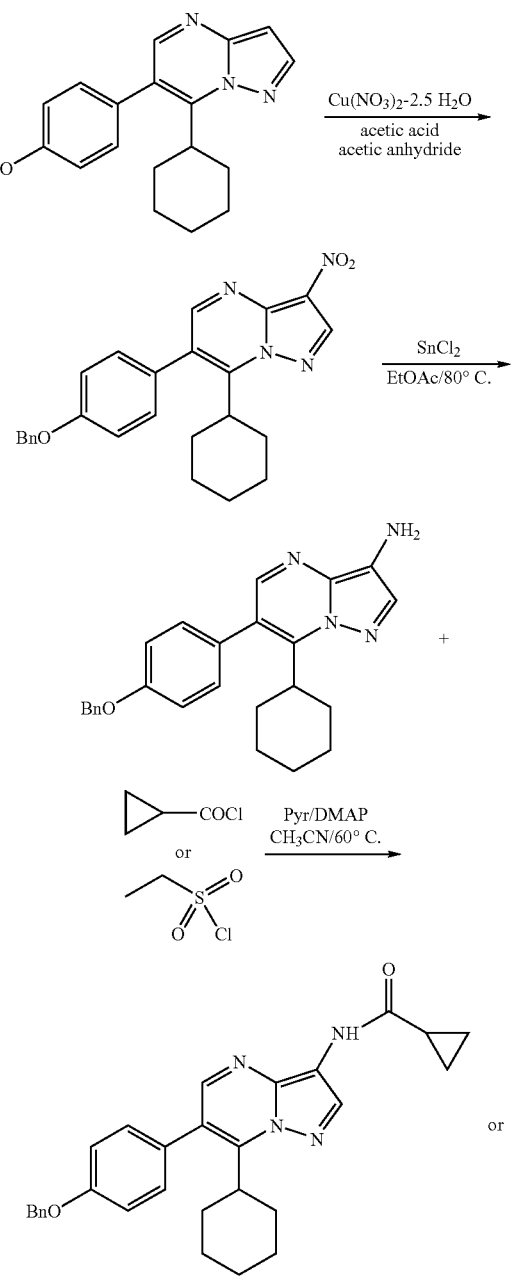

-continued

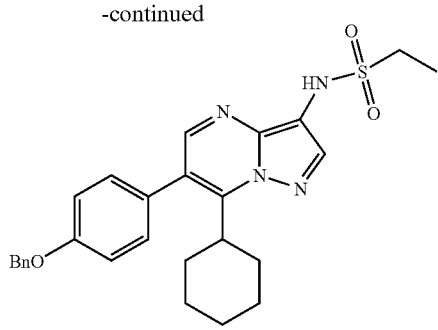

To a mixture of 25 mg (0.109 mmol) of copper (II) nitrate dihydrate ($Cu(NO_3)_2 \cdot 2.5H_2O$) in 1.5 mL of acetic acid and 3 mL of acetic anhydride at 35° C. was added portionwise (over 15 min) 40 mg (0.104 mmol) of 6-(4-benzyloxy-phenyl)-7-cyclohexyl-pyrazolo[1,5-a]pyrimidine and the resulting mixture was stirred at 35° C. overnight. The reaction mixture was diluted with dichloromethane, and washed with 0.1 N sodium hydroxide solution, water and brine. The organic extract was dried over sodium sulfate and evaporated to give 43 mg of purple residue which was chromatographed on silica gel (Biotage; dichloromethane) to afford 18 mg (41%) of 6-(4-benzyloxy-phenyl)-7-cyclohexyl-3-nitro-pyrazolo[1,5-a]pyrimidine as an off-white residue (90% purity) as indicated by $^1H$ NMR; LC-MS—calcd for $C_{25}H_{24}N_4O_3$ $[M^++H]^+$: 429.18, found: 429.2.

To a solution of 18 mg (0.042 mmol) of 6-(4-benzyloxy-phenyl)-7-cyclohexyl-3-nitro-pyrazolo[1,5-a]pyrimidine in 3 mL of ethyl acetate (EtOAc) was added 40 mg (0.21 mmol) of tin (II) chloride ($SnCl_2$) and the resulting mixture was stirred at 80° C. under argon for 8 h when analysis by TLC indicated only 75% conversion of starting material to product. Therefore, 40 mg (0.21 mmol) of tin (II) chloride ($SnCl_2$) was added, the reaction mixture was heated at 80° C. for 8 h when analysis by TLC indicated complete conversion of starting material to product. The mixture was diluted with ethyl acetate, washed with saturated sodium bicarbonate solution, water, brine, dried over sodium sulfate and evaporated to give (after lyophilization) 6 mg (36% yield) of 6-(4-benzyloxy-phenyl)-7-cyclohexyl-pyrazolo[1,5-a]pyrimidin-3-ylamine as a yellow solid as indicated by $^1H$ NMR; LC-MS—calcd for $C_{25}H_{26}N_4O$ $[M^++H]^+$: 399.21, found: 399.2.

To a solution of 30 mg (0.075 mmol) 6-(4-benzyloxy-phenyl)-7-cyclohexyl-pyrazolo[1,5-a]pyridin-3-ylamine in 2 mL of acetonitrile ($CH_3CN$) was added 0.018 mL (0.225 mmol) of pyridine (pyr), followed by 16 mg (0.2 mmol) of cyclopropylcarbonyl chloride or 19 mg (0.15 mmol) of ethanesulfonyl chloride, and 1 mg of dimethylaminopyridine (DMAP) and the resulting mixture was stirred at 60° C. overnight. Since analysis by LC-MS revealed product formation, the reaction mixture was concentrated to give a residue which was purified via reverse-phase chromatography to afford (after lyophilization) 17 mg (49% yield) of cyclopropanecarboxylic acid [6-(4-benzyloxy-phenyl)-7-cyclohexyl-pyrazolo[1,5-a]pyrimidin-3-yl]-amide (415) as a yellow solid or 17 mg (46% yield) of ethanesulfonic acid [6-(4-benzyloxy-phenyl)-7-cyclohexyl-pyrazolo[1,5-a]pyrimidin-3-yl]-amide (421) as a yellow solid as indicated by LC-MS—calcd for $C_{29}H_{30}N_4O_2$ $[M^++H]^+$: 467.24, found: 467.2; calcd for $C_{27}H_{30}N_4O_3S$ $[M^++H]^+$: 491.2, found: 491.2.

Example 30

Synthesis of 2-{[7-Cyclohexyl-6-(4-fluoro-phenyl)-2-methyl-pyrazolo[1,5-a]pyrimidine-3-carbonyl]-amino}-3-(4-hydroxy-phenyl)-propionic acid

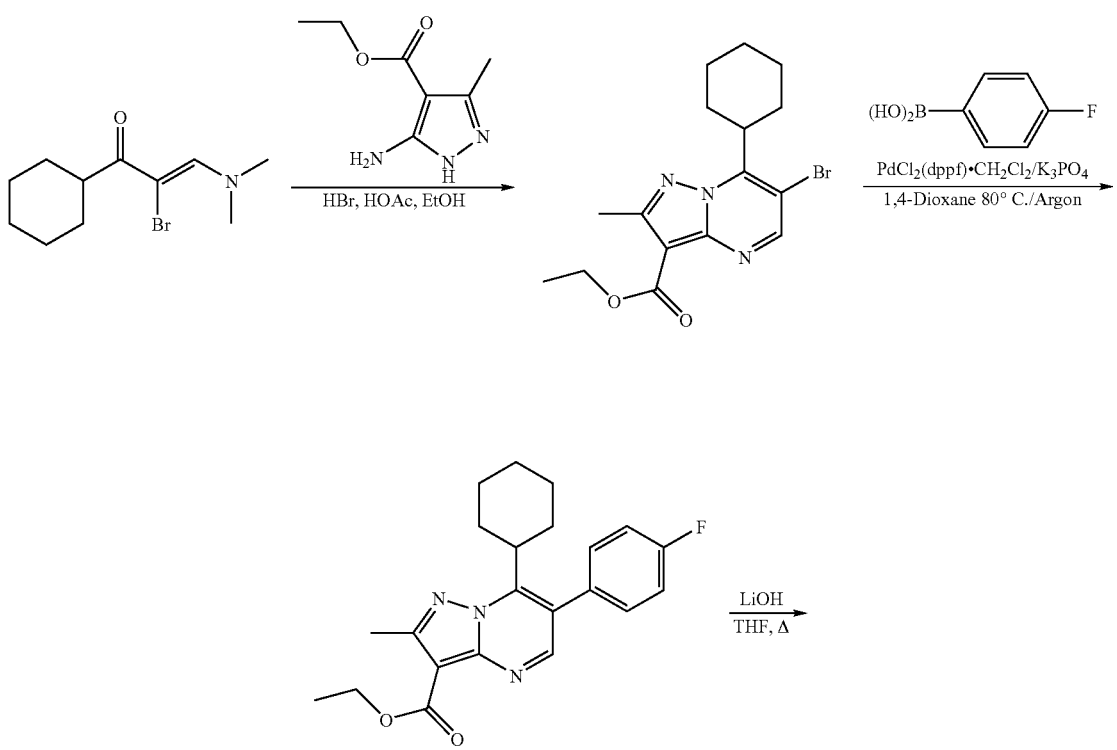

-continued

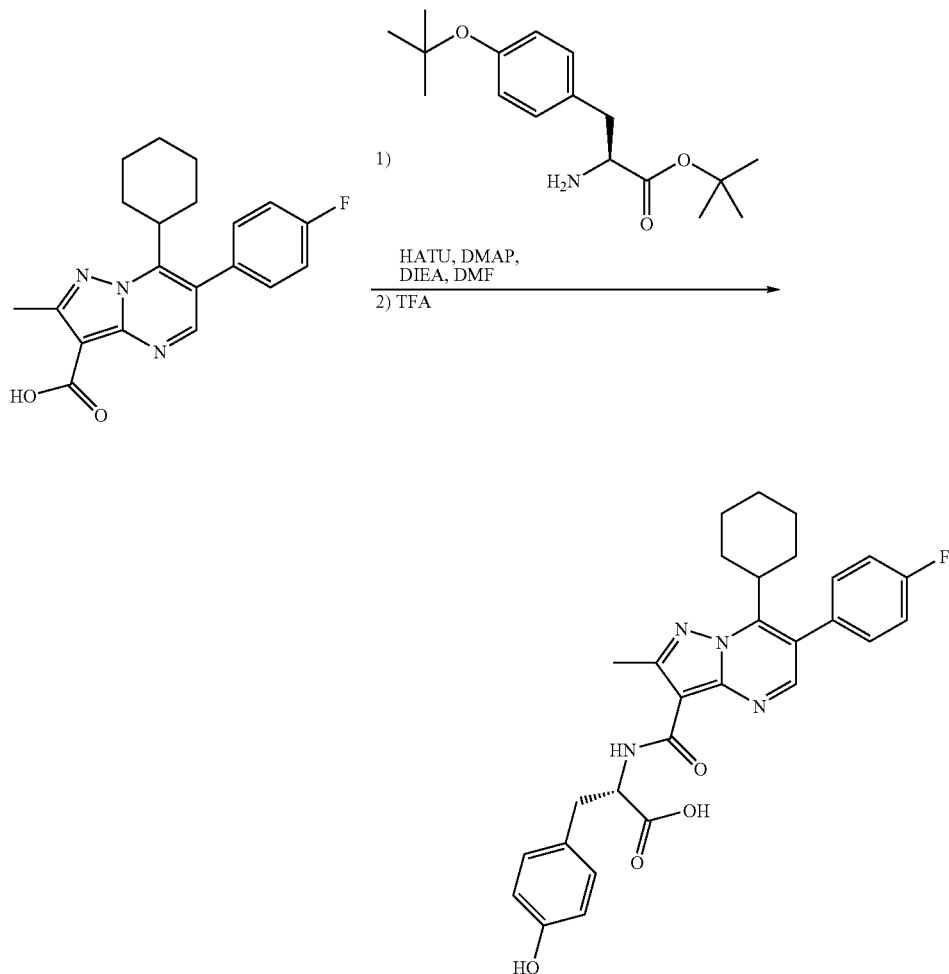

A solution of 1.04 (4 mmol) of 2-bromo-1-cyclohexyl-3-dimethylamino-propenone and 0.676 g (4 mmol) of 5-amino-3-methyl-1H-pyrazole-4-carboxylic acid ethyl ester in 10 mL of ethanol was added 0.65 mL of 30% hydrogen bromide in acetic acid solution, and the resulting mixture was heated at reflux for 1 h. The reaction mixture was cooled to rt and concentrated to give a brown residue which sonicated with 30% ethyl acetate in hexane to give a precipitate which was filtered, and then washed twice with ethyl acetate. The combined organic extracts were evaporated to give 1.32 g of a orange solid which was chromatographed on silica gel (gradient elution with dichloromethane, followed by 2% to 10% ethyl acetate in dichloromethane) to afford 0.756 g (52%) of 6-bromo-7-cyclohexyl-2-methyl-pyrazolo[1,5-a]pyrimidine-3-carboxylic acid ethyl ester as a yellow solid as indicated by $^1$H NMR; LC-MS—calcd for $C_{16}H_{20}BrN_3O_2$ [M$^+$+H]$^+$: 366.07, found: 366.1.

A mixture of 187 mg (0.5 mmol) of 6-bromo-7-cyclohexyl-2-methyl-pyrazolo[1,5-a]pyrimidine-3-carboxylic acid ethyl ester, 105 mg (0.75 mmol, 1.5 equiv) of 4-fluorophenylboronic acid, 20 mg (0.025 mmol, 5 mol %) of Pd catalyst, and 318 mg (1.5 mmol, 3 equiv) of potassium phosphate was placed into a carousel tube. After a vacuum and argon cycle, 1,4-dioxane (7 mL) was added, and the resulting mixture was heated at 80° C. under argon for 14 h. The reaction mixture was diluted with ethyl acetate, filtered through a small pad of Celite, dried over sodium sulfate and evaporated to give a brown residue which was chromatographed on silica gel (gradient elution with 2%, 5% to 10% ethyl acetate in dichloromethane) to afford 0.178 g (94%) of 7-cyclohexyl-6-(4-fluoro-phenyl)-2-methyl-pyrazolo[1,5-a]pyrimidine-3-carboxylic acid ethyl ester as an off-white solid as indicated by $^1$H NMR; LC-MS—calcd for $C_{22}H_{24}FN_3O_2$ [M$^+$+H]$^+$: 382.19, found: 382.1.

To a solution of 178 mg (0.46 mmol) of 7-cyclohexyl-6-(4-fluoro-phenyl)-2-methyl-pyrazolo[1,5-a]pyrimidine-3-carboxylic acid ethyl ester in 9 mL of tetrahydrofuran was added 2.8 mL (2.8 mmol) of 1 M LiOH solution, and the mixture was heated at reflux for 15 h. Since analysis by TLC revealed that starting material was still present, 2.8 mL (2.8 mmol) of 1 M LiOH solution was added, and reflux was continued for 60 h. The reaction mixture was then cooled to rt, concentrated, diluted with water, acidified with 10% HCl solution to pH=2, and extracted with ethyl acetate. The combined organic extracts were dried over sodium sulfate, and evaporated to give 156 mg (96% yield, 90% purity) of 7-cyclohexyl-6-(4-fluoro-phenyl)-2-methyl-pyrazolo[1,5-a]pyrimidine-3-carboxylic acid (515) as a beige solid as indicated by $^1$H NMR; LC-MS—calcd for $C_{20}H_{20}FN_3O_2$ $[M^++H]^+$: 354.15, found: 354.2.

A solution of 36 mg (0.1 mmol) 7-cyclohexyl-6-(4-fluoro-phenyl)-2-methyl-pyrazolo[1,5-a]pyrimidine-3-carboxylic acid in 2 mL of dimethylformamide was cooled at 0° C. To the above cold solution was added 0.053 mL (0.3 mmol) of N,N-diisopropylethylamine (DIEA), followed by 38 mg (0.1 mmol) of HATU, and 37 mg (0.11 mmol) of 2-amino-3-(4-tert-butoxy-phenyl)-propionic acid tert-butyl ester, and a few crystals of 4-dimethylaminopyridine (DMAP), and the resulting mixture was allowed to warm up to rt, and stirred at rt overnight. The reaction mixture was then diluted with ethyl acetate, washed with 0.1 N NaOH solution, water, and brine, dried over sodium sulfate and evaporated to give a residue which was treated with 2 mL of 95:5 trifluoroacetic acid (TFA):water, and stirred at rt for 2.5 h. The mixture was quenched by the addition of 10 mL of 1:1 acetonitrile:water solution, and concentrated to give a residue which was purified via reverse-phase chromatography using Gilson to afford (after lyophilization) 8 mg (16% over 2 steps) of 2-{[7-Cyclohexyl-6-(4-fluoro-phenyl)-2-methyl-pyrazolo[1,5-a]pyrimidine-3-carbonyl]-amino}-3-(4-hydroxy-phenyl)-propionic acid as a white solid (92% purity, entry 517), as indicated by $^1$H-NMR. (LC-MS calcd for $C_{29}H_{29}FN_4O_4$ $[M+H]^+$ 517.22; found 517.2).

Example 31

Synthesis of 4'-chloro-2-{4-[7-cyclohexyl-3-(1H-tetrazol-5-yl)-pyrazolo[1,5-a]pyrimidin-6-yl]-phenoxymethyl}-biphenyl-4-carboxylic acid

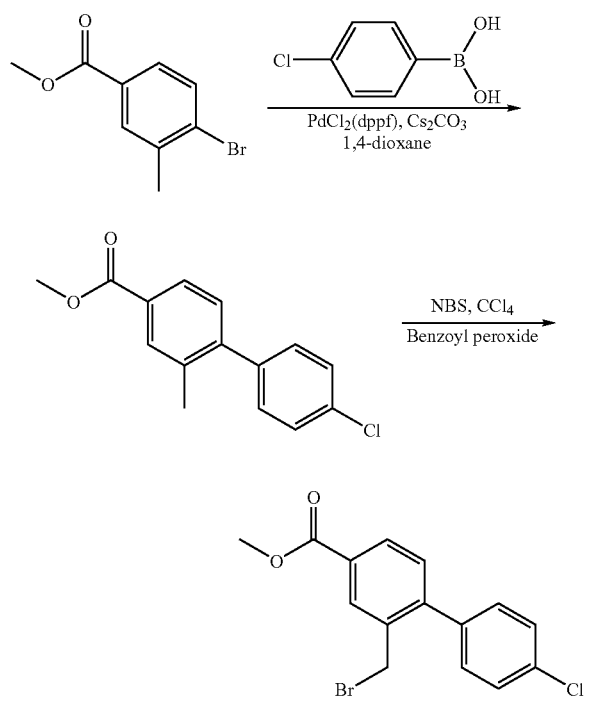

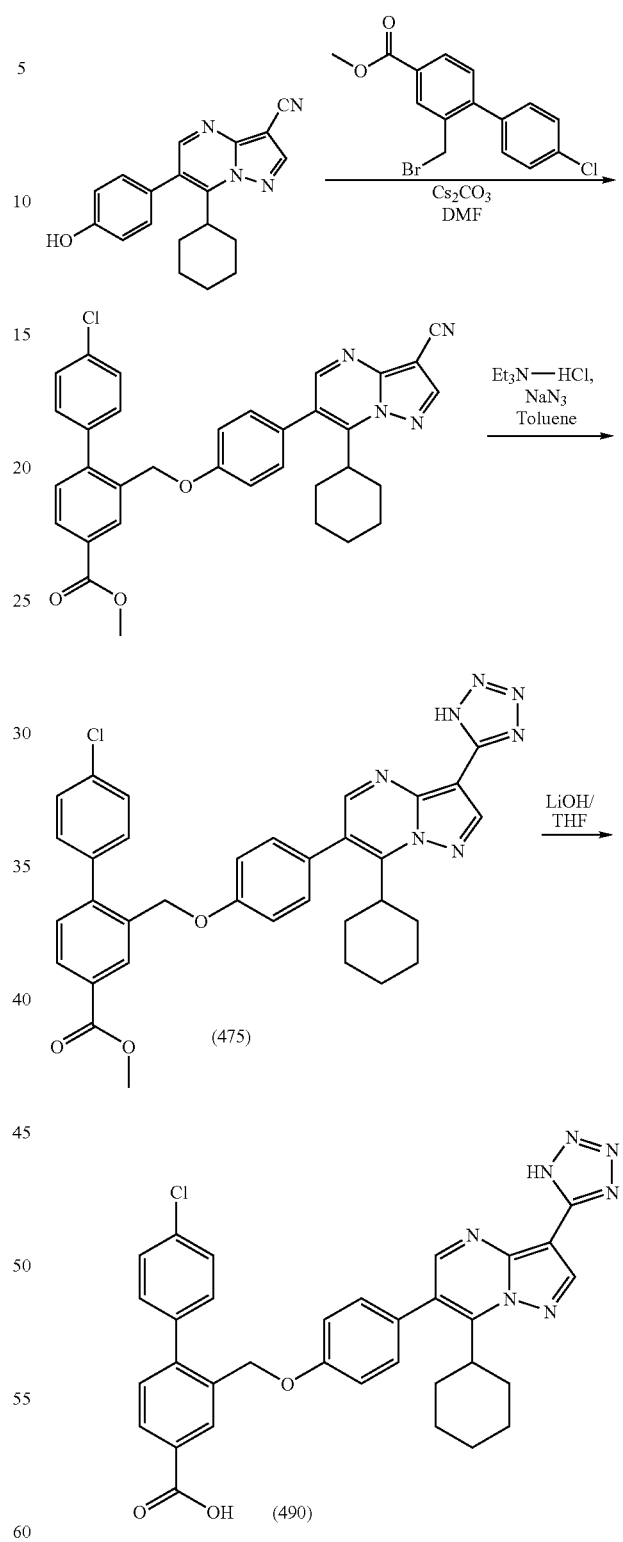

A mixture of 250 mg (1.09 mmol) of 4-bromo-3-methyl-benzoic acid methyl ester, 204 mg (1.31 mmol) of 4-chlorophenylboronic acid, 1.06 g (3.27 mmol) of cesium carbonate ($Cs_2CO_3$) and $PdCl_2(dppf)$ catalyst (5 mol %) was flushed with argon. To this mixture was added 3 mL of 1,4-dioxane and the reaction mixture was heated to 80° C. overnight. The mixture was then cooled to rt, and filtered through a pad of Celite while rinsing the pad with ethyl acetate. The filtrate was washed with brine, dried over sodium sulfate and concentrated to give a residue which was chromatographed on silica gel (5% ethyl acetate in hexane) to afford 191 mg (67%) of desired 4'-chloro-2-methyl-biphenyl-4-carboxylic acid methyl ester, as an oil as indicated by $^1$H NMR; LC-MS calcd for $C_{15}H_{13}ClO_2$ [M$^+$+H]$^+$: 261.07, found: 261.1.

To a solution of 191 mg (0.73 mmol) of 4'-chloro-2-methyl-biphenyl-4-carboxylic acid methyl ester in 4 mL of carbon tetrachloride (CCl$_4$) was added 9.7 mg (0.04 mmol) of benzoyl peroxide, followed by 124 mg (0.696 mmol) of N-bromosuccinimide (NBS), and the reaction mixture was heated at reflux for 6 h. The mixture was cooled to rt, diluted with dichloromethane and washed with water and brine. The organic layer was dried over sodium sulfate and concentrated to give 132 mg (53%) of 2-bromomethyl-4'-chloro-biphenyl-4-carboxylic acid methyl ester, as an oil, which was used without any further purification in the next step. $^1$H NMR δCDCl$_3$ 8.10 (s, 1H), 7.91-7.89 (d, J=8.0 Hz, 1-H), 7.37-7.35 (d, J=8.3 Hz, 2H), 7.30-7.18 (d, J=8.7 Hz, 2H), 7.22-7.20 (d, J=8.0 Hz, 1H), 4.30 (s, 2H), 3.87 (s, 3H).

Alkylation of 7-cyclohexyl-6-(4-hydroxy-phenyl)-pyrazolo[1,5-a]pyrimidine-3-carbonitrile with 2-bromomethyl-4'-chloro-biphenyl-4-carboxylic acid methyl ester was carried out in dimethylformamide (DMF) using cesium carbonate and following a previously described experimental procedure to give 4'-chloro-2-[4-(3-cyano-7-cyclohexyl-pyrazolo[1,5-a]pyrimidin-6-yl)-phenoxymethyl]-biphenyl-4-carboxylic acid methyl ester. This compound was converted to its corresponding tetrazole 4'-chloro-2-{4-[7-cyclohexyl-3-(1H-tetrazol-5-yl)-pyrazolo[1,5-a]pyrimidin-6-yl]-phenoxymethyl}-biphenyl-4-carboxylic acid methyl ester (475) via a previously described procedure. Finally, 4'-chloro-2-{4-[7-cyclohexyl-3-(1H-tetrazol-5-yl)-pyrazolo[1,5-a]pyrimidin-6-yl]-phenoxymethyl}-biphenyl-4-carboxylic acid (490) was obtained following a standard LiOH saponification protocol.

Example 32

Synthesis of 5-(4-benzyloxy-phenyl)-6-cyclohexyl-7-oxo-4,7-dihydro-pyrazolo[1,5-a]pyrimidine-2-carboxylic acid

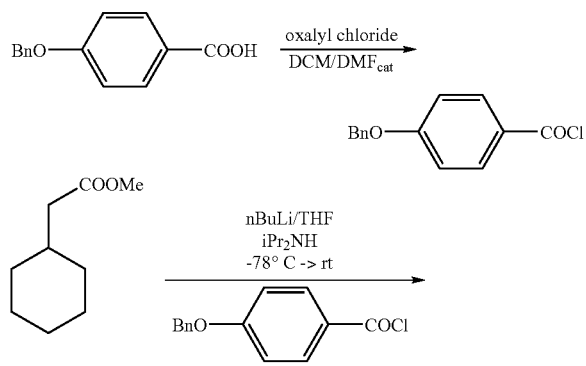

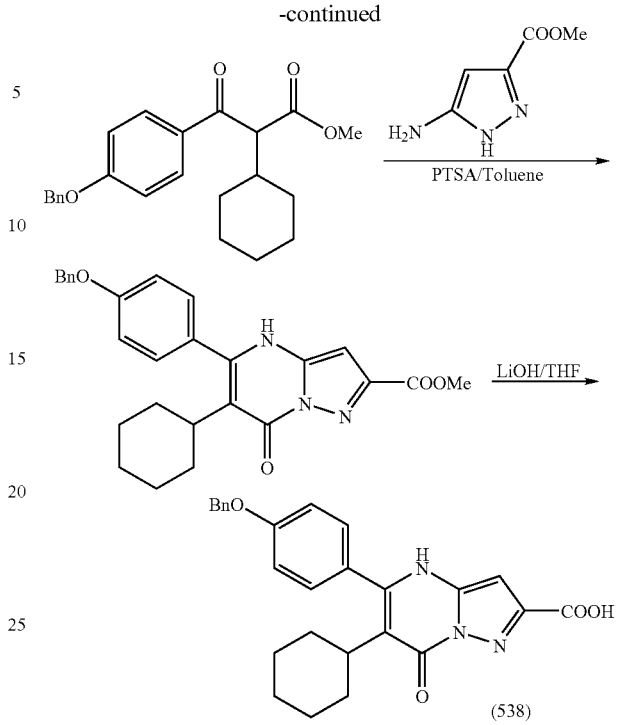

To a mixture of 5.0 g (21.9 mmol) of 4-benzyloxy-benzoic acid in 25 mL of dichloromethane (DCM) was added dropwise 10 mL (114 mmol) of oxalyl chloride, followed by 5 □L of dimethylformamide (DMF cat) and the reaction mixture was heated at reflux for 3 h, and concentrated to give 5.32 g (98%) of desired 4-benzyloxy-benzoyl chloride as a yellow solid as indicated by $^1$H NMR. The product was used without any further purification in the next step.

A solution of 0.35 mL (2.5 mmol) of diisopropylamine (iPr$_2$NH) in 7 mL of tetrahydrofuran (THF) was flushed with argon and cooled to −78° C. To this solution was added dropwise 1 mL (2.5 mmol) of n-butyllithium (nBuLi) 2.5 M solution in hexane, and the resulting mixture was stirred at −78° C. for 20 min, after which time 0.33 mL (2 mmol) of methyl cyclohexylacetate was added dropwise. The mixture was allowed to warm up to rt for 40 min, then it was cooled again to −78° C., and a solution of 0.592 g (2.4 mmol) of 4-benzyloxy-benzoyl chloride in 8 mL of THF was added dropwise, and the resulting mixture was allowed to warm up to rt, and stirred at rt overnight under argon. The reaction mixture was quenched on ice by the addition of saturated ammonium chloride solution, and extracted with ethyl acetate. The combined organic extracts were washed with water, brine, dried over sodium sulfate and concentrated to give 0.83 g of a yellow solid residue which was chromatographed on silica gel (Biotage; 25% hexane in dichloromethane) to afford 0.306 g (42% yield) of desired 3-(4-benzyloxy-phenyl)-2-cyclohexyl-3-oxo-propionic acid methyl ester as a white solid as indicated by $^1$H NMR; LC-MS—calcd for $C_{23}H_{26}O_4$ [M$^+$+H]$^+$: 367.18, found: 367.2.

A mixture of 274 mg (0.747 mmol) of 3-(4-benzyloxy-phenyl)-2-cyclohexyl-3-oxo-propionic acid methyl ester, 106 mg (0.747 mmol) of 5-amino-1H-pyrazole-3-carboxylic acid methyl ester, 15 mg (10 mol %) of p-toluenesulfonic acid monohydrate (PTSA), and 10 mL of toluene was heated at reflux for 88 h. The reaction mixture was then concentrated to a residue which was chromatographed on silica gel (Biotage;

gradient elution 2% to 20% ethyl acetate in dichloromethane) to afford 55 mg (16% yield) of desired 5-(4-benzyloxy-phenyl)-6-cyclohexyl-7-oxo-4,7-dihydro-pyrazolo[1,5-a]pyrimidine-2-carboxylic acid methyl ester as a solid as indicated by $^1$H NMR; LC-MS—calcd for $C_{27}H_{27}N_3O_4$ [M$^+$+H]$^+$: 458.2, found: 458.2.

This material was then converted to 5-(4-benzyloxy-phenyl)-6-cyclohexyl-7-oxo-4,7-dihydro-pyrazolo[1,5-a]pyrimidine-2-carboxylic acid via the well known LiOH saponification protocol (55% yield, entry 538); LC-MS—calcd for $C_{26}H_{25}N_3O_4$ [M$^+$+H]$^+$: 444.18, found: 444.2.

Example 33

Synthesis of 5-(4-benzyloxy-phenyl)-6-cyclohexyl-2-(1H-tetrazol-5-yl)-4H-pyrazolo[1,5-a]pyrimidin-7-one

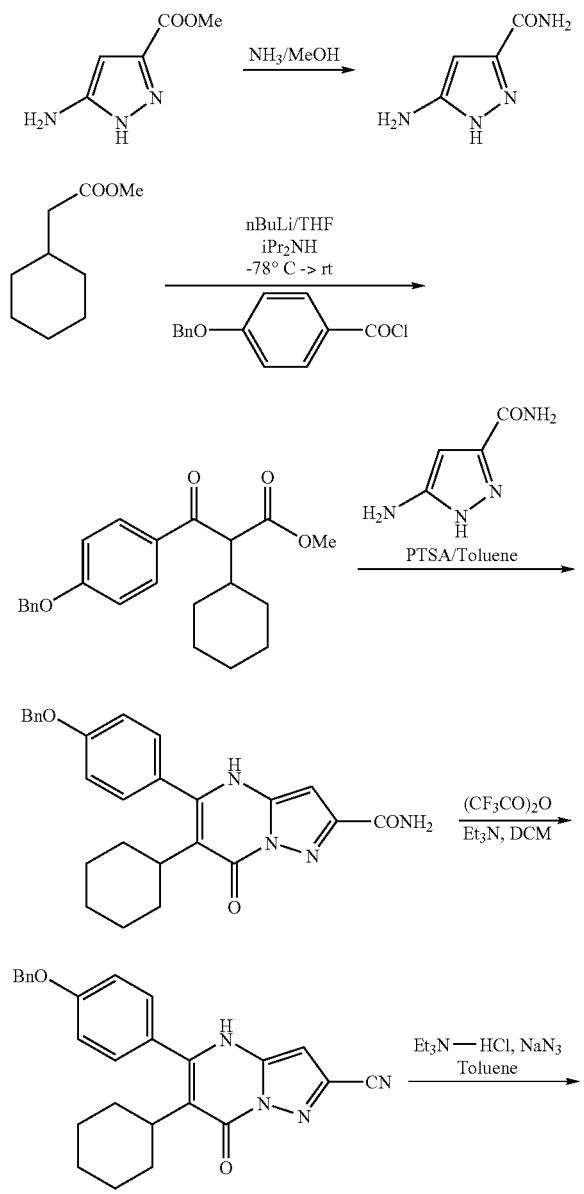

-continued

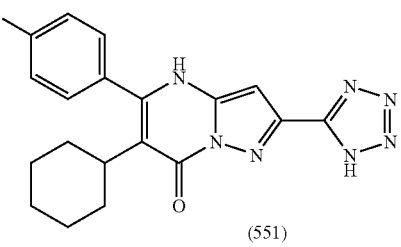

(551)

A solution of 1.0 g (7 mmol) of 5-amino-1H-pyrazole-3-carboxylic acid methyl ester in 10 mL of methanol (MeOH) in a sealed tube was saturated with ammonia (NH$_3$), and the sealed tube mixture was stirred at rt overnight. Since analysis by thin layer chromatography (TLC) revealed that the reaction was not complete, the mixture was then heated at 80° for 1 day. The reaction mixture was then cooled, the sealed tube was opened, and the solvent was evaporated to give 0.9 g of desired 5-amino-1H-pyrazole-3-carboxylic acid amide as indicated by $^1$H NMR; LC-MS—calcd for $C_4H_6N_4O$ [M$^+$+H]$^+$: 127.05, found: 127.2.

The preparation of 3-(4-benzyloxy-phenyl)-2-cyclohexyl-3-oxo-propionic acid methyl ester is described elsewhere in this document.

A mixture of 1.0 g (2.7 mmol) of 3-(4-benzyloxy-phenyl)-2-cyclohexyl-3-oxo-propionic acid methyl ester, 340 mg (2.7 mmol) of 5-amino-1H-pyrazole-3-carboxylic acid amide, 51 mg (10 mol %) of p-toluenesulfonic acid monohydrate (PTSA), and 15 mL of toluene was heated at reflux for 72 h. The reaction mixture was then concentrated to a residue which chromatographed on silica gel (Biotage; gradient elution 15% ethyl acetate in dichloromethane to 6% methanol in dichloromethane) to give a residue which was further purified via reverse-phase chromatography (Gilson) to afford (after lyophilization) 22 mg (2% yield) of desired 5-(4-benzyloxy-phenyl)-6-cyclohexyl-7-oxo-4,7-dihydro-pyrazolo[1,5-a]pyrimidine-2-carboxylic acid amide as indicated by $^1$H-NMR; LC-MS calcd for $C_{26}H_{26}N_4O_3$ [M$^+$+H]$^+$: 443.2, found: 443.2.

To a mixture of 22 mg (0.05 mmol) of 5-(4-benzyloxy-phenyl)-6-cyclohexyl-7-oxo-4,7-dihydro-pyrazolo[1,5-a]pyrimidine-2-carboxylic acid amide in 1 mL of dichloromethane (DCM) was added 0.04 mL (0.3 mmol) of triethylamine (Et$_3$N), and the resulting mixture was cooled in an ice bath. Then 0.021 mL (0.15 mmol) of trifluoroacetic anhydride ((CF$_3$CO)$_2$O) was added during which time the mixture became homogeneous, and was stirred for 2.5 h. The reaction mixture was quenched by the addition of water, and concentrated to a residue which was purified via reverse-phase chromatography to afford (after lyophilization) 3 mg (14% yield) of desired 5-(4-benzyloxy-phenyl)-6-cyclohexyl-7-oxo-4,7-dihydro-pyrazolo[1,5-a]pyrimidine-2-carbonitrile as indicated by LC-MS calcd for $C_{26}H_{24}N_4O_2$ [M$^+$+H]$^+$: 425.19, found: 425.2.

This material was then converted to the corresponding tetrazole 5-(4-benzyloxy-phenyl)-6-cyclohexyl-2-(1H-tetrazol-5-yl)-4H-pyrazolo[1,5-a]pyrimidin-7-one (551) via a previously described (sodium azide, triethylamine hydrochloride) experimental procedure (54% yield); LC-MS—calcd for $C_{26}H_{25}N_7O_2$ [M$^+$+H]$^+$: 468.21, found: 468.2.

Example 34

Synthesis of 5-(4-benzyloxy-phenyl)-6-cyclohexyl-7-methoxy-pyrazolo[1,5-a]pyrimidine-2-carboxylic acid

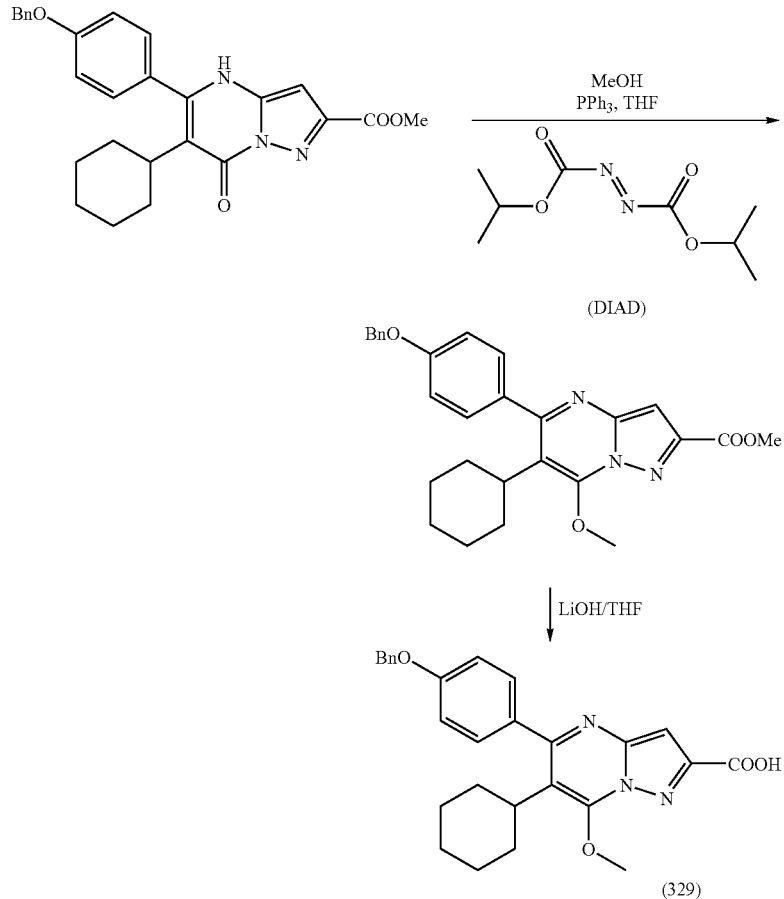

(329)

To an ice cold mixture of 22 mg (0.048 mmol) of 5-(4-benzyloxy-phenyl)-6-cyclohexyl-7-oxo-4,7-dihydro-pyrazolo[1,5-a]pyrimidine-2-carboxylic acid methyl ester in 3 mL of tetrahydrofuran (THF) was added 0.008 mL (0.192 mmol) of methanol (MeOH), 50 mg (0.192 mmol) of triphenylphosphine (PPh$_3$), followed by 0.038 mL (0.192 mmol) of diisopropyl azodicarboxylate (DIAD) and the mixture was allowed to warm up to rt and stirred at rt for 2 h when analysis by thin layer chromatography (TLC) revealed complete consumption of starting material. The reaction mixture was then concentrated and the residue was chromatographed on silica gel (Biotage; gradient elution dichloromethane (DCM) to 10% ethyl acetate in DCM) to give 24 mg of desired 5-(4-benzyloxy-phenyl)-6-cyclohexyl-7-methoxy-pyrazolo[1,5-a]pyrimidine-2-carboxylic acid methyl ester as indicated by $^1$H-NMR (containing traces of impurities).

Note that 5-(4-benzyloxy-phenyl)-6-cyclohexyl-7-methoxy-pyrazolo[1,5-a]pyrimidine-2-carboxylic acid methyl ester was also obtained using an alkylation procedure (dimethylsulfate, with acetonitrile as solvent).

Conversion of 5-(4-benzyloxy-phenyl)-6-cyclohexyl-7-methoxy-pyrazolo[1,5-a]pyrimidine-2-carboxylic acid methyl ester to the corresponding acid 5-(4-benzyloxy-phenyl)-6-cyclohexyl-7-methoxy-pyrazolo[1,5-a]pyrimidine-2-carboxylic acid (329) was accomplished via the well known LiOH saponification protocol; LC-MS—calcd for $C_{27}H_{27}N_3O_4$ [M$^+$+H]$^+$: 458.2, found: 458.2.

Example 35

Synthesis of 2-{[5-(4-benzyloxy-phenyl)-6-cyclohexyl-7-oxo-4,7-dihydro-pyrazolo[1,5-a]pyrimidine-2-carbonyl]-amino}-3-hydroxy-propionic acid

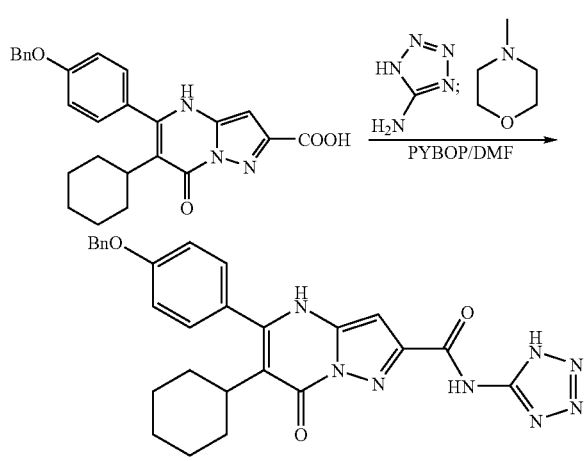

111

-continued

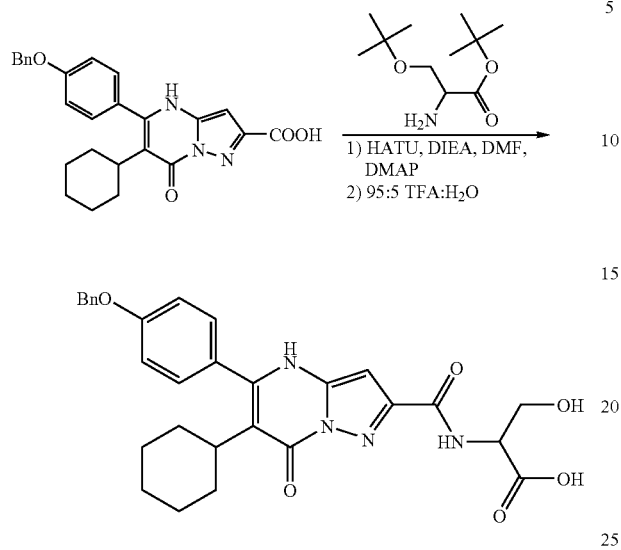

To a solution of 71 mg (0.16 mmol) of 5-(4-benzyloxy-phenyl)-6-cyclohexyl-7-oxo-4,7-dihydro-pyrazolo[1,5-a]pyrimidine-2-carboxylic acid in 4 mL of dimethylformamide (DMF) was added 0.053 mL (0.48 mmol) of 4-methyl-morpholine, 14 mg (0.164 mmol) of 5-aminotetrazole, followed by 100 mg (0.192 mmol) of PYBOP when the solution turned yellow, and the resulting mixture was stirred at rt for 41 h. The reaction mixture was concentrated to give a residue which was purified via reverse-phase chromatography to afford 29 mg (35% yield) of desired 5-(4-benzyloxy-phenyl)-6-cyclohexyl-7-oxo-4,7-dihydro-pyrazolo[1,5-a]pyrimidine-2-carboxylic acid (1H-tetrazol-5-yl)-amide (540) as a solid as indicated by $^1$H-NMR; LC-MS calcd. for $C_{27}H_{26}N_8O_3$ $[M^++H]^+$: 511.21; found: 511.1.

To a solution of 67 mg (0.15 mmol) of 5-(4-benzyloxy-phenyl)-6-cyclohexyl-7-oxo-4,7-dihydro-pyrazolo[1,5-a]pyrimidine-2-carboxylic acid in 3 mL of DMF was added 0.13 mL (0.75 mmol) of diisopropylethylamine (DIEA), a few crystals of dimethylaminopyridine (DMAP cat), 50 mg (0.195 mmol) of 2-amino-3-tert-butoxy-propionic acid tert-butyl ester hydrochloride, followed by 74 mg (0.195 mmol) of HATU, and the resulting mixture was stirred at rt overnight. The reaction mixture was diluted with ethyl acetate, washed with 0.1 N sodium hydroxide solution (2 times) and brine. The separated organic layer was dried over sodium sulfate and concentrated to give a residue which was treated with 3 mL of 95:5 trifluoroacetic acid (TFA):water, stirred at rt for 2 h, and quenched by the addition of 1:1 acetonitrile:water. The resulting mixture was concentrated to give a residue which was purified via reverse-phase chromatography to afford (after lyophilization) 14 mg (17%) of desired 2-{[5-(4-benzyloxy-phenyl)-6-cyclohexyl-7-oxo-4,7-dihydro-pyrazolo[1,5-a]pyrimidine-2-carbonyl]-amino}-3-hydroxy-propionic acid (544) as a white solid as indicated by $^1$H-NMR; LC-MS calcd. for $C_{29}H_{30}N_4O_6$ $[M^++H]^+$: 531.22; found: 531.2.

112

Example 36

Synthesis of 5-(4-benzyloxy-phenyl)-6-(2-cyclohexylethyl)-7-oxo-4,7-dihydro-pyrazolo[1,5-a]pyrimidine-2-carboxylic acid and 6-(2-cyclohexylethyl)-5-furan-3-yl-7-oxo-4,7-dihydro-pyrazolo[1,5-a]pyrimidine-2-carboxylic acid

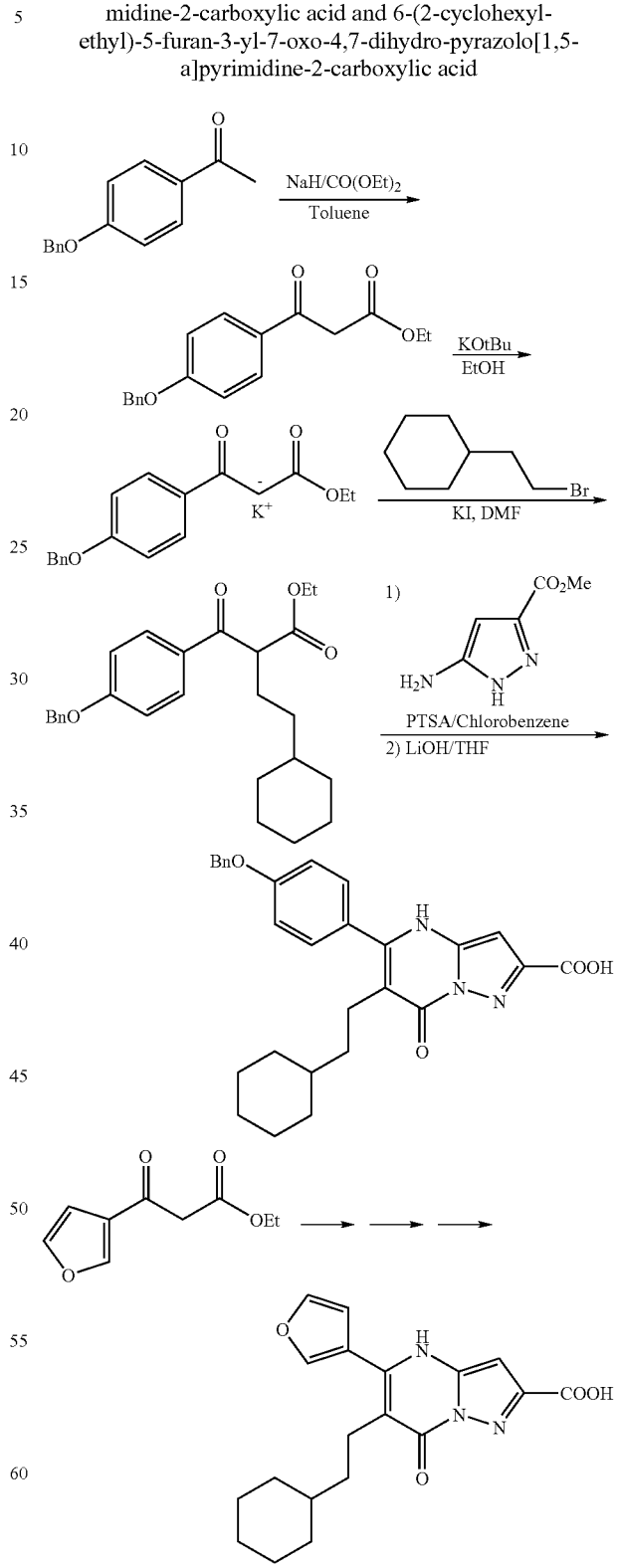

To a refluxing mixture of 7.0 g (175 mmol) of sodium hydride (NaH 60% dispersion in mineral oil) and 10.45 g (88.5 mmol) of diethyl carbonate (CO(OEt)$_2$) in 100 mL of toluene was added dropwise via an addition funnel a mixture of 10 g (44.3 mmol) of 1-(4-benzyloxy-phenyl)-ethanone in 20 mL of toluene, and the resulting mixture was heated at reflux under argon for 1 h. The reaction mixture was then cooled to 0° C., quenched by the addition of 40 mL of acetic acid, during which time a yellow precipitate formed, and it dissolved upon subsequent addition of water. The separated organic layer was washed with saturated sodium bicarbonate solution, water and brine, dried over sodium sulfate and concentrated to give a residue which was chromatographed on silica gel (10% hexane in dichloromethane) to afford 9.2 g (70% yield) of desired 3-(4-benzyloxy-phenyl)-3-oxo-propionic acid ethyl ester as indicated by $^1$H NMR.

To a solution of 2 g (6.7 mmol) of 3-(4-benzyloxy-phenyl)-3-oxo-propionic acid ethyl ester in 12 mL of ethanol (heated slightly for complete dissolution) was added dropwise 7 mL (7 mmol) of potassium t-butoxide (KOtBu 1 M solution in t-butanol), during which time a precipitate formed. The reaction mixture was stirred at rt for 20 min, then diethyl ether was added and the precipitate was collected by filtration, washed with ether and dried to afford 2.2 g (98% yield) of desired 3-(4-benzyloxy-phenyl)-3-oxo-propionic acid ethyl ester potassium salt as indicated by $^1$H NMR.

A mixture 100 mg (0.3 mmol) of 3-(4-benzyloxy-phenyl)-3-oxo-propionic acid ethyl ester potassium salt, 86 mg (0.45 mmol) of 2-cyclohexylethyl bromide, and 17 mg (0.1 mmol) of potassium iodide (KI) in 1 mL of dimethylformamide (DMF) in a 4 mL vial was shaken in a sand bath at 80° C. overnight. The mixture was then concentrated to give a residue which was purified via reverse-phase chromatography (Gilson) to afford (after lyophilization) 85 mg (70% yield) of 2-(4-benzyloxy-benzoyl)-4-cyclohexyl-butyric acid ethyl ester as a solid as indicated by LC-MS—calcd for C$_{26}$H$_{32}$O$_2$ [M$^+$+H]$^+$: 409.23, found: 409.2.

A mixture of 71 mg (0.171 mmol) of 2-(4-benzyloxy-benzoyl)-4-cyclohexyl-butyric acid ethyl ester, 24 mg (0.171 mmol) of 5-amino-1H-pyrazole-3-carboxylic acid methyl ester, 7 mg (20 mol %) of p-toluenesulfonic acid monohydrate (PTSA), and 3 mL of chlorobenzene was heated at 120° C. overnight. The reaction mixture was then concentrated to a residue which was purified via reverse-phase chromatography (Gilson) to afford (after lyophilization) desired 5-(4-benzyloxy-phenyl)-6-(2-cyclohexyl-ethyl)-7-oxo-4,7-dihydro-pyrazolo[1,5-a]pyrimidine-2-carboxylic acid methyl ester as a solid as indicated by LC-MS—calcd for C$_{29}$H$_{31}$N$_3$O$_4$ [M$^+$+H]$^+$: 486.23, found: 486.2. This material was then converted to 5-(4-benzyloxy-phenyl)-6-(2-cyclohexyl-ethyl)-7-oxo-4,7-dihydro-pyrazolo[1,5-a]pyrimidine-2-carboxylic acid (559) via the well known. LiOH saponification protocol (10% yield over 2 steps); LC-MS—calcd for C$_{28}$H$_{29}$N$_3$O$_4$ [M$^+$+H]$^+$: 472.22, found: 472.2.

Note that the same synthetic sequence was carried out from the commercially available 3-furan-3-yl-3-oxo-propionic acid ethyl ester as depicted above to give 6-(2-cyclohexyl-ethyl)-5-furan-3-yl-7-oxo-4,7-dihydro-pyrazolo[1,5-a]pyrimidine-2-carboxylic acid (612).

Example 37

Synthesis of 4-(3-trifluoromethyl-phenoxy)-benzoic acid

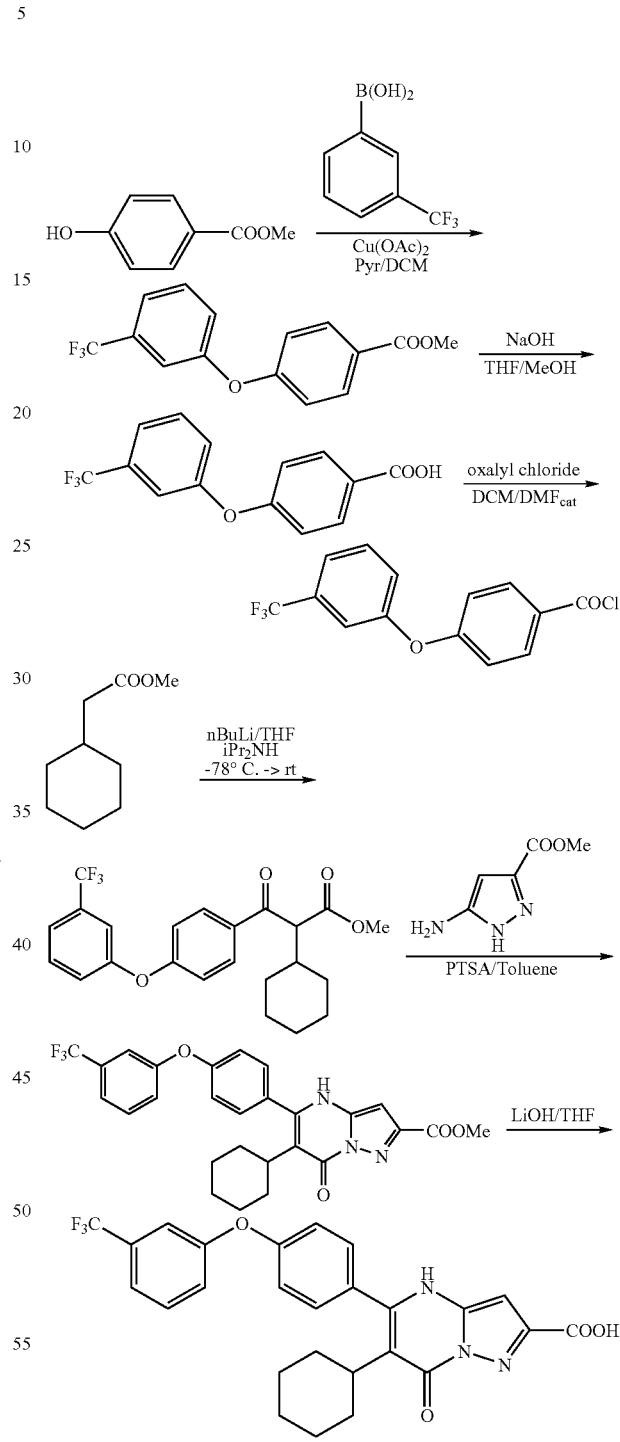

According to a modification of a literature procedure from (*J. Org. Chem.* 2002, 67, 1699-1702) an aqua-green mixture of 2.74 g (18 mmol) of 4-hydroxy-benzoic acid methyl ester, 4.9 g (27 mmol) of copper (II) acetate (Cu(OAc)$_2$), 6.84 g (36 mmol) of 3-trifluoromethyl-phenoxy-boronic acid, 2.92 mL (36 mmol) of pyridine (pyr), and 120 mL of DCM was stirred at rt for 68 h while opened to air. The reaction mixture was filtered through Celite, while rinsing the Celite pad with ethyl acetate and chloroform. The combined organic filtrates were concentrated to a green solid residue, which was partitioned between ethyl acetate and water and extracted with ethyl acetate. The combined organic extracts were washed with water (3 times), brine, dried over sodium sulfate and evaporated to give 4.6 g of a brown residue which was chromatographed on silica gel (Biotage; 1:1 hexane:DCM) to give 3.56 (67% yield) of desired 4-(3-trifluoromethyl-phenoxy)-benzoic acid methyl ester as a pale yellow oil as indicated by $^1$H-NMR and $^{19}$F-NMR; LC-MS—calcd for $C_{15}H_{11}F_3O_3$ [M$^+$+H]$^+$: 297.07, found: 297.1.

A mixture of 3.56 g (12 mmol) of 4-(3-trifluoromethyl-phenoxy)-benzoic acid methyl ester, and 15 mL (60 mmol) of 4 N sodium hydroxide (NaOH) solution in 45 mL of tetrahydrofuran (THF) and 15 mL of methanol (MeOH) was heated at 50° C. for 25 h, when analysis by thin layer chromatography revealed complete conversion of starting material to product. The reaction mixture was concentrated and acidified with 2N HCl solution while keeping the flask in an ice bath, when a white precipitate formed. The solid was filtered and dried to give 3.02 g (89%) of desired 4-(3-trifluoromethyl-phenoxy)-benzoic acid as a white solid as indicated by $^1$H NMR and $^{19}$F-NMR.

Synthesis of 6-Cyclohexyl-7-oxo-5-[4-(3-trifluoromethyl-phenoxy)-phenyl]-4,7-dihydro-pyrazolo[1,5-a]pyrimidine-2-carboxylic acid (543) was accomplished as depicted in the above scheme, starting from 4-(3-trifluoromethyl-phenoxy)-benzoic acid via transformations that were described for the synthesis of 5-(4-Benzyloxy-phenyl)-6-cyclohexyl-7-oxo-4,7-dihydro-pyrazolo[1,5-a]pyrimidine-2-carboxylic acid (538). For entry 543: LC-MS—calcd for $C_{26}H_{22}F_3N_3O_4$ [M$^+$+H]$^+$: 498.16, found: 498.1.

Example 38

Synthesis of 6-cyclohexyl-7-oxo-5-[4-(3-trifluoromethyl-benzyloxy)-phenyl]-4,7-dihydro-pyrazolo[1,5-a]pyrimidine-2-carboxylic acid

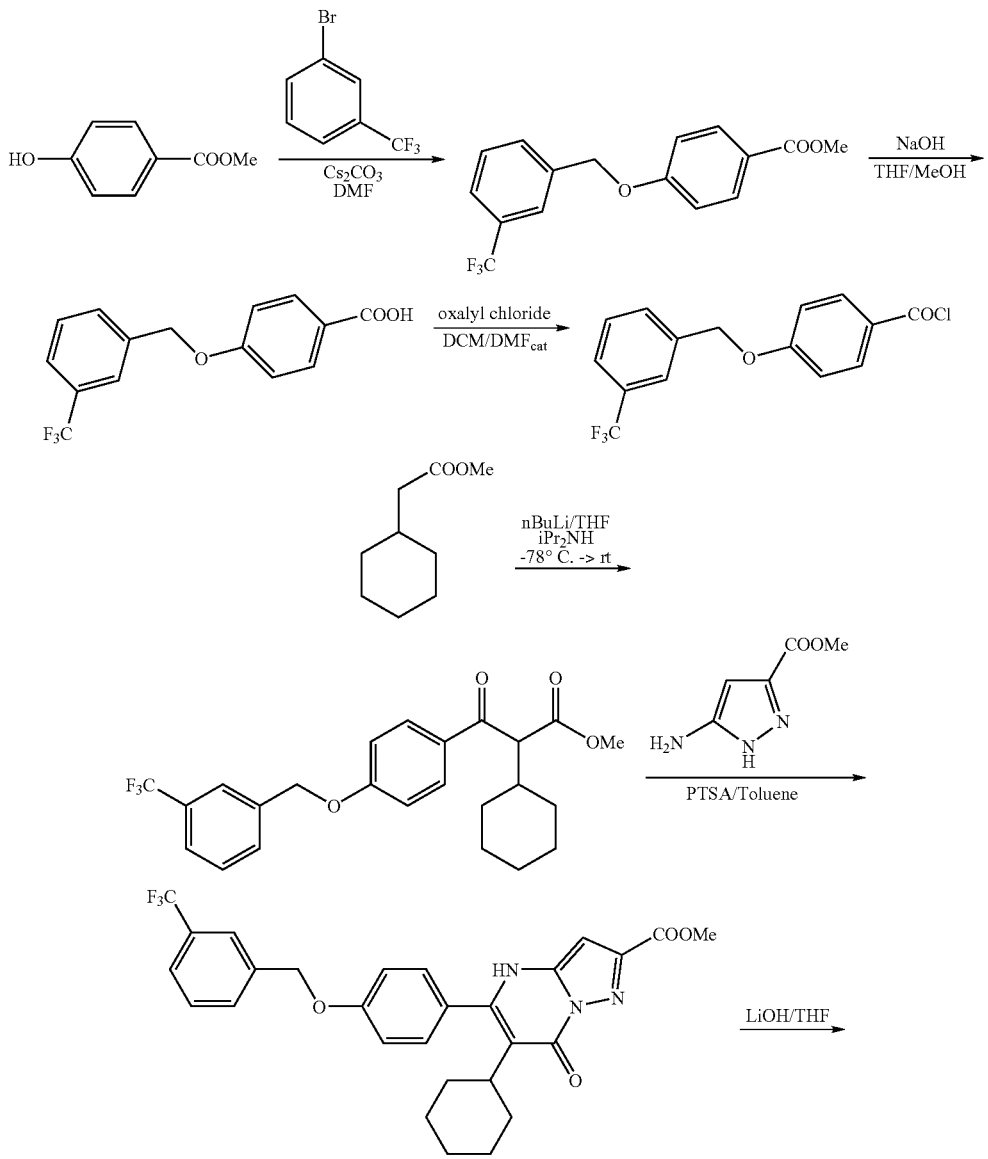

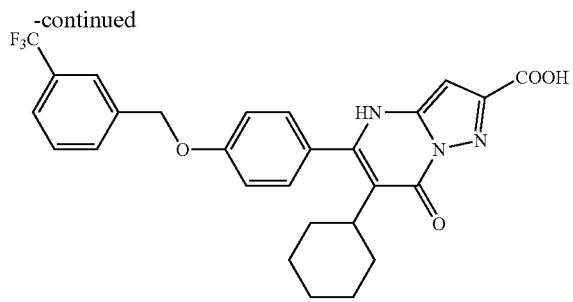

To a solution of 2.28 g (15 mmol) of 4-hydroxy-benzoic acid methyl ester in 30 mL of dimethylformamide (DMF) was added 5.38 g (16.5 mmol) of cesium carbonate (Cs$_2$CO$_3$), followed by 2.75 mL (18 mmol) of 3-(trifluoromethyl)-benzyl bromide, and the resulting heterogeneous mixture was stirred at rt overnight. The reaction mixture was filtered and concentrated, diluted with water and extracted with ethyl acetate, and the combined organic extracts were washed with water and brine, and concentrated to give 4.75 g of desired 4-(3-trifluoromethyl-benzyloxy)-benzoic acid methyl ester as indicated by $^1$H NMR and $^{19}$F-NMR (containing traces of residual 3-(trifluoromethyl)-benzyl bromide).

This product was used without any further purification in the synthesis of 6-cyclohexyl-7-oxo-5-[4-(3-trifluoromethyl-benzyloxy)-phenyl]-4,7-dihydro-pyrazolo[1,5-a]pyrimidine-2-carboxylic acid (545), which was accomplished as depicted in the above scheme, via standard transformations that were previously described for the synthesis of 5-(4-Benzyloxy-phenyl)-6-cyclohexyl-7-oxo-4,7-dihydro-pyrazolo[1,5-a]pyrimidine-2-carboxylic acid.

Example 39

Synthesis of 6-cyclohexyl-5-[4-(3,5-dimethyl-isoxazol-4-yl)-phenyl]-7-oxo-4,7-dihydro-pyrazolo[1,5-a]pyrimidine-2-carboxylic acid, 5-(4-benzyl-phenyl)-6-cyclohexyl-7-oxo-4,7-dihydro-pyrazolo[1,5-a]pyrimidine-2-carboxylic acid, and 5-(4-(3-trifluoromethoxyphenyl)-phenyl)-6-cyclohexyl-7-oxo-4,7-dihydro-pyrazolo[1,5-a]pyrimidine-2-carboxylic acid

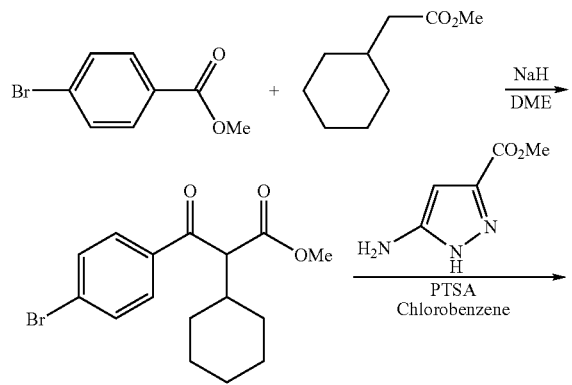

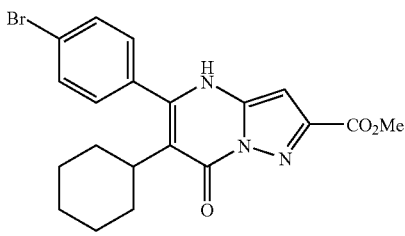

The product of the above sequence was synthesized following the same experimental procedure that was used to prepare a related intermediate where the 4-bromo-phenyl group was replaced by 2-furyl group. This aryl bromide compound was used as a synthetic intermediate, which was transformed using some of the representative reactions below.

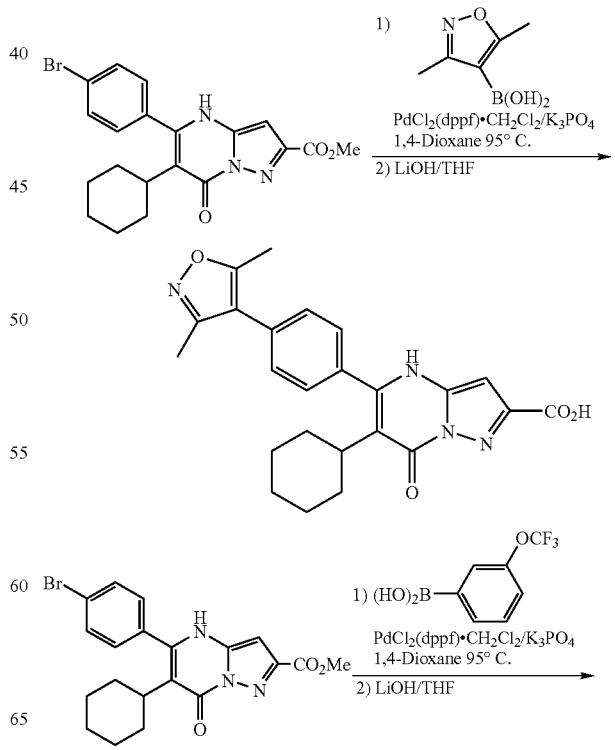

-continued

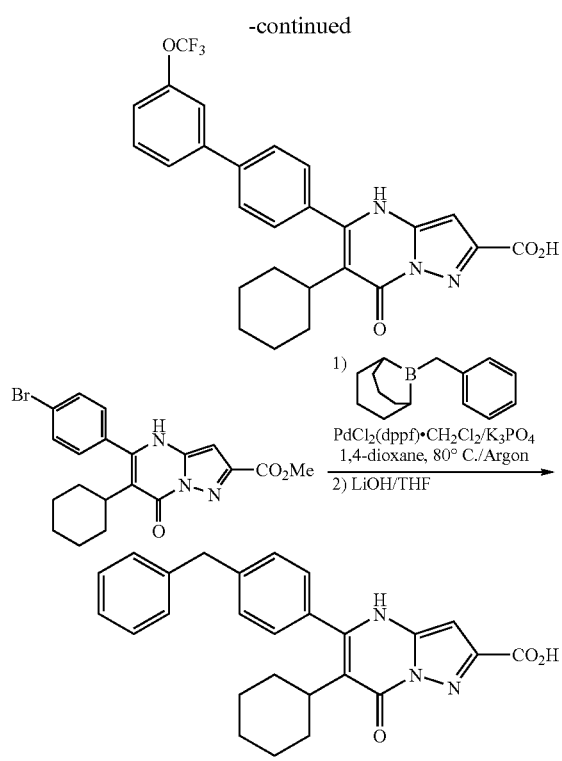

A mixture of 42 mg (0.1 mmol) of 5-(4-bromo-phenyl)-6-cyclohexyl-7-oxo-4,7-dihydro-pyrazolo[1,5-a]pyrimidine-2-carboxylic acid methyl ester, 21 mg (0.15 mmol) of 3,5-dimethyl-isoxazoleboronic acid, 7.3 mg (0.01 mmol) of Pd catalyst, and 63 mg (0.3 mmol) of potassium phosphate in 1 mL of 1,4-dioxane was shaken at 95° C. in a sandbath overnight. The reaction mixture was then diluted with dichloromethane, filtered through a small pad of Celite, dried over sodium sulfate and evaporated to give a residue, which was purified via reverse-phase chromatography (Gilson) to afford desired 6-cyclohexyl-5-[4-(3,5-dimethyl-isoxazol-4-yl)-phenyl]-7-oxo-4,7-dihydro-pyrazolo[1,5-a]pyrimidine-2-carboxylic acid methyl ester as a solid as indicated by LC-MS—calcd for $C_{25}H_{26}N_4O_4$ $[M^++H]^+$: 447.19, found: 447.3. This material was then converted to 6-cyclohexyl-5-[4-(3,5-dimethyl-isoxazol-4-yl)-phenyl]-7-oxo-4,7-dihydro-pyrazolo[1,5-a]pyrimidine-2-carboxylic acid (591) via the well known LiOH saponification protocol (37% yield over 2 steps); LC-MS—calcd for $C_{24}H_{24}N_4O_4$ $[M^++H]^+$: 433.18, found: 433.1.

According to a modification of a literature procedure (Suzuki, A. et al *Tetrahedron Lett.* 1986, 27, 6369-6372) a mixture of 43 mg (0.1 mmol) of 5-(4-bromo-phenyl)-6-cyclohexyl-7-oxo-4,7-dihydro-pyrazolo[1,5-a]pyrimidine-2-carboxylic acid methyl ester, 7.3 mg (0.01 mmol) of Pd catalyst, 0.4 mL (0.2 mmol) of B-Benzyl-9-BBN 0.5 M solution in THF, and 63 mg (0.3 mmol) of potassium phosphate, was purged with argon, 1 mL of 1,4-dioxane was added, and the resulting mixture was shaken at 80° C. in a sandbath overnight. The reaction mixture was then diluted with dichloromethane, filtered through a small pad of Celite, dried over sodium sulfate and evaporated to give a residue, which was purified via reverse-phase chromatography (Gilson) to afford desired 5-(4-benzyl-phenyl)-6-cyclohexyl-7-oxo-4,7-dihydro-pyrazolo[1,5-a]pyrimidine-2-carboxylic acid methyl ester as a solid as indicated by LC-MS—calcd for $C_{27}H_{27}N_3O_3$ $[M^++H]^+$: 442.21, found: 442.2. This material was then converted to 5-(4-benzyl-phenyl)-6-cyclohexyl-7-oxo-4,7-dihydro-pyrazolo[1,5-a]pyrimidine-2-carboxylic acid (581) via a LiOH saponification (33% yield over 2 steps); LC-MS—calcd for $C_{26}H_{25}N_3O_3$ $[M^++H]^+$: 428.19, found: 428.2.

Example 40

Synthesis of 6-cyclohexyl-5-furan-2-yl-7-oxo-4,7-dihydro-pyrazolo[1,5-a]pyrimidine-2-carboxylic acid and 6-cyclohexyl-5-(3-fluoro-phenyl)-7-oxo-4,7-dihydro-pyrazolo[1,5-a]pyrimidine-2-carboxylic acid

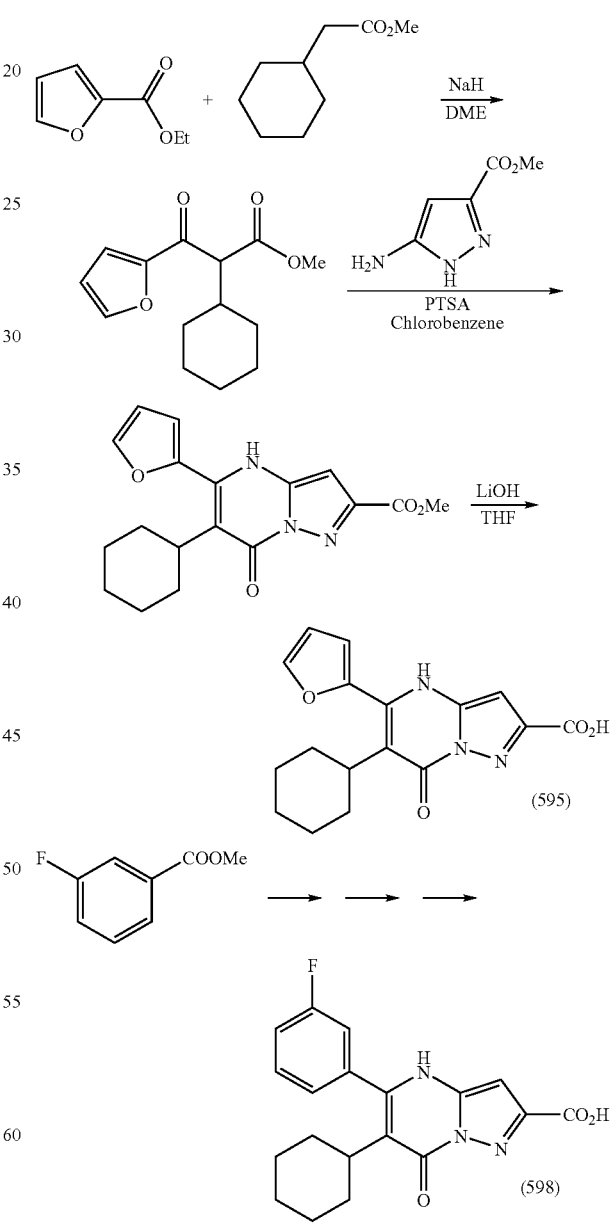

To an ice cold suspension of 0.92 g (23 mmol) of sodium hydride (NaH 60% dispersion in mineral oil) (previously washed with hexane and dried under vacuum) in 25 mL of 1,2-dimethoxyethane (DME) was added 0.9 g (5.76 mmol) of methyl cyclohexylacetate, and the resulting mixture was stirred at 0° C. for 20 min. Then 1.2 g (8.56 mmol) of ethyl 2-furoate was added, and the reaction mixture was heated at reflux overnight. The mixture was then cooled to 0° C., quenched by the addition of 1 M HCl solution to pH=3, and extracted with ethyl acetate. The combined organic extracts were washed with brine, dried over sodium sulfate and concentrated to give a brown oil which was chromatographed on silica gel (Biotage; 10% hexane in dichloromethane) to afford 1.1 g (76% yield) of desired 2-cyclohexyl-3-furan-2-yl-3-oxo-propionic acid methyl ester as indicated by $^1$H NMR.

A mixture of 1.1 g (4.4 mmol) of 2-cyclohexyl-3-furan-2-yl-3-oxo-propionic acid methyl ester, 0.592 g (4.2 mmol) of 5-amino-1H-pyrazole-3-carboxylic acid methyl ester, 76 mg (0.4 mmol, 10 mol %) of p-toluenesulfonic acid monohydrate (PTSA), and 50 mL of chlorobenzene was heated at 120° C. overnight. The reaction mixture was then concentrated to a residue which was chromatographed on silica gel (7% methanol in dichloromethane) to afford 0.46 g (32% yield) of desired 6-cyclohexyl-5-furan-2-yl-7-oxo-4,7-dihydro-pyrazolo[1,5-a]pyrimidine-2-carboxylic acid methyl ester as indicated by $^1$H NMR; LC-MS—calcd for $C_{18}H_{19}N_3O_4$ $[M^++H]^+$: 342.14, found: 342.3.

Conversion of 6-cyclohexyl-5-furan-2-yl-7-oxo-4,7-dihydro-pyrazolo[1,5-a]pyrimidine-2-carboxylic acid methyl ester to 6-cyclohexyl-5-furan-2-yl-7-oxo-4,7-dihydro-pyrazolo[1,5-a]pyrimidine-2-carboxylic acid (595) was accomplished via the well known LiOH saponification protocol where the yield was 77%. LC-MS—calcd for $C_{17}H_{17}N_3O_4$ $[M^++H]^+$: 328.13, found: 328.1. $^1$H NMR (DMSO-$d_6$) δ8.06-8.05d. J=2 Hz,⃞6.99-6.98 (d, J=3.6 Hz, 1H), 6.80-6.78 (d of d, J=3.6 Hz, J=2 Hz, 1H), 6.39s, 1H), 2.79-2.71 (m, 1H), 2.25-2.16 (m, 2H), 1.77-1.75 (m, 2H), 1.66-1.65 (m, 1H), 1.59-1.55 (m, 2H), 1.25-1.20 (m, 3H).

Note that the same synthetic scheme was carried out for 3-fluoro-benzoic acid methyl ester as depicted above to afford 6-cyclohexyl-5-(3-fluoro-phenyl)-7-oxo-4,7-dihydro-pyrazolo[1,5-a]pyrimidine-2-carboxylic acid (598); the cyclization yield was slightly improved (54%).

Example 41

Synthesis of 2-[(6-cyclohexyl-5-furan-2-yl-7-oxo-4,7-dihydro-pyrazolo[1,5-a]pyrimidine-2-carbonyl)-amino]-3-(1H-indol-2-yl)-propionic acid

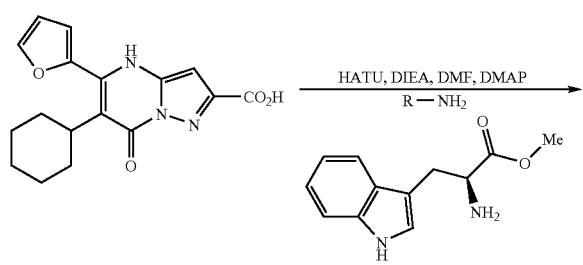

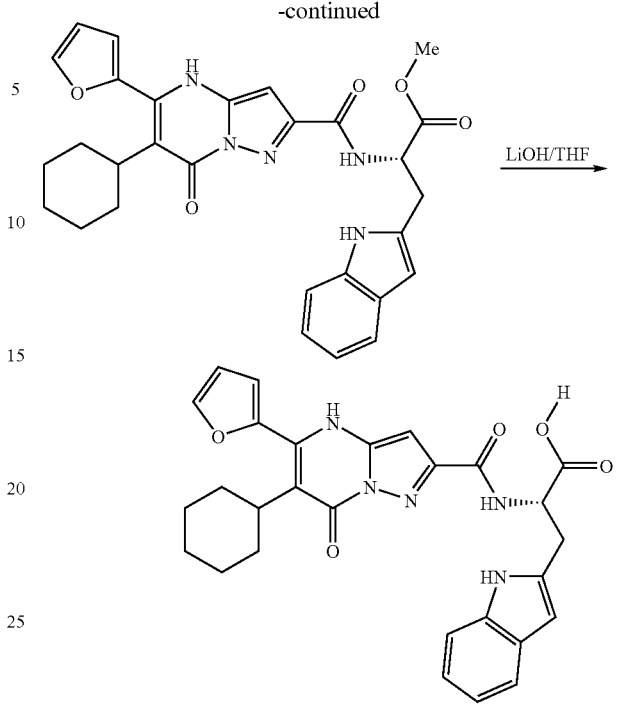

To a solution of 8.2 mg (0.025 mmol) of 6-cyclohexyl-5-furan-2-yl-7-oxo-4,7-dihydro-pyrazolo[1,5-a]pyrimidine-2-carboxylic acid in 2 mL of dimethylformamide (DMF) was added 0.009 mL (0.05 mmol) of diisopropylethylamine (DIEA), a few crystals of dimethylaminopyridine (DMAP cat), 7 mg (0.027 mmol) of L-tryptophan methyl ester hydrochloride, followed by 11 mg (0.03 mmol) of HATU, and the resulting mixture was stirred at rt overnight. The reaction mixture was diluted with ethyl acetate, washed with 0.1 N sodium hydroxide solution (2 times) and brine. The separated organic layer was dried over sodium sulfate and concentrated to give a residue which was purified via reverse-phase chromatography (Gilson) to afford desired 2-[(6-cyclohexyl-5-furan-2-yl-7-oxo-4,7-dihydro-pyrazolo[1,5-a]pyrimidine-2-carbonyl)-amino]-3-(1H-indol-2-yl)-propionic acid methyl ester (606). This compound was then converted to 2-[(6-cyclohexyl-5-furan-2-yl-7-oxo-4,7-dihydro-pyrazolo[1,5-a]pyrimidine-2-carbonyl)-amino]-3-(1H-indol-2-yl)-propionic acid (599) via the well known LiOH saponification protocol (39% yield over 2 steps); LC-MS calcd. for $C_{28}H_{27}N_5O_5$ $[M^++H]^+$: 514.2; found: 514.2.

Note that this protocol was used for most of the amides in this series, however for expediency in some cases a different amidation protocol was utilized as follows: To a solution of the acid in tetrahydrofuran (THF) was added 4 equiv of amine (R—NH$_2$), followed by 2 equiv of 1-hydroxybenzotriazole (HOBt) and 4 equiv of PS-carbodiimide resin, and the resulting mixture was stirred at rt overnight. The reaction mixture was then treated with 4 equiv of MP-carbonate resin and 4.8 equiv of PS-TsOH resin, and stirring was continued at rt for 4 h. The mixture was then filtered and washed with THF, and the combined THF extracts were concentrated to afford the crude coupling product.

In the second (deprotection) step, a typical aqueous LiOH mediated saponification was employed for those amine building blocks containing methyl or ethyl esters, and for those amine building blocks containing t-butyl esters or ethers a typical 95:5 TFA:water deprotection protocol was carried out.

Example 42

Synthesis of N-(6-cyclohexyl-5-furan-2-yl-7-oxo-4,7-dihydro-pyrazolo[1,5-a]pyrimidine-2-carbonyl)-C-phenyl-methanesulfonamide

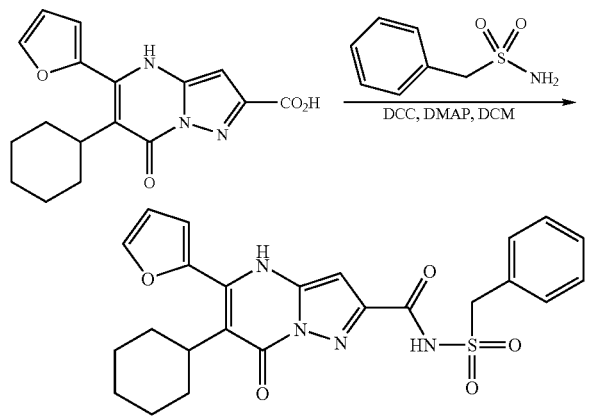

To a solution of 20 mg (0.06 mmol) of 6-cyclohexyl-5-furan-2-yl-7-oxo-4,7-dihydro-pyrazolo[1,5-a]pyrimidine-2-carboxylic acid in 2 mL of dichloromethane (DCM) was a few crystals of DMAP (cat), 12 mg (0.071 mmol) of toluenesulfonamide, followed by 0.071 mL (0.071 mmol) of 1 M dicyclohexylcarbodiimide (DCC) solution in DCM. The reaction mixture was stirred at rt overnight, concentrated, and the resulting residue was purified by reverse-phase chromatography (Gilson) to afford (after lyophilization) 5 mg (17% yield) of desired N-(6-cyclohexyl-5-furan-2-yl-7-oxo-4,7-dihydro-pyrazolo[1,5-a]pyrimidine-2-carbonyl)-C-phenyl-methanesulfonamide (616) as a solid as indicated by LC-MS calcd. for $C_{24}H_{24}N_4O_5S$ $[M^++H]^+$: 481.15; found: 481.1.

Note that N-(6-Cyclohexyl-5-furan-2-yl-7-oxo-4,7-dihydro-pyrazolo[1,5-a]pyrimidine-2-carbonyl)-C,C,C-trifluoro-methanesulfonamide (617) was also synthesized using this protocol.

Example 43

Assay for HCV RNA-Dependent RNA Polymerase Activity

Overview

HCV RNA-dependent RNA polymerase (RdRp) was assayed by scintillation proximity assay (SPA), using an RNA homopolymer (polyC) complexed with a biotinylated oligoG$_{12}$ primer. The primer can be added directly to the template without a denaturing and annealing process. The assay specifically measures the incorporation of [$^3$H] labeled GTP into PolyG. The biotinylated G$_{12}$ enables the capture of the [$^3$H] labeled products by streptavidin-coated SPA beads.

The HCV NS5B RdRp used in this assay was modified by the removal of a 55 amino acid portion from the C-terminus, which contains a hydrophobic domain of 21 amino acids. The HCV NS5B RdRp protein was purified as a polyhistidine (His$_6$) fusion protein expressed in E. coli, and the His-tag was then removed by specific proteolysis.

The assay was carried out at room temperature (~22° C.) in a 96-well plate for 50 minutes. No preincubation was required. The reaction was initiated by adding the enzyme to the RNA substrate in the presence or absence of test compounds. To stop the reaction, 50 μl of 10 mg/mL streptavidin-coated SPA beads supplemented with 100 mM EDTA was added to each well, and the plate was incubated by shaking at room temperature for 15 minutes. After harvesting and a wash by filtration, the radioactivity in each well was counted using a TopCount Scintillation/Luminescence Counter.

The assay conditions are: 50 μl reaction volume incubated at room temperature for 50 minutes in 20 mM Hepes pH 7.3, 7.5 mM DTT, 20 units/mL RNasin, 0.5 ug/mL oligo (G)$_{12}$, 5 μg/mL Poly (C), 0.5 μM GTP, 1 μCi/mL 3H-GTP, 1 mM MgCl$_2$, 60 mM NaCl, 100 μg/mL BSA, 6 nM NS5B CT55 enzyme.

| MATERIALS Buffer: | | |
|---|---|---|
| | 1X | 1 Liter |
| Hepes (pH7.3), | 20 mM | 20 mLs 1M |
| MgCl$_2$ | 10 mM | 10 mLs 1M |
| NaCl | 60 mM | 12 mLs 5M |
| BSA | 100 μg/mL | 100 mgs |
| RNAse-free H20 | | to 1 Liter |

Sterile filter. Store buffer at 4° C.

RNA Template:

A stock solution of 5 mgs/mL was prepared in 20 mM Hepes pH 7.3. Buffer (4 mL) was added to 5 mg of polycytidylic acid [Sigma, #P4903], and the solution was checked for absorbance at OD$_{260}$, and quantitated using the conversion: OD$_{260}$ of 1=40 μg/mL. The solution was then corrected to 5 mg/mL in buffer, aliquoted, and stored at −80° C.

RNA Primer:

A stock solution of 0.5 mg/mL of the primer was prepared in 20 mM Hepes pH 7.3. The solution was checked for absorbance at OD$_{260}$, and quantitated using the conversion: OD$_{260}$ of 1=32 μg/mL, then aliquoted and stored at −80° C.

GTP Substrate:

A stock solution (2 mM) was prepared in 20 mM Hepes pH 7.3, and then aliquoted and stored at −80° C.

NS5BΔCT55 RdRp:

HCV NS5BΔCT55 (from 1b BK strain) was purified as a polyhistidine (His$_6$) fusion protein expressed in E. coli. The protein was modified by removing a 55 amino acid portion from the C-terminus containing a hydrophobic domain of 21 amino acids and a His$_6$-tag was fused to the protein at the C-terminus. After purification, the His-tag was removed by specific proteolysis. The M.W. of the protein is 60323. For a working stock the enzyme was diluted 1:10 from 53 μM down to 5.4 μM, then aliquoted and stored at −80° C. 6 nM of the enzyme was required for each reaction.

Enzyme Storage Buffer:

25 mM Hepes (pH7.5), 5 mM DTT, 0.6 M NaCl, 15% Glycerol, 0.1% Octylglucoside, 2 mg/L Leupeptin, 100 μM PMSF.

The buffer was stored at −20° C.

Zinc Acetate Control Inhibitor:
  50× stock solutions of zinc acetate were made up at 16, 8, 4 and 2 mM in 100% DMSO. Stocks were stored at 4° C.

Filter Plate Wash Buffer:
  200 mL of 20×SSC Buffer and 80 mLs of 1M Hepes pH 7.3 were brought up to 4 Liters in milli-$Q^R$ water. The solution was stored at room temperature.

| INSTRUMENTS AND SUPPLIES | |
|---|---|
| TopCount.NXT Microplate Reader | [Packard, A991200] |
| Mach 3U Harvester 96 | [TomTec, 96-3] |
| Microtest U Bottom Tissue Culture Plate | [Falcon, 353077] |
| Unifilter-96, GF/B white microplate | [Packard, 6005177] |
| Nunc Polypropylene Microplate | [Nunc, 442587] |
| TopSeal-A: 96-well Microplate sealing film | [Packard, 6005185] |
| Mini Orbital Shaker | [Bellco, 7744-08096] |
| CHEMICALS | |
| RNA homopolymer/Poly(C) | [Sigma, #P4903] |
| Biotin-Oligo(G)$_{12}$ | [Oligo, Etc., EO-1/22/98] |
| Unlabeled GTP | [Novagen, 69176-1] |
| [$^3$H] labeled GTP | [Amersham, TRK314] |
| 1 M Hepes (pH7.3) | [USB, 16924] |
| 0.5 M EDTA (pH8.0) | [GibcoBRL, 15575-012] |
| DTT [dithiothreitol] | [GibcoBRL, 15508-013] |
| MgCl$_2$ | [Sigma, M1028] |
| BSA (Fraction V) | [Boehringer Mannheim, 100350] |
| RNaseIN | [Promega, N2515] |
| Leupeptin | [Sigma, L9783] |
| n-Octylglucoside | [Boehringer Mannheim, 1359088] |
| PMSF | [Sigma, 7626] |
| 5 M NaCl | [GibcoBRL, 24740-011] |
| Glycerol | [GibcoBRL, 15514-011] |
| Streptavidin-coated SPA beads | [Amersham, RPNQ0007] |
| PBS (w/o Mg$^{++}$ and Ca$^{++}$) | [GibcoBRL, 14190-144] |
| DMSO | [Sigma, D5879] |
| ZnOAc | [Sigma, Z0625] |
| Rnase-free Water | [USB, US70783] |
| 20X SSC Buffer | [GibcoBRL, 15557-044] |

Assay Procedures

Dilution of Test Compounds
  Stock solutions were prepared at a concentration of 1 mg/mL in 100% DMSO. Compounds were serially diluted in a 96-well polypropylene microplate [Nunc] using a multichannel pipetter as follows:
(1) To Rows B, E and H were added 15 μl DMSO; to Rows C, D, F, and G were added 20 μl DMSO. 12 Compounds were added undiluted across Row A, and then 5 μl of each compound was transferred from Row A to Row B, triturating 10-12 times to mix. Another 5 μl was then transferred from Row B to Row C and so on to Row H, producing 7 serial dilutions of the stock.
(2) 1 μl of each dilution (50×) was transferred to assay plates as described below, producing final concentrations of 20, 5, 1, 0.2, 0.05, 0.01, 0.002, and 0.0005 μg/mL.

Assay Set up: 1 Plate

Enzyme/RNA Mixture (700 μl total, 5 μl/reaction)
660 μl of 1× Buffer
  7 μl 5 mg/mL template polyC
  7 μl 0.5 mg/mL primer oligorG$_{12}$
  3.5 μl 40 U/μl RNAsin
  10 μl 1 M DTT
8 μl of 5.3 μM enzyme (10× for 6 nM final)

Nucleotide Mixture (2 mL total, 20 μl/reaction):
2.0 mL of 1× Buffer
30 μl of 1M DTT
5 μl of ~1 mCi/mL [3H]-GTP
1.3 μl of 2 mM cold GTP Reaction Mixture:
24 μl of 1× Buffer
20 μl of Nucleotide mixture
1 μl of Compound
5 μl of Enzyme Protocol
(1) 24 μl of 1× buffer was placed in each well on a 96-well Plate (Microtest U Bottom Tissue Culture Plate from Falcon).
(2) In order of addition, 1× Buffer, DTT, unlabeled GTP, and $^3$H-GTP were mixed. 20 μl of this nucleotide mixture in 1× Buffer was added to each well.
(3) 1 μl of each test compound dilution was added in triplicate to each well except for the Enzyme/RNA and RNA alone control wells. The control wells received 1 μl of 100% DMSO.
(4) 1 μl of each stock solution of zinc acetate control inhibitor was added to wells in duplicate. 50× zinc acetate stock solutions used were 16, 8, 4 and 2 mM for final concentrations of 320, 160, 80, and 40 μM.
(5) In order of addition, 1× Buffer, DTT, RNasin, Biotin-Oligo(G)$_{12}$, and polyC were mixed and incubated at room temperature for 15 minutes. Enzyme was added, mixed, and 5 μl of the Enzyme/RNA/Buffer Mix was added to each well except for the RNA alone control wells. 5 μl of RNA/1× Buffer Mix was added to the RNA alone control wells.
(6) The plate was shaken for 1 min on a mini-orbital shaker (Bellco) to mix the reaction components thoroughly. Plate was incubated at room temperature (~22° C.) for 50 minutes.
(7) The reaction was stopped by adding 50 μl of streptavidin SPA beads (10 mg/mL in PBS w/o Mg$^{++}$ and Ca$^{++}$ supplemented with 100 mM EDTA) to each well. The plate was then shaken again for 15 minutes at room temperature as in (5) to mix the beads.
(8) The plate was then harvested and washed with Filter Plate Wash Buffer by transferring to a filter plate (Unifilter-96 GF/B white microplate from Packard) using a harvester (Tomtec). Plate was allowed to dry for 30 minutes at 37° C. After drying, the adhesive backing tape (supplied by manufacturer) was applied to the bottom of the Unifilter plate. The top was covered with TopSeal microplate sealing film.
(9) The radioactivity in each well was counted using a TopCount Scintillation/Luminescence Counter.

Representative date for HCV RdRp inhibitors of the invention are shown in Table 1.

Example 43

High Throughput Assay for HCV NS5B RNA-Dependent RNA Polymerase

The Scintillation Proximity Assay (SPA) for HCV NS5B RdRp we developed uses an RNA homopolymer (polyC) complexed with a biotinylated oligoG12 primer. The primer can be added directly to the template without a denaturing and annealing process. The assay specifically measures the incorporation of [3H] labeled GMP into PolyG. The biotinylated G12 enables the capture of the [3H] labeled products by streptavidin-coated SPA beads.

The NS5B enzymes, NS5BCT21-His and NS5BCT55, used in this assay were purified as polyhistidine (His6) fusion proteins expressed in *E. coli*. The NS5BCT21-His protein has been modified by removing a 21 amino acid hydrophobic domain from the C-terminus. A His6-tag was fused to the protein at the C-terminus, replacing the deleted hydrophobic domain. The NS5BCT55 protein has been modified by removing a 55 amino acid portion from the C-terminus containing the hydrophobic domain of 21 amino acids and a His6-tag was fused to the protein at the N-terminus. After purification, the His-tag was removed by specific proteolysis.

The substrate of this assay is a RNA homopolymer template (polyC) complexed with a biotinylated primer (oligoG12). [3H]-GTPs are polymerized into polyG complementing the PolyC template.

The assay is carried out at room temperature (~22° C.) in a 96-well plate for three hours. No preincubation is required. The reaction is initiated by mixing the RNA substrate and the enzyme in the presence or absence of test compounds. EDTA is added to a final concentration of 50 mM to stop the reaction. Streptavidin-coated SPA beads (0.5 mg) are then added to each well. After harvesting and a wash by filtration, the radioactivity in each well was counted using a TopCount Scintillation/Luminescence Counter.

The assay conditions were: 50 μl reaction volume at room temperature for three hours in :20 mM Hepes (pH7.3), 7.5 mM DTT, 10 mM MgCl2, 121 mM NaCl, 100 μg/ml BSA, 2% DMSO, 0.05% glycerol, 5 μM GTP, 1.0 μCi [3H]-GTP, 0.25 μg poly(C)/0.025 μg oligo(G)12, 1 unit of RNaseIN and 0.05 μM NS5BDCT21-His or NS5BDCT55.

| MATERIALS | | | |
|---|---|---|---|
| | 1X | 1.25X | 5X Stock |
| Enzyme buffers: | | | |
| Hepes (pH7.3), | 20 mM | 25 mM | 100 mM |
| MgCl$_2$ | 10 mM | 12.5 mM | 50 mM |
| NaCl120 mM | 150 mM | 600 mM | |
| Reaction buffers: | | | |
| Hepes (pH7.3), | 20 mM | 25 mM | 100 mM |
| MgCl$_2$ | 10 mM | 12.5 mM | 50 mM |
| BSA | 100 μg/ml | 125 μg/ml | 500 μg/ml |

Store buffers at 4° C.

Store substrates and enzyme at −80° C.

NS5BCT21-His Enzyme Storage Buffer:

50 mM Hepes (pH7.3), 5 mM DTT, 0.5 M NaCl, 20% Glycerol, 200 ng/ml Antipain, 100 ng/ml Leupeptin, 50 μM PMSF.

Store buffer at −20° C.

NS5BCT55 Enzyme Storage Buffer:

25 mM Hepes (pH7.5), 10 mM □-Mercaptoethanol, 0.6 M NaCl, 15% Glycerol, 0.1% Octyl-glucaside, 2 mg/L Leupeptin, 100 μM PMSF.

Store buffer at −20° C.

Assay Procedures (1) 9 μl of Rnase-free water is placed in each well on a 96-well Plate (Microtest U Bottom Tissue Culture Plate from Falcon).

(2) In order of addition, Rnase-free H$_2$O, 5× reaction buffer (with BSA), DTT, cold GTP, and $^3$H-GTP are mixed. 20 μl of this nucleotide mixture in 1.25× Reaction buffer is added to each well.

(3) In order of addition, Rnase-free H$_2$O, 5× enzyme buffer (with NaCl), DTT, RNaseIN, Oligo(G)$_{12}$, and polyC are mixed and incubated at room temperature for 15 minutes. Enzyme is added, mixed, and 20 μl of the Enzyme/RNA mixture in 1.25× Enzyme buffer is added to each well except for the RNA alone control wells. 20 ul of Enzyme storage buffer/RNA mixture in 1.25× Enzyme buffer is added to the RNA alone control wells.

(4) 1 μl of each test compound [100% DMSO, 100 μg/ml] is added to each well except for the Enzyme/RNA and RNA alone control wells. The control wells received 1 μl of 100% DMSO.

(5) The plate is shaken gently for 1 min on a mini-orbital shaker (Bellco) to mix the reaction components thoroughly and then incubated at room temperature for 3 hours.

(6) The reaction is stopped by adding 50 μl of streptavidin SPA beads (0.5 mg, resuspended in PBS w/o Mg$^{++}$ and Ca$^{++}$ supplement with 100 mM EDTA to each well. The plate is shaken again as above to mix the beads and incubated at room temperature for 15 minutes.

(7) The plate is then harvested, washed, and transferred to a filter plate using a harvester (Tomtec). The radioactivity in each well is counted using a TopCount Scintillation/Luminescence Counter.

TABLE 1

Inhibition of HCV RdRp[1]

| Compound | MOLSTRUCTURE | Δ-55 Activity | Δ-21 Activity |
|---|---|---|---|
| 1 | 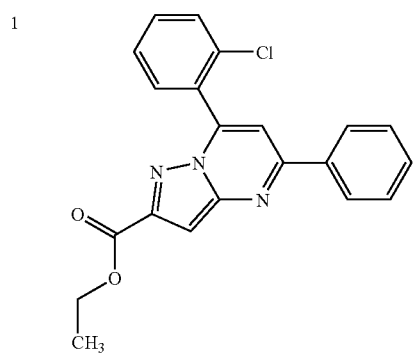 | A | |

TABLE 1-continued

Inhibition of HCV RdRp[1]

| Compound | MOLSTRUCTURE | Δ-55 Activity | Δ-21 Activity |
|---|---|---|---|
| 2 | | | A |
| 3 | | | A |
| 4 | | | A |
| 5 | | | A |

TABLE 1-continued

Inhibition of HCV RdRp[1]

| Compound | MOLSTRUCTURE | Δ-55 Activity | Δ-21 Activity |
|---|---|---|---|
| 6 | ethyl 7-(2-chlorophenyl)-5-(4-fluorophenyl)pyrazolo[1,5-a]pyrimidine-3-carboxylate | | A |
| 7 | ethyl 7-(2-chlorophenyl)-5-(4-fluorophenyl)pyrazolo[1,5-a]pyrimidine-2-carboxylate | | A |
| 8 | ethyl 7-(4-chlorophenyl)-5-(4-fluorophenyl)pyrazolo[1,5-a]pyrimidine-3-carboxylate | | A |
| 9 | ethyl 7-(4-chlorophenyl)-5-(4-fluorophenyl)pyrazolo[1,5-a]pyrimidine-2-carboxylate | | A |

TABLE 1-continued

Inhibition of HCV RdRp[1]

| Compound | MOLSTRUCTURE | Δ-55 Activity | Δ-21 Activity |
|---|---|---|---|
| 10 | | A | |
| 11 | | A | |
| 12 | | A | |
| 13 | | A | |
| 14 | | A | |

TABLE 1-continued

Inhibition of HCV RdRp[1]

| Compound | MOLSTRUCTURE | Δ-55 Activity | Δ-21 Activity |
|---|---|---|---|
| 15 | | | B |
| 16 | | | B |
| 17 | | | A |
| 18 | | | B |
| 19 | | | A |
| 20 | | | A |

TABLE 1-continued

Inhibition of HCV RdRp[1]

| Compound | MOLSTRUCTURE | Δ-55 Activity | Δ-21 Activity |
|---|---|---|---|
| 21 | | | A |
| 22 | | | A |
| 23 | | | A |
| 24 | | | B |
| 25 | | | A |

TABLE 1-continued

Inhibition of HCV RdRp[1]

| Compound | MOLSTRUCTURE | Δ-55 Activity | Δ-21 Activity |
|---|---|---|---|
| 26 | | | A |
| 27 | | | B |
| 28 | | | A |
| 29 | | | A |
| 30 | | | A |

TABLE 1-continued
Inhibition of HCV RdRp[1]
| Compound | MOLSTRUCTURE | Δ-55 Activity | Δ-21 Activity |
|---|---|---|---|
| 31 | 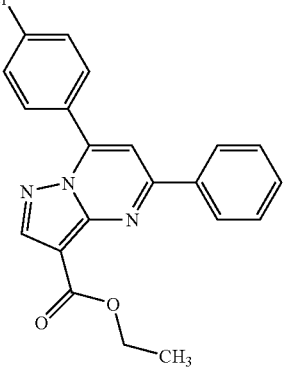 | | A |
| 32 | 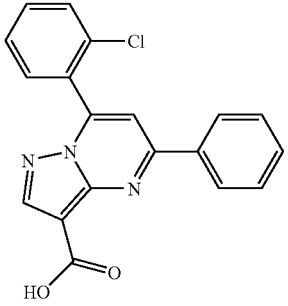 | | A |
| 33 | 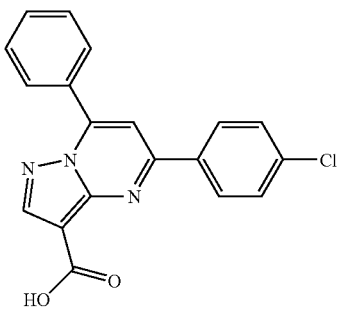 | | A |
| 34 | 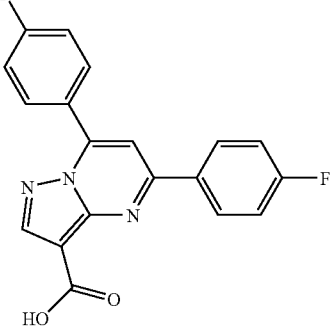 | | A |

TABLE 1-continued

Inhibition of HCV RdRp[1]

| Compound | MOLSTRUCTURE | Δ-55 Activity | Δ-21 Activity |
|---|---|---|---|
| 35 | 7-(2-chlorophenyl)-5-(4-fluorophenyl)pyrazolo[1,5-a]pyrimidine-3-carboxylic acid | | A |
| 36 | 7-(4-chlorophenyl)-5-(4-fluorophenyl)pyrazolo[1,5-a]pyrimidine-3-carboxylic acid | | A |
| 37 | 7-(2-chlorophenyl)-5-phenylpyrazolo[1,5-a]pyrimidine-2-carboxylic acid | | A |
| 38 | 5-(4-chlorophenyl)-7-phenylpyrazolo[1,5-a]pyrimidine-2-carboxylic acid | | A |

TABLE 1-continued
Inhibition of HCV RdRp[1]
| Compound | MOLSTRUCTURE | Δ-55 Activity | Δ-21 Activity |
|---|---|---|---|
| 39 | 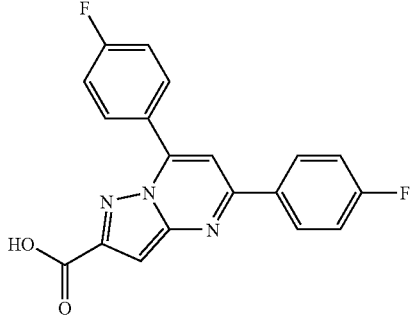 | | A |
| 40 | 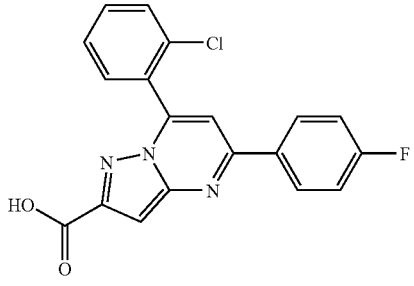 | | A |
| 41 | 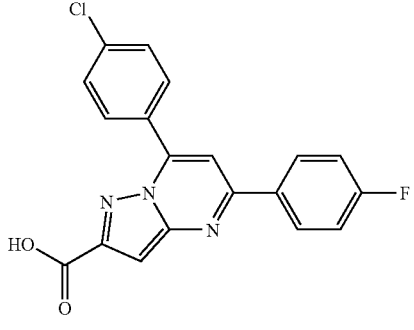 | | A |
| 42 | 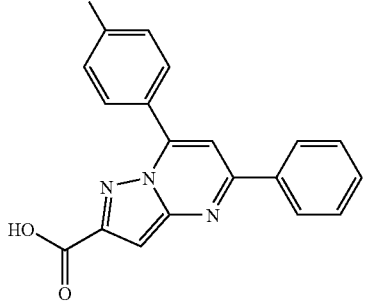 | | A |

TABLE 1-continued

Inhibition of HCV RdRp[1]

| Compound | MOLSTRUCTURE | Δ-55 Activity | Δ-21 Activity |
|---|---|---|---|
| 43 | | | A |
| 44 | | | A |
| 45 | | | A |
| 46 | | | A |
| 47 | | | A |

TABLE 1-continued

Inhibition of HCV RdRp[1]

| Compound | MOLSTRUCTURE | Δ-55 Activity | Δ-21 Activity |
|---|---|---|---|
| 48 | | A | |
| 49 | | A | |
| 50 | | A | |
| 51 | | A | |
| 52 | | A | |
| 53 | | A | |

TABLE 1-continued

Inhibition of HCV RdRp[1]

| Compound | MOLSTRUCTURE | Δ-55 Activity | Δ-21 Activity |
|---|---|---|---|
| 54 | | | A |
| 55 | | | A |
| 56 | | | A |
| 57 | | | A |
| 58 | | | A |

TABLE 1-continued
Inhibition of HCV RdRp[1]
| Compound | MOLSTRUCTURE | Δ-55 Activity | Δ-21 Activity |
|---|---|---|---|
| 59 | 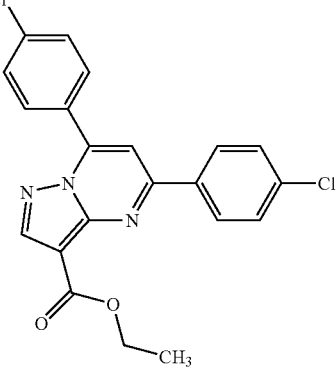 | | A |
| 60 | 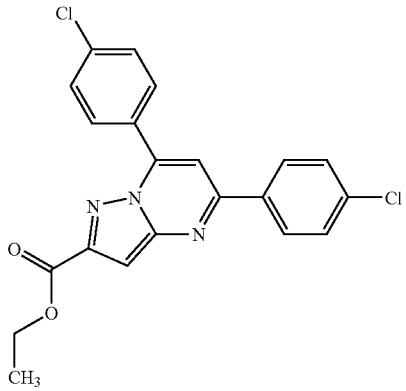 | | A |
| 61 | 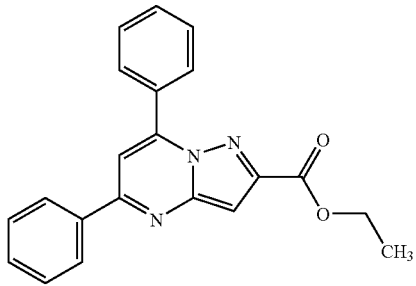 | | A |
| 62 | 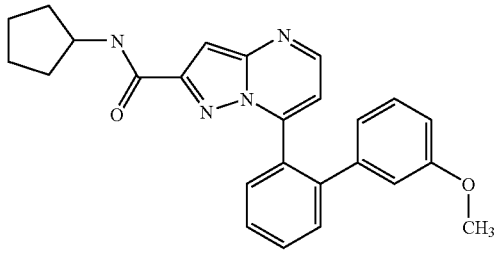 | | A |

TABLE 1-continued

Inhibition of HCV RdRp[1]

| Compound | MOLSTRUCTURE | Δ-55 Activity | Δ-21 Activity |
|---|---|---|---|
| 63 | | | A |
| 64 | | | B |
| 65 | | | A |
| 66 | | | A |

TABLE 1-continued

Inhibition of HCV RdRp[1]

| Compound | MOLSTRUCTURE | Δ-55 Activity | Δ-21 Activity |
|---|---|---|---|
| 67 | | | A |
| 68 | | | A |
| 69 | | | A |
| 70 | | | A |

TABLE 1-continued

Inhibition of HCV RdRp[1]

| Compound | MOLSTRUCTURE | Δ-55 Activity | Δ-21 Activity |
|---|---|---|---|
| 71 | | | A |
| 72 | | | A |
| 73 | | | A |

TABLE 1-continued
Inhibition of HCV RdRp[1]
| Compound | MOLSTRUCTURE | Δ-55 Activity | Δ-21 Activity |
|---|---|---|---|
| 74 | 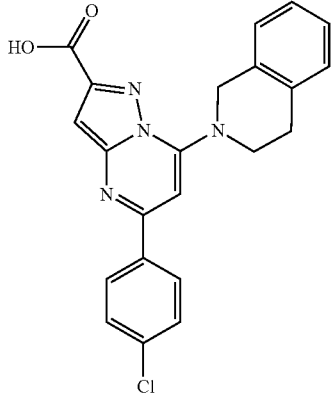 | | A |
| 75 | 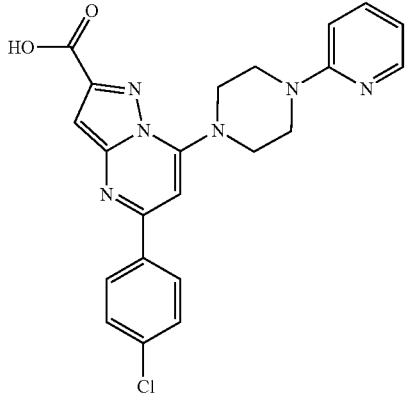 | | A |
| 76 | 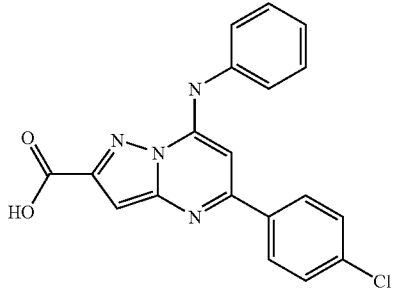 | | A |
| 77 | 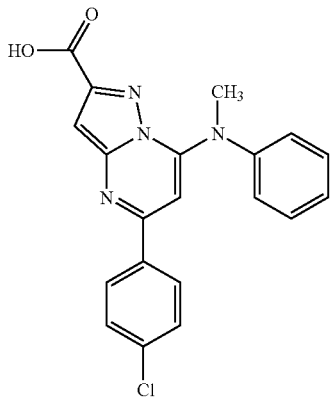 | | A |

TABLE 1-continued

Inhibition of HCV RdRp[1]

| Compound | MOLSTRUCTURE | Δ-55 Activity | Δ-21 Activity |
|---|---|---|---|
| 78 | | | A |
| 79 | | | A |
| 80 | | | A |

TABLE 1-continued

Inhibition of HCV RdRp[1]

| Compound | MOLSTRUCTURE | Δ-55 Activity | Δ-21 Activity |
|---|---|---|---|
| 81 | | A | |
| 82 | | A | |
| 83 | | A | |
| 84 | | A | |

TABLE 1-continued

Inhibition of HCV RdRp[1]

| Compound | MOLSTRUCTURE | Δ-55 Activity | Δ-21 Activity |
| --- | --- | --- | --- |
| 85 | | | A |
| 86 | | | A |
| 87 | | | A |
| 88 | | | A |
| 89 | | | A |

TABLE 1-continued
Inhibition of HCV RdRp[1]
| Compound | MOLSTRUCTURE | Δ-55 Activity | Δ-21 Activity |
|---|---|---|---|
| 90 | 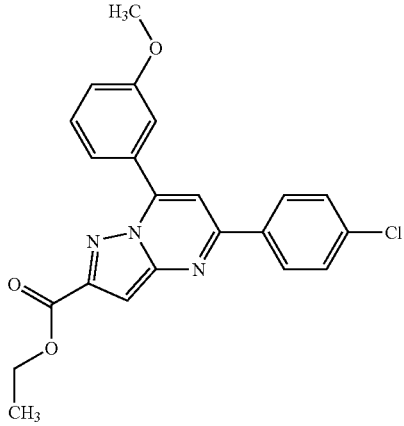 | A | |
| 91 | 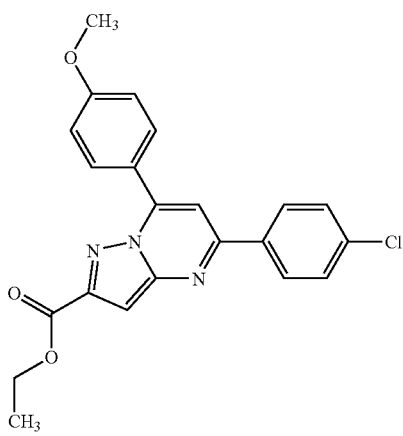 | A | |
| 92 | 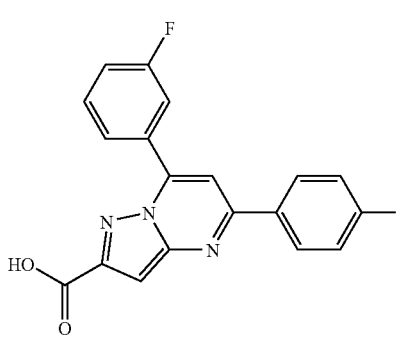 | A | |
| 93 | 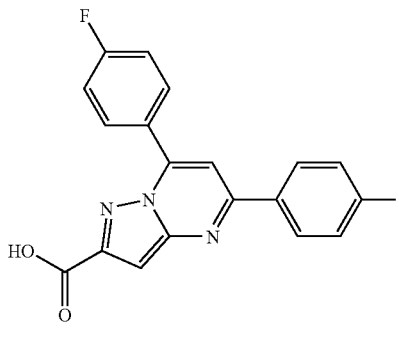 | A | |

TABLE 1-continued

Inhibition of HCV RdRp[1]

| Compound | MOLSTRUCTURE | Δ-55 Activity | Δ-21 Activity |
|---|---|---|---|
| 94 | | | A |
| 95 | | | A |
| 96 | | | A |
| 97 | | | A |

TABLE 1-continued

Inhibition of HCV RdRp[1]

| Compound | MOLSTRUCTURE | A-55 Activity | A-21 Activity |
|---|---|---|---|
| 98 | | A | |
| 99 | | A | |
| 100 | | B | B |
| 101 | | A | |

TABLE 1-continued

Inhibition of HCV RdRp[1]

| Compound | MOLSTRUCTURE | Δ-55 Activity | Δ-21 Activity |
|---|---|---|---|
| 102 | | A | |
| 103 | | A | |
| 104 | | A | |
| 105 | | A | |

TABLE 1-continued

Inhibition of HCV RdRp[1]

| Compound | MOLSTRUCTURE | Δ-55 Activity | Δ-21 Activity |
|---|---|---|---|
| 106 | | | A |
| 107 | | | A |
| 108 | | | A |
| 109 | | | A |
| 110 | | | A |

TABLE 1-continued

Inhibition of HCV RdRp[1]

| Compound | MOLSTRUCTURE | Δ-55 Activity | Δ-21 Activity |
|---|---|---|---|
| 111 | 7-(3-chlorophenyl)-5-(2,4-dichlorophenyl)pyrazolo[1,5-a]pyrimidine-2-carboxylic acid | | A |
| 112 | 7-(4-chlorophenyl)-5-(2,4-dichlorophenyl)pyrazolo[1,5-a]pyrimidine-2-carboxylic acid | | A |
| 113 | 5-(2,4-dichlorophenyl)-7-(3-methoxyphenyl)pyrazolo[1,5-a]pyrimidine-2-carboxylic acid | | A |
| 114 | 5-(2,4-dichlorophenyl)-7-(4-methoxyphenyl)pyrazolo[1,5-a]pyrimidine-2-carboxylic acid | | A |

TABLE 1-continued

Inhibition of HCV RdRp[1]

| Compound | MOLSTRUCTURE | Δ-55 Activity | Δ-21 Activity |
|---|---|---|---|
| 115 | | A | |
| 116 | | B | B |
| 117 | | A | |
| 118 | | A | |

TABLE 1-continued

Inhibition of HCV RdRp[1]

| Compound | MOLSTRUCTURE | Δ-55 Activity | Δ-21 Activity |
|---|---|---|---|
| 119 | 7-(biphenyl-4-yl)-5-(4-fluorophenyl)pyrazolo[1,5-a]pyrimidine-2-carboxylic acid | B | B |
| 120 | 7-phenyl-5-(4-phenoxyphenyl)pyrazolo[1,5-a]pyrimidine-2-carboxylic acid | A | |
| 121 | 7-(3-fluorophenyl)-5-(4-phenoxyphenyl)pyrazolo[1,5-a]pyrimidine-2-carboxylic acid | A | |
| 122 | 7-(3-chlorophenyl)-5-(4-phenoxyphenyl)pyrazolo[1,5-a]pyrimidine-2-carboxylic acid | B | B |

TABLE 1-continued

Inhibition of HCV RdRp[1]

| Compound | MOLSTRUCTURE | Δ-55 Activity | Δ-21 Activity |
|---|---|---|---|
| 123 | (4-chlorophenyl)-(4-phenoxyphenyl)-pyrazolo[1,5-a]pyrimidine-2-carboxylic acid | B | B |
| 124 | (3-methoxyphenyl)-(4-phenoxyphenyl)-pyrazolo[1,5-a]pyrimidine-2-carboxylic acid | B | B |
| 125 | (4-methoxyphenyl)-(4-phenoxyphenyl)-pyrazolo[1,5-a]pyrimidine-2-carboxylic acid | B | B |
| 126 | (4-phenoxyphenyl)-(4-chlorophenyl)-pyrazolo[1,5-a]pyrimidine-2-carboxylic acid | B | B |

TABLE 1-continued

Inhibition of HCV RdRp[1]

| Compound | MOLSTRUCTURE | Δ-55 Activity | Δ-21 Activity |
|---|---|---|---|
| 127 | | A | |
| 128 | | B | B |
| 129 | | B | B |

TABLE 1-continued

Inhibition of HCV RdRp[1]

| Compound | MOLSTRUCTURE | Δ-55 Activity | Δ-21 Activity |
|---|---|---|---|
| 130 | | B | B |
| 131 | | | A |
| 132 | | | A |
| 133 | | B | B |

TABLE 1-continued

Inhibition of HCV RdRp[1]

| Compound | MOLSTRUCTURE | Δ-55 Activity | Δ-21 Activity |
|---|---|---|---|
| 134 | | B | B |
| 135 | | B | B |
| 136 | | A | |
| 137 | | B | |

TABLE 1-continued

Inhibition of HCV RdRp[1]

| Compound | MOLSTRUCTURE | A-55 Activity | A-21 Activity |
| --- | --- | --- | --- |
| 138 | | A | |
| 139 | | A | |
| 140 | | B | B |
| 141 | | A | |

TABLE 1-continued

Inhibition of HCV RdRp[1]

| Compound | MOLSTRUCTURE | Δ-55 Activity | Δ-21 Activity |
|---|---|---|---|
| 142 | | | A |
| 143 | | | A |
| 144 | | | A |
| 145 | | | A |
| 146 | | | A |

TABLE 1-continued

Inhibition of HCV RdRp[1]

| Compound | MOLSTRUCTURE | Δ-55 Activity | Δ-21 Activity |
|---|---|---|---|
| 147 | | | A |
| 148 | | | A |
| 149 | | | A |
| 150 | | | A |

TABLE 1-continued

Inhibition of HCV RdRp[1]

| Compound | MOLSTRUCTURE | Δ-55 Activity | Δ-21 Activity |
|---|---|---|---|
| 151 | | | A |
| 152 | | | A |
| 153 | | | A |
| 154 | | | A |

TABLE 1-continued

Inhibition of HCV RdRp[1]

| Compound | MOLSTRUCTURE | A-55 Activity | A-21 Activity |
|---|---|---|---|
| 155 | | A | |
| 156 | | A | |
| 157 | | B | B |
| 158 | | A | |

TABLE 1-continued
Inhibition of HCV RdRp[1]
| Compound | MOLSTRUCTURE | Δ-55 Activity | Δ-21 Activity |
|---|---|---|---|
| 159 | 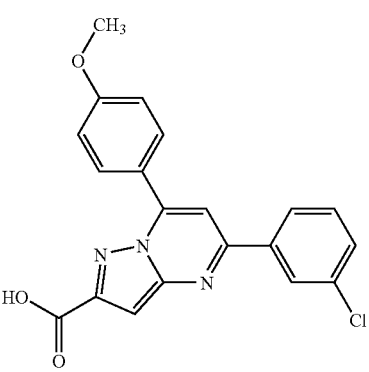 | | A |
| 160 | 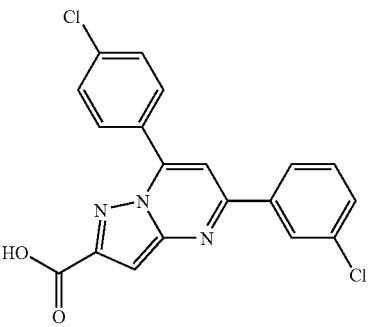 | | A |
| 161 | 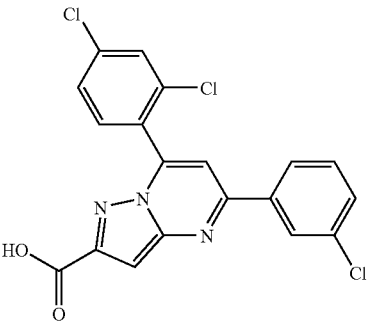 | | A |
| 162 | 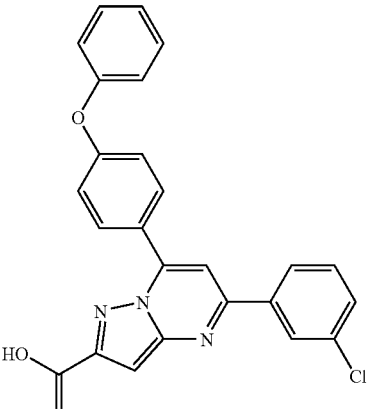 | B | B |

TABLE 1-continued

Inhibition of HCV RdRp[1]

| Compound | MOLSTRUCTURE | A-55 Activity | A-21 Activity |
|---|---|---|---|
| 163 | | B | B |
| 164 | | A | |
| 165 | | A | B |
| 166 | | A | |

TABLE 1-continued

Inhibition of HCV RdRp[1]

| Compound | MOLSTRUCTURE | Δ-55 Activity | Δ-21 Activity |
|---|---|---|---|
| 167 | | | A |
| 168 | | | B |
| 169 | | | A |
| 170 | | | A |

TABLE 1-continued
Inhibition of HCV RdRp[1]
| Compound | MOLSTRUCTURE | Δ-55 Activity | Δ-21 Activity |
| --- | --- | --- | --- |
| 171 | 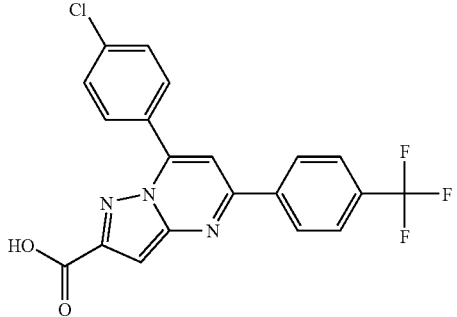 | | A |
| 172 | 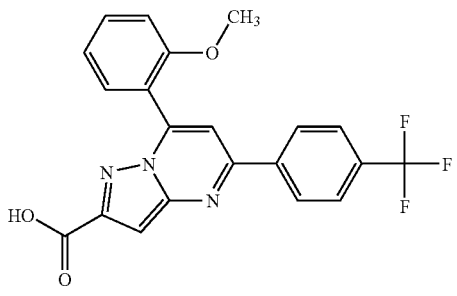 | | A |
| 173 | 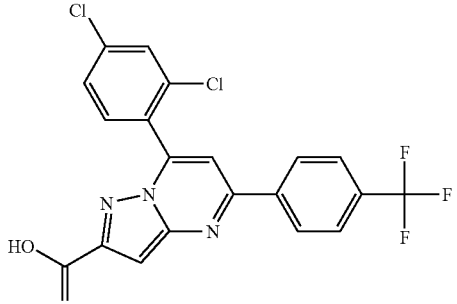 | | A |
| 174 | 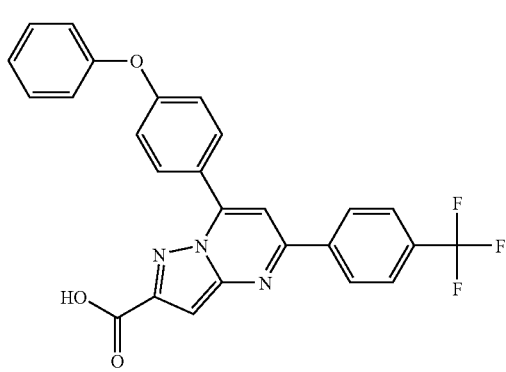 | | B |

TABLE 1-continued
Inhibition of HCV RdRp[1]
| Compound | MOLSTRUCTURE | Δ-55 Activity | Δ-21 Activity |
|---|---|---|---|
| 175 | 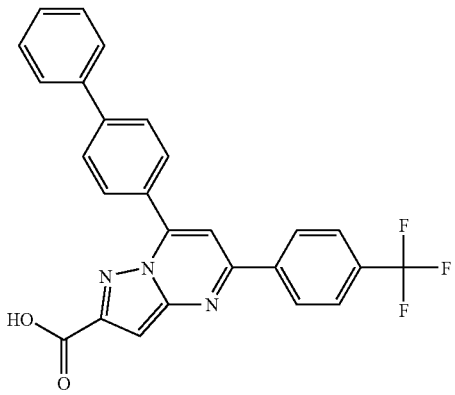 | B | |
| 176 | 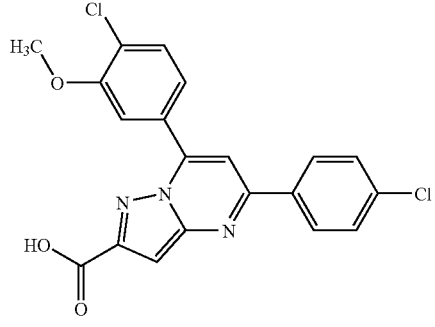 | A | |
| 177 | 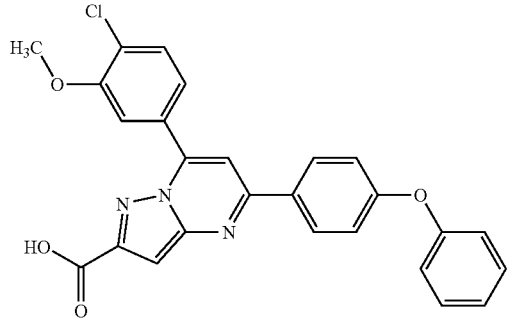 | B | |
| 178 | 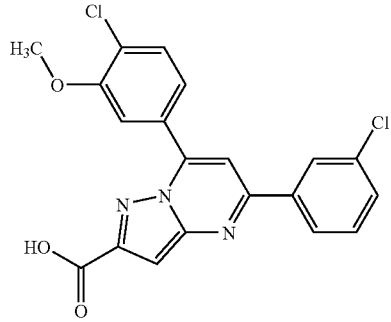 | A | |

TABLE 1-continued

Inhibition of HCV RdRp[1]

| Compound | MOLSTRUCTURE | Δ-55 Activity | Δ-21 Activity |
|---|---|---|---|
| 179 | (structure) | | A |
| 180 | (structure) | | B |
| 181 | (structure) | | B |
| 182 | (structure) | | A |

TABLE 1-continued

Inhibition of HCV RdRp[1]

| Compound | MOLSTRUCTURE | Δ-55 Activity | Δ-21 Activity |
|---|---|---|---|
| 183 | | | B |
| 184 | | | B |
| 185 | | | B |

TABLE 1-continued

Inhibition of HCV RdRp[1]

| Compound | MOLSTRUCTURE | Δ-55 Activity | Δ-21 Activity |
|---|---|---|---|
| 186 | | B | |
| 187 | | B | B |
| 188 | | B | B |

TABLE 1-continued

Inhibition of HCV RdRp[1]

| Compound | MOLSTRUCTURE | Δ-55 Activity | Δ-21 Activity |
|---|---|---|---|
| 189 | | A | |
| 190 | | B | B |
| 191 | | B | B |
| 192 | | A | |

TABLE 1-continued

Inhibition of HCV RdRp[1]

| Compound | MOLSTRUCTURE | Δ-55 Activity | Δ-21 Activity |
|---|---|---|---|
| 193 | 7-(3,5-dichlorophenyl)-5-(4-(trifluoromethyl)phenyl)pyrazolo[1,5-a]pyrimidine-2-carboxylic acid | | A |
| 194 | 7-(3-fluoro-5-methoxyphenyl)-5-(4-(trifluoromethyl)phenyl)pyrazolo[1,5-a]pyrimidine-2-carboxylic acid | | A |
| 195 | 7-(3,4-dichlorophenyl)-5-(4-fluorophenyl)pyrazolo[1,5-a]pyrimidine-2-carboxylic acid | | B |
| 196 | 7-(3-fluoro-4-methoxyphenyl)-5-(4-(trifluoromethyl)phenyl)pyrazolo[1,5-a]pyrimidine-2-carboxylic acid | | A |

TABLE 1-continued
Inhibition of HCV RdRp[1]
| Compound | MOLSTRUCTURE | Δ-55 Activity | Δ-21 Activity |
|---|---|---|---|
| 197 | 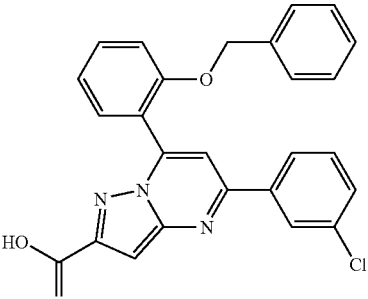 | B | B |
| 198 | 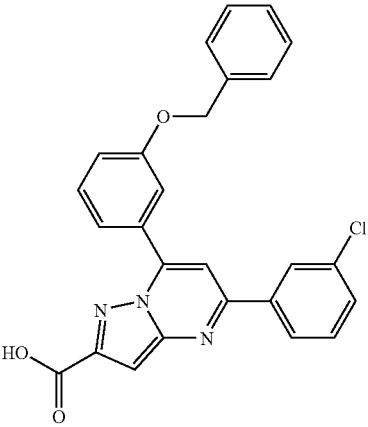 | B | B |
| 199 | 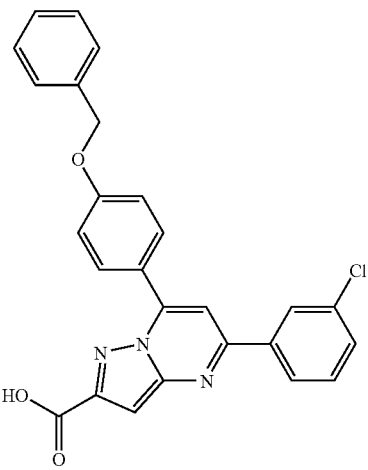 | B | B |
| 200 | 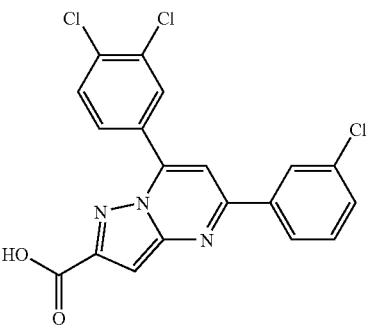 | B | A |

TABLE 1-continued

Inhibition of HCV RdRp[1]

| Compound | MOLSTRUCTURE | Δ-55 Activity | Δ-21 Activity |
|---|---|---|---|
| 201 | | A | |
| 202 | | B | B |
| 203 | | B | |
| 204 | | A | |

TABLE 1-continued

Inhibition of HCV RdRp[1]

| Compound | MOLSTRUCTURE | Δ-55 Activity | Δ-21 Activity |
|---|---|---|---|
| 205 | | B | B |
| 206 | | B | B |
| 207 | | | A |
| 208 | | | A |

TABLE 1-continued

Inhibition of HCV RdRp[1]

| Compound | MOLSTRUCTURE | Δ-55 Activity | Δ-21 Activity |
|---|---|---|---|
| 209 | | A | |
| 210 | | A | |
| 211 | | B | B |
| 212 | | B | B |

TABLE 1-continued

Inhibition of HCV RdRp[1]

| Compound | MOLSTRUCTURE | Δ-55 Activity | Δ-21 Activity |
|---|---|---|---|
| 213 | | A | |
| 214 | | B | B |
| 215 | | A | |
| 216 | | B | |

TABLE 1-continued
Inhibition of HCV RdRp[1]
| Compound | MOLSTRUCTURE | Δ-55 Activity | Δ-21 Activity |
|---|---|---|---|
| 217 | 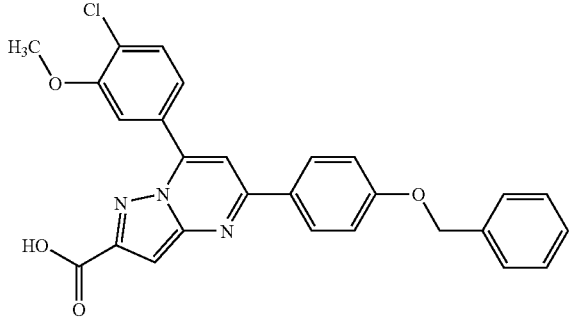 | B | B |
| 218 | 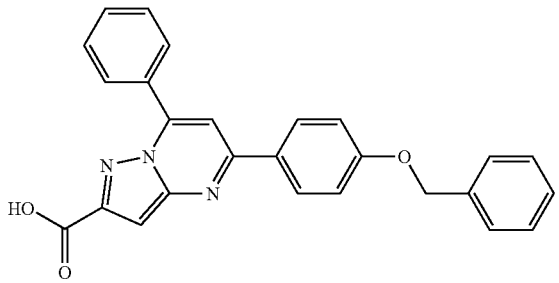 | A | |
| 219 | 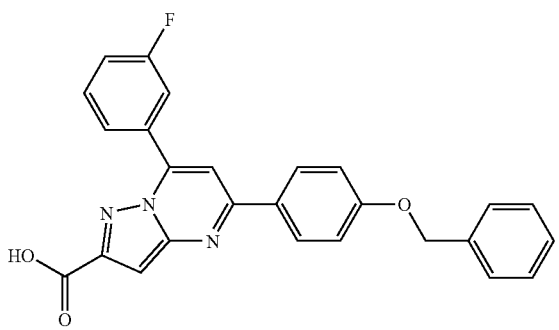 | A | |
| 220 | 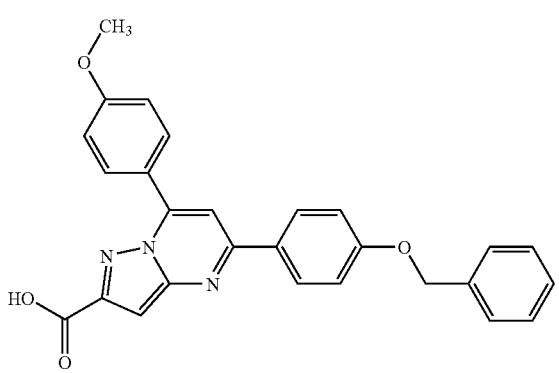 | B | B |

TABLE 1-continued

Inhibition of HCV RdRp[1]

| Compound | MOLSTRUCTURE | Δ-55 Activity | Δ-21 Activity |
|---|---|---|---|
| 221 | | | A |
| 222 | | | A |
| 223 | | | B |
| 224 | | | A |

TABLE 1-continued

Inhibition of HCV RdRp[1]

| Compound | MOLSTRUCTURE | Δ-55 Activity | Δ-21 Activity |
|---|---|---|---|
| 225 | | | A |
| 226 | | | A |
| 227 | | | B |
| 228 | | | B |

TABLE 1-continued

Inhibition of HCV RdRp[1]

| Compound | MOLSTRUCTURE | Δ-55 Activity | Δ-21 Activity |
|---|---|---|---|
| 229 | | | B |
| 230 | | | A |
| 231 | | | A |
| 232 | | | A |

TABLE 1-continued

Inhibition of HCV RdRp[1]

| Compound | MOLSTRUCTURE | Δ-55 Activity | Δ-21 Activity |
|---|---|---|---|
| 233 | | | A |
| 234 | | | A |
| 235 | | | A |
| 236 | | | A |

TABLE 1-continued

Inhibition of HCV RdRp[1]

| Compound | MOLSTRUCTURE | Δ-55 Activity | Δ-21 Activity |
|---|---|---|---|
| 237 | | | A |
| 238 | | | A |
| 239 | | | A |
| 240 | | | A |

TABLE 1-continued

Inhibition of HCV RdRp[1]

| Compound | MOLSTRUCTURE | Δ-55 Activity | Δ-21 Activity |
|---|---|---|---|
| 241 | | | A |
| 242 | | | A |
| 243 | | | A |

TABLE 1-continued

Inhibition of HCV RdRp[1]

| Compound | MOLSTRUCTURE | A-55 Activity | A-21 Activity |
|---|---|---|---|
| 244 | | A | |
| 245 | | A | |
| 246 | | A | |

TABLE 1-continued

Inhibition of HCV RdRp[1]

| Compound | MOLSTRUCTURE | A-55 Activity | A-21 Activity |
|---|---|---|---|
| 247 | | | A |
| 248 | | | A |
| 249 | | | A |

TABLE 1-continued

Inhibition of HCV RdRp[1]

| Compound | MOLSTRUCTURE | Δ-55 Activity | Δ-21 Activity |
|---|---|---|---|
| 250 | | | A |
| 251 | | | A |
| 252 | | | A |

TABLE 1-continued
Inhibition of HCV RdRp[1]
| Compound | MOLSTRUCTURE | Δ-55 Activity | Δ-21 Activity |
|---|---|---|---|
| 253 | 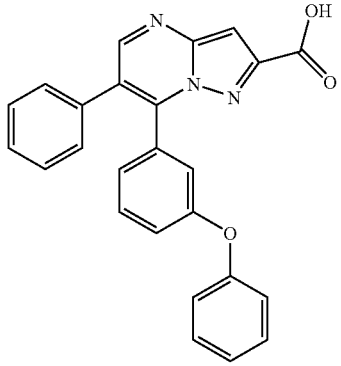 | | A |
| 254 | 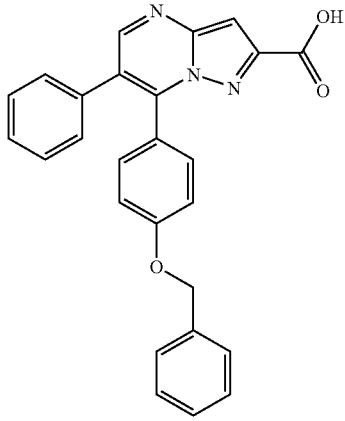 | | A |
| 255 | 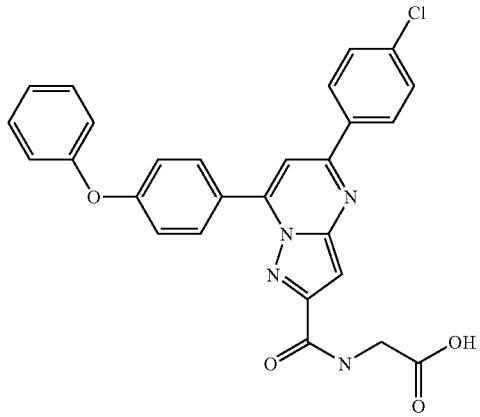 | | B |

TABLE 1-continued

Inhibition of HCV RdRp[1]

| Compound | MOLSTRUCTURE | Δ-55 Activity | Δ-21 Activity |
|---|---|---|---|
| 256 | | | B |
| 257 | | | A |
| 258 | | | B |

TABLE 1-continued

Inhibition of HCV RdRp[1]

| Compound | MOLSTRUCTURE | Δ-55 Activity | Δ-21 Activity |
|---|---|---|---|
| 259 | 4-chlorophenyl / 4-phenoxyphenyl pyrazolo[1,5-a]pyrimidine-2-carboxamide with N-(2-hydroxyethyl) | A | |
| 260 | 4-chlorophenyl / 4-phenoxyphenyl pyrazolo[1,5-a]pyrimidine-2-carboxamide with L-serine | B | |
| 261 | 4-chlorophenyl / 4-phenoxyphenyl pyrazolo[1,5-a]pyrimidine-2-(N-methyl)carboxamide | A | |

TABLE 1-continued

Inhibition of HCV RdRp[1]

| Compound | MOLSTRUCTURE | A-55 Activity | A-21 Activity |
|---|---|---|---|
| 262 | | A | |
| 263 | | B | |
| 264 | | A | |

TABLE 1-continued

Inhibition of HCV RdRp[1]

| Compound | MOLSTRUCTURE | A-55 Activity | A-21 Activity |
|---|---|---|---|
| 265 | | A | |
| 266 | | A | |
| 267 | | A | |
| 268 | | A | |

TABLE 1-continued

Inhibition of HCV RdRp[1]

| Compound | MOLSTRUCTURE | Δ-55 Activity | Δ-21 Activity |
|---|---|---|---|
| 269 | | | A |
| 270 | | | A |
| 271 | | | A |
| 272 | | | A |

TABLE 1-continued

Inhibition of HCV RdRp[1]

| Compound | MOLSTRUCTURE | Δ-55 Activity | Δ-21 Activity |
|---|---|---|---|
| 273 | | | A |
| 274 | | | A |
| 275 | | | A |
| 276 | | | B |

TABLE 1-continued
Inhibition of HCV RdRp[1]
| Compound | MOLSTRUCTURE | Δ-55 Activity | Δ-21 Activity |
|---|---|---|---|
| 277 | 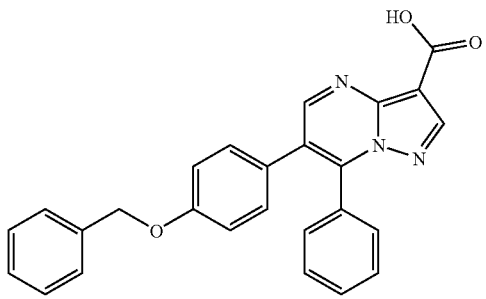 | A | |
| 278 | 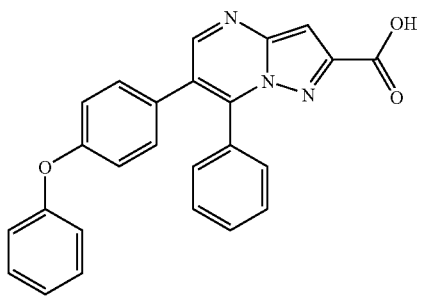 | A | |
| 279 | 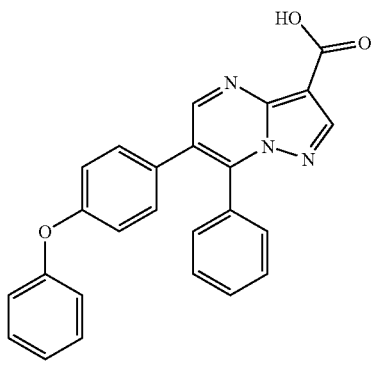 | A | |
| 280 | 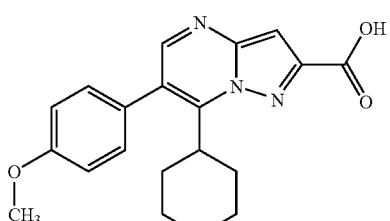 | A | |
| 281 | 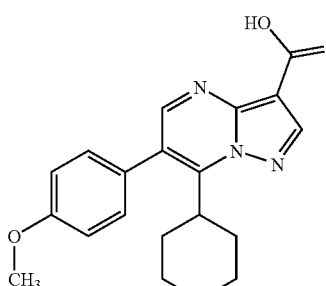 | B | |

TABLE 1-continued

Inhibition of HCV RdRp[1]

| Compound | MOLSTRUCTURE | Δ-55 Activity | Δ-21 Activity |
|---|---|---|---|
| 282 | | | B |
| 283 | | | B |
| 284 | | | A |
| 285 | | | A |

TABLE 1-continued

Inhibition of HCV RdRp[1]

| Compound | MOLSTRUCTURE | Δ-55 Activity | Δ-21 Activity |
|---|---|---|---|
| 286 | | B | |
| 287 | | C | C |
| 288 | | A | |
| 289 | | A | |

TABLE 1-continued

Inhibition of HCV RdRp[1]

| Compound | MOLSTRUCTURE | Δ-55 Activity | Δ-21 Activity |
|---|---|---|---|
| 290 | | | B |
| 291 | | | B |
| 292 | | | A |
| 293 | | | A |

TABLE 1-continued

Inhibition of HCV RdRp[1]

| Compound | MOLSTRUCTURE | Δ-55 Activity | Δ-21 Activity |
|---|---|---|---|
| 294 | | B | |
| 295 | | B | |
| 296 | | B | |

TABLE 1-continued

Inhibition of HCV RdRp[1]

| Compound | MOLSTRUCTURE | Δ-55 Activity | Δ-21 Activity |
|---|---|---|---|
| 297 | | B | |
| 298 | | B | |
| 299 | | B | |

TABLE 1-continued
Inhibition of HCV RdRp[1]
| Compound | MOLSTRUCTURE | Δ-55 Activity | Δ-21 Activity |
|---|---|---|---|
| 300 | 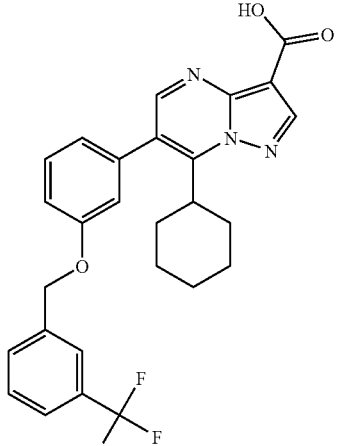 | A | |
| 301 | 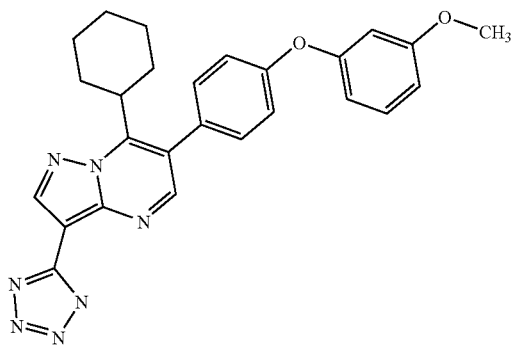 | C | C |
| 302 | 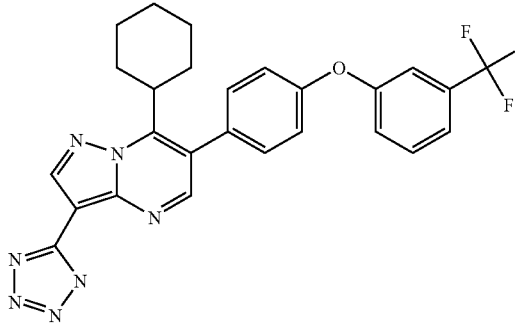 | B | B |
| 303 | 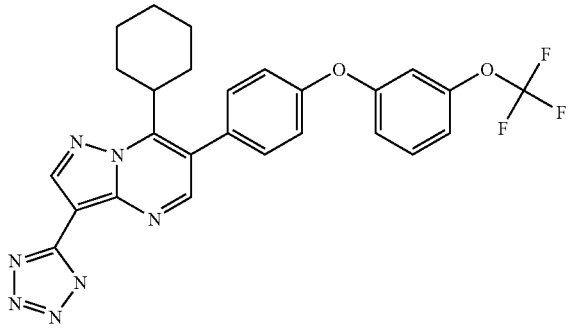 | B | B |

TABLE 1-continued
Inhibition of HCV RdRp[1]
| Compound | MOLSTRUCTURE | Δ-55 Activity | Δ-21 Activity |
|---|---|---|---|
| 304 | 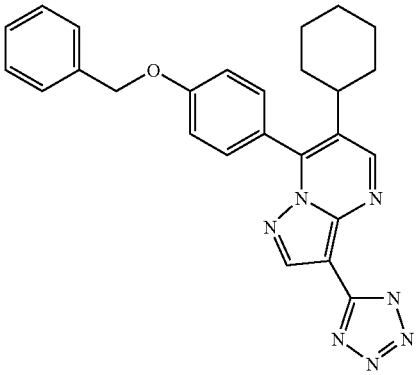 | B | |
| 305 | 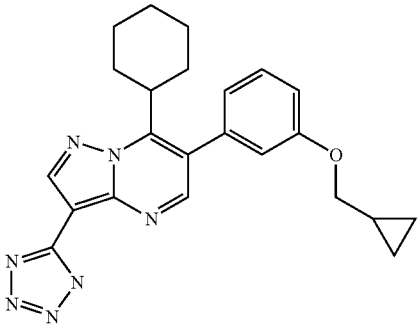 | B | |
| 306 | 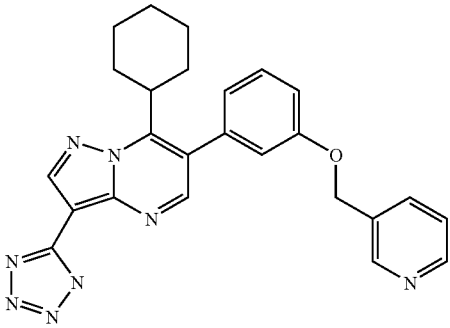 | B | |
| 307 | 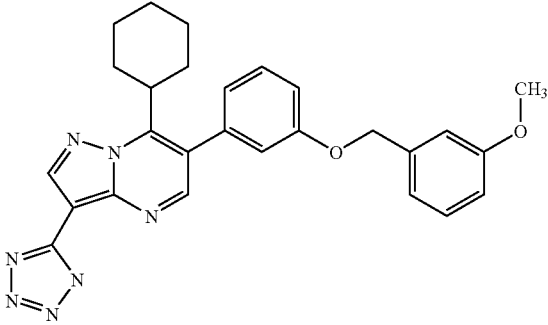 | B | B |

TABLE 1-continued

Inhibition of HCV RdRp[1]

| Compound | MOLSTRUCTURE | Δ-55 Activity | Δ-21 Activity |
|---|---|---|---|
| 308 | | B | B |
| 309 | | B | |
| 310 | | B | |
| 311 | | B | |

TABLE 1-continued

Inhibition of HCV RdRp[1]

| Compound | MOLSTRUCTURE | Δ-55 Activity | Δ-21 Activity |
|---|---|---|---|
| 312 | | B | |
| 313 | | B | |
| 314 | | B | |
| 315 | | B | |

TABLE 1-continued

Inhibition of HCV RdRp[1]

| Compound | MOLSTRUCTURE | A-55 Activity | A-21 Activity |
|---|---|---|---|
| 316 | | | B |
| 317 | | | B |
| 318 | | | B |
| 319 | | | B |

TABLE 1-continued
Inhibition of HCV RdRp[1]
| Compound | MOLSTRUCTURE | Δ-55 Activity | Δ-21 Activity |
|---|---|---|---|
| 320 | 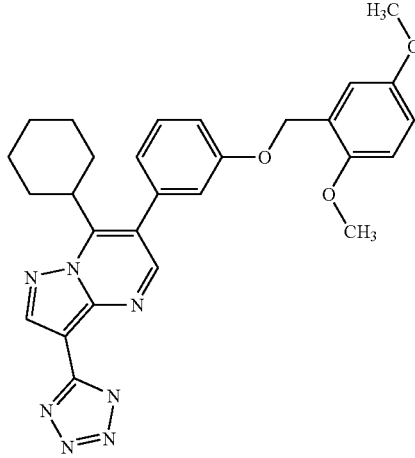 | | B |
| 321 | 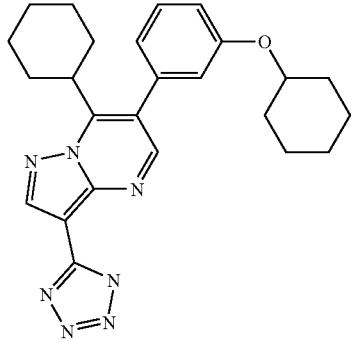 | | B |
| 322 | 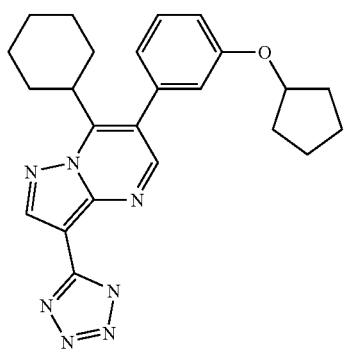 | | B |

TABLE 1-continued

Inhibition of HCV RdRp[1]

| Compound | MOLSTRUCTURE | Δ-55 Activity | Δ-21 Activity |
|---|---|---|---|
| 323 | | | B |
| 324 | | | B |
| 325 | | | A |

TABLE 1-continued

Inhibition of HCV RdRp[1]

| Compound | MOLSTRUCTURE | Δ-55 Activity | Δ-21 Activity |
|---|---|---|---|
| 326 | | B | |
| 327 | | B | |
| 328 | | A | |

TABLE 1-continued

Inhibition of HCV RdRp[1]

| Compound | MOLSTRUCTURE | Δ-55 Activity | Δ-21 Activity |
|---|---|---|---|
| 329 | | A | |
| 330 | | B | C |
| 331 | | B | C |
| 332 | | B | |
| 333 | | B | |

TABLE 1-continued

Inhibition of HCV RdRp[1]

| Compound | MOLSTRUCTURE | Δ-55 Activity | Δ-21 Activity |
|---|---|---|---|
| 334 | | A | |
| 335 | | A | |
| 336 | | A | |
| 337 | | B | B |
| 338 | | B | B |

TABLE 1-continued

Inhibition of HCV RdRp[1]

| Compound | MOLSTRUCTURE | Δ-55 Activity | Δ-21 Activity |
|---|---|---|---|
| 339 | | B | B |
| 340 | | B | C |
| 341 | | B | B |
| 342 | | B | C |
| 343 | | C | C |

TABLE 1-continued

Inhibition of HCV RdRp[1]

| Compound | MOLSTRUCTURE | Δ-55 Activity | Δ-21 Activity |
|---|---|---|---|
| 344 | | B | B |
| 345 | | B | B |
| 346 | | C | C |
| 347 | | B | |

TABLE 1-continued

Inhibition of HCV RdRp[1]

| Compound | MOLSTRUCTURE | Δ-55 Activity | Δ-21 Activity |
|---|---|---|---|
| 348 | | C | C |
| 349 | | B | C |
| 350 | | B | |

TABLE 1-continued
Inhibition of HCV RdRp[1]
| Compound | MOLSTRUCTURE | A-55 Activity | A-21 Activity |
|---|---|---|---|
| 351 | 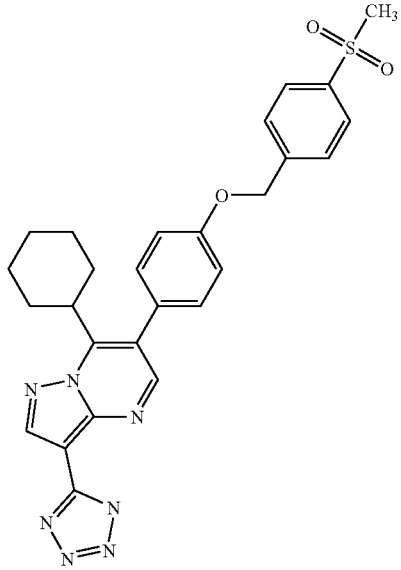 | B | C |
| 352 | 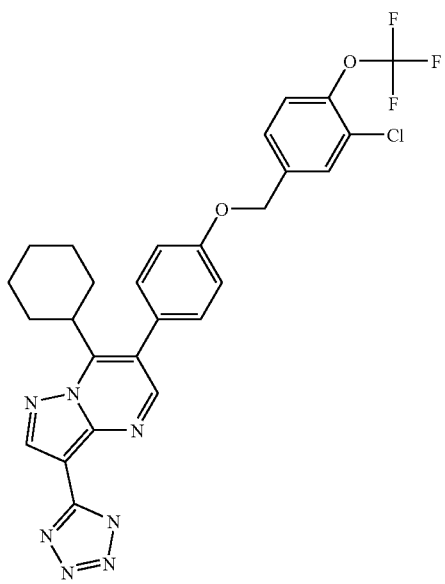 | B | |

TABLE 1-continued
Inhibition of HCV RdRp[1]
| Compound | MOLSTRUCTURE | Δ-55 Activity | Δ-21 Activity |
|---|---|---|---|
| 353 | 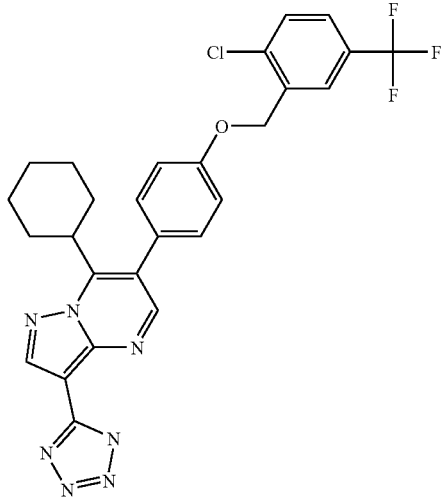 | | B |
| 354 | 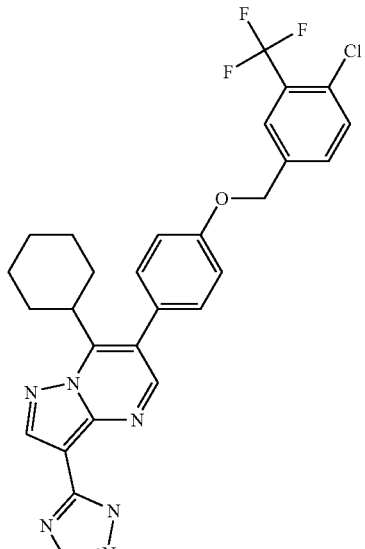 | | B |

TABLE 1-continued
Inhibition of HCV RdRp[1]
| Compound | MOLSTRUCTURE | Δ-55 Activity | Δ-21 Activity |
|---|---|---|---|
| 355 | 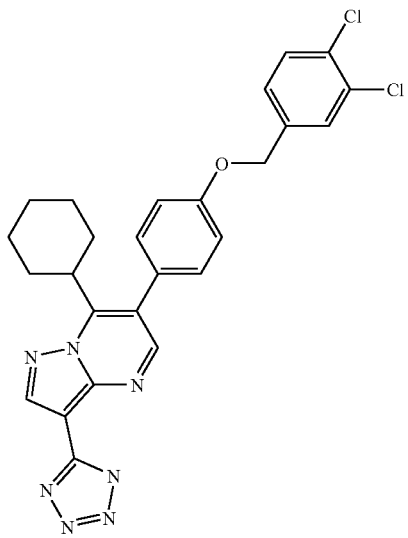 | B | |
| 356 | 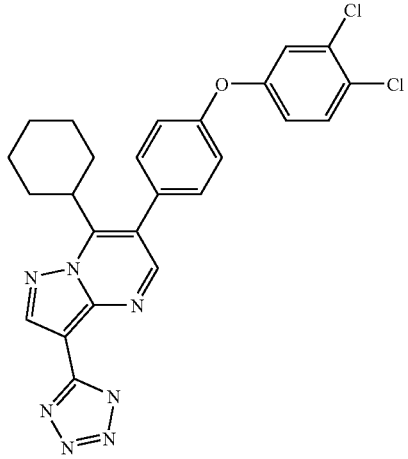 | B | |
| 357 | 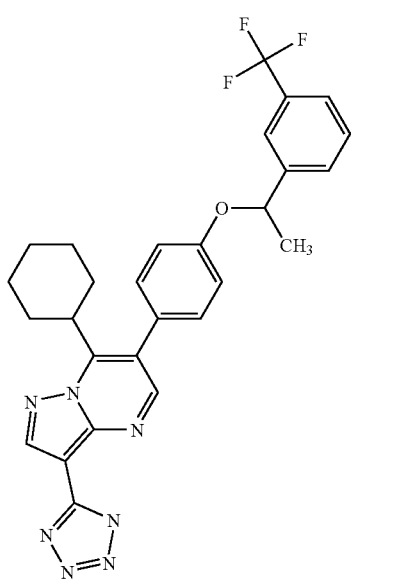 | B | |

TABLE 1-continued

Inhibition of HCV RdRp[1]

| Compound | MOLSTRUCTURE | Δ-55 Activity | Δ-21 Activity |
|---|---|---|---|
| 358 | | B | C |
| 359 | | B | |
| 360 | | B | C |

TABLE 1-continued

Inhibition of HCV RdRp[1]

| Compound | MOLSTRUCTURE | Δ-55 Activity | Δ-21 Activity |
|---|---|---|---|
| 361 | | B | C |
| 362 | | B | |
| 363 | | A | |

TABLE 1-continued

Inhibition of HCV RdRp[1]

| Compound | MOLSTRUCTURE | Δ-55 Activity | Δ-21 Activity |
|---|---|---|---|
| 364 | | | A |
| 365 | | | A |
| 366 | | | B |
| 367 | | | B |

TABLE 1-continued
Inhibition of HCV RdRp[1]
| Compound | MOLSTRUCTURE | Δ-55 Activity | Δ-21 Activity |
|---|---|---|---|
| 368 | 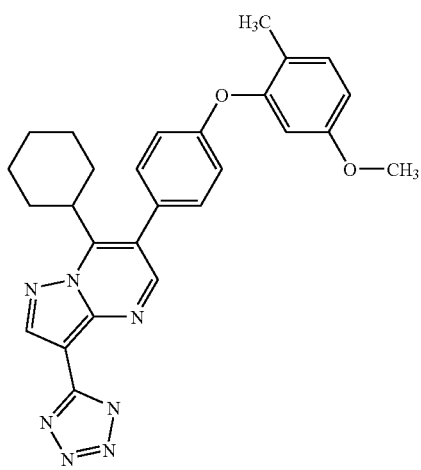 | B | |
| 369 | 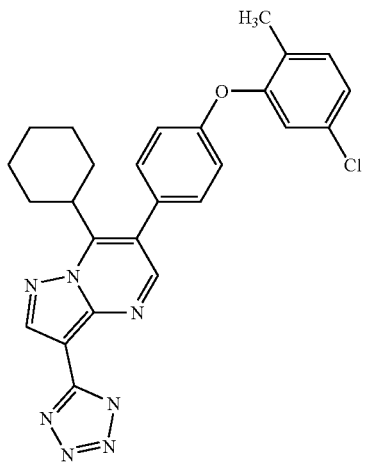 | B | |
| 370 | 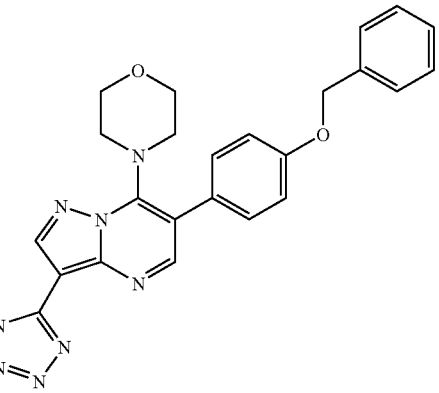 | A | A |

TABLE 1-continued
Inhibition of HCV RdRp[1]
| Compound | MOLSTRUCTURE | Δ-55 Activity | Δ-21 Activity |
| --- | --- | --- | --- |
| 371 | 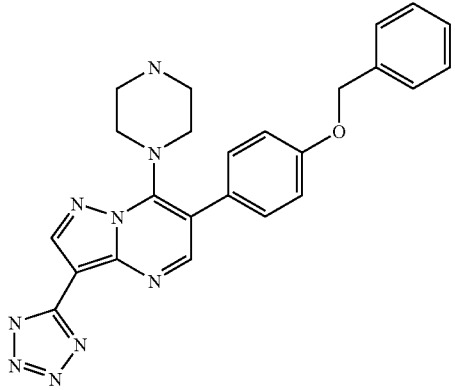 | A | A |
| 372 | 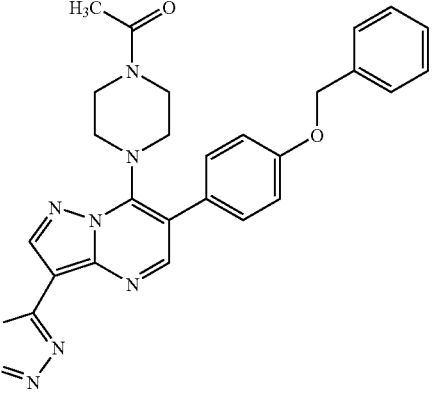 | A | A |
| 373 | 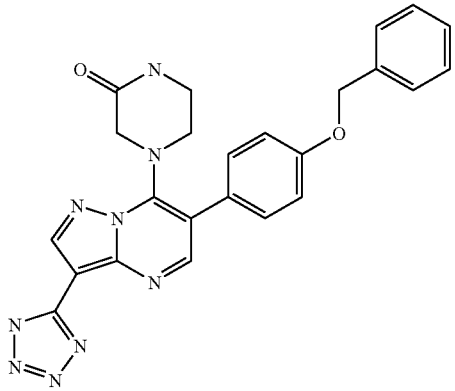 | A | A |

TABLE 1-continued

Inhibition of HCV RdRp[1]

| Compound | MOLSTRUCTURE | Δ-55 Activity | Δ-21 Activity |
|---|---|---|---|
| 374 | | B | B |
| 375 | | B | B |
| 376 | | A | |
| 377 | | A | |

TABLE 1-continued
Inhibition of HCV RdRp[1]
| Compound | MOLSTRUCTURE | Δ-55 Activity | Δ-21 Activity |
|---|---|---|---|
| 378 | 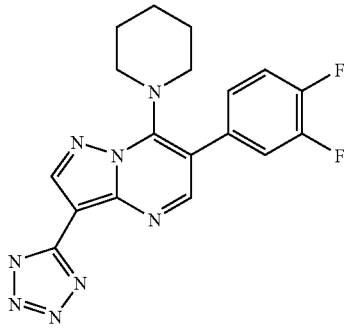 | B | C |
| 379 | 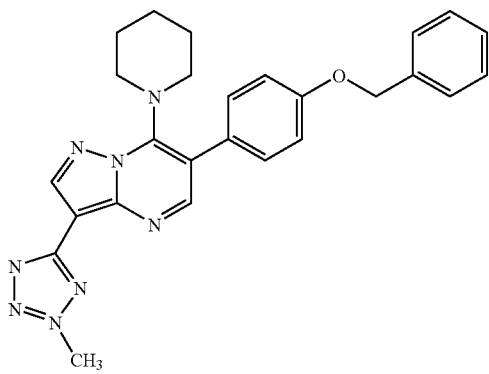 | A | |
| 380 | 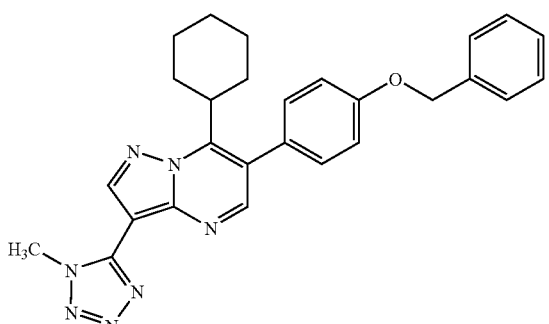 | A | |
| 381 | 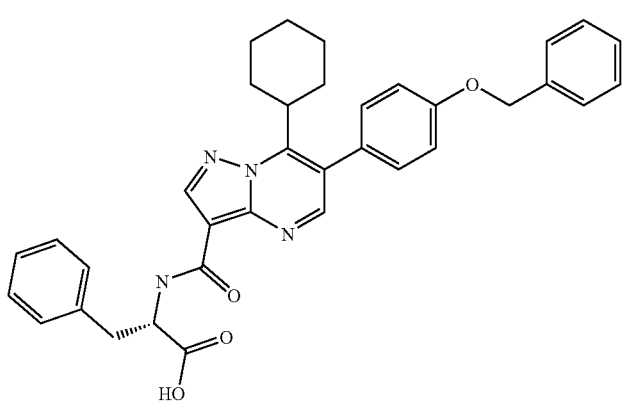 | B | C |

TABLE 1-continued

Inhibition of HCV RdRp[1]

| Compound | MOLSTRUCTURE | Δ-55 Activity | Δ-21 Activity |
|---|---|---|---|
| 382 | | B | |
| 383 | | C | C |
| 384 | | B | |
| 385 | | A | |

TABLE 1-continued

Inhibition of HCV RdRp[1]

| Compound | MOLSTRUCTURE | Δ-55 Activity | Δ-21 Activity |
|---|---|---|---|
| 386 | | A | |
| 387 | | B | |
| 388 | | B | |
| 389 | | A | |
| 390 | | A | |

TABLE 1-continued

Inhibition of HCV RdRp[1]

| Compound | MOLSTRUCTURE | Δ-55 Activity | Δ-21 Activity |
|---|---|---|---|
| 391 | | A | A |
| 392 | | A | A |
| 393 | | A | A |
| 394 | | A | A |

TABLE 1-continued

Inhibition of HCV RdRp[1]

| Compound | MOLSTRUCTURE | Δ-55 Activity | Δ-21 Activity |
|---|---|---|---|
| 395 | | A | B |
| 396 | | B | C |
| 397 | | A | B |
| 398 | | C | C |

TABLE 1-continued
Inhibition of HCV RdRp[1]
| Compound | MOLSTRUCTURE | Δ-55 Activity | Δ-21 Activity |
|---|---|---|---|
| 399 | 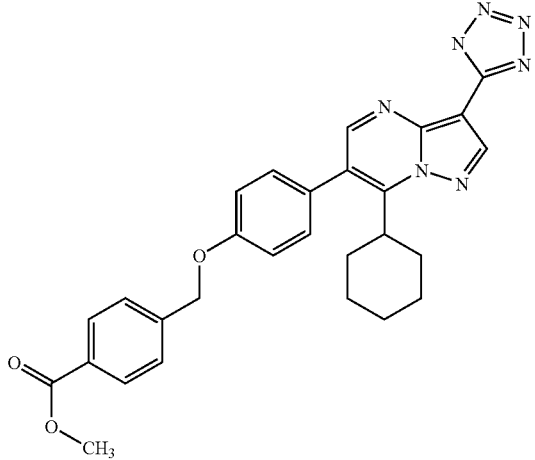 | C | C |
| 400 | 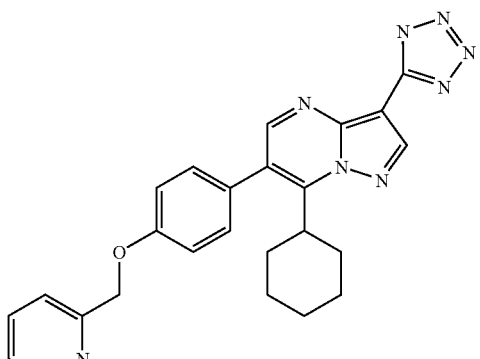 | B | C |
| 401 | 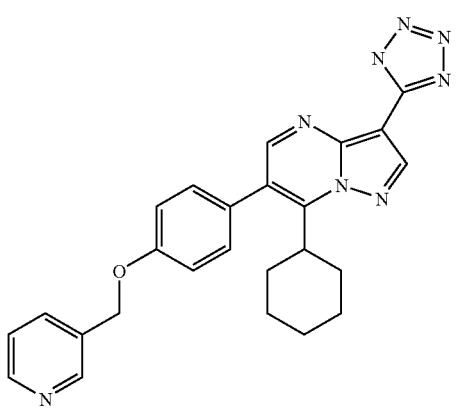 | B | C |

TABLE 1-continued
Inhibition of HCV RdRp[1]
| Compound | MOLSTRUCTURE | Δ-55 Activity | Δ-21 Activity |
| --- | --- | --- | --- |
| 402 | 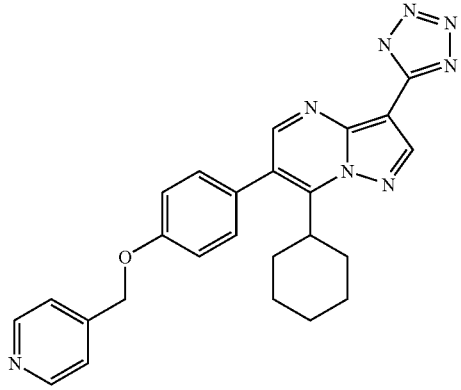 | C | C |
| 403 | 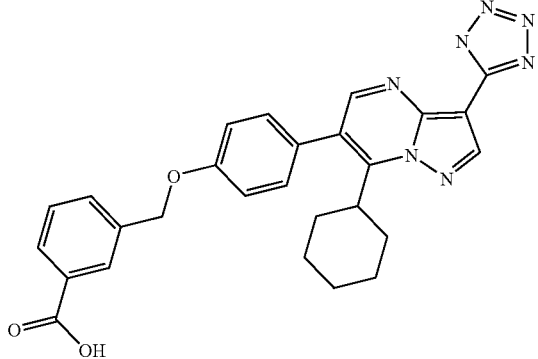 | B | C |
| 404 | 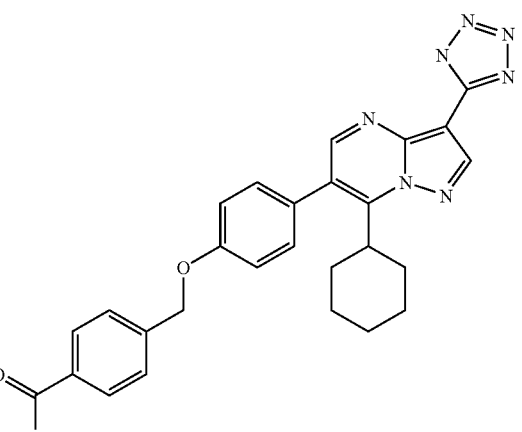 | C | C |

TABLE 1-continued

Inhibition of HCV RdRp[1]

| Compound | MOLSTRUCTURE | Δ-55 Activity | Δ-21 Activity |
|---|---|---|---|
| 405 | | A | A |
| 406 | | A | A |
| 407 | | A | A |
| 408 | | A | A |

TABLE 1-continued

Inhibition of HCV RdRp[1]

| Compound | MOLSTRUCTURE | Δ-55 Activity | Δ-21 Activity |
|---|---|---|---|
| 409 | | A | B |
| 410 | | B | B |
| 411 | | A | B |
| 412 | | A | A |

TABLE 1-continued

Inhibition of HCV RdRp[1]

| Compound | MOLSTRUCTURE | Δ-55 Activity | Δ-21 Activity |
|---|---|---|---|
| 413 | | A | A |
| 414 | | A | A |
| 415 | | A | A |
| 416 | | A | A |

TABLE 1-continued

Inhibition of HCV RdRp[1]

| Compound | MOLSTRUCTURE | Δ-55 Activity | Δ-21 Activity |
|---|---|---|---|
| 417 | | | A |
| 418 | | | A |
| 419 | | | A |
| 420 | | | A |

TABLE 1-continued

Inhibition of HCV RdRp[1]

| Compound | MOLSTRUCTURE | Δ-55 Activity | Δ-21 Activity |
|---|---|---|---|
| 421 | | A | |
| 422 | | A | |
| 423 | | A | |

TABLE 1-continued

Inhibition of HCV RdRp[1]

| Compound | MOLSTRUCTURE | Δ-55 Activity | Δ-21 Activity |
|---|---|---|---|
| 424 | | A | |
| 425 | | A | |
| 426 | | A | |

TABLE 1-continued
Inhibition of HCV RdRp[1]
| Compound | MOLSTRUCTURE | Δ-55 Activity | Δ-21 Activity |
|---|---|---|---|
| 427 | 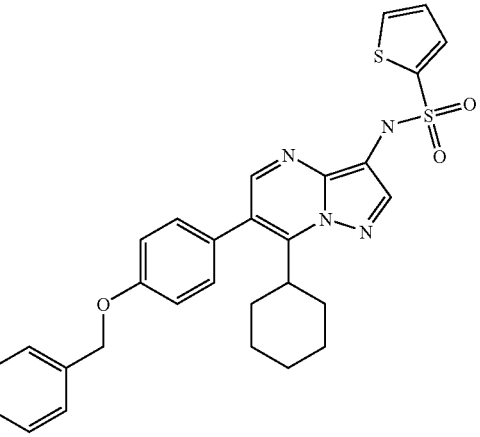 | A | |
| 428 | 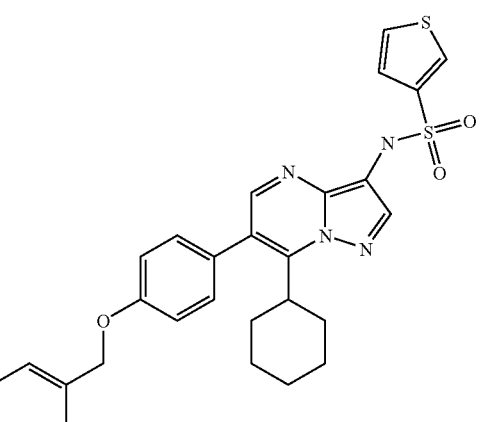 | A | |
| 429 | 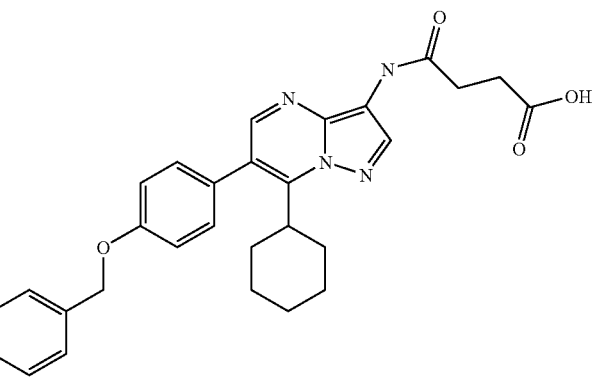 | B | B |

TABLE 1-continued

Inhibition of HCV RdRp[1]

| Compound | MOLSTRUCTURE | Δ-55 Activity | Δ-21 Activity |
|---|---|---|---|
| 430 | | B | B |
| 431 | | B | B |
| 432 | | B | C |
| 433 | | B | C |

TABLE 1-continued

Inhibition of HCV RdRp[1]

| Compound | MOLSTRUCTURE | Δ-55 Activity | Δ-21 Activity |
|---|---|---|---|
| 434 | | B | B |
| 435 | | B | C |
| 436 | | A | A |
| 437 | | C | C |

TABLE 1-continued

Inhibition of HCV RdRp[1]

| Compound | MOLSTRUCTURE | Δ-55 Activity | Δ-21 Activity |
| --- | --- | --- | --- |
| 438 | | B | B |
| 439 | | B | B |
| 440 | | B | B |
| 441 | | B | B |

TABLE 1-continued

Inhibition of HCV RdRp[1]

| Compound | MOLSTRUCTURE | Δ-55 Activity | Δ-21 Activity |
|---|---|---|---|
| 442 | | B | C |
| 443 | | B | C |
| 444 | | B | B |
| 445 | | B | B |

TABLE 1-continued

Inhibition of HCV RdRp[1]

| Compound | MOLSTRUCTURE | Δ-55 Activity | Δ-21 Activity |
|---|---|---|---|
| 446 | | B | B |
| 447 | | B | B |
| 448 | | B | B |
| 449 | | A | |

TABLE 1-continued
Inhibition of HCV RdRp[1]
| Compound | MOLSTRUCTURE | Δ-55 Activity | Δ-21 Activity |
|---|---|---|---|
| 450 | 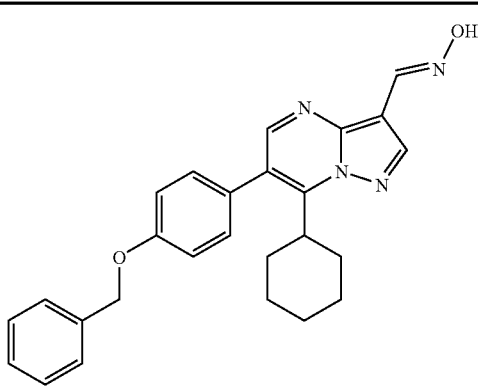 | A | |
| 451 | 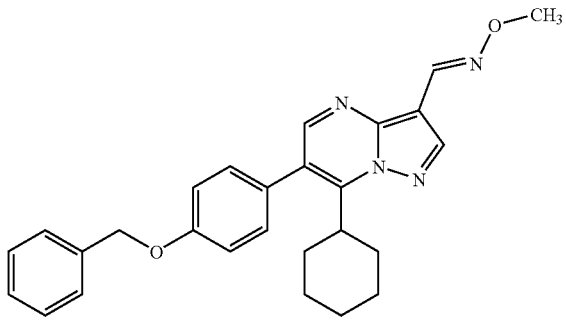 | A | |
| 452 | 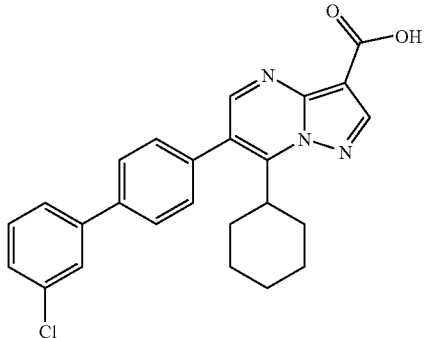 | B | B |
| 453 | 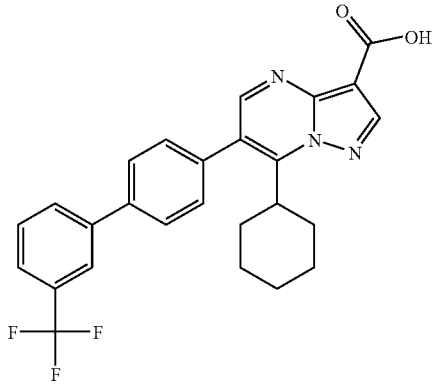 | A | B |

TABLE 1-continued
Inhibition of HCV RdRp[1]
| Compound | MOLSTRUCTURE | Δ-55 Activity | Δ-21 Activity |
|---|---|---|---|
| 454 | 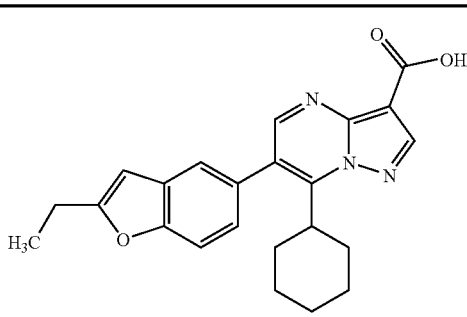 | | B |
| 455 | 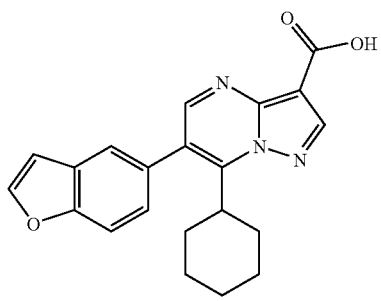 | | B |
| 456 | 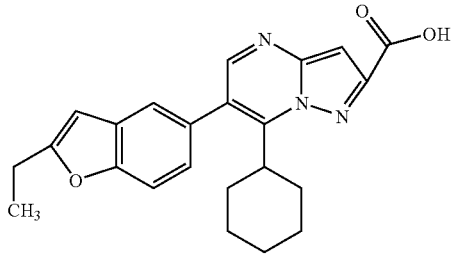 | | B |
| 457 | 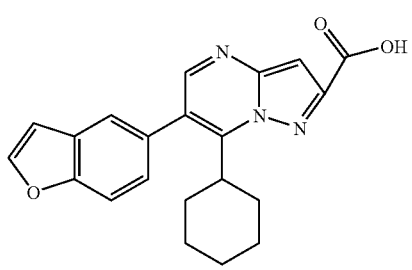 | | A |
| 458 | 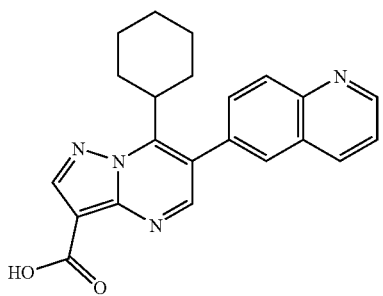 | A | A |

TABLE 1-continued

Inhibition of HCV RdRp[1]

| Compound | MOLSTRUCTURE | Δ-55 Activity | Δ-21 Activity |
|---|---|---|---|
| 459 | | A | |
| 460 | | A | |
| 461 | | B | C |
| 462 | | B | B |
| 463 | | A | A |

TABLE 1-continued

Inhibition of HCV RdRp[1]

| Compound | MOLSTRUCTURE | Δ-55 Activity | Δ-21 Activity |
|---|---|---|---|
| 464 | | A | |
| 465 | | B | B |
| 466 | | A | A |
| 467 | | B | B |
| 468 | | B | B |

TABLE 1-continued

Inhibition of HCV RdRp[1]

| Compound | MOLSTRUCTURE | Δ-55 Activity | Δ-21 Activity |
|---|---|---|---|
| 469 | | A | |
| 470 | | A | B |
| 471 | | B | B |
| 472 | | B | B |
| 473 | | B | B |

TABLE 1-continued

Inhibition of HCV RdRp[1]

| Compound | MOLSTRUCTURE | A-55 Activity | A-21 Activity |
|----------|--------------|---------------|---------------|
| 474 | | A | A |
| 475 | | C | C |
| 476 | | A | A |
| 477 | | B | B |

TABLE 1-continued

Inhibition of HCV RdRp[1]

| Compound | MOLSTRUCTURE | A-55 Activity | A-21 Activity |
|---|---|---|---|
| 478 | | B | B |
| 479 | | A | A |
| 480 | | A | B |
| 481 | | A | A |

TABLE 1-continued

Inhibition of HCV RdRp[1]

| Compound | MOLSTRUCTURE | Δ-55 Activity | Δ-21 Activity |
|---|---|---|---|
| 482 | | C | C |
| 483 | | A | B |
| 484 | | B | C |
| 485 | | B | B |

TABLE 1-continued
Inhibition of HCV RdRp[1]
| Compound | MOLSTRUCTURE | Δ-55 Activity | Δ-21 Activity |
|---|---|---|---|
| 486 | 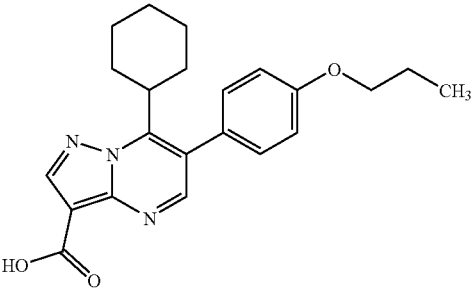 | B | B |
| 487 | 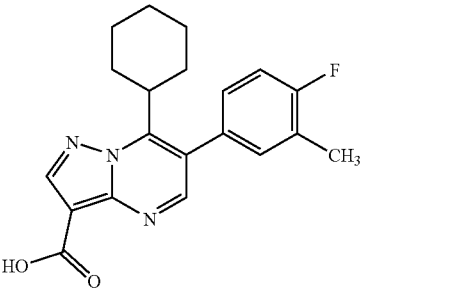 | B | B |
| 488 | 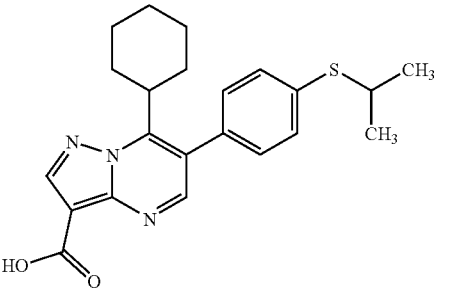 | B | B |
| 489 | 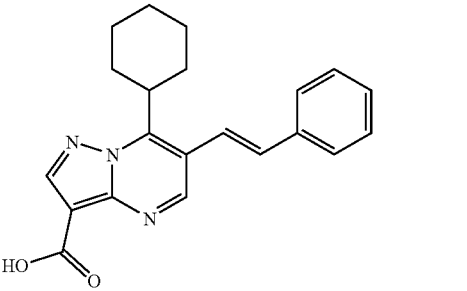 | B | B |

TABLE 1-continued

Inhibition of HCV RdRp[1]

| Compound | MOLSTRUCTURE | Δ-55 Activity | Δ-21 Activity |
|---|---|---|---|
| 490 | | C | C |
| 491 | | A | A |
| 492 | | A | A |
| 493 | | A | B |

TABLE 1-continued

Inhibition of HCV RdRp[1]

| Compound | MOLSTRUCTURE | Δ-55 Activity | Δ-21 Activity |
|---|---|---|---|
| 494 | | C | C |
| 495 | | A | B |
| 496 | | A | A |
| 497 | | B | C |

TABLE 1-continued

Inhibition of HCV RdRp[1]

| Compound | MOLSTRUCTURE | Δ-55 Activity | Δ-21 Activity |
|---|---|---|---|
| 498 | | A | A |
| 499 | | B | C |
| 500 | | B | C |
| 501 | | B | C |

TABLE 1-continued

Inhibition of HCV RdRp[1]

| Compound | MOLSTRUCTURE | Δ-55 Activity | Δ-21 Activity |
|---|---|---|---|
| 502 | | C | C |
| 503 | | B | C |
| 504 | | B | B |
| 505 | | C | C |

US 7,449,488 B2
387                                                                                                        388
TABLE 1-continued
Inhibition of HCV RdRp[1]
| Compound | MOLSTRUCTURE | Δ-55 Activity | Δ-21 Activity |
|---|---|---|---|
| 506 | 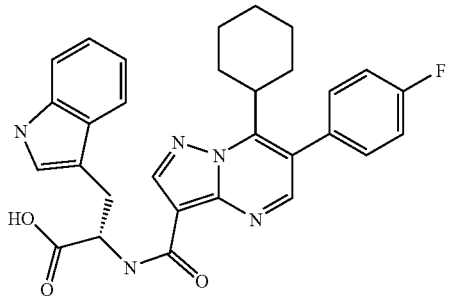 | C | C |
| 507 | 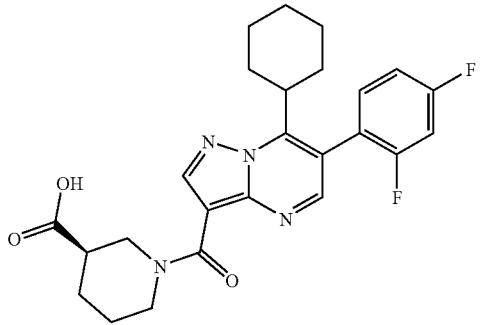 | A | A |
| 508 | 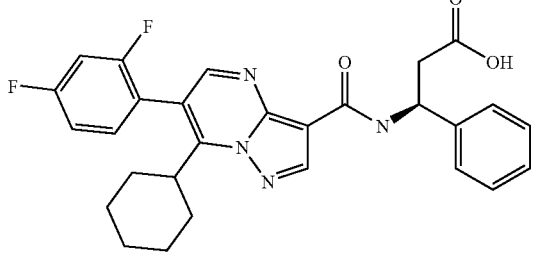 | B | B |
| 509 | 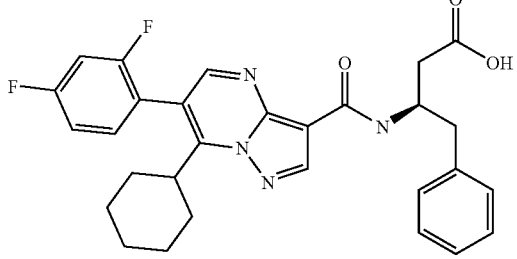 | A | B |
| 510 | 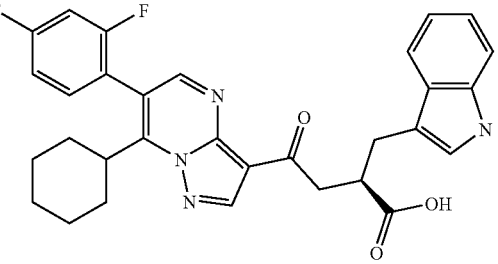 | C | C |

TABLE 1-continued

Inhibition of HCV RdRp[1]

| Compound | MOLSTRUCTURE | Δ-55 Activity | Δ-21 Activity |
|---|---|---|---|
| 511 | | A | B |
| 512 | | B | C |
| 513 | | A | C |
| 514 | | B | C |
| 515 | | | A |

TABLE 1-continued

Inhibition of HCV RdRp[1]

| Compound | MOLSTRUCTURE | Δ-55 Activity | Δ-21 Activity |
|---|---|---|---|
| 516 | | | A |
| 517 | | | C |
| 518 | | | C |
| 519 | | | B |

TABLE 1-continued

Inhibition of HCV RdRp[1]

| Compound | MOLSTRUCTURE | Δ-55 Activity | Δ-21 Activity |
|---|---|---|---|
| 520 | | C | C |
| 521 | | | C |
| 522 | | | C |

TABLE 1-continued

Inhibition of HCV RdRp[1]

| Compound | MOLSTRUCTURE | Δ-55 Activity | Δ-21 Activity |
|---|---|---|---|
| 523 | | | C |
| 524 | | | C |
| 525 | | | C |
| 526 | | | C |

TABLE 1-continued

Inhibition of HCV RdRp[1]

| Compound | MOLSTRUCTURE | Δ-55 Activity | Δ-21 Activity |
|---|---|---|---|
| 527 | | | C |
| 528 | | | C |
| 529 | | | C |
| 530 | | | C |

TABLE 1-continued

Inhibition of HCV RdRp[1]

| Compound | MOLSTRUCTURE | Δ-55 Activity | Δ-21 Activity |
|---|---|---|---|
| 531 | | | C |
| 532 | | | C |
| 533 | | B | C |
| 534 | | | B |

TABLE 1-continued

Inhibition of HCV RdRp[1]

| Compound | MOLSTRUCTURE | Δ-55 Activity | Δ-21 Activity |
|---|---|---|---|
| 535 | | | A |
| 536 | | | A |
| 537 | | | A |
| 538 | | | B |

TABLE 1-continued

Inhibition of HCV RdRp[1]

| Compound | MOLSTRUCTURE | Δ-55 Activity | Δ-21 Activity |
|---|---|---|---|
| 539 | | | B |
| 540 | | B | C |
| 541 | | | A |
| 542 | | | C |

TABLE 1-continued

Inhibition of HCV RdRp[1]

| Compound | MOLSTRUCTURE | Δ-55 Activity | Δ-21 Activity |
|---|---|---|---|
| 543 | | C | |
| 544 | | B | |
| 545 | | B | C |

TABLE 1-continued

Inhibition of HCV RdRp[1]

| Compound | MOLSTRUCTURE | Δ-55 Activity | Δ-21 Activity |
|---|---|---|---|
| 546 | | | B |
| 547 | | | B |
| 548 | | | B |

TABLE 1-continued

Inhibition of HCV RdRp[1]

| Compound | MOLSTRUCTURE | Δ-55 Activity | Δ-21 Activity |
|---|---|---|---|
| 549 | | B | |
| 550 | | B | B |
| 551 | | C | C |
| 552 | | A | B |

TABLE 1-continued

Inhibition of HCV RdRp[1]

| Compound | MOLSTRUCTURE | Δ-55 Activity | Δ-21 Activity |
|---|---|---|---|
| 553 | | A | B |
| 554 | | B | B |
| 555 | | B | C |
| 556 | | A | B |

TABLE 1-continued

Inhibition of HCV RdRp[1]

| Compound | MOLSTRUCTURE | Δ-55 Activity | Δ-21 Activity |
|---|---|---|---|
| 557 | | B | C |
| 558 | | B | B |
| 559 | | C | C |
| 560 | | B | B |

TABLE 1-continued

Inhibition of HCV RdRp[1]

| Compound | MOLSTRUCTURE | Δ-55 Activity | Δ-21 Activity |
|---|---|---|---|
| 561 | | A | A |
| 562 | | A | B |
| 563 | | A | A |
| 564 | | A | B |

TABLE 1-continued

Inhibition of HCV RdRp[1]

| Compound | MOLSTRUCTURE | Δ-55 Activity | Δ-21 Activity |
|---|---|---|---|
| 565 | | B | B |
| 566 | | B | B |
| 567 | | A | A |
| 568 | | A | B |

TABLE 1-continued

Inhibition of HCV RdRp[1]

| Compound | MOLSTRUCTURE | Δ-55 Activity | Δ-21 Activity |
|---|---|---|---|
| 569 | | B | B |
| 570 | | A | B |
| 571 | | A | B |
| 572 | | B | B |

TABLE 1-continued

Inhibition of HCV RdRp[1]

| Compound | MOLSTRUCTURE | Δ-55 Activity | Δ-21 Activity |
|---|---|---|---|
| 573 | | B | B |
| 574 | | A | B |
| 575 | | A | A |
| 576 | | B | B |

TABLE 1-continued

Inhibition of HCV RdRp[1]

| Compound | MOLSTRUCTURE | Δ-55 Activity | Δ-21 Activity |
|---|---|---|---|
| 577 | | B | B |
| 578 | | B | B |
| 579 | | B | B |
| 580 | | B | B |
| 581 | | B | B |

TABLE 1-continued

Inhibition of HCV RdRp[1]

| Compound | MOLSTRUCTURE | Δ-55 Activity | Δ-21 Activity |
|---|---|---|---|
| 582 | | B | B |
| 583 | | B | B |
| 584 | | B | B |
| 585 | | B | B |
| 586 | | B | |

TABLE 1-continued

Inhibition of HCV RdRp[1]

| Compound | MOLSTRUCTURE | Δ-55 Activity | Δ-21 Activity |
|---|---|---|---|
| 587 | | B | B |
| 588 | | B | B |
| 589 | | B | B |
| 590 | | B | B |
| 591 | | B | B |

TABLE 1-continued

Inhibition of HCV RdRp[1]

| Compound | MOLSTRUCTURE | Δ-55 Activity | Δ-21 Activity |
|---|---|---|---|
| 592 | | B | B |
| 593 | | B | B |
| 594 | | B | B |
| 595 | | B | C |
| 596 | | B | C |
| 597 | | B | B |

TABLE 1-continued

Inhibition of HCV RdRp[1]

| Compound | MOLSTRUCTURE | Δ-55 Activity | Δ-21 Activity |
|---|---|---|---|
| 598 | | B | C |
| 599 | | B | C |
| 600 | | C | C |
| 601 | | B | C |

TABLE 1-continued

Inhibition of HCV RdRp[1]

| Compound | MOLSTRUCTURE | Δ-55 Activity | Δ-21 Activity |
|---|---|---|---|
| 602 | | B | C |
| 603 | | B | C |
| 604 | | A | B |
| 605 | | | B |

TABLE 1-continued
Inhibition of HCV RdRp[1]
| Compound | MOLSTRUCTURE | Δ-55 Activity | Δ-21 Activity |
|---|---|---|---|
| 606 | 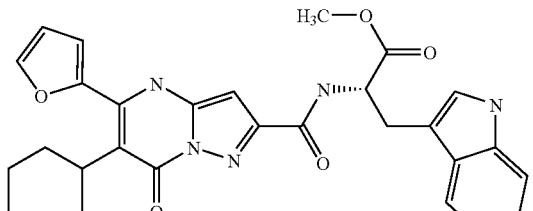 | | C |
| 607 | 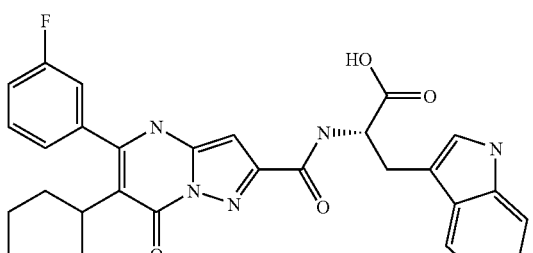 | | C |
| 608 | 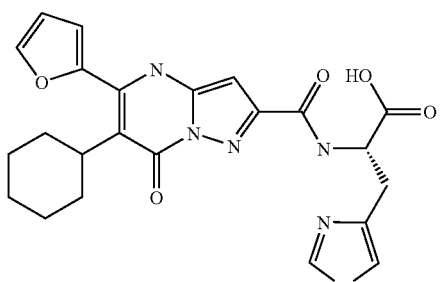 | | C |
| 609 | 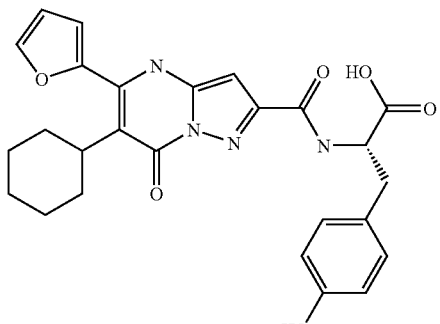 | | C |

TABLE 1-continued
Inhibition of HCV RdRp[1]
| Compound | MOLSTRUCTURE | Δ-55 Activity | Δ-21 Activity |
|---|---|---|---|
| 610 | 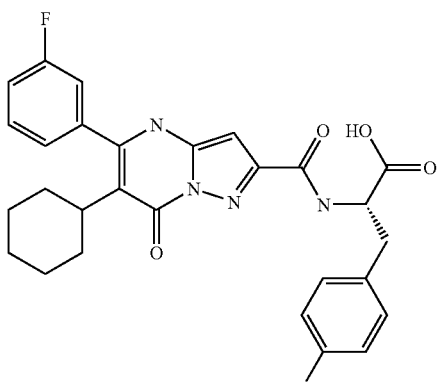 | | C |
| 611 | 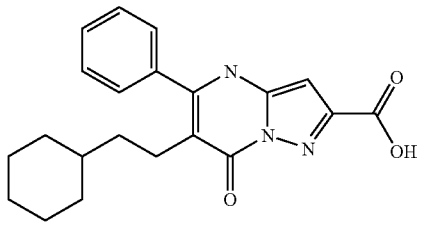 | | C |
| 612 | 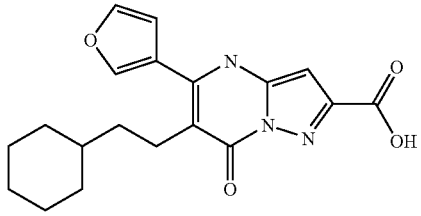 | | C |
| 613 | 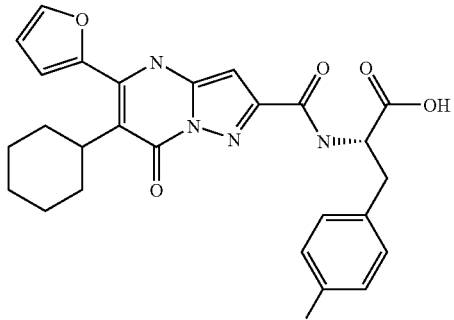 | | C |
| 614 | 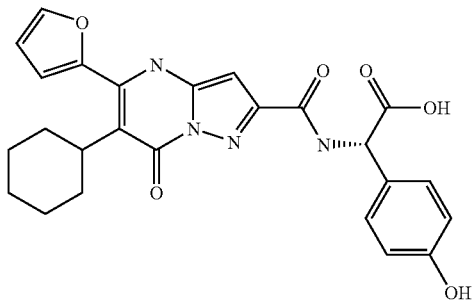 | | C |

TABLE 1-continued
Inhibition of HCV RdRp[1]
| Compound | MOLSTRUCTURE | Δ-55 Activity | Δ-21 Activity |
|---|---|---|---|
| 615 | 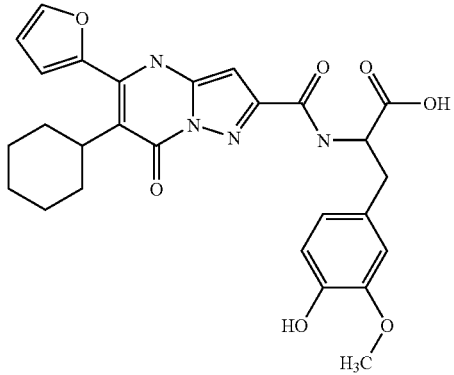 | | C |
| 616 | 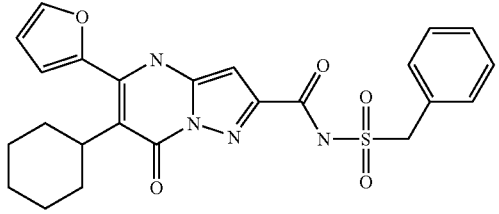 | | C |
| 617 | 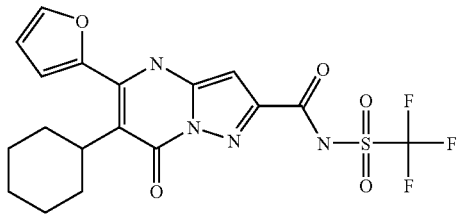 | | B |
| 618 | 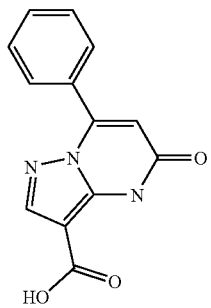 | | A |
| 619 | 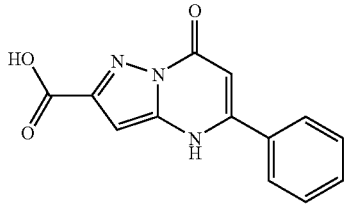 | | A |

TABLE 1-continued

Inhibition of HCV RdRp[1]

| Compound | MOLSTRUCTURE | Δ-55 Activity | Δ-21 Activity |
|---|---|---|---|
| 620 | 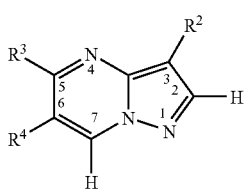 | A | |

[1] All nitrogen atoms have three valences; where a bond is not explicitly identified, a hydrogen bond is assumed.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention and appended claims.

What is claimed is:

1. A compound represented by the structural formula (VII):

(VII)

or a pharmaceutically acceptable salt, or ester of the compound of Formula (VII), wherein:

$R^2$ is halo;

$R^3$ is a saturated or partially unsaturated six-membered heterocyclic radical with one nitrogen; and $R^4$ is selected from the group consisting of H, halo, haloalkyl, alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —$NR^8R^9$, —$NR^8COR^9$, —$NR^8SO_2R^9$, —$COR^8$, —$CO_2R^8$, —$CONR^8R^9$, —$CH_2OR^8$, —$OR^8$, —$SR^8$, —$SO_2R^8$, —$S(O_2)NR^8R^9$, —$S(O_2)$aryl, —$S(O_2)$heteroaryl, —$C(O)OR^9$, —$C(O)$aryl, —$C(O)$heteroaryl, —$(CHR^5)_n$-aryl, —$(CHR^5)_n$-heteroaryl,

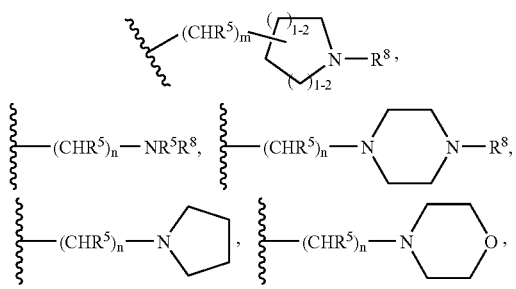

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for $R^4$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$;

$R^5$ is selected from the group consisting of H, alkyl, aryl or cycloalkyl;

$R^6$ is selected from the group consisting of H, alkyl, alkenyl, aryl, arylalkyl, arylalkenyl, cycloalkyl, heterocyclyl, heterocyclylalkyl heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —$CF_3$, —$OCF_3$, —CN, —$OR^5$, —$NR^5R^{10}$, —$C(R^5R^{11})_p$—$R^9$, —$N(R^5)$ Boc, —$(CR^5R^{11})_pOR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^7$ is selected from the group consisting of alkyl, cycloalkyl, aryl, arylalkenyl, heteroaryl, arylalkyl, heteroarylalkyl, heteroarylalkenyl, and heterocyclyl, wherein each of the alkyl, cycloalkyl, heteroarylalkyl, aryl, arylalkenyl, heteroaryl, arylalkyl, heteroarylalkyl, heteroarylalkenyl, and heterocyclyl can be unsubstituted or optionally independently substituted with one or more moieties which can be the same or different, each moiety being independently selected from the group consisting of halo, alkyl, aryl, cycloalkyl, $CF_3$, $OCF_3$, $CN$, $-OR^5$, $-NR^5R^{10}$, $-CH_2OR^5$, $-C(O_2)R^5$, $-C(O)NR^5R^{10}$, $-C(O)R^5$, $-SR^{10}$, $-S(O_2)R^{10}$, $-S(O_2)NR^5R^{10}$, $-N(R^5)S(O_2)R^{10}$, $-N(R^5)C(O)R^{10}$ and $-N(R^5)C(O)NR^5R^{10}$;

$R^8$ is selected from the group consisting of H, $-OR^6$, $-NR^5R^6$, $-C(O)NR^5R^{10}$, $-S(O_2)NR^5R^{10}$, $-C(O)R^7$, $-C(=N-CN)-NH_2$, $-C(=NH)-NHR^5$, heterocyclyl, $-S(O_2)R^7$,

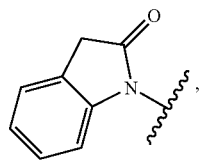

$-OR^{10}$, $-CF_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, $-CF_3$, $-OCF_3$, $-CN$, $-OR^5$, $-NR^5R^{10}$, $-C(R^5R^{11})_p-R^9$, $-N(R^5)Boc$, $-(CR^5R^{11})_pOR^5$, $-C(O_2)R^5$, $-C(O)R^5$, $-C(O)NR^5R^{10}$, $-SO_3H$, $-SR^{10}$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

$R^9$ is selected from the group consisting of H, $-OR^6$, $-NR^5R^6$, $-C(O)NR^5R^{10}$, $-S(O_2)NR^5R^{10}$, $-C(O)R^7$, $-C(=N-CN)-NH_2$, $-C(=NH)-NHR^5$, heterocyclyl, $-S(O_2)R^7$,

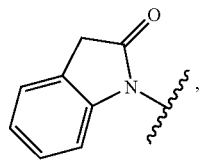

$-OR^{10}$, $-CF_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, $-CF_3$, $-OCF_3$, $-CN$, $-OR^5$, $-NR^5R^{10}$, $-C(R^5R^{11})_p-R^9$, $-N(R^5)Boc$, $-(CR^5R^{11})_pOR^5$, $-C(O_2)R^5$, $-C(O)R^5$, $-C(O)NR^5R^{10}$, $-SO_3H$, $-SR^{10}$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

$R^{10}$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, $-CF_3$, $-OCF_3$, $-CN$, $-OR^5$, $-NR^5R^{11}$, $-C(R^5R^{11})_p-R^9$, $-N(R^5)Boc$, $-(CR^5R^{11})_pOR^5$, $-C(O_2)R^5$, $-C(O)R^5$, $-C(O)NR^5R^{11}$, $-SO_3H$, $-SR^{11}$, $-S(O_2)R^7$, $-S(O_2)NR^5R^{11}$, $-N(R^5)S(O_2)R^7$, $-N(R^5)C(O)R^7$ and $-N(R^5)C(O)NR^5R^{11}$;

or optionally (i) $R^5$ and $R^{11}$ in the moiety $-NR^5R^{11}$, or (ii) $R^5$ and $R^6$ in the moiety $-NR^5R^6$, may be joined together to form a cycloalkyl or heterocyclyl moiety, with each of the cycloalkyl or heterocyclyl moiety being unsubstituted or optionally independently being substituted with one or more $R^9$ groups; and $R^{11}$ is H, halo or alkyl;

m is 0 to 4;

n is 1 to 4; and p is 1 to 4.

2. The compound according to claim 1, wherein $R^2$ is selected from the group consisting of Cl, Br, F, and I.

3. The compound according to claim 1, wherein $R^3$ is selected from the group consisting of piperidinyl, tetrahydroquinolinyl, tetrahydroisoquinolinyl, and decahydroquinolinyl.

4. The compound according to claim 1, wherein $R^4$ is H.

5. The compound according to claim 1, wherein $R^4$ is selected from the group consisting of Cl, Br, $-OH$, $-SH$, alkyl, alkenyl, alkynyl, haloalkyl and cyclopropyl.

6. The compound according to claim 1, wherein $R^4$ is $-NH_2$.

7. The compound according to claim 1, wherein $R^4$ is $-OH$.

8. The compound according to claim 1, wherein $R^4$ is alkoxy.

9. The compound according to claim 1, wherein $R^4$ is alkylthio.

10. The compound according to claim 1, wherein $R^4$ is halo.

11. The compound according to claim 1, wherein n is 1.

12. The compound according to claim 1, wherein p is 1.

13. The compound according to claim 1, wherein the compound is

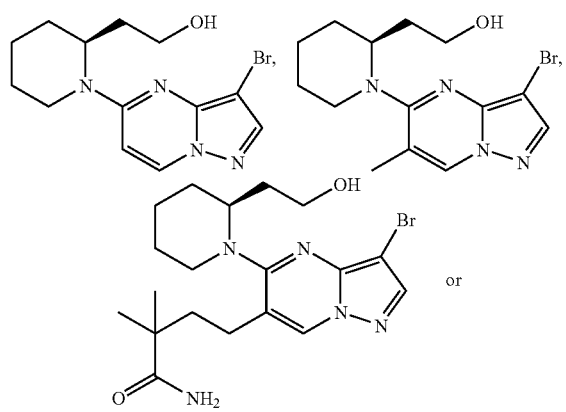

-continued

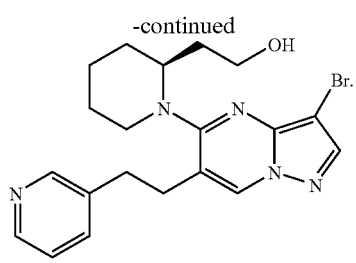

14. A compound according to claim 1 or a pharmaceutically acceptable salt, or ester thereof in purified form.

15. A compound according to claim 1 or a pharmaceutically acceptable salt, or ester thereof in isolated form.

16. A pharmaceutical composition comprising a therapeutically effective amount of at least one compound of claim 1 or a pharmaceutically acceptable salt, or ester thereof in combination with at least one pharmaceutically acceptable carrier.

* * * * *